(12) United States Patent
Griffith et al.

(10) Patent No.: US 7,494,795 B2
(45) Date of Patent: Feb. 24, 2009

(54) CRYSTAL STRUCTURE OF FMS-LIKE TYROSINE KINASE

(76) Inventors: James Paul Griffith, 15 Wood Ridge Cir., Weston, MA (US) 02493; James Roger Black, 40 Cherry St., Wenham, MA (US) 01984; Carlos H. Faerman, 41 Mohawk Dr., Acton, MA (US) 01720; Lovorka Lora Swenson, 5 David Rd., Belmont, MA (US) 02478; Michael Andrew Wynn, 19 Cross St., Salem, MA (US) 01970; Fan Lu, 59 Bridge St., Newton, MA (US) 02458; Judith A. Lippke, 307 South St., Chestnut Hill, MA (US) 02467; Kumkum Saxena, 8 Dotty Ann Dr., Framingham, MA (US) 01701

( * ) Notice: Subject to any disclaimer, the term of this patent is extended or adjusted under 35 U.S.C. 154(b) by 534 days.

(21) Appl. No.: 10/941,387

(22) Filed: Sep. 15, 2004

(65) Prior Publication Data

US 2005/0181975 A1 Aug. 18, 2005

Related U.S. Application Data

(60) Provisional application No. 60/540,391, filed on Jan. 29, 2004, provisional application No. 60/503,270, filed on Sep. 15, 2003.

(51) Int. Cl.
 *C12N 9/10* (2006.01)
 *G01N 31/00* (2006.01)
(52) U.S. Cl. .......................... 435/193; 436/4
(58) Field of Classification Search ............... 436/4; 435/193
See application file for complete search history.

(56) References Cited

U.S. PATENT DOCUMENTS

| | | | |
|---|---|---|---|
| 4,886,646 | A | 12/1989 | Carter et al. |
| 5,096,676 | A | 3/1992 | McPherson et al. |
| 5,130,105 | A | 7/1992 | Carter et al. |
| 5,221,410 | A | 6/1993 | Kushner et al. |
| 5,400,741 | A | 3/1995 | DeTitta et al. |
| 5,884,230 | A | 3/1999 | Srinivasan et al. |

OTHER PUBLICATIONS

McPherson, A. Current Approaches to Macromolecular Crystallization. European Journal of Biochemistry. 1990. vol. 189, pp. 1-23.*
Drenth, "Principles of Protein X-Ray Crystallography", 2nd Edition, 1999 Springer-Verlag New York Inc., Chapter 1, p. 1-21.*
Cudney R. Protein Crystallization and Dumb Luck. The Rigaku Journal. 1999. vol. 16, No. 1, pp. 1-7.*
Kundrot, C.E. Which Strategy for a Protein Crystallization Project? Cellular Molecular Life Science. 2004. vol. 61, pp. 525-536.*
Abu-Duhier et al., "Identification of Novel *FLT-3* Asp835 Mutations in Adult Acute Myeloid Leukaemia", *Br. J. Haematol.*, 113: 983-988 (2001).

Agnès et al., "Genomic Structure of the Downstream Part of the Human *FLT3* Gene: Exon/Intron Structure Conservation among Genes Encoding Receptor Tyrosine Kinases (RTK) of Subclass III", *Gene*, 145: 283-288 (1994).
Balbes et al., "A Perspective of Modern Methods in Computer-Aided Drug Design", *Rev. in Comp. Chem.*, 5: 337-379 (1994).
Bartlett et al., "CAVEAT: A Progam to Facilitate the Structure-Derived Design of Biologically Active Molecules", *Mol. Rec. in Chem. and Biol. Prob.*, 78: 182-196 (1989).
Blundell et al., "Knowledge-Based Prediction of Protein Structures and the Design of Novel Molecules", *Nature*, 326: 347-352 (1987).
Böhm, "The Computer Program LUDI: A New Method for the De Novo Design of Enzyme Inhibitors", *J. Comp. Aid. Molec. Design*, 6: 61-78 (1992).
Bossemeyer et al., "Phosphotransferase and Substrate Binding Mechanism of the cAMP-Dependent Protein Kinase Catalytic Subunit from Porcine Heart as Deduced from the 2.0 Å Structure of the Complex with $Mn^{2+}$ Adenylyl Imidodiphosphate and Inhibitor Peptide PKI(5-24)", *EMBO J.*, 12: 849-859 (1993).
Brasel et al., "Expression of the flt3 Receptor and its Ligand on Hematopoietic Cells", *Leukemia*, 9: 1212-1218 (1995).
Brünger et al., "Crystallography & NMR System: A New Software Suite for Macromolecular Structure Determination", *Acta Cryst.*, D54: 905-921 (1998).
Carson, "Ribbons 2.0", *J. Appl. Cryst.*, 24: 958-961 (1991).
Chan et al., "Autoinhibition of the Kit Receptor Tyrosine Kinase by the Cytosolic Juxtamembrane Region", *Mol. Cell. Biol.*, 23: 3067-3078 (2003).
Chayen, "A Novel Technique to Control the Rate of Vapour Diffusion, Giving Larger Protein Crystals", *J. Appl. Cryst.*, 30: 198-202 (1997).
Chayen, "The Role of Oil in Macromolecular Crystallization", *Structure*, 5: 1269-1274 (1997).
Chayen, "Comparative Studies of Protein Crystallization by Vapour-Diffusion and Microbatch Techniques", *Acta Cryst.*, D54: 8-15 (1998).
Claesson-Welsh et al., "Cloning and Expression of Human Platelet-Derived Growth Factor α and β Receptors", *Methods in Enzymol.*, 198: 72-77 (1991).

(Continued)

*Primary Examiner*—Suzanne M. Noakes
(74) *Attorney, Agent, or Firm*—James F. Haley, Jr.; Raymond M. Doss; Ropes & Gray LLP

(57) ABSTRACT

The invention relates to FMS-like tyrosine kinase (FLT3), FLT3 binding pockets or FLT3-like binding pockets. The invention relates to a computer comprising a data storage medium encoded with the structure coordinates of such binding pockets. The invention also relates to methods of using the structure coordinates to solve the structure of homologous proteins or protein complexes. The invention relates to methods of using the structure coordinates to screen for and design compounds that bind to FMS-like tyrosine kinase protein, complexes of FMS-like tyrosine kinase protein, homologues thereof, or FLT-3-like protein or protein complexes. The invention also relates to crystallizable compositions and crystals comprising an FMS-like tyrosine kinase cytoplasmic domain or homologues thereof. The invention also relates to methods of identifying inhibitors of the cytoplasmic domain of FMS-like tyrosine kinase protein.

12 Claims, 59 Drawing Sheets

OTHER PUBLICATIONS

Claesson-Welsh et al., "cDNA Cloning and Expression of the Human A-type Platelet-Derived Growth Factor (PDGF) Receptor Establishes Structural Similarity to the B-Type PDGF Receptor", *Proc. Natl. Acad. Sci. USA*, 86: 4917-4921 (1989).
Cohen et al., "Molecular Modeling Software and Methods for Medicinal Chemistry", *J. Med. Chem.*, 33: 883-894 (1990).
Cory and Bentley, "MATCHMOL, An Interactive Computer Graphics Procedure for Superposition of Molecular Models", *J. Mol. Graphics*, 2: 39-42 (1984).
D'Arcy et al., "A Novel Approach to Crystallising Proteins Under Oil", *J. Cryst. Growth*, 168: 175-180 (1996).
Dayhoff et al., "Transfer RNA", *Atlas Of Protein Sequence and Structure*, 5: D345-D352 (1978).
deLapeyrière et al., "Expression of *Flt3* Tyrosine Kinase Receptor Gene in Mouse Hematopoietic and Nervous Tissues", *Differentiation*, 58: 351-359 (1995).
Drexler, "Expression of FLT3 Receptor and Response to FLT3 Ligand by Leukemic Cells", *Leukemia*, 10: 588-599 (1996).
Eisen et al., "HOOK: A Program for Finding Novel Molecular Architectures that Satisfy the Chemical and Steric Requirements of a Macromolecule Binding Site", *Proteins Struct. Funct. Genet.*, 19: 199-221 (1994).
Fabbro et al., "PKC412—A Protein Kinase Inhibitor with a Broad Therapeutic Potential", *Anti-Cancer Drug Design*, 15: 17-28 (2000).
Fetrow and Bryant, "New Programs for Protein Tertiary Structure Prediction", *Bio/Tech.*, 11: 479-484 (1993).
Giles et al., "SU5416, a Small Molecule Tyrosine Kinase Receptor Inhibitor, Has Biologic Activity in Patients with Refactory Acute Myeloid Leukemia or Myelodysplastic Syndromes", *Blood*, 102: 795-801 (2003).
Gillet et al., "SPROUT: A Program for Structure Generation", *J. Comp. Aid. Molec. Des.*, 7: 127-153 (1993).
Gilliland and Griffin, "The Roles of FLT3 in Hematopoiesis and Leukemia", *Blood*, 100: 1532-1542 (2002).
Goodford, "A Computational Procedure for Determining Energetically Favorable Binding Sites on Biologically Important Macromolecules", *J. Med. Chem.*, 28: 849-857 (1985).
Goodsell and Olson, "Automated Docking of Substrates to Proteins by Simulated Annealing", *Proteins Struct. Funct. Genet.*, 8: 195-202 (1990).
Greer, "Comparative Modeling of Homologous Proteins", *Meth. in Enzymol.*, 202: 239-252 (1991).
Griffith et al., "The Structural Basis for Autoinhibition of FLT3 by the Juxtamembrane Domain", *Mol. Cell*, 13: 169-178 (2004).
Gschwend et al., "Molecular Docking Towards Drug Discovery", *J. Mol. Recog.*, 9: 175-186 (1996).
Guex and Peitsch, "Swiss-Model and the Swiss-PdbViewer: An Environment for Comparative Protein Modeling", *Electrophoresis*, 18: 2714-2723 (1997).
Guida, "Software for Structure-Based Drug Design", *Curr. Opin. Struct. Biol.*, 4: 777-781 (1994).
Hanks et al., "The Protein Kinase Family: Conserved Features and Deduced Phylogeny of the Catalytic Domains", *Science*, 241: 42-52 (1988).
Hanks and Quinn, "Protein Kinase Catalytic Domain Sequence Database: Identification of Conserved Features of Primary Structure and Classification of Family Members", *Methods in Enzymol.*, 200: 38-62 (1991).
Hannum et al., "Ligand for FLT3/FLK2 Receptor Tyrosine Kinase Regulates Growth of Haematopoietic Stem Cells and is Encoded by Variant RNAs", *Nature*, 368: 643-648 (1994).
Hayakawa et al., "Tandem-Duplicated Flt3 Constitutively Activates STAT5 and MAP Kinase and Introduces Autonomous Cell Growth in IL-3-Dependent Cell Lines", *Oncogene*, 19: 624-631 (2000).
Heldin, "Dimerization of Cell Surface Receptors in Signal Transduction", *Cell*, 80: 213-223 (1995).
Higgins et al., "Using CLUSTAL for Multiple Sequence Alignments", *Methods in Enzymol.*, 266: 383-402 (1996).
Horiike et al., "Tandem Duplications of the *FLT3* Receptor Gene are Associated with Leukemic Transformation of *Myelodysplasia*", *Leukemia*, 11: 1442-1446 (1997).
Hubbard, "Crystal Structure of the Activated Insulin Receptor Tyrosine Kinase in Complex with Peptide Substrate and ATP Analog", *EMBO J.*, 16: 5573-5581 (1997).
Huse et al., "Crystal Structure of the Cytoplasmic Domain of the Type I TGFβ Receptor in Complex with FKBP12", *Cell*, 96: 425-436 (1999).
Huse and Kuriyan, "The Conformational Plasticity of Protein Kinases", *Cell*, 109: 275-282 (2002).
Irusta et al., "Definition of an Inhibitory Juxtamembrane WW-Like Domain in the Platelet-Derived Growth Factor β Receptors", *J. Biol. Chem.*, 277: 38627-38634 (2002).
Johnson et al., "Knowledge-Based Protein Modeling", *Crit. Rev. Biochem. Mol. Biol.*, 29: 1-68 (1994).
Jones et al., "Improved Methods for Building Protein Models in Electron Density Maps and the Location of Errors in these Models", *Acta Cryst.*, A47: 110-119 (1991).
Kelly et al., "CT53518, a Novel Selective FLT3 Antagonist for the Treatment of Acute Myelogenous Leukemia (AML)", *Cancer Cell*, 1: 421-432 (2002).
Knighton et al., "Crystal Structure of the Catalytic Subunit of Cyclic Adenosine Monophosphate—Dependent Protein Kinase", *Science*, 253: 407-414 (1991).
Kottaridis et al., "FLT3 Mutations and Leukemia", *Br. J. Haematol.*, 122: 523-538 (2003).
Lattman, "Use of the Rotation and Translation Functions", *Meth. in Enzymol.*, 115: 55-77 (1985).
Lauri and Bartlett, "CAVEAT: A Program to Facilitate the Design of Organic Molecules", *J. Comp. Aid. Molec. Des.*, 8: 51-66 (1994).
Lyman et al., "The flt3 Ligand: A Hematopoietic Stem Cell Factor Whose Activities Are Distinct from Steel Factor", *Stem Cells*, 12: 99-110 (1994).
Lyman et al., "Structural Analysis of Human and Murine flt3 Ligand Genomic Loci", *Oncogene*, 11: 1165-1172 (1995).
Maroc et al., "Biochemical Characterization and Analysis of the Transforming Potential of the FLT3/FLK2 Receptor Tyrosine Kinase", *Oncogene*, 8: 909-918 (1993).
Martin, "3D Database Searching in Drug Design", *J. Med. Chem.*, 35: 2145-2154 (1992).
Matsui et al., "Isolation of a Novel Receptor cDNA Establishes the Existence of Two PDGF Receptor Genes", *Science*, 243: 800-804 (1989).
Matthews et al., "A Receptor Tyrosine Kinase Specific to Hematopoietic Stem and Progenitor Cell-Enriched Populations", *Cell*, 65: 1143-1152 (1991).
McTigue et al., "Crystal Structure of the Kinase Domain of Human Vascular Endothelial Growth Factor Receptor 2: A Key Enzyme in Angiogenesis", *Structure*, 7: 319-330 (1999).
Meng et al., "Automated Docking with Grid-Based Energy Evaluation", *J. Comp. Chem.*, 13: 505-524 (1992).
Miranker and Karplus, "Functionality Maps of Binding Sites: A Multiple Copy Simultaneous Search Method", *Proteins Struct. Funct. Genet.*, 11: 29-34 (1991).
Mizuki et al., "Flt3 Mutations from Patients with Acute Myeloid Leukemia Induce Transformation of 32D Cells Mediated by the Ras and STAT5 Pathways", *Blood*, 96: 3907-3914 (2000).
Mizuki et al., "Suppression of Myeloid Transcription Factors and Induction of STAT Response Genes by AML-Specific Flt3 Mutations", *Blood*, 101: 3164-3173 (2003).
Mohammadi et al., "Structure of the FGF Receptor Tyrosine Kinase Domain Reveals a Novel Autoinhibitory Mechanism", *Cell*, 86: 577-587 (1996).
Mol et al., "Structure of a c-Kit Product Complex Reveals the Basis for Kinase Transactivation", *J. Biol. Chem.*, 278: 31461-31464 (2003).
Nakao et al., "Internal Tandem Duplication of the flt3 Gene Found in Acute Myeloid Leukemia", *Leukemia*, 10: 1911-1918 (1996).
Navia and Murcko, "Use of Structural Information in Drug Design", *Curr. Opin. Struct. Biol.*, 2: 202-210 (1992).
Nishibata and Itai, "Automatic Creation of Drug Candidate Structures Based on Receptor Structure. Starting Point for Artificial Lead Generation", *Tetrahedron*, 47: 8985-8990 (1991).

O'Farrell et al., "SU11248 is a Novel FLT3 Tyrosine Kinase Inhibitor With Potent Activity In Vitro and In Vivo", *Blood*, 101: 3597-3605 (2003).

Pav et al., "Microtube Batch Protein Crystallization: Applications to Human Immunodefficiency Virus Type 2 (HIV-2) Protease and Human Renin", *Proteins Struct. Funct. Genet.*, 20: 98-102 (1994).

Redington, "MOLFIT: A Computer Program for Molecular Superposition", *Comput. Chem.*, 16: 217-222 (1992).

Rosnet et al., "Isolation and Chromosomal Localization of a Novel FMS-Like Tyrosine Kinase Gene", *Genomics*, 9: 380-385 (1991).

Rosnet et al., "Murine *flt3*, a Gene Encoding a Novel Tyrosine Kinase Receptor of the PDGFR/CSF1R Family", *Oncogene*, 6: 1641-1650 (1991).

Rosnet et al., "Human *FLT3/FLK2* Gene: cDNA Cloning and Expression in Hematopoietic Cells", *Blood*, 82: 1110-1119 (1993).

Rosnet and Birnbaum, "Hematopoietic Receptors of Class III Receptor-Type Tyrosine Kinases", *Crit. Rev. Oncog.*, 4: 595-613 (1993).

Rosnet et al., "Expression and Signal Transduction of the FLT3 Tyrosine Kinase Receptor", *Acta Haematol.*, 95: 218-223 (1996).

Savvides et al., "Flt3 Ligand Structure and Unexpected Commonalities of Helical Bundles and Cystine Knots", *Nat. Struct. Biol.*, 7: 486-491 (2000).

Scheijen and Griffin, "Tyrosine Kinase Oncogenes in Normal Hematopoiesis and Hematological Disease", *Oncogene*, 21: 3314-3333 (2002).

Schnare et al., "Comprehensive Comparison of Structural Characteristis in Eukaryotic Cytoplasmic Large Subunit (23 S-like) Ribosomal RNA", *J. Mol. Biol.*, 256: 701-719 (1996).

Small et al., "STK-1, the Human Homolog of Flk-2/Flt-3, is Selectively Expressed in CD34+ Human Bone Marrow Cells and is Involved in the Proliferation of Early Progenitor/Stem Cells", *Proc. Natl. Acad. Sci. USA*, 91: 459-463 (1994).

Smith and Waterman, "Comparison of Biosequences", *Adv. In App. Math.*, 2: 482-489 (1981).

Spiekermann et al., "The Protein Tyrosine Kinase Inhibitor SU5614 Inhibits FLT3 and Induces Growth Arrest and Apoptosis in AML-Derived Cell Lines Expressing a Constitutively Activated FLT3", *Blood*, 101: 1494-1504 (2003).

Stirewalt and Radich, "The Role of FLT3 in Haematopoietic Malignancies", *Nature Rev. Cancer*, 3: 650-665 (2003).

Stanley et al., "CSF-1-A Mononuclear Phagocyte Lineage-Specific Hemopoietic Growth Factor", *J. Cell. Biochem.*, 21: 151-159 (1983).

Szklarz and Halpert, "Use of Homology Modeling in Conjunction with Site-Directed Mutagenesis for Analysis of Structure-Function Relationships of Mammalian Cytochromes P450", *Life Sci.*, 61: 2507-2520 (1997).

Thiede et al., "Analysis of FLT3-Activating Mutations in 979 Patients with Acute Myelogenous Leukemia: Association with FAB Subtypes and Identification of Subgroups with Poor Prognosis", *Blood*, 99: 4326-4335 (2002).

Turner et al., "FLT3 Receptor Expression on the Surface of Normal and Malignant Human Hematopoietic Cells", *Blood*, 88: 3383-3390 (1996).

Weisberg et al., "Inhibition of Mutant FLT3 Receptors in Leukemia Cells by the Small Molecule Tyrosine Kinase Inhibitor PKC412", *Cancer Cell*, 1: 433-443 (2002).

Wishart et al., "Constrained Multiple Sequence Alignment Using XALIGN", *Comput. Appl. Biosci.*, 10: 687-688 (1994).

Wybenga-Groot et al., "Structural Basis for Autoinhibition of the EphB2 Receptor Tyrosine Kinase by the Unphosphorylated Juxtamembrane Region", *Cell*, 106: 745-757 (2001).

Yamamoto et al., "Activating Mutation of D835 within the Activation Loop of FLT3 in Human Hematologic Malignancies", *Blood*, 97: 2434-2439 (2001).

Yarden et al., "Human Proto-Oncogene c-*kit*: A New Cell Surface Receptor Tyrosine Kinase for an Unidentified Ligand", *EMBO J.*, 6: 3341-3351 (1987).

Yarden et al., "Structure of the Receptor for Platelet-Derived Growth Factor Helps Define a Family of Closely Related Growth Factor Receptors", *Nature*, 323: 226-232 (1986).

Yokota et al., "Internal Tandem Duplication of the FLT3 Gene Is Preferentially Seen in Acute Myeloid Leukemia and Myelodysplastic Syndrome Among Various Hematological Malignancies. A Study on a Large Series of Patients and Cell Lines", *Leukemia*, 11: 1605-1609 (1997).

Zhang et al., "Essential Role of Signal Transducer and Activator of Transcription (Stat)5a but Not Stat5b for Flt3-Dependent Signaling", *J. Exp. Med.*, 192: 719-728 (2000).

\* cited by examiner

FIGURE 1A-1

| ATOM | Type | Resid | # | X | Y | Z | Occ | B | | |
|------|------|-------|---|---|---|---|-----|---|---|---|
| ATOM | 1 | CB | PHE A 570 | 83.564 | 47.422 | 11.477 | 1.00 | 43.36 | A | C |
| ATOM | 2 | CG | PHE A 570 | 83.013 | 48.352 | 12.517 | 1.00 | 47.09 | A | C |
| ATOM | 3 | CD1 | PHE A 570 | 83.687 | 49.521 | 12.845 | 1.00 | 45.04 | A | C |
| ATOM | 4 | CD2 | PHE A 570 | 81.827 | 48.057 | 13.176 | 1.00 | 49.21 | A | C |
| ATOM | 5 | CE1 | PHE A 570 | 83.191 | 50.383 | 13.814 | 1.00 | 47.14 | A | C |
| ATOM | 6 | CE2 | PHE A 570 | 81.322 | 48.914 | 14.147 | 1.00 | 50.62 | A | C |
| ATOM | 7 | CZ | PHE A 570 | 82.005 | 50.079 | 14.467 | 1.00 | 44.51 | A | C |
| ATOM | 8 | C | PHE A 570 | 85.047 | 46.454 | 13.207 | 1.00 | 53.42 | A | C |
| ATOM | 9 | O | PHE A 570 | 84.250 | 45.605 | 13.604 | 1.00 | 58.22 | A | O |
| ATOM | 10 | N | PHE A 570 | 85.402 | 45.883 | 10.818 | 1.00 | 42.85 | A | N |
| ATOM | 11 | CA | PHE A 570 | 84.987 | 46.961 | 11.771 | 1.00 | 51.40 | A | C |
| ATOM | 12 | N | ARG A 571 | 85.980 | 46.998 | 13.983 | 1.00 | 53.72 | A | N |
| ATOM | 13 | CA | ARG A 571 | 86.180 | 46.596 | 15.370 | 1.00 | 56.29 | A | C |
| ATOM | 14 | CB | ARG A 571 | 87.675 | 46.358 | 15.601 | 1.00 | 60.11 | A | C |
| ATOM | 15 | CG | ARG A 571 | 88.268 | 45.356 | 14.629 | 1.00 | 65.95 | A | C |
| ATOM | 16 | CD | ARG A 571 | 89.727 | 45.077 | 14.904 | 1.00 | 71.67 | A | C |
| ATOM | 17 | NE | ARG A 571 | 90.242 | 44.076 | 13.973 | 1.00 | 80.39 | A | N |
| ATOM | 18 | CZ | ARG A 571 | 91.478 | 43.582 | 14.002 | 1.00 | 87.65 | A | C |
| ATOM | 19 | NH1 | ARG A 571 | 92.342 | 43.995 | 14.922 | 1.00 | 88.21 | A | N |
| ATOM | 20 | NH2 | ARG A 571 | 91.851 | 42.671 | 13.109 | 1.00 | 90.85 | A | N |
| ATOM | 21 | C | ARG A 571 | 85.660 | 47.593 | 16.409 | 1.00 | 53.15 | A | C |
| ATOM | 22 | O | ARG A 571 | 85.272 | 48.715 | 16.082 | 1.00 | 49.58 | A | O |
| ATOM | 23 | N | TYR A 572 | 85.636 | 47.166 | 17.667 | 1.00 | 53.79 | A | N |
| ATOM | 24 | CA | TYR A 572 | 85.204 | 48.050 | 18.740 | 1.00 | 47.05 | A | C |
| ATOM | 25 | CB | TYR A 572 | 84.906 | 47.304 | 20.042 | 1.00 | 51.42 | A | C |
| ATOM | 26 | CG | TYR A 572 | 84.690 | 48.267 | 21.198 | 1.00 | 43.63 | A | C |
| ATOM | 27 | CD1 | TYR A 572 | 83.583 | 49.114 | 21.210 | 1.00 | 32.83 | A | C |
| ATOM | 28 | CE1 | TYR A 572 | 83.381 | 50.034 | 22.227 | 1.00 | 43.51 | A | C |
| ATOM | 29 | CD2 | TYR A 572 | 85.606 | 48.365 | 22.250 | 1.00 | 38.04 | A | C |
| ATOM | 30 | CE2 | TYR A 572 | 85.414 | 49.291 | 23.292 | 1.00 | 34.63 | A | C |
| ATOM | 31 | CZ | TYR A 572 | 84.294 | 50.124 | 23.270 | 1.00 | 37.73 | A | C |
| ATOM | 32 | OH | TYR A 572 | 84.057 | 51.069 | 24.247 | 1.00 | 34.65 | A | O |
| ATOM | 33 | C | TYR A 572 | 86.344 | 48.997 | 19.044 | 1.00 | 34.51 | A | C |
| ATOM | 34 | O | TYR A 572 | 87.518 | 48.606 | 19.006 | 1.00 | 37.71 | A | O |
| ATOM | 35 | N | GLU A 573 | 85.990 | 50.235 | 19.366 | 1.00 | 38.92 | A | N |
| ATOM | 36 | CA | GLU A 573 | 86.974 | 51.240 | 19.721 | 1.00 | 35.77 | A | C |
| ATOM | 37 | CB | GLU A 573 | 87.706 | 51.705 | 18.464 | 1.00 | 41.14 | A | C |
| ATOM | 38 | CG | GLU A 573 | 88.947 | 52.536 | 18.750 | 1.00 | 61.33 | A | C |
| ATOM | 39 | CD | GLU A 573 | 89.653 | 52.994 | 17.485 | 1.00 | 64.41 | A | C |
| ATOM | 40 | OE1 | GLU A 573 | 90.675 | 53.702 | 17.598 | 1.00 | 77.64 | A | O |
| ATOM | 41 | OE2 | GLU A 573 | 89.189 | 52.646 | 16.381 | 1.00 | 73.74 | A | O |
| ATOM | 42 | C | GLU A 573 | 86.244 | 52.412 | 20.363 | 1.00 | 35.50 | A | C |
| ATOM | 43 | O | GLU A 573 | 85.194 | 52.831 | 19.865 | 1.00 | 31.71 | A | O |
| ATOM | 44 | N | SER A 574 | 86.755 | 52.937 | 21.473 | 1.00 | 29.83 | A | N |
| ATOM | 45 | CA | SER A 574 | 86.083 | 54.089 | 22.057 | 1.00 | 31.01 | A | C |
| ATOM | 46 | CB | SER A 574 | 86.569 | 54.402 | 23.479 | 1.00 | 38.07 | A | C |
| ATOM | 47 | OG | SER A 574 | 85.879 | 55.551 | 24.009 | 1.00 | 30.19 | A | O |
| ATOM | 48 | C | SER A 574 | 86.418 | 55.272 | 21.154 | 1.00 | 27.72 | A | C |
| ATOM | 49 | O | SER A 574 | 87.531 | 55.376 | 20.622 | 1.00 | 29.82 | A | O |
| ATOM | 50 | N | GLN A 575 | 85.459 | 56.164 | 20.989 | 1.00 | 22.86 | A | N |
| ATOM | 51 | CA | GLN A 575 | 85.679 | 57.341 | 20.166 | 1.00 | 25.74 | A | C |
| ATOM | 52 | CB | GLN A 575 | 84.364 | 57.771 | 19.504 | 1.00 | 26.92 | A | C |
| ATOM | 53 | CG | GLN A 575 | 83.775 | 56.660 | 18.625 | 1.00 | 24.47 | A | C |
| ATOM | 54 | CD | GLN A 575 | 84.785 | 56.102 | 17.620 | 1.00 | 33.51 | A | C |

FIGURE 1A-2

```
ATOM    55  OE1 GLN A 575      84.830  54.895  17.365  1.00 44.25      A  O
ATOM    56  NE2 GLN A 575      85.595  56.976  17.054  1.00 34.77      A  N
ATOM    57  C   GLN A 575      86.273  58.441  21.027  1.00 30.14      A  C
ATOM    58  O   GLN A 575      86.612  59.504  20.532  1.00 25.98      A  O
ATOM    59  N   LEU A 576      86.390  58.179  22.327  1.00 25.21      A  N
ATOM    60  CA  LEU A 576      87.011  59.148  23.227  1.00 30.81      A  C
ATOM    61  CB  LEU A 576      86.478  58.981  24.654  1.00 32.02      A  C
ATOM    62  CG  LEU A 576      86.936  60.022  25.679  1.00 39.10      A  C
ATOM    63  CD1 LEU A 576      86.539  61.405  25.215  1.00 41.43      A  C
ATOM    64  CD2 LEU A 576      86.307  59.727  27.037  1.00 44.20      A  C
ATOM    65  C   LEU A 576      88.501  58.758  23.140  1.00 25.46      A  C
ATOM    66  O   LEU A 576      88.887  57.636  23.489  1.00 27.21      A  O
ATOM    67  N   GLN A 577      89.333  59.675  22.668  1.00 25.85      A  N
ATOM    68  CA  GLN A 577      90.744  59.344  22.467  1.00 26.38      A  C
ATOM    69  CB  GLN A 577      90.985  59.031  21.000  1.00 31.20      A  C
ATOM    70  CG  GLN A 577      90.182  57.884  20.474  1.00 44.95      A  C
ATOM    71  CD  GLN A 577      91.058  56.792  19.928  1.00 55.40      A  C
ATOM    72  OE1 GLN A 577      92.288  56.862  20.020  1.00 64.42      A  O
ATOM    73  NE2 GLN A 577      90.437  55.767  19.360  1.00 66.74      A  N
ATOM    74  C   GLN A 577      91.720  60.437  22.849  1.00 25.76      A  C
ATOM    75  O   GLN A 577      91.425  61.629  22.688  1.00 28.93      A  O
ATOM    76  N   MET A 578      92.892  60.030  23.333  1.00 23.99      A  N
ATOM    77  CA  MET A 578      93.911  61.014  23.647  1.00 27.80      A  C
ATOM    78  CB  MET A 578      94.822  60.520  24.777  1.00 26.94      A  C
ATOM    79  CG  MET A 578      95.737  61.603  25.337  1.00 38.65      A  C
ATOM    80  SD  MET A 578      96.706  60.995  26.753  1.00 45.88      A  S
ATOM    81  CE  MET A 578      95.401  60.775  27.948  1.00 38.12      A  C
ATOM    82  C   MET A 578      94.733  61.214  22.374  1.00 24.77      A  C
ATOM    83  O   MET A 578      94.966  60.263  21.625  1.00 24.27      A  O
ATOM    84  N   VAL A 579      95.139  62.456  22.122  1.00 28.51      A  N
ATOM    85  CA  VAL A 579      95.965  62.776  20.961  1.00 36.10      A  C
ATOM    86  CB  VAL A 579      95.203  63.635  19.895  1.00 27.98      A  C
ATOM    87  CG1 VAL A 579      93.944  62.905  19.420  1.00 28.06      A  C
ATOM    88  CG2 VAL A 579      94.870  65.026  20.471  1.00 24.38      A  C
ATOM    89  C   VAL A 579      97.187  63.581  21.417  1.00 38.90      A  C
ATOM    90  O   VAL A 579      97.229  64.089  22.538  1.00 30.82      A  O
ATOM    91  N   GLN A 580      98.182  63.674  20.544  1.00 35.35      A  N
ATOM    92  CA  GLN A 580      99.397  64.448  20.823  1.00 31.01      A  C
ATOM    93  CB  GLN A 580     100.603  63.555  21.095  1.00 31.18      A  C
ATOM    94  CG  GLN A 580     101.895  64.378  21.287  1.00 36.79      A  C
ATOM    95  CD  GLN A 580     103.003  63.550  21.867  1.00 49.98      A  C
ATOM    96  OE1 GLN A 580     104.162  63.653  21.455  1.00 59.67      A  O
ATOM    97  NE2 GLN A 580     102.658  62.715  22.836  1.00 45.64      A  N
ATOM    98  C   GLN A 580      99.679  65.276  19.597  1.00 29.18      A  C
ATOM    99  O   GLN A 580      99.957  64.733  18.526  1.00 28.82      A  O
ATOM   100  N   VAL A 581      99.586  66.589  19.762  1.00 31.68      A  N
ATOM   101  CA  VAL A 581      99.803  67.526  18.673  1.00 40.70      A  C
ATOM   102  CB  VAL A 581      99.219  68.894  19.043  1.00 40.96      A  C
ATOM   103  CG1 VAL A 581      99.406  69.865  17.912  1.00 49.10      A  C
ATOM   104  CG2 VAL A 581      97.729  68.735  19.356  1.00 41.03      A  C
ATOM   105  C   VAL A 581     101.291  67.630  18.323  1.00 50.21      A  C
ATOM   106  O   VAL A 581     102.147  67.722  19.204  1.00 45.26      A  O
ATOM   107  N   THR A 582     101.571  67.592  17.024  1.00 48.35      A  N
ATOM   108  CA  THR A 582     102.924  67.622  16.483  1.00 53.37      A  C
ATOM   109  CB  THR A 582     103.117  66.431  15.532  1.00 49.45      A  C
ATOM   110  OG1 THR A 582     103.235  65.230  16.302  1.00 60.95      A  O
```

FIGURE 1A-3

| | | | | | | | | | | | |
|---|---|---|---|---|---|---|---|---|---|---|---|
| ATOM | 111 | CG2 | THR | A | 582 | 104.349 | 66.613 | 14.674 | 1.00 | 69.01 | A C |
| ATOM | 112 | C | THR | A | 582 | 103.290 | 68.901 | 15.733 | 1.00 | 56.17 | A C |
| ATOM | 113 | O | THR | A | 582 | 104.463 | 69.177 | 15.499 | 1.00 | 61.58 | A O |
| ATOM | 114 | N | GLY | A | 583 | 102.288 | 69.671 | 15.336 | 1.00 | 61.93 | A N |
| ATOM | 115 | CA | GLY | A | 583 | 102.557 | 70.900 | 14.618 | 1.00 | 55.51 | A C |
| ATOM | 116 | C | GLY | A | 583 | 101.440 | 71.884 | 14.862 | 1.00 | 59.87 | A C |
| ATOM | 117 | O | GLY | A | 583 | 100.548 | 71.631 | 15.672 | 1.00 | 52.55 | A O |
| ATOM | 118 | N | SER | A | 584 | 101.487 | 73.008 | 14.159 | 1.00 | 57.09 | A N |
| ATOM | 119 | CA | SER | A | 584 | 100.472 | 74.038 | 14.311 | 1.00 | 57.20 | A C |
| ATOM | 120 | CB | SER | A | 584 | 101.087 | 75.413 | 14.027 | 1.00 | 56.53 | A C |
| ATOM | 121 | OG | SER | A | 584 | 101.628 | 75.462 | 12.718 | 1.00 | 47.46 | A O |
| ATOM | 122 | C | SER | A | 584 | 99.293 | 73.779 | 13.367 | 1.00 | 52.26 | A C |
| ATOM | 123 | O | SER | A | 584 | 98.218 | 74.342 | 13.532 | 1.00 | 51.60 | A O |
| ATOM | 124 | N | SER | A | 585 | 99.510 | 72.923 | 12.379 | 1.00 | 51.63 | A N |
| ATOM | 125 | CA | SER | A | 585 | 98.471 | 72.586 | 11.418 | 1.00 | 53.02 | A C |
| ATOM | 126 | CB | SER | A | 585 | 99.111 | 72.066 | 10.135 | 1.00 | 53.40 | A C |
| ATOM | 127 | OG | SER | A | 585 | 98.126 | 71.775 | 9.166 | 1.00 | 69.93 | A O |
| ATOM | 128 | C | SER | A | 585 | 97.511 | 71.538 | 11.991 | 1.00 | 49.98 | A C |
| ATOM | 129 | O | SER | A | 585 | 97.931 | 70.600 | 12.678 | 1.00 | 46.58 | A O |
| ATOM | 130 | N | ASP | A | 586 | 96.225 | 71.695 | 11.687 | 1.00 | 46.84 | A N |
| ATOM | 131 | CA | ASP | A | 586 | 95.189 | 70.786 | 12.182 | 1.00 | 40.56 | A C |
| ATOM | 132 | CB | ASP | A | 586 | 93.856 | 71.065 | 11.475 | 1.00 | 43.61 | A C |
| ATOM | 133 | CG | ASP | A | 586 | 93.147 | 72.296 | 12.013 | 1.00 | 50.82 | A C |
| ATOM | 134 | OD1 | ASP | A | 586 | 93.743 | 73.034 | 12.839 | 1.00 | 48.17 | A O |
| ATOM | 135 | OD2 | ASP | A | 586 | 91.985 | 72.528 | 11.601 | 1.00 | 46.33 | A O |
| ATOM | 136 | C | ASP | A | 586 | 95.499 | 69.302 | 12.067 | 1.00 | 36.05 | A C |
| ATOM | 137 | O | ASP | A | 586 | 95.198 | 68.536 | 12.976 | 1.00 | 33.88 | A O |
| ATOM | 138 | N | ASN | A | 587 | 96.109 | 68.884 | 10.963 | 1.00 | 31.81 | A N |
| ATOM | 139 | CA | ASN | A | 587 | 96.381 | 67.467 | 10.778 | 1.00 | 35.75 | A C |
| ATOM | 140 | CB | ASN | A | 587 | 96.347 | 67.118 | 9.282 | 1.00 | 39.60 | A C |
| ATOM | 141 | CG | ASN | A | 587 | 97.551 | 67.651 | 8.524 | 1.00 | 50.18 | A C |
| ATOM | 142 | OD1 | ASN | A | 587 | 98.361 | 68.411 | 9.058 | 1.00 | 52.07 | A O |
| ATOM | 143 | ND2 | ASN | A | 587 | 97.667 | 67.256 | 7.265 | 1.00 | 60.20 | A N |
| ATOM | 144 | C | ASN | A | 587 | 97.678 | 66.956 | 11.409 | 1.00 | 29.12 | A C |
| ATOM | 145 | O | ASN | A | 587 | 97.994 | 65.775 | 11.302 | 1.00 | 34.45 | A O |
| ATOM | 146 | N | GLU | A | 588 | 98.404 | 67.833 | 12.088 | 1.00 | 32.62 | A N |
| ATOM | 147 | CA | GLU | A | 588 | 99.660 | 67.441 | 12.721 | 1.00 | 37.35 | A C |
| ATOM | 148 | CB | GLU | A | 588 | 100.657 | 68.612 | 12.641 | 1.00 | 38.18 | A C |
| ATOM | 149 | CG | GLU | A | 588 | 100.821 | 69.092 | 11.190 | 1.00 | 45.42 | A C |
| ATOM | 150 | CD | GLU | A | 588 | 101.737 | 70.291 | 11.019 | 1.00 | 47.21 | A C |
| ATOM | 151 | OE1 | GLU | A | 588 | 101.609 | 71.280 | 11.775 | 1.00 | 54.64 | A O |
| ATOM | 152 | OE2 | GLU | A | 588 | 102.581 | 70.244 | 10.100 | 1.00 | 62.42 | A O |
| ATOM | 153 | C | GLU | A | 588 | 99.457 | 66.970 | 14.163 | 1.00 | 34.73 | A C |
| ATOM | 154 | O | GLU | A | 588 | 99.636 | 67.713 | 15.141 | 1.00 | 34.29 | A O |
| ATOM | 155 | N | TYR | A | 589 | 99.067 | 65.712 | 14.282 | 1.00 | 32.68 | A N |
| ATOM | 156 | CA | TYR | A | 589 | 98.841 | 65.116 | 15.591 | 1.00 | 35.00 | A C |
| ATOM | 157 | CB | TYR | A | 589 | 97.538 | 65.646 | 16.208 | 1.00 | 29.53 | A C |
| ATOM | 158 | CG | TYR | A | 589 | 96.291 | 65.100 | 15.535 | 1.00 | 26.21 | A C |
| ATOM | 159 | CD1 | TYR | A | 589 | 95.798 | 63.826 | 15.861 | 1.00 | 25.32 | A C |
| ATOM | 160 | CE1 | TYR | A | 589 | 94.704 | 63.279 | 15.181 | 1.00 | 28.26 | A C |
| ATOM | 161 | CD2 | TYR | A | 589 | 95.653 | 65.815 | 14.511 | 1.00 | 27.47 | A C |
| ATOM | 162 | CE2 | TYR | A | 589 | 94.555 | 65.271 | 13.820 | 1.00 | 34.19 | A C |
| ATOM | 163 | CZ | TYR | A | 589 | 94.089 | 64.005 | 14.162 | 1.00 | 38.35 | A C |
| ATOM | 164 | OH | TYR | A | 589 | 93.020 | 63.454 | 13.491 | 1.00 | 33.94 | A O |
| ATOM | 165 | C | TYR | A | 589 | 98.711 | 63.641 | 15.314 | 1.00 | 33.68 | A C |
| ATOM | 166 | O | TYR | A | 589 | 98.557 | 63.241 | 14.160 | 1.00 | 33.75 | A O |

FIGURE 1A-4

```
ATOM   167  N    PHE A 590      98.808  62.832  16.359  1.00 32.05      A  N
ATOM   168  CA   PHE A 590      98.623  61.400  16.207  1.00 27.34      A  C
ATOM   169  CB   PHE A 590      99.973  60.661  16.039  1.00 37.99      A  C
ATOM   170  CG   PHE A 590     100.914  60.791  17.205  1.00 34.01      A  C
ATOM   171  CD1  PHE A 590     100.995  59.787  18.163  1.00 34.73      A  C
ATOM   172  CD2  PHE A 590     101.745  61.907  17.327  1.00 32.76      A  C
ATOM   173  CE1  PHE A 590     101.900  59.891  19.238  1.00 31.65      A  C
ATOM   174  CE2  PHE A 590     102.648  62.021  18.392  1.00 35.06      A  C
ATOM   175  CZ   PHE A 590     102.722  61.003  19.351  1.00 30.69      A  C
ATOM   176  C    PHE A 590      97.840  60.922  17.415  1.00 30.01      A  C
ATOM   177  O    PHE A 590      97.779  61.618  18.428  1.00 30.17      A  O
ATOM   178  N    TYR A 591      97.194  59.769  17.298  1.00 28.78      A  N
ATOM   179  CA   TYR A 591      96.425  59.240  18.410  1.00 36.21      A  C
ATOM   180  CB   TYR A 591      95.316  58.292  17.920  1.00 34.07      A  C
ATOM   181  CG   TYR A 591      94.300  58.946  17.016  1.00 39.78      A  C
ATOM   182  CD1  TYR A 591      94.331  58.747  15.630  1.00 39.62      A  C
ATOM   183  CE1  TYR A 591      93.436  59.413  14.789  1.00 38.62      A  C
ATOM   184  CD2  TYR A 591      93.352  59.820  17.539  1.00 38.88      A  C
ATOM   185  CE2  TYR A 591      92.462  60.495  16.714  1.00 43.65      A  C
ATOM   186  CZ   TYR A 591      92.508  60.291  15.348  1.00 41.14      A  C
ATOM   187  OH   TYR A 591      91.650  61.002  14.548  1.00 36.49      A  O
ATOM   188  C    TYR A 591      97.325  58.474  19.360  1.00 33.63      A  C
ATOM   189  O    TYR A 591      98.167  57.698  18.928  1.00 30.27      A  O
ATOM   190  N    VAL A 592      97.137  58.690  20.654  1.00 31.34      A  N
ATOM   191  CA   VAL A 592      97.910  57.966  21.644  1.00 27.53      A  C
ATOM   192  CB   VAL A 592      97.865  58.679  23.017  1.00 24.27      A  C
ATOM   193  CG1  VAL A 592      98.558  57.840  24.066  1.00 23.71      A  C
ATOM   194  CG2  VAL A 592      98.507  60.063  22.913  1.00 26.60      A  C
ATOM   195  C    VAL A 592      97.284  56.569  21.766  1.00 28.49      A  C
ATOM   196  O    VAL A 592      96.095  56.436  22.021  1.00 35.84      A  O
ATOM   197  N    ASP A 593      98.084  55.536  21.542  1.00 27.46      A  N
ATOM   198  CA   ASP A 593      97.623  54.155  21.650  1.00 33.92      A  C
ATOM   199  CB   ASP A 593      98.115  53.365  20.437  1.00 35.73      A  C
ATOM   200  CG   ASP A 593      97.647  51.929  20.440  1.00 44.25      A  C
ATOM   201  OD1  ASP A 593      97.468  51.358  21.529  1.00 52.56      A  O
ATOM   202  OD2  ASP A 593      97.479  51.360  19.343  1.00 54.63      A  O
ATOM   203  C    ASP A 593      98.227  53.591  22.957  1.00 37.78      A  C
ATOM   204  O    ASP A 593      99.449  53.546  23.129  1.00 32.74      A  O
ATOM   205  N    PHE A 594      97.372  53.173  23.882  1.00 32.40      A  N
ATOM   206  CA   PHE A 594      97.850  52.663  25.168  1.00 36.77      A  C
ATOM   207  CB   PHE A 594      96.797  52.916  26.255  1.00 28.87      A  C
ATOM   208  CG   PHE A 594      96.651  54.364  26.634  1.00 37.91      A  C
ATOM   209  CD1  PHE A 594      95.833  55.218  25.896  1.00 28.57      A  C
ATOM   210  CD2  PHE A 594      97.359  54.880  27.713  1.00 30.68      A  C
ATOM   211  CE1  PHE A 594      95.724  56.573  26.229  1.00 28.99      A  C
ATOM   212  CE2  PHE A 594      97.258  56.234  28.053  1.00 35.29      A  C
ATOM   213  CZ   PHE A 594      96.438  57.081  27.307  1.00 30.07      A  C
ATOM   214  C    PHE A 594      98.197  51.185  25.163  1.00 33.52      A  C
ATOM   215  O    PHE A 594      98.502  50.612  26.206  1.00 31.72      A  O
ATOM   216  N    ARG A 595      98.157  50.559  23.998  1.00 25.75      A  N
ATOM   217  CA   ARG A 595      98.432  49.133  23.947  1.00 26.58      A  C
ATOM   218  CB   ARG A 595      98.372  48.639  22.500  1.00 31.18      A  C
ATOM   219  CG   ARG A 595      98.516  47.127  22.352  1.00 43.19      A  C
ATOM   220  CD   ARG A 595      98.044  46.657  20.973  1.00 50.46      A  C
ATOM   221  NE   ARG A 595      98.603  47.476  19.900  1.00 59.66      A  N
ATOM   222  CZ   ARG A 595      98.217  47.419  18.628  1.00 63.36      A  C
```

FIGURE 1A-5

| | | | | | | | | | | |
|---|---|---|---|---|---|---|---|---|---|---|
| ATOM | 223 | NH1 | ARG A 595 | 97.260 | 46.580 | 18.255 | 1.00 | 63.23 | A | N |
| ATOM | 224 | NH2 | ARG A 595 | 98.793 | 48.201 | 17.725 | 1.00 | 61.97 | A | N |
| ATOM | 225 | C | ARG A 595 | 99.768 | 48.756 | 24.609 | 1.00 | 31.49 | A | C |
| ATOM | 226 | O | ARG A 595 | 99.829 | 47.780 | 25.359 | 1.00 | 29.15 | A | O |
| ATOM | 227 | N | GLU A 596 | 100.822 | 49.539 | 24.369 | 1.00 | 25.76 | A | N |
| ATOM | 228 | CA | GLU A 596 | 102.127 | 49.234 | 24.962 | 1.00 | 28.77 | A | C |
| ATOM | 229 | CB | GLU A 596 | 103.279 | 49.837 | 24.118 | 1.00 | 25.41 | A | C |
| ATOM | 230 | CG | GLU A 596 | 103.293 | 49.476 | 22.616 | 1.00 | 27.30 | A | C |
| ATOM | 231 | CD | GLU A 596 | 103.454 | 47.984 | 22.337 | 1.00 | 35.77 | A | C |
| ATOM | 232 | OE1 | GLU A 596 | 103.223 | 47.569 | 21.184 | 1.00 | 41.43 | A | O |
| ATOM | 233 | OE2 | GLU A 596 | 103.815 | 47.223 | 23.258 | 1.00 | 33.16 | A | O |
| ATOM | 234 | C | GLU A 596 | 102.266 | 49.715 | 26.418 | 1.00 | 24.51 | A | C |
| ATOM | 235 | O | GLU A 596 | 103.254 | 49.402 | 27.064 | 1.00 | 27.13 | A | O |
| ATOM | 236 | N | TYR A 597 | 101.303 | 50.479 | 26.935 | 1.00 | 26.41 | A | N |
| ATOM | 237 | CA | TYR A 597 | 101.406 | 50.957 | 28.322 | 1.00 | 31.65 | A | C |
| ATOM | 238 | CB | TYR A 597 | 100.575 | 52.224 | 28.512 | 1.00 | 23.48 | A | C |
| ATOM | 239 | CG | TYR A 597 | 101.169 | 53.439 | 27.831 | 1.00 | 27.92 | A | C |
| ATOM | 240 | CD1 | TYR A 597 | 101.228 | 53.529 | 26.428 | 1.00 | 25.02 | A | C |
| ATOM | 241 | CE1 | TYR A 597 | 101.855 | 54.620 | 25.796 | 1.00 | 28.71 | A | C |
| ATOM | 242 | CD2 | TYR A 597 | 101.742 | 54.463 | 28.583 | 1.00 | 29.46 | A | C |
| ATOM | 243 | CE2 | TYR A 597 | 102.373 | 55.548 | 27.969 | 1.00 | 24.29 | A | C |
| ATOM | 244 | CZ | TYR A 597 | 102.427 | 55.616 | 26.574 | 1.00 | 36.13 | A | C |
| ATOM | 245 | OH | TYR A 597 | 103.078 | 56.670 | 25.974 | 1.00 | 31.22 | A | O |
| ATOM | 246 | C | TYR A 597 | 100.973 | 49.875 | 29.323 | 1.00 | 28.46 | A | C |
| ATOM | 247 | O | TYR A 597 | 100.385 | 48.871 | 28.927 | 1.00 | 26.21 | A | O |
| ATOM | 248 | N | GLU A 598 | 101.285 | 50.045 | 30.605 | 1.00 | 27.50 | A | N |
| ATOM | 249 | CA | GLU A 598 | 100.882 | 49.021 | 31.581 | 1.00 | 27.48 | A | C |
| ATOM | 250 | CB | GLU A 598 | 102.017 | 48.688 | 32.565 | 1.00 | 33.21 | A | C |
| ATOM | 251 | CG | GLU A 598 | 103.283 | 48.036 | 31.957 | 1.00 | 36.27 | A | C |
| ATOM | 252 | CD | GLU A 598 | 102.989 | 46.850 | 31.041 | 1.00 | 41.53 | A | C |
| ATOM | 253 | OE1 | GLU A 598 | 102.074 | 46.055 | 31.340 | 1.00 | 48.55 | A | O |
| ATOM | 254 | OE2 | GLU A 598 | 103.687 | 46.705 | 30.021 | 1.00 | 43.48 | A | O |
| ATOM | 255 | C | GLU A 598 | 99.656 | 49.482 | 32.367 | 1.00 | 26.25 | A | C |
| ATOM | 256 | O | GLU A 598 | 99.477 | 50.665 | 32.618 | 1.00 | 35.44 | A | O |
| ATOM | 257 | N | TYR A 599 | 98.808 | 48.533 | 32.734 | 1.00 | 29.16 | A | N |
| ATOM | 258 | CA | TYR A 599 | 97.600 | 48.829 | 33.492 | 1.00 | 26.70 | A | C |
| ATOM | 259 | CB | TYR A 599 | 96.541 | 47.752 | 33.189 | 1.00 | 24.96 | A | C |
| ATOM | 260 | CG | TYR A 599 | 95.393 | 47.665 | 34.179 | 1.00 | 23.24 | A | C |
| ATOM | 261 | CD1 | TYR A 599 | 95.194 | 46.497 | 34.906 | 1.00 | 24.35 | A | C |
| ATOM | 262 | CE1 | TYR A 599 | 94.124 | 46.345 | 35.772 | 1.00 | 25.37 | A | C |
| ATOM | 263 | CD2 | TYR A 599 | 94.484 | 48.715 | 34.346 | 1.00 | 23.81 | A | C |
| ATOM | 264 | CE2 | TYR A 599 | 93.378 | 48.575 | 35.235 | 1.00 | 31.21 | A | C |
| ATOM | 265 | CZ | TYR A 599 | 93.228 | 47.363 | 35.940 | 1.00 | 25.88 | A | C |
| ATOM | 266 | OH | TYR A 599 | 92.211 | 47.146 | 36.834 | 1.00 | 30.07 | A | O |
| ATOM | 267 | C | TYR A 599 | 97.915 | 48.885 | 34.988 | 1.00 | 26.58 | A | C |
| ATOM | 268 | O | TYR A 599 | 98.561 | 47.991 | 35.520 | 1.00 | 26.45 | A | O |
| ATOM | 269 | N | ASP A 600 | 97.465 | 49.945 | 35.654 | 1.00 | 25.85 | A | N |
| ATOM | 270 | CA | ASP A 600 | 97.720 | 50.117 | 37.084 | 1.00 | 26.71 | A | C |
| ATOM | 271 | CB | ASP A 600 | 97.621 | 51.608 | 37.444 | 1.00 | 23.78 | A | C |
| ATOM | 272 | CG | ASP A 600 | 98.063 | 51.898 | 38.879 | 1.00 | 29.70 | A | C |
| ATOM | 273 | OD1 | ASP A 600 | 98.445 | 53.050 | 39.132 | 1.00 | 26.74 | A | O |
| ATOM | 274 | OD2 | ASP A 600 | 98.017 | 50.994 | 39.751 | 1.00 | 27.18 | A | O |
| ATOM | 275 | C | ASP A 600 | 96.717 | 49.285 | 37.888 | 1.00 | 24.33 | A | C |
| ATOM | 276 | O | ASP A 600 | 95.523 | 49.584 | 37.902 | 1.00 | 25.03 | A | O |
| ATOM | 277 | N | LEU A 601 | 97.216 | 48.243 | 38.546 | 1.00 | 23.65 | A | N |
| ATOM | 278 | CA | LEU A 601 | 96.375 | 47.319 | 39.307 | 1.00 | 27.48 | A | C |

FIGURE 1A-6

```
ATOM   279  CB   LEU A 601      97.182  46.094  39.743  1.00 22.94      A  C
ATOM   280  CG   LEU A 601      97.724  45.293  38.546  1.00 35.71      A  C
ATOM   281  CD1  LEU A 601      98.847  44.335  38.970  1.00 26.24      A  C
ATOM   282  CD2  LEU A 601      96.558  44.550  37.897  1.00 30.79      A  C
ATOM   283  C    LEU A 601      95.626  47.877  40.496  1.00 31.27      A  C
ATOM   284  O    LEU A 601      94.836  47.165  41.100  1.00 30.72      A  O
ATOM   285  N    LYS A 602      95.845  49.142  40.833  1.00 28.21      A  N
ATOM   286  CA   LYS A 602      95.113  49.697  41.963  1.00 30.20      A  C
ATOM   287  CB   LYS A 602      95.690  51.054  42.387  1.00 26.03      A  C
ATOM   288  CG   LYS A 602      95.536  52.167  41.362  1.00 31.91      A  C
ATOM   289  CD   LYS A 602      95.881  53.523  41.962  1.00 32.94      A  C
ATOM   290  CE   LYS A 602      95.815  54.608  40.899  1.00 40.06      A  C
ATOM   291  NZ   LYS A 602      96.369  55.903  41.383  1.00 39.62      A  N
ATOM   292  C    LYS A 602      93.643  49.840  41.564  1.00 38.89      A  C
ATOM   293  O    LYS A 602      92.790  50.038  42.418  1.00 24.66      A  O
ATOM   294  N    TRP A 603      93.349  49.725  40.266  1.00 32.89      A  N
ATOM   295  CA   TRP A 603      91.962  49.837  39.784  1.00 30.82      A  C
ATOM   296  CB   TRP A 603      91.923  50.375  38.346  1.00 28.28      A  C
ATOM   297  CG   TRP A 603      92.342  51.807  38.233  1.00 17.01      A  C
ATOM   298  CD2  TRP A 603      91.500  52.949  38.383  1.00 21.34      A  C
ATOM   299  CE2  TRP A 603      92.316  54.097  38.224  1.00 18.36      A  C
ATOM   300  CE3  TRP A 603      90.126  53.120  38.632  1.00 22.88      A  C
ATOM   301  CD1  TRP A 603      93.615  52.290  37.991  1.00 22.17      A  C
ATOM   302  NE1  TRP A 603      93.602  53.668  37.990  1.00 18.21      A  N
ATOM   303  CZ2  TRP A 603      91.803  55.398  38.302  1.00 27.81      A  C
ATOM   304  CZ3  TRP A 603      89.622  54.423  38.713  1.00 24.95      A  C
ATOM   305  CH2  TRP A 603      90.461  55.539  38.545  1.00 25.75      A  C
ATOM   306  C    TRP A 603      91.184  48.519  39.801  1.00 25.51      A  C
ATOM   307  O    TRP A 603      89.955  48.518  39.634  1.00 27.44      A  O
ATOM   308  N    GLU A 604      91.906  47.413  39.975  1.00 22.74      A  N
ATOM   309  CA   GLU A 604      91.324  46.079  39.960  1.00 28.71      A  C
ATOM   310  CB   GLU A 604      92.454  45.052  40.076  1.00 24.85      A  C
ATOM   311  CG   GLU A 604      92.117  43.643  39.609  1.00 31.81      A  C
ATOM   312  CD   GLU A 604      91.749  43.568  38.131  1.00 35.97      A  C
ATOM   313  OE1  GLU A 604      92.121  44.462  37.342  1.00 33.55      A  O
ATOM   314  OE2  GLU A 604      91.094  42.585  37.751  1.00 32.35      A  O
ATOM   315  C    GLU A 604      90.290  45.910  41.091  1.00 40.46      A  C
ATOM   316  O    GLU A 604      90.571  46.191  42.255  1.00 32.59      A  O
ATOM   317  N    PHE A 605      89.096  45.447  40.722  1.00 33.92      A  N
ATOM   318  CA   PHE A 605      87.974  45.271  41.645  1.00 30.25      A  C
ATOM   319  CB   PHE A 605      86.810  46.146  41.165  1.00 33.33      A  C
ATOM   320  CG   PHE A 605      85.660  46.238  42.128  1.00 36.35      A  C
ATOM   321  CD1  PHE A 605      85.748  47.031  43.278  1.00 30.75      A  C
ATOM   322  CD2  PHE A 605      84.481  45.543  41.880  1.00 34.29      A  C
ATOM   323  CE1  PHE A 605      84.677  47.126  44.155  1.00 39.35      A  C
ATOM   324  CE2  PHE A 605      83.400  45.633  42.760  1.00 41.88      A  C
ATOM   325  CZ   PHE A 605      83.499  46.427  43.896  1.00 40.52      A  C
ATOM   326  C    PHE A 605      87.566  43.806  41.655  1.00 35.10      A  C
ATOM   327  O    PHE A 605      87.684  43.121  40.640  1.00 37.23      A  O
ATOM   328  N    PRO A 606      87.082  43.295  42.806  1.00 35.02      A  N
ATOM   329  CD   PRO A 606      86.969  43.929  44.126  1.00 35.00      A  C
ATOM   330  CA   PRO A 606      86.671  41.883  42.881  1.00 39.33      A  C
ATOM   331  CB   PRO A 606      86.423  41.668  44.386  1.00 33.85      A  C
ATOM   332  CG   PRO A 606      87.218  42.743  45.041  1.00 37.36      A  C
ATOM   333  C    PRO A 606      85.387  41.694  42.064  1.00 35.10      A  C
ATOM   334  O    PRO A 606      84.393  42.348  42.348  1.00 34.22      A  O
```

FIGURE 1A-7

```
ATOM    335  N    ARG A 607      85.387  40.814  41.067  1.00 35.16      A  N
ATOM    336  CA   ARG A 607      84.171  40.666  40.279  1.00 41.24      A  C
ATOM    337  CB   ARG A 607      84.424  39.817  39.021  1.00 39.34      A  C
ATOM    338  CG   ARG A 607      84.893  38.398  39.260  1.00 45.43      A  C
ATOM    339  CD   ARG A 607      85.273  37.714  37.936  1.00 44.25      A  C
ATOM    340  NE   ARG A 607      86.420  38.332  37.259  1.00 45.03      A  N
ATOM    341  CZ   ARG A 607      86.359  38.942  36.073  1.00 51.49      A  C
ATOM    342  NH1  ARG A 607      85.206  39.029  35.421  1.00 39.50      A  N
ATOM    343  NH2  ARG A 607      87.456  39.450  35.519  1.00 45.31      A  N
ATOM    344  C    ARG A 607      82.987  40.129  41.100  1.00 45.59      A  C
ATOM    345  O    ARG A 607      81.834  40.314  40.721  1.00 41.44      A  O
ATOM    346  N    GLU A 608      83.265  39.509  42.246  1.00 47.40      A  N
ATOM    347  CA   GLU A 608      82.188  38.993  43.090  1.00 42.35      A  C
ATOM    348  CB   GLU A 608      82.738  37.987  44.115  1.00 51.99      A  C
ATOM    349  CG   GLU A 608      83.561  38.600  45.247  1.00 60.86      A  C
ATOM    350  CD   GLU A 608      84.156  37.549  46.179  1.00 64.57      A  C
ATOM    351  OE1  GLU A 608      84.700  37.930  47.237  1.00 56.00      A  O
ATOM    352  OE2  GLU A 608      84.086  36.344  45.852  1.00 63.54      A  O
ATOM    353  C    GLU A 608      81.456  40.138  43.808  1.00 39.67      A  C
ATOM    354  O    GLU A 608      80.343  39.959  44.288  1.00 39.70      A  O
ATOM    355  N    ASN A 609      82.072  41.313  43.894  1.00 31.34      A  N
ATOM    356  CA   ASN A 609      81.401  42.439  44.540  1.00 31.76      A  C
ATOM    357  CB   ASN A 609      82.407  43.435  45.115  1.00 41.05      A  C
ATOM    358  CG   ASN A 609      83.143  42.883  46.323  1.00 44.62      A  C
ATOM    359  OD1  ASN A 609      83.775  43.627  47.066  1.00 54.73      A  O
ATOM    360  ND2  ASN A 609      83.076  41.576  46.509  1.00 38.59      A  N
ATOM    361  C    ASN A 609      80.463  43.182  43.593  1.00 30.25      A  C
ATOM    362  O    ASN A 609      79.996  44.281  43.909  1.00 35.22      A  O
ATOM    363  N    LEU A 610      80.218  42.586  42.434  1.00 36.33      A  N
ATOM    364  CA   LEU A 610      79.329  43.161  41.426  1.00 45.19      A  C
ATOM    365  CB   LEU A 610      79.958  43.105  40.021  1.00 38.66      A  C
ATOM    366  CG   LEU A 610      81.122  44.024  39.656  1.00 37.75      A  C
ATOM    367  CD1  LEU A 610      81.588  43.733  38.216  1.00 32.58      A  C
ATOM    368  CD2  LEU A 610      80.673  45.470  39.793  1.00 37.14      A  C
ATOM    369  C    LEU A 610      78.031  42.363  41.382  1.00 44.80      A  C
ATOM    370  O    LEU A 610      78.056  41.150  41.180  1.00 38.15      A  O
ATOM    371  N    GLU A 611      76.904  43.040  41.577  1.00 39.96      A  N
ATOM    372  CA   GLU A 611      75.614  42.360  41.493  1.00 49.76      A  C
ATOM    373  CB   GLU A 611      74.748  42.715  42.700  1.00 51.96      A  C
ATOM    374  CG   GLU A 611      73.599  41.752  42.925  1.00 69.04      A  C
ATOM    375  CD   GLU A 611      73.033  41.870  44.324  1.00 80.23      A  C
ATOM    376  OE1  GLU A 611      73.822  41.745  45.289  1.00 78.50      A  O
ATOM    377  OE2  GLU A 611      71.808  42.085  44.457  1.00 86.52      A  O
ATOM    378  C    GLU A 611      74.968  42.866  40.201  1.00 38.14      A  C
ATOM    379  O    GLU A 611      74.473  43.981  40.152  1.00 32.98      A  O
ATOM    380  N    PHE A 612      74.998  42.053  39.155  1.00 33.39      A  N
ATOM    381  CA   PHE A 612      74.451  42.471  37.872  1.00 41.27      A  C
ATOM    382  CB   PHE A 612      74.903  41.511  36.765  1.00 39.20      A  C
ATOM    383  CG   PHE A 612      76.360  41.670  36.383  1.00 43.73      A  C
ATOM    384  CD1  PHE A 612      77.280  40.654  36.638  1.00 51.74      A  C
ATOM    385  CD2  PHE A 612      76.813  42.853  35.788  1.00 44.01      A  C
ATOM    386  CE1  PHE A 612      78.638  40.810  36.308  1.00 50.31      A  C
ATOM    387  CE2  PHE A 612      78.164  43.022  35.455  1.00 37.47      A  C
ATOM    388  CZ   PHE A 612      79.077  42.001  35.715  1.00 42.89      A  C
ATOM    389  C    PHE A 612      72.938  42.637  37.843  1.00 48.01      A  C
ATOM    390  O    PHE A 612      72.194  41.824  38.385  1.00 47.90      A  O
```

FIGURE 1A-8

```
ATOM   391  N    GLY A 613      72.508  43.727  37.216  1.00 50.17      A  N
ATOM   392  CA   GLY A 613      71.101  44.039  37.091  1.00 44.84      A  C
ATOM   393  C    GLY A 613      70.683  43.974  35.633  1.00 46.54      A  C
ATOM   394  O    GLY A 613      71.026  43.023  34.930  1.00 40.96      A  O
ATOM   395  N    LYS A 614      69.962  44.993  35.173  1.00 41.11      A  N
ATOM   396  CA   LYS A 614      69.476  45.036  33.788  1.00 51.71      A  C
ATOM   397  CB   LYS A 614      68.256  45.953  33.688  1.00 52.29      A  C
ATOM   398  CG   LYS A 614      68.622  47.429  33.797  1.00 57.08      A  C
ATOM   399  CD   LYS A 614      67.417  48.336  33.623  1.00 72.15      A  C
ATOM   400  CE   LYS A 614      67.818  49.808  33.698  1.00 73.84      A  C
ATOM   401  NZ   LYS A 614      66.639  50.723  33.629  1.00 76.54      A  N
ATOM   402  C    LYS A 614      70.503  45.526  32.765  1.00 49.84      A  C
ATOM   403  O    LYS A 614      71.447  46.253  33.102  1.00 46.80      A  O
ATOM   404  N    VAL A 615      70.292  45.131  31.513  1.00 52.06      A  N
ATOM   405  CA   VAL A 615      71.145  45.547  30.407  1.00 51.19      A  C
ATOM   406  CB   VAL A 615      70.883  44.703  29.145  1.00 47.27      A  C
ATOM   407  CG1  VAL A 615      71.719  45.223  27.983  1.00 45.95      A  C
ATOM   408  CG2  VAL A 615      71.203  43.259  29.420  1.00 51.28      A  C
ATOM   409  C    VAL A 615      70.769  46.994  30.106  1.00 45.24      A  C
ATOM   410  O    VAL A 615      69.587  47.318  30.027  1.00 50.21      A  O
ATOM   411  N    LEU A 616      71.761  47.866  29.964  1.00 45.86      A  N
ATOM   412  CA   LEU A 616      71.493  49.274  29.668  1.00 43.05      A  C
ATOM   413  CB   LEU A 616      72.583  50.167  30.256  1.00 49.15      A  C
ATOM   414  CG   LEU A 616      72.689  50.275  31.770  1.00 52.13      A  C
ATOM   415  CD1  LEU A 616      73.719  51.327  32.106  1.00 48.02      A  C
ATOM   416  CD2  LEU A 616      71.331  50.656  32.359  1.00 53.50      A  C
ATOM   417  C    LEU A 616      71.423  49.525  28.167  1.00 45.07      A  C
ATOM   418  O    LEU A 616      70.830  50.501  27.712  1.00 49.73      A  O
ATOM   419  N    GLY A 617      72.051  48.644  27.408  1.00 43.36      A  N
ATOM   420  CA   GLY A 617      72.066  48.781  25.969  1.00 40.49      A  C
ATOM   421  C    GLY A 617      73.016  47.728  25.462  1.00 42.97      A  C
ATOM   422  O    GLY A 617      73.956  47.338  26.160  1.00 38.38      A  O
ATOM   423  N    SER A 618      72.787  47.262  24.246  1.00 41.22      A  N
ATOM   424  CA   SER A 618      73.638  46.235  23.694  1.00 30.30      A  C
ATOM   425  CB   SER A 618      72.946  44.891  23.832  1.00 35.66      A  C
ATOM   426  OG   SER A 618      73.863  43.845  23.578  1.00 56.84      A  O
ATOM   427  C    SER A 618      73.972  46.518  22.236  1.00 39.89      A  C
ATOM   428  O    SER A 618      73.317  47.326  21.592  1.00 44.92      A  O
ATOM   429  N    GLY A 619      74.991  45.848  21.715  1.00 37.72      A  N
ATOM   430  CA   GLY A 619      75.375  46.081  20.338  1.00 50.39      A  C
ATOM   431  C    GLY A 619      76.113  44.904  19.748  1.00 50.62      A  C
ATOM   432  O    GLY A 619      76.098  43.811  20.309  1.00 50.73      A  O
ATOM   433  N    ALA A 620      76.781  45.132  18.626  1.00 47.43      A  N
ATOM   434  CA   ALA A 620      77.507  44.068  17.951  1.00 49.06      A  C
ATOM   435  CB   ALA A 620      77.875  44.519  16.539  1.00 50.34      A  C
ATOM   436  C    ALA A 620      78.757  43.567  18.656  1.00 50.29      A  C
ATOM   437  O    ALA A 620      79.161  42.420  18.463  1.00 48.76      A  O
ATOM   438  N    PHE A 621      79.372  44.414  19.472  1.00 51.01      A  N
ATOM   439  CA   PHE A 621      80.618  44.043  20.131  1.00 44.91      A  C
ATOM   440  CB   PHE A 621      81.598  45.207  20.030  1.00 50.13      A  C
ATOM   441  CG   PHE A 621      81.838  45.658  18.632  1.00 58.03      A  C
ATOM   442  CD1  PHE A 621      82.577  44.867  17.755  1.00 60.69      A  C
ATOM   443  CD2  PHE A 621      81.289  46.853  18.173  1.00 52.97      A  C
ATOM   444  CE1  PHE A 621      82.766  45.257  16.436  1.00 64.43      A  C
ATOM   445  CE2  PHE A 621      81.469  47.253  16.860  1.00 61.94      A  C
ATOM   446  CZ   PHE A 621      82.212  46.451  15.986  1.00 66.03      A  C
```

FIGURE 1A-9

```
ATOM    447  C   PHE A 621      80.509  43.628  21.580  1.00 40.88      A  C
ATOM    448  O   PHE A 621      81.409  42.980  22.108  1.00 39.04      A  O
ATOM    449  N   GLY A 622      79.424  44.016  22.231  1.00 40.48      A  N
ATOM    450  CA  GLY A 622      79.273  43.677  23.629  1.00 38.45      A  C
ATOM    451  C   GLY A 622      78.113  44.450  24.178  1.00 43.25      A  C
ATOM    452  O   GLY A 622      77.153  44.717  23.450  1.00 37.54      A  O
ATOM    453  N   LYS A 623      78.203  44.844  25.443  1.00 32.63      A  N
ATOM    454  CA  LYS A 623      77.104  45.566  26.058  1.00 36.92      A  C
ATOM    455  CB  LYS A 623      75.982  44.578  26.394  1.00 46.90      A  C
ATOM    456  CG  LYS A 623      76.435  43.492  27.379  1.00 52.73      A  C
ATOM    457  CD  LYS A 623      75.345  42.499  27.732  1.00 46.08      A  C
ATOM    458  CE  LYS A 623      75.884  41.459  28.703  1.00 52.27      A  C
ATOM    459  NZ  LYS A 623      74.915  40.364  28.942  1.00 52.94      A  N
ATOM    460  C   LYS A 623      77.521  46.274  27.331  1.00 38.33      A  C
ATOM    461  O   LYS A 623      78.621  46.070  27.838  1.00 35.52      A  O
ATOM    462  N   VAL A 624      76.612  47.096  27.842  1.00 33.60      A  N
ATOM    463  CA  VAL A 624      76.817  47.825  29.078  1.00 37.17      A  C
ATOM    464  CB  VAL A 624      76.752  49.352  28.856  1.00 40.64      A  C
ATOM    465  CG1 VAL A 624      76.944  50.086  30.173  1.00 33.42      A  C
ATOM    466  CG2 VAL A 624      77.832  49.769  27.869  1.00 43.62      A  C
ATOM    467  C   VAL A 624      75.678  47.367  29.996  1.00 49.00      A  C
ATOM    468  O   VAL A 624      74.488  47.467  29.640  1.00 35.47      A  O
ATOM    469  N   MET A 625      76.059  46.851  31.164  1.00 38.01      A  N
ATOM    470  CA  MET A 625      75.120  46.326  32.150  1.00 40.77      A  C
ATOM    471  CB  MET A 625      75.578  44.954  32.626  1.00 45.08      A  C
ATOM    472  CG  MET A 625      75.663  43.887  31.580  1.00 50.16      A  C
ATOM    473  SD  MET A 625      74.053  43.279  31.215  1.00 62.88      A  S
ATOM    474  CE  MET A 625      73.518  42.696  32.868  1.00 54.19      A  C
ATOM    475  C   MET A 625      75.025  47.190  33.385  1.00 43.65      A  C
ATOM    476  O   MET A 625      76.004  47.836  33.785  1.00 39.17      A  O
ATOM    477  N   ASN A 626      73.850  47.210  34.002  1.00 37.49      A  N
ATOM    478  CA  ASN A 626      73.741  47.938  35.250  1.00 44.74      A  C
ATOM    479  CB  ASN A 626      72.309  48.406  35.549  1.00 48.44      A  C
ATOM    480  CG  ASN A 626      72.119  48.779  37.028  1.00 60.57      A  C
ATOM    481  OD1 ASN A 626      71.678  47.954  37.835  1.00 59.97      A  O
ATOM    482  ND2 ASN A 626      72.482  50.013  37.390  1.00 41.73      A  N
ATOM    483  C   ASN A 626      74.159  46.897  36.285  1.00 38.91      A  C
ATOM    484  O   ASN A 626      74.187  45.692  36.004  1.00 36.93      A  O
ATOM    485  N   ALA A 627      74.541  47.368  37.458  1.00 44.17      A  N
ATOM    486  CA  ALA A 627      74.900  46.468  38.538  1.00 37.38      A  C
ATOM    487  CB  ALA A 627      76.187  45.688  38.208  1.00 33.51      A  C
ATOM    488  C   ALA A 627      75.081  47.283  39.797  1.00 38.31      A  C
ATOM    489  O   ALA A 627      75.102  48.517  39.775  1.00 36.95      A  O
ATOM    490  N   THR A 628      75.152  46.573  40.911  1.00 39.38      A  N
ATOM    491  CA  THR A 628      75.384  47.198  42.193  1.00 43.88      A  C
ATOM    492  CB  THR A 628      74.406  46.658  43.275  1.00 53.25      A  C
ATOM    493  OG1 THR A 628      73.059  47.013  42.926  1.00 52.74      A  O
ATOM    494  CG2 THR A 628      74.740  47.248  44.633  1.00 47.54      A  C
ATOM    495  C   THR A 628      76.805  46.764  42.528  1.00 34.47      A  C
ATOM    496  O   THR A 628      77.183  45.600  42.311  1.00 33.84      A  O
ATOM    497  N   ALA A 629      77.602  47.691  43.036  1.00 33.05      A  N
ATOM    498  CA  ALA A 629      78.964  47.338  43.387  1.00 37.76      A  C
ATOM    499  CB  ALA A 629      79.972  48.198  42.590  1.00 23.80      A  C
ATOM    500  C   ALA A 629      79.177  47.522  44.882  1.00 40.49      A  C
ATOM    501  O   ALA A 629      78.933  48.598  45.437  1.00 40.31      A  O
ATOM    502  N   TYR A 630      79.650  46.466  45.527  1.00 44.40      A  N
```

FIGURE 1A-10

```
ATOM    503  CA   TYR A 630      79.902  46.521  46.959  1.00 50.26      A    C
ATOM    504  CB   TYR A 630      79.856  45.119  47.572  1.00 62.37      A    C
ATOM    505  CG   TYR A 630      78.524  44.411  47.488  1.00 81.92      A    C
ATOM    506  CD1  TYR A 630      77.321  45.113  47.614  1.00 89.18      A    C
ATOM    507  CE1  TYR A 630      76.092  44.446  47.614  1.00 91.03      A    C
ATOM    508  CD2  TYR A 630      78.466  43.020  47.356  1.00 90.09      A    C
ATOM    509  CE2  TYR A 630      77.244  42.344  47.359  1.00 94.61      A    C
ATOM    510  CZ   TYR A 630      76.063  43.061  47.489  1.00 95.13      A    C
ATOM    511  OH   TYR A 630      74.860  42.390  47.508  1.00 93.23      A    O
ATOM    512  C    TYR A 630      81.252  47.143  47.304  1.00 41.70      A    C
ATOM    513  O    TYR A 630      82.290  46.582  47.003  1.00 42.93      A    O
ATOM    514  N    GLY A 631      81.220  48.308  47.935  1.00 43.76      A    N
ATOM    515  CA   GLY A 631      82.436  48.961  48.372  1.00 48.95      A    C
ATOM    516  C    GLY A 631      83.383  49.548  47.352  1.00 55.84      A    C
ATOM    517  O    GLY A 631      84.553  49.753  47.662  1.00 49.74      A    O
ATOM    518  N    ILE A 632      82.905  49.836  46.147  1.00 55.56      A    N
ATOM    519  CA   ILE A 632      83.780  50.405  45.139  1.00 47.34      A    C
ATOM    520  CB   ILE A 632      83.150  50.297  43.737  1.00 54.91      A    C
ATOM    521  CG2  ILE A 632      82.090  51.400  43.553  1.00 37.83      A    C
ATOM    522  CG1  ILE A 632      84.250  50.386  42.670  1.00 46.82      A    C
ATOM    523  CD1  ILE A 632      83.777  50.083  41.265  1.00 44.47      A    C
ATOM    524  C    ILE A 632      84.020  51.873  45.475  1.00 52.26      A    C
ATOM    525  O    ILE A 632      85.083  52.429  45.188  1.00 50.61      A    O
ATOM    526  N    SER A 633      83.017  52.481  46.101  1.00 58.20      A    N
ATOM    527  CA   SER A 633      83.041  53.890  46.491  1.00 70.76      A    C
ATOM    528  CB   SER A 633      81.606  54.395  46.673  1.00 76.04      A    C
ATOM    529  OG   SER A 633      80.874  53.538  47.540  1.00 69.49      A    O
ATOM    530  C    SER A 633      83.822  54.115  47.779  1.00 76.60      A    C
ATOM    531  O    SER A 633      83.860  53.243  48.646  1.00 80.36      A    O
ATOM    532  N    LYS A 634      84.425  55.296  47.902  1.00 80.55      A    N
ATOM    533  CA   LYS A 634      85.225  55.660  49.074  1.00 90.86      A    C
ATOM    534  CB   LYS A 634      85.312  57.186  49.194  1.00 91.44      A    C
ATOM    535  CG   LYS A 634      85.939  57.863  47.982  1.00 91.50      A    C
ATOM    536  CD   LYS A 634      86.169  59.350  48.220  1.00 95.83      A    C
ATOM    537  CE   LYS A 634      87.172  59.592  49.346  1.00 94.53      A    C
ATOM    538  NZ   LYS A 634      87.477  61.041  49.529  1.00 92.15      A    N
ATOM    539  C    LYS A 634      84.732  55.067  50.400  1.00 93.86      A    C
ATOM    540  O    LYS A 634      85.524  54.839  51.322  1.00 89.00      A    O
ATOM    541  N    THR A 635      83.429  54.816  50.491  1.00 94.53      A    N
ATOM    542  CA   THR A 635      82.842  54.251  51.699  1.00 94.10      A    C
ATOM    543  CB   THR A 635      81.558  55.007  52.093  1.00 94.09      A    C
ATOM    544  OG1  THR A 635      80.714  55.145  50.943  1.00 94.95      A    O
ATOM    545  CG2  THR A 635      81.898  56.383  52.645  1.00 95.25      A    C
ATOM    546  C    THR A 635      82.509  52.768  51.544  1.00 92.44      A    C
ATOM    547  O    THR A 635      82.456  52.245  50.428  1.00 85.52      A    O
ATOM    548  N    GLY A 636      82.291  52.100  52.677  1.00 88.49      A    N
ATOM    549  CA   GLY A 636      81.956  50.687  52.663  1.00 80.99      A    C
ATOM    550  C    GLY A 636      80.501  50.487  52.282  1.00 81.65      A    C
ATOM    551  O    GLY A 636      79.832  49.583  52.782  1.00 78.97      A    O
ATOM    552  N    VAL A 637      80.020  51.341  51.382  1.00 79.02      A    N
ATOM    553  CA   VAL A 637      78.642  51.301  50.908  1.00 77.82      A    C
ATOM    554  CB   VAL A 637      78.072  52.729  50.825  1.00 78.44      A    C
ATOM    555  CG1  VAL A 637      76.586  52.691  50.517  1.00 76.51      A    C
ATOM    556  CG2  VAL A 637      78.338  53.460  52.127  1.00 78.57      A    C
ATOM    557  C    VAL A 637      78.554  50.665  49.519  1.00 77.02      A    C
ATOM    558  O    VAL A 637      79.565  50.515  48.830  1.00 80.17      A    O
```

FIGURE 1A-11

```
ATOM   559  N    SER A 638      77.347  50.283  49.112  1.00 66.76      A  N
ATOM   560  CA   SER A 638      77.156  49.700  47.790  1.00 64.50      A  C
ATOM   561  CB   SER A 638      76.260  48.466  47.858  1.00 51.47      A  C
ATOM   562  OG   SER A 638      74.916  48.851  48.062  1.00 63.75      A  O
ATOM   563  C    SER A 638      76.498  50.762  46.910  1.00 62.94      A  C
ATOM   564  O    SER A 638      75.627  51.504  47.371  1.00 61.82      A  O
ATOM   565  N    ILE A 639      76.925  50.845  45.651  1.00 51.41      A  N
ATOM   566  CA   ILE A 639      76.358  51.822  44.734  1.00 45.19      A  C
ATOM   567  CB   ILE A 639      77.284  53.034  44.526  1.00 51.19      A  C
ATOM   568  CG2  ILE A 639      77.532  53.730  45.852  1.00 54.99      A  C
ATOM   569  CG1  ILE A 639      78.597  52.585  43.874  1.00 45.12      A  C
ATOM   570  CD1  ILE A 639      79.478  53.738  43.418  1.00 52.68      A  C
ATOM   571  C    ILE A 639      76.070  51.226  43.372  1.00 38.27      A  C
ATOM   572  O    ILE A 639      76.489  50.107  43.057  1.00 38.54      A  O
ATOM   573  N    GLN A 640      75.325  51.985  42.576  1.00 43.70      A  N
ATOM   574  CA   GLN A 640      74.966  51.576  41.226  1.00 45.27      A  C
ATOM   575  CB   GLN A 640      73.693  52.301  40.785  1.00 48.75      A  C
ATOM   576  CG   GLN A 640      72.496  51.984  41.655  1.00 55.36      A  C
ATOM   577  CD   GLN A 640      72.266  50.496  41.763  1.00 64.27      A  C
ATOM   578  OE1  GLN A 640      71.944  49.832  40.772  1.00 63.04      A  O
ATOM   579  NE2  GLN A 640      72.449  49.953  42.966  1.00 68.68      A  N
ATOM   580  C    GLN A 640      76.111  51.943  40.286  1.00 37.27      A  C
ATOM   581  O    GLN A 640      76.716  53.008  40.416  1.00 35.66      A  O
ATOM   582  N    VAL A 641      76.400  51.063  39.340  1.00 39.47      A  N
ATOM   583  CA   VAL A 641      77.468  51.328  38.379  1.00 40.45      A  C
ATOM   584  CB   VAL A 641      78.787  50.616  38.799  1.00 30.50      A  C
ATOM   585  CG1  VAL A 641      79.211  51.056  40.199  1.00 36.49      A  C
ATOM   586  CG2  VAL A 641      78.594  49.123  38.741  1.00 22.84      A  C
ATOM   587  C    VAL A 641      77.040  50.818  36.998  1.00 34.76      A  C
ATOM   588  O    VAL A 641      76.034  50.132  36.878  1.00 34.92      A  O
ATOM   589  N    ALA A 642      77.807  51.172  35.970  1.00 34.06      A  N
ATOM   590  CA   ALA A 642      77.549  50.753  34.598  1.00 30.42      A  C
ATOM   591  CB   ALA A 642      77.430  51.978  33.678  1.00 27.73      A  C
ATOM   592  C    ALA A 642      78.764  49.916  34.227  1.00 28.24      A  C
ATOM   593  O    ALA A 642      79.887  50.351  34.389  1.00 34.75      A  O
ATOM   594  N    VAL A 643      78.541  48.716  33.724  1.00 28.91      A  N
ATOM   595  CA   VAL A 643      79.639  47.823  33.398  1.00 29.93      A  C
ATOM   596  CB   VAL A 643      79.457  46.470  34.148  1.00 32.26      A  C
ATOM   597  CG1  VAL A 643      80.642  45.581  33.910  1.00 27.72      A  C
ATOM   598  CG2  VAL A 643      79.253  46.723  35.635  1.00 34.15      A  C
ATOM   599  C    VAL A 643      79.785  47.525  31.912  1.00 38.30      A  C
ATOM   600  O    VAL A 643      78.895  46.920  31.301  1.00 31.80      A  O
ATOM   601  N    LYS A 644      80.907  47.938  31.327  1.00 33.48      A  N
ATOM   602  CA   LYS A 644      81.144  47.660  29.910  1.00 32.73      A  C
ATOM   603  CB   LYS A 644      82.114  48.665  29.287  1.00 32.17      A  C
ATOM   604  CG   LYS A 644      81.602  50.079  29.102  1.00 33.49      A  C
ATOM   605  CD   LYS A 644      82.490  50.816  28.074  1.00 37.89      A  C
ATOM   606  CE   LYS A 644      82.074  52.267  27.931  1.00 40.51      A  C
ATOM   607  NZ   LYS A 644      82.750  52.931  26.789  1.00 42.15      A  N
ATOM   608  C    LYS A 644      81.759  46.282  29.777  1.00 31.87      A  C
ATOM   609  O    LYS A 644      82.613  45.892  30.578  1.00 35.08      A  O
ATOM   610  N    MET A 645      81.347  45.539  28.763  1.00 29.84      A  N
ATOM   611  CA   MET A 645      81.908  44.208  28.537  1.00 33.05      A  C
ATOM   612  CB   MET A 645      81.239  43.177  29.449  1.00 33.07      A  C
ATOM   613  CG   MET A 645      79.719  43.182  29.400  1.00 42.66      A  C
ATOM   614  SD   MET A 645      79.008  42.007  30.585  1.00 48.33      A  S
```

FIGURE 1A-12

```
ATOM    615  CE   MET A 645      78.703  43.032  31.965  1.00 39.72      A    C
ATOM    616  C    MET A 645      81.753  43.788  27.084  1.00 37.20      A    C
ATOM    617  O    MET A 645      80.947  44.345  26.349  1.00 38.43      A    O
ATOM    618  N    LEU A 646      82.531  42.801  26.675  1.00 40.40      A    N
ATOM    619  CA   LEU A 646      82.473  42.336  25.300  1.00 47.04      A    C
ATOM    620  CB   LEU A 646      83.880  42.033  24.771  1.00 37.49      A    C
ATOM    621  CG   LEU A 646      84.862  43.200  24.652  1.00 46.35      A    C
ATOM    622  CD1  LEU A 646      86.188  42.681  24.126  1.00 46.18      A    C
ATOM    623  CD2  LEU A 646      84.296  44.257  23.720  1.00 39.81      A    C
ATOM    624  C    LEU A 646      81.631  41.095  25.126  1.00 49.65      A    C
ATOM    625  O    LEU A 646      81.313  40.397  26.088  1.00 44.84      A    O
ATOM    626  N    LYS A 647      81.294  40.839  23.868  1.00 48.65      A    N
ATOM    627  CA   LYS A 647      80.538  39.673  23.453  1.00 57.47      A    C
ATOM    628  CB   LYS A 647      80.473  39.641  21.922  1.00 60.62      A    C
ATOM    629  CG   LYS A 647      79.186  39.114  21.319  1.00 69.39      A    C
ATOM    630  CD   LYS A 647      78.111  40.189  21.272  1.00 76.88      A    C
ATOM    631  CE   LYS A 647      76.895  39.708  20.485  1.00 79.80      A    C
ATOM    632  NZ   LYS A 647      75.825  40.740  20.403  1.00 78.62      A    N
ATOM    633  C    LYS A 647      81.371  38.485  23.931  1.00 57.31      A    C
ATOM    634  O    LYS A 647      82.600  38.552  23.932  1.00 56.98      A    O
ATOM    635  N    GLU A 648      80.715  37.404  24.336  1.00 63.50      A    N
ATOM    636  CA   GLU A 648      81.434  36.215  24.783  1.00 60.69      A    C
ATOM    637  CB   GLU A 648      80.446  35.151  25.256  1.00 69.22      A    C
ATOM    638  CG   GLU A 648      79.627  35.571  26.471  1.00 84.99      A    C
ATOM    639  CD   GLU A 648      78.505  34.597  26.789  1.00 91.86      A    C
ATOM    640  OE1  GLU A 648      78.777  33.378  26.864  1.00 91.66      A    O
ATOM    641  OE2  GLU A 648      77.353  35.055  26.969  1.00 96.48      A    O
ATOM    642  C    GLU A 648      82.267  35.669  23.628  1.00 56.91      A    C
ATOM    643  O    GLU A 648      83.440  35.344  23.795  1.00 61.48      A    O
ATOM    644  N    ARG A 655      89.377  42.664  22.924  1.00 34.48      A    N
ATOM    645  CA   ARG A 655      89.818  42.630  24.329  1.00 47.68      A    C
ATOM    646  CB   ARG A 655      90.327  41.240  24.738  1.00 45.12      A    C
ATOM    647  CG   ARG A 655      89.247  40.174  24.880  1.00 58.39      A    C
ATOM    648  CD   ARG A 655      89.701  38.999  25.760  1.00 56.97      A    C
ATOM    649  NE   ARG A 655      90.903  38.331  25.256  1.00 68.56      A    N
ATOM    650  CZ   ARG A 655      90.992  37.712  24.080  1.00 74.29      A    C
ATOM    651  NH1  ARG A 655      89.946  37.663  23.262  1.00 77.19      A    N
ATOM    652  NH2  ARG A 655      92.133  37.140  23.717  1.00 70.02      A    N
ATOM    653  C    ARG A 655      90.917  43.650  24.596  1.00 42.77      A    C
ATOM    654  O    ARG A 655      90.842  44.391  25.574  1.00 36.69      A    O
ATOM    655  N    GLU A 656      91.929  43.692  23.728  1.00 36.63      A    N
ATOM    656  CA   GLU A 656      93.024  44.648  23.894  1.00 41.57      A    C
ATOM    657  CB   GLU A 656      94.130  44.379  22.863  1.00 52.95      A    C
ATOM    658  CG   GLU A 656      95.513  44.843  23.312  1.00 56.67      A    C
ATOM    659  CD   GLU A 656      95.849  44.352  24.714  1.00 67.95      A    C
ATOM    660  OE1  GLU A 656      95.896  43.119  24.918  1.00 65.65      A    O
ATOM    661  OE2  GLU A 656      96.052  45.198  25.614  1.00 58.47      A    O
ATOM    662  C    GLU A 656      92.453  46.061  23.720  1.00 43.61      A    C
ATOM    663  O    GLU A 656      92.867  47.018  24.395  1.00 37.38      A    O
ATOM    664  N    ALA A 657      91.474  46.178  22.825  1.00 38.29      A    N
ATOM    665  CA   ALA A 657      90.825  47.460  22.584  1.00 34.62      A    C
ATOM    666  CB   ALA A 657      89.815  47.321  21.462  1.00 37.02      A    C
ATOM    667  C    ALA A 657      90.127  47.933  23.865  1.00 26.00      A    C
ATOM    668  O    ALA A 657      90.169  49.121  24.216  1.00 28.64      A    O
ATOM    669  N    LEU A 658      89.498  47.003  24.578  1.00 31.22      A    N
ATOM    670  CA   LEU A 658      88.811  47.374  25.812  1.00 33.43      A    C
```

FIGURE 1A-13

```
ATOM  671  CB   LEU A 658    87.869  46.246  26.260  1.00 30.92  A C
ATOM  672  CG   LEU A 658    86.818  46.603  27.321  1.00 30.14  A C
ATOM  673  CD1  LEU A 658    86.011  47.817  26.890  1.00 25.83  A C
ATOM  674  CD2  LEU A 658    85.907  45.389  27.569  1.00 32.07  A C
ATOM  675  C    LEU A 658    89.876  47.681  26.881  1.00 28.75  A C
ATOM  676  O    LEU A 658    89.703  48.584  27.696  1.00 34.18  A O
ATOM  677  N    MET A 659    90.983  46.945  26.862  1.00 32.67  A N
ATOM  678  CA   MET A 659    92.063  47.215  27.814  1.00 30.40  A C
ATOM  679  CB   MET A 659    93.187  46.166  27.692  1.00 24.50  A C
ATOM  680  CG   MET A 659    92.861  44.819  28.358  1.00 31.26  A C
ATOM  681  SD   MET A 659    92.330  44.983  30.139  1.00 39.36  A S
ATOM  682  CE   MET A 659    93.938  45.365  30.933  1.00 38.92  A C
ATOM  683  C    MET A 659    92.632  48.620  27.570  1.00 33.86  A C
ATOM  684  O    MET A 659    92.938  49.337  28.521  1.00 32.09  A O
ATOM  685  N    SER A 660    92.750  49.020  26.299  1.00 29.97  A N
ATOM  686  CA   SER A 660    93.290  50.341  25.965  1.00 25.42  A C
ATOM  687  CB   SER A 660    93.556  50.474  24.443  1.00 26.59  A C
ATOM  688  OG   SER A 660    94.689  49.689  24.068  1.00 26.44  A O
ATOM  689  C    SER A 660    92.368  51.445  26.412  1.00 21.54  A C
ATOM  690  O    SER A 660    92.808  52.522  26.828  1.00 28.49  A O
ATOM  691  N    GLU A 661    91.070  51.201  26.282  1.00 23.25  A N
ATOM  692  CA   GLU A 661    90.116  52.186  26.716  1.00 21.02  A C
ATOM  693  CB   GLU A 661    88.685  51.743  26.379  1.00 23.02  A C
ATOM  694  CG   GLU A 661    87.660  52.698  26.929  1.00 26.69  A C
ATOM  695  CD   GLU A 661    86.215  52.315  26.601  1.00 36.00  A C
ATOM  696  OE1  GLU A 661    85.327  53.055  27.047  1.00 31.84  A O
ATOM  697  OE2  GLU A 661    85.972  51.300  25.911  1.00 33.64  A O
ATOM  698  C    GLU A 661    90.275  52.309  28.242  1.00 16.64  A C
ATOM  699  O    GLU A 661    90.282  53.405  28.776  1.00 18.21  A O
ATOM  700  N    LEU A 662    90.372  51.170  28.923  1.00 22.26  A N
ATOM  701  CA   LEU A 662    90.560  51.149  30.380  1.00 24.71  A C
ATOM  702  CB   LEU A 662    90.758  49.704  30.862  1.00 19.90  A C
ATOM  703  CG   LEU A 662    91.185  49.491  32.327  1.00 26.57  A C
ATOM  704  CD1  LEU A 662    90.207  50.194  33.271  1.00 19.50  A C
ATOM  705  CD2  LEU A 662    91.244  48.010  32.632  1.00 23.12  A C
ATOM  706  C    LEU A 662    91.799  51.981  30.758  1.00 24.21  A C
ATOM  707  O    LEU A 662    91.718  52.919  31.567  1.00 26.37  A O
ATOM  708  N    LYS A 663    92.949  51.639  30.161  1.00 25.07  A N
ATOM  709  CA   LYS A 663    94.186  52.353  30.478  1.00 25.31  A C
ATOM  710  CB   LYS A 663    95.352  51.843  29.625  1.00 28.56  A C
ATOM  711  CG   LYS A 663    95.772  50.403  29.912  1.00 29.60  A C
ATOM  712  CD   LYS A 663    96.731  49.926  28.829  1.00 23.27  A C
ATOM  713  CE   LYS A 663    96.835  48.445  28.794  1.00 31.62  A C
ATOM  714  NZ   LYS A 663    97.763  48.008  27.726  1.00 25.86  A N
ATOM  715  C    LYS A 663    94.017  53.830  30.244  1.00 30.66  A C
ATOM  716  O    LYS A 663    94.456  54.650  31.043  1.00 25.08  A O
ATOM  717  N    MET A 664    93.360  54.172  29.142  1.00 30.76  A N
ATOM  718  CA   MET A 664    93.149  55.572  28.823  1.00 26.62  A C
ATOM  719  CB   MET A 664    92.466  55.688  27.451  1.00 31.70  A C
ATOM  720  CG   MET A 664    92.252  57.112  26.938  1.00 41.46  A C
ATOM  721  SD   MET A 664    90.818  57.962  27.641  1.00 50.85  A S
ATOM  722  CE   MET A 664    90.297  58.914  26.235  1.00 49.19  A C
ATOM  723  C    MET A 664    92.325  56.267  29.919  1.00 29.68  A C
ATOM  724  O    MET A 664    92.679  57.357  30.380  1.00 26.27  A O
ATOM  725  N    MET A 665    91.238  55.640  30.359  1.00 24.22  A N
ATOM  726  CA   MET A 665    90.409  56.281  31.381  1.00 29.78  A C
```

FIGURE 1A-14

```
ATOM    727  CB   MET A 665      89.058  55.568  31.501  1.00 26.98      A  C
ATOM    728  CG   MET A 665      88.192  55.647  30.222  1.00 32.44      A  C
ATOM    729  SD   MET A 665      87.881  57.347  29.676  1.00 33.13      A  S
ATOM    730  CE   MET A 665      86.522  57.905  30.841  1.00 25.44      A  C
ATOM    731  C    MET A 665      91.097  56.363  32.756  1.00 26.95      A  C
ATOM    732  O    MET A 665      90.786  57.251  33.544  1.00 27.90      A  O
ATOM    733  N    THR A 666      92.017  55.444  33.049  1.00 26.19      A  N
ATOM    734  CA   THR A 666      92.733  55.511  34.331  1.00 35.66      A  C
ATOM    735  CB   THR A 666      93.589  54.256  34.619  1.00 29.43      A  C
ATOM    736  OG1  THR A 666      94.579  54.099  33.593  1.00 36.22      A  O
ATOM    737  CG2  THR A 666      92.725  53.015  34.729  1.00 27.56      A  C
ATOM    738  C    THR A 666      93.702  56.708  34.348  1.00 37.32      A  C
ATOM    739  O    THR A 666      94.115  57.156  35.407  1.00 33.00      A  O
ATOM    740  N    GLN A 667      94.054  57.212  33.169  1.00 31.30      A  N
ATOM    741  CA   GLN A 667      94.982  58.333  33.043  1.00 33.09      A  C
ATOM    742  CB   GLN A 667      95.837  58.165  31.785  1.00 40.55      A  C
ATOM    743  CG   GLN A 667      96.665  56.907  31.757  1.00 61.37      A  C
ATOM    744  CD   GLN A 667      98.126  57.171  32.049  1.00 74.23      A  C
ATOM    745  OE1  GLN A 667      98.487  57.604  33.144  1.00 80.71      A  O
ATOM    746  NE2  GLN A 667      98.979  56.920  31.060  1.00 79.12      A  N
ATOM    747  C    GLN A 667      94.296  59.683  32.951  1.00 35.56      A  C
ATOM    748  O    GLN A 667      94.920  60.713  33.164  1.00 32.61      A  O
ATOM    749  N    LEU A 668      93.010  59.674  32.619  1.00 37.25      A  N
ATOM    750  CA   LEU A 668      92.256  60.907  32.439  1.00 36.90      A  C
ATOM    751  CB   LEU A 668      90.882  60.585  31.836  1.00 37.69      A  C
ATOM    752  CG   LEU A 668      90.305  61.312  30.623  1.00 38.91      A  C
ATOM    753  CD1  LEU A 668      88.812  61.499  30.860  1.00 37.93      A  C
ATOM    754  CD2  LEU A 668      90.973  62.640  30.381  1.00 41.25      A  C
ATOM    755  C    LEU A 668      92.034  61.753  33.685  1.00 36.89      A  C
ATOM    756  O    LEU A 668      92.128  62.980  33.634  1.00 34.43      A  O
ATOM    757  N    GLY A 669      91.741  61.104  34.805  1.00 39.02      A  N
ATOM    758  CA   GLY A 669      91.430  61.855  36.003  1.00 41.45      A  C
ATOM    759  C    GLY A 669      89.916  62.050  35.922  1.00 50.42      A  C
ATOM    760  O    GLY A 669      89.331  61.896  34.853  1.00 53.01      A  O
ATOM    761  N    SER A 670      89.272  62.393  37.027  1.00 42.82      A  N
ATOM    762  CA   SER A 670      87.825  62.555  37.020  1.00 38.73      A  C
ATOM    763  CB   SER A 670      87.249  61.982  38.313  1.00 41.43      A  C
ATOM    764  OG   SER A 670      87.802  62.671  39.419  1.00 50.51      A  O
ATOM    765  C    SER A 670      87.324  63.989  36.844  1.00 35.64      A  C
ATOM    766  O    SER A 670      88.044  64.966  37.075  1.00 33.35      A  O
ATOM    767  N    HIS A 671      86.068  64.097  36.418  1.00 34.15      A  N
ATOM    768  CA   HIS A 671      85.425  65.385  36.227  1.00 32.96      A  C
ATOM    769  CB   HIS A 671      85.725  65.945  34.836  1.00 31.48      A  C
ATOM    770  CG   HIS A 671      85.104  67.288  34.592  1.00 34.08      A  C
ATOM    771  CD2  HIS A 671      83.829  67.637  34.295  1.00 29.52      A  C
ATOM    772  ND1  HIS A 671      85.802  68.471  34.723  1.00 32.51      A  N
ATOM    773  CE1  HIS A 671      84.984  69.490  34.519  1.00 31.51      A  C
ATOM    774  NE2  HIS A 671      83.780  69.010  34.258  1.00 34.97      A  N
ATOM    775  C    HIS A 671      83.909  65.194  36.416  1.00 26.94      A  C
ATOM    776  O    HIS A 671      83.370  64.128  36.130  1.00 35.74      A  O
ATOM    777  N    GLU A 672      83.233  66.215  36.925  1.00 32.67      A  N
ATOM    778  CA   GLU A 672      81.794  66.110  37.152  1.00 38.90      A  C
ATOM    779  CB   GLU A 672      81.237  67.380  37.828  1.00 38.43      A  C
ATOM    780  CG   GLU A 672      79.687  67.426  37.736  1.00 57.25      A  C
ATOM    781  CD   GLU A 672      78.986  68.339  38.748  1.00 56.88      A  C
ATOM    782  OE1  GLU A 672      79.310  69.545  38.831  1.00 58.72      A  O
```

FIGURE 1A-15

```
ATOM   783  OE2 GLU A 672      78.083  67.838  39.450  1.00 51.46      A  O
ATOM   784  C   GLU A 672      80.965  65.836  35.885  1.00 33.94      A  C
ATOM   785  O   GLU A 672      79.952  65.142  35.946  1.00 31.56      A  O
ATOM   786  N   ASN A 673      81.408  66.370  34.752  1.00 37.52      A  N
ATOM   787  CA  ASN A 673      80.685  66.227  33.486  1.00 28.53      A  C
ATOM   788  CB  ASN A 673      80.640  67.582  32.815  1.00 24.98      A  C
ATOM   789  CG  ASN A 673      80.066  68.642  33.740  1.00 26.61      A  C
ATOM   790  OD1 ASN A 673      80.695  69.666  33.998  1.00 37.47      A  O
ATOM   791  ND2 ASN A 673      78.854  68.391  34.242  1.00 27.30      A  N
ATOM   792  C   ASN A 673      81.207  65.171  32.531  1.00 36.30      A  C
ATOM   793  O   ASN A 673      80.993  65.253  31.309  1.00 27.68      A  O
ATOM   794  N   ILE A 674      81.879  64.175  33.105  1.00 26.45      A  N
ATOM   795  CA  ILE A 674      82.409  63.045  32.348  1.00 28.61      A  C
ATOM   796  CB  ILE A 674      83.972  63.034  32.354  1.00 32.67      A  C
ATOM   797  CG2 ILE A 674      84.491  61.765  31.681  1.00 27.03      A  C
ATOM   798  CG1 ILE A 674      84.516  64.286  31.658  1.00 34.52      A  C
ATOM   799  CD1 ILE A 674      84.176  64.352  30.181  1.00 30.42      A  C
ATOM   800  C   ILE A 674      81.933  61.797  33.071  1.00 35.54      A  C
ATOM   801  O   ILE A 674      81.799  61.809  34.293  1.00 28.46      A  O
ATOM   802  N   VAL A 675      81.642  60.736  32.331  1.00 26.22      A  N
ATOM   803  CA  VAL A 675      81.263  59.477  32.963  1.00 23.60      A  C
ATOM   804  CB  VAL A 675      80.575  58.522  32.008  1.00 31.48      A  C
ATOM   805  CG1 VAL A 675      80.472  57.153  32.646  1.00 29.53      A  C
ATOM   806  CG2 VAL A 675      79.160  59.051  31.662  1.00 32.24      A  C
ATOM   807  C   VAL A 675      82.614  58.892  33.363  1.00 39.31      A  C
ATOM   808  O   VAL A 675      83.386  58.433  32.513  1.00 27.73      A  O
ATOM   809  N   ASN A 676      82.893  58.922  34.663  1.00 36.56      A  N
ATOM   810  CA  ASN A 676      84.177  58.464  35.190  1.00 30.67      A  C
ATOM   811  CB  ASN A 676      84.488  59.233  36.489  1.00 27.74      A  C
ATOM   812  CG  ASN A 676      84.401  60.747  36.314  1.00 29.25      A  C
ATOM   813  OD1 ASN A 676      85.129  61.344  35.512  1.00 31.53      A  O
ATOM   814  ND2 ASN A 676      83.511  61.378  37.073  1.00 32.66      A  N
ATOM   815  C   ASN A 676      84.337  56.974  35.441  1.00 22.27      A  C
ATOM   816  O   ASN A 676      83.401  56.273  35.832  1.00 32.36      A  O
ATOM   817  N   LEU A 677      85.556  56.491  35.225  1.00 22.53      A  N
ATOM   818  CA  LEU A 677      85.883  55.092  35.483  1.00 24.82      A  C
ATOM   819  CB  LEU A 677      87.248  54.761  34.890  1.00 35.72      A  C
ATOM   820  CG  LEU A 677      87.752  53.357  35.195  1.00 30.00      A  C
ATOM   821  CD1 LEU A 677      87.091  52.366  34.247  1.00 27.33      A  C
ATOM   822  CD2 LEU A 677      89.266  53.337  35.073  1.00 29.82      A  C
ATOM   823  C   LEU A 677      85.962  54.919  37.011  1.00 28.65      A  C
ATOM   824  O   LEU A 677      86.449  55.807  37.696  1.00 26.09      A  O
ATOM   825  N   LEU A 678      85.505  53.787  37.536  1.00 29.63      A  N
ATOM   826  CA  LEU A 678      85.548  53.548  38.982  1.00 33.25      A  C
ATOM   827  CB  LEU A 678      84.124  53.325  39.529  1.00 26.62      A  C
ATOM   828  CG  LEU A 678      83.146  54.502  39.408  1.00 30.79      A  C
ATOM   829  CD1 LEU A 678      81.744  54.093  39.901  1.00 25.28      A  C
ATOM   830  CD2 LEU A 678      83.693  55.686  40.193  1.00 27.76      A  C
ATOM   831  C   LEU A 678      86.413  52.324  39.311  1.00 38.38      A  C
ATOM   832  O   LEU A 678      86.999  52.234  40.394  1.00 30.91      A  O
ATOM   833  N   GLY A 679      86.482  51.383  38.375  1.00 28.98      A  N
ATOM   834  CA  GLY A 679      87.280  50.192  38.587  1.00 27.06      A  C
ATOM   835  C   GLY A 679      87.220  49.257  37.394  1.00 30.88      A  C
ATOM   836  O   GLY A 679      86.577  49.573  36.391  1.00 27.19      A  O
ATOM   837  N   ALA A 680      87.884  48.109  37.505  1.00 27.66      A  N
ATOM   838  CA  ALA A 680      87.907  47.113  36.433  1.00 33.97      A  C
```

FIGURE 1A-16

```
ATOM    839  CB  ALA A 680      88.957  47.490  35.360  1.00 26.09       A C
ATOM    840  C   ALA A 680      88.214  45.722  36.967  1.00 28.74       A C
ATOM    841  O   ALA A 680      88.835  45.567  38.004  1.00 34.14       A O
ATOM    842  N   CYS A 681      87.773  44.719  36.225  1.00 28.05       A N
ATOM    843  CA  CYS A 681      87.987  43.315  36.539  1.00 26.41       A C
ATOM    844  CB  CYS A 681      86.640  42.616  36.764  1.00 27.71       A C
ATOM    845  SG  CYS A 681      85.615  43.433  37.968  1.00 33.71       A S
ATOM    846  C   CYS A 681      88.644  42.790  35.268  1.00 32.30       A C
ATOM    847  O   CYS A 681      88.007  42.702  34.222  1.00 33.16       A O
ATOM    848  N   THR A 682      89.911  42.419  35.366  1.00 30.00       A N
ATOM    849  CA  THR A 682      90.670  41.993  34.198  1.00 33.51       A C
ATOM    850  CB  THR A 682      91.674  43.089  33.835  1.00 40.59       A C
ATOM    851  OG1 THR A 682      92.676  43.155  34.870  1.00 32.21       A O
ATOM    852  CG2 THR A 682      90.979  44.448  33.760  1.00 31.63       A C
ATOM    853  C   THR A 682      91.506  40.732  34.364  1.00 38.51       A C
ATOM    854  O   THR A 682      92.184  40.334  33.429  1.00 37.58       A O
ATOM    855  N   LEU A 683      91.460  40.098  35.529  1.00 41.75       A N
ATOM    856  CA  LEU A 683      92.335  38.962  35.769  1.00 37.80       A C
ATOM    857  CB  LEU A 683      93.135  39.230  37.048  1.00 42.41       A C
ATOM    858  CG  LEU A 683      94.038  40.468  37.055  1.00 46.29       A C
ATOM    859  CD1 LEU A 683      94.527  40.772  38.473  1.00 45.42       A C
ATOM    860  CD2 LEU A 683      95.210  40.224  36.115  1.00 41.50       A C
ATOM    861  C   LEU A 683      91.792  37.548  35.829  1.00 42.32       A C
ATOM    862  O   LEU A 683      92.380  36.643  35.248  1.00 44.24       A O
ATOM    863  N   SER A 684      90.692  37.342  36.536  1.00 43.72       A N
ATOM    864  CA  SER A 684      90.153  35.992  36.678  1.00 46.79       A C
ATOM    865  CB  SER A 684      89.880  35.704  38.153  1.00 44.18       A C
ATOM    866  OG  SER A 684      88.883  36.584  38.647  1.00 44.14       A O
ATOM    867  C   SER A 684      88.883  35.730  35.886  1.00 52.99       A C
ATOM    868  O   SER A 684      88.099  34.850  36.243  1.00 51.82       A O
ATOM    869  N   GLY A 685      88.679  36.488  34.814  1.00 53.16       A N
ATOM    870  CA  GLY A 685      87.487  36.302  34.009  1.00 50.10       A C
ATOM    871  C   GLY A 685      87.384  37.347  32.921  1.00 49.53       A C
ATOM    872  O   GLY A 685      88.316  38.112  32.714  1.00 42.96       A O
ATOM    873  N   PRO A 686      86.261  37.405  32.200  1.00 48.76       A N
ATOM    874  CD  PRO A 686      85.003  36.659  32.355  1.00 49.96       A C
ATOM    875  CA  PRO A 686      86.150  38.411  31.145  1.00 47.01       A C
ATOM    876  CB  PRO A 686      84.731  38.198  30.608  1.00 41.10       A C
ATOM    877  CG  PRO A 686      84.000  37.635  31.787  1.00 53.53       A C
ATOM    878  C   PRO A 686      86.380  39.825  31.673  1.00 46.99       A C
ATOM    879  O   PRO A 686      86.127  40.122  32.850  1.00 36.52       A O
ATOM    880  N   ILE A 687      86.857  40.693  30.787  1.00 31.42       A N
ATOM    881  CA  ILE A 687      87.138  42.074  31.135  1.00 33.47       A C
ATOM    882  CB  ILE A 687      87.978  42.739  30.036  1.00 31.43       A C
ATOM    883  CG2 ILE A 687      88.227  44.199  30.392  1.00 29.90       A C
ATOM    884  CG1 ILE A 687      89.288  41.966  29.854  1.00 34.57       A C
ATOM    885  CD1 ILE A 687      90.136  42.432  28.689  1.00 47.57       A C
ATOM    886  C   ILE A 687      85.900  42.936  31.372  1.00 39.72       A C
ATOM    887  O   ILE A 687      85.005  43.000  30.529  1.00 39.87       A O
ATOM    888  N   TYR A 688      85.852  43.603  32.523  1.00 29.27       A N
ATOM    889  CA  TYR A 688      84.745  44.496  32.824  1.00 25.72       A C
ATOM    890  CB  TYR A 688      83.928  44.052  34.053  1.00 38.66       A C
ATOM    891  CG  TYR A 688      83.315  42.675  34.033  1.00 42.19       A C
ATOM    892  CD1 TYR A 688      82.905  42.071  32.842  1.00 39.59       A C
ATOM    893  CE1 TYR A 688      82.273  40.819  32.853  1.00 42.64       A C
ATOM    894  CD2 TYR A 688      83.085  42.000  35.233  1.00 45.89       A C
```

FIGURE 1A-17

```
ATOM    895  CE2 TYR A 688      82.459  40.763  35.261  1.00 50.36      A    C
ATOM    896  CZ  TYR A 688      82.055  40.175  34.077  1.00 59.63      A    C
ATOM    897  OH  TYR A 688      81.439  38.945  34.141  1.00 52.97      A    O
ATOM    898  C   TYR A 688      85.282  45.868  33.181  1.00 31.84      A    C
ATOM    899  O   TYR A 688      86.171  45.983  34.029  1.00 32.61      A    O
ATOM    900  N   LEU A 689      84.744  46.914  32.564  1.00 27.86      A    N
ATOM    901  CA  LEU A 689      85.171  48.259  32.935  1.00 27.04      A    C
ATOM    902  CB  LEU A 689      85.454  49.121  31.704  1.00 29.71      A    C
ATOM    903  CG  LEU A 689      86.372  48.551  30.605  1.00 36.47      A    C
ATOM    904  CD1 LEU A 689      87.018  49.738  29.891  1.00 26.28      A    C
ATOM    905  CD2 LEU A 689      87.441  47.631  31.161  1.00 25.77      A    C
ATOM    906  C   LEU A 689      83.971  48.794  33.717  1.00 34.12      A    C
ATOM    907  O   LEU A 689      82.841  48.753  33.227  1.00 33.67      A    O
ATOM    908  N   ILE A 690      84.218  49.273  34.931  1.00 30.20      A    N
ATOM    909  CA  ILE A 690      83.167  49.770  35.809  1.00 27.33      A    C
ATOM    910  CB  ILE A 690      83.374  49.222  37.255  1.00 33.17      A    C
ATOM    911  CG2 ILE A 690      82.164  49.551  38.141  1.00 25.16      A    C
ATOM    912  CG1 ILE A 690      83.588  47.707  37.200  1.00 26.86      A    C
ATOM    913  CD1 ILE A 690      84.149  47.114  38.522  1.00 34.29      A    C
ATOM    914  C   ILE A 690      83.132  51.291  35.841  1.00 23.81      A    C
ATOM    915  O   ILE A 690      84.105  51.962  36.232  1.00 30.36      A    O
ATOM    916  N   PHE A 691      81.997  51.836  35.425  1.00 26.29      A    N
ATOM    917  CA  PHE A 691      81.819  53.270  35.377  1.00 22.57      A    C
ATOM    918  CB  PHE A 691      81.470  53.711  33.940  1.00 35.76      A    C
ATOM    919  CG  PHE A 691      82.604  53.549  32.941  1.00 25.97      A    C
ATOM    920  CD1 PHE A 691      82.826  52.337  32.306  1.00 32.51      A    C
ATOM    921  CD2 PHE A 691      83.432  54.630  32.633  1.00 33.73      A    C
ATOM    922  CE1 PHE A 691      83.863  52.192  31.363  1.00 25.93      A    C
ATOM    923  CE2 PHE A 691      84.470  54.497  31.694  1.00 37.06      A    C
ATOM    924  CZ  PHE A 691      84.682  53.273  31.061  1.00 28.00      A    C
ATOM    925  C   PHE A 691      80.716  53.760  36.298  1.00 24.09      A    C
ATOM    926  O   PHE A 691      79.924  52.964  36.817  1.00 29.28      A    O
ATOM    927  N   GLU A 692      80.688  55.076  36.485  1.00 25.31      A    N
ATOM    928  CA  GLU A 692      79.645  55.750  37.241  1.00 29.80      A    C
ATOM    929  CB  GLU A 692      79.847  57.271  37.181  1.00 31.85      A    C
ATOM    930  CG  GLU A 692      80.981  57.802  38.043  1.00 34.44      A    C
ATOM    931  CD  GLU A 692      81.183  59.300  37.892  1.00 42.13      A    C
ATOM    932  OE1 GLU A 692      81.660  59.926  38.863  1.00 49.31      A    O
ATOM    933  OE2 GLU A 692      80.883  59.860  36.808  1.00 39.33      A    O
ATOM    934  C   GLU A 692      78.353  55.406  36.489  1.00 40.95      A    C
ATOM    935  O   GLU A 692      78.362  55.268  35.260  1.00 37.91      A    O
ATOM    936  N   TYR A 693      77.254  55.267  37.221  1.00 38.34      A    N
ATOM    937  CA  TYR A 693      75.953  54.945  36.627  1.00 40.47      A    C
ATOM    938  CB  TYR A 693      75.196  53.953  37.516  1.00 41.02      A    C
ATOM    939  CG  TYR A 693      73.781  53.664  37.068  1.00 51.15      A    C
ATOM    940  CD1 TYR A 693      73.522  53.085  35.821  1.00 50.78      A    C
ATOM    941  CE1 TYR A 693      72.216  52.827  35.403  1.00 53.64      A    C
ATOM    942  CD2 TYR A 693      72.692  53.979  37.890  1.00 54.26      A    C
ATOM    943  CE2 TYR A 693      71.380  53.726  37.484  1.00 49.55      A    C
ATOM    944  CZ  TYR A 693      71.151  53.150  36.243  1.00 58.15      A    C
ATOM    945  OH  TYR A 693      69.861  52.883  35.849  1.00 57.14      A    O
ATOM    946  C   TYR A 693      75.132  56.224  36.470  1.00 39.18      A    C
ATOM    947  O   TYR A 693      75.164  57.107  37.326  1.00 40.79      A    O
ATOM    948  N   CYS A 694      74.417  56.334  35.359  1.00 37.48      A    N
ATOM    949  CA  CYS A 694      73.593  57.512  35.106  1.00 36.04      A    C
ATOM    950  CB  CYS A 694      74.072  58.213  33.817  1.00 36.46      A    C
```

FIGURE 1A-18

```
ATOM    951  SG  CYS A 694      75.758  58.936  33.940  1.00 35.68      A  S
ATOM    952  C   CYS A 694      72.149  56.994  34.988  1.00 42.76      A  C
ATOM    953  O   CYS A 694      71.762  56.422  33.962  1.00 41.97      A  O
ATOM    954  N   CYS A 695      71.370  57.183  36.057  1.00 35.68      A  N
ATOM    955  CA  CYS A 695      69.995  56.684  36.123  1.00 41.20      A  C
ATOM    956  CB  CYS A 695      69.376  57.026  37.497  1.00 27.96      A  C
ATOM    957  SG  CYS A 695      69.455  58.757  38.003  1.00 50.80      A  S
ATOM    958  C   CYS A 695      69.003  57.046  35.009  1.00 37.65      A  C
ATOM    959  O   CYS A 695      68.152  56.230  34.680  1.00 44.73      A  O
ATOM    960  N   TYR A 696      69.117  58.228  34.407  1.00 45.28      A  N
ATOM    961  CA  TYR A 696      68.161  58.635  33.368  1.00 42.35      A  C
ATOM    962  CB  TYR A 696      67.759  60.085  33.612  1.00 34.34      A  C
ATOM    963  CG  TYR A 696      67.234  60.321  35.010  1.00 52.87      A  C
ATOM    964  CD1 TYR A 696      66.202  59.539  35.532  1.00 52.31      A  C
ATOM    965  CE1 TYR A 696      65.724  59.746  36.831  1.00 60.55      A  C
ATOM    966  CD2 TYR A 696      67.776  61.318  35.816  1.00 59.24      A  C
ATOM    967  CE2 TYR A 696      67.308  61.535  37.110  1.00 68.24      A  C
ATOM    968  CZ  TYR A 696      66.286  60.746  37.613  1.00 64.52      A  C
ATOM    969  OH  TYR A 696      65.852  60.954  38.901  1.00 69.94      A  O
ATOM    970  C   TYR A 696      68.523  58.449  31.884  1.00 41.98      A  C
ATOM    971  O   TYR A 696      67.965  59.132  31.025  1.00 40.28      A  O
ATOM    972  N   GLY A 697      69.436  57.520  31.593  1.00 41.80      A  N
ATOM    973  CA  GLY A 697      69.848  57.247  30.224  1.00 41.27      A  C
ATOM    974  C   GLY A 697      70.498  58.378  29.429  1.00 32.40      A  C
ATOM    975  O   GLY A 697      70.848  59.429  29.968  1.00 32.35      A  O
ATOM    976  N   ASP A 698      70.634  58.153  28.122  1.00 38.28      A  N
ATOM    977  CA  ASP A 698      71.270  59.117  27.225  1.00 28.42      A  C
ATOM    978  CB  ASP A 698      71.559  58.454  25.871  1.00 33.36      A  C
ATOM    979  CG  ASP A 698      70.293  58.207  25.060  1.00 31.03      A  C
ATOM    980  OD1 ASP A 698      69.761  57.075  25.078  1.00 30.63      A  O
ATOM    981  OD2 ASP A 698      69.835  59.166  24.415  1.00 32.40      A  O
ATOM    982  C   ASP A 698      70.441  60.388  27.031  1.00 23.75      A  C
ATOM    983  O   ASP A 698      69.190  60.349  26.980  1.00 31.53      A  O
ATOM    984  N   LEU A 699      71.130  61.522  26.945  1.00 22.87      A  N
ATOM    985  CA  LEU A 699      70.461  62.810  26.781  1.00 24.47      A  C
ATOM    986  CB  LEU A 699      71.504  63.914  26.688  1.00 26.41      A  C
ATOM    987  CG  LEU A 699      71.008  65.345  26.427  1.00 28.83      A  C
ATOM    988  CD1 LEU A 699      70.158  65.866  27.630  1.00 31.42      A  C
ATOM    989  CD2 LEU A 699      72.229  66.231  26.215  1.00 20.90      A  C
ATOM    990  C   LEU A 699      69.487  62.911  25.561  1.00 29.36      A  C
ATOM    991  O   LEU A 699      68.529  63.669  25.616  1.00 26.66      A  O
ATOM    992  N   LEU A 700      69.725  62.174  24.473  1.00 31.76      A  N
ATOM    993  CA  LEU A 700      68.817  62.262  23.313  1.00 31.55      A  C
ATOM    994  CB  LEU A 700      69.351  61.488  22.098  1.00 24.24      A  C
ATOM    995  CG  LEU A 700      68.449  61.570  20.846  1.00 28.86      A  C
ATOM    996  CD1 LEU A 700      68.283  63.037  20.416  1.00 27.44      A  C
ATOM    997  CD2 LEU A 700      69.060  60.740  19.712  1.00 26.25      A  C
ATOM    998  C   LEU A 700      67.432  61.715  23.666  1.00 24.81      A  C
ATOM    999  O   LEU A 700      66.423  62.365  23.428  1.00 29.69      A  O
ATOM   1000  N   ASN A 701      67.391  60.510  24.215  1.00 27.74      A  N
ATOM   1001  CA  ASN A 701      66.123  59.931  24.628  1.00 31.40      A  C
ATOM   1002  CB  ASN A 701      66.318  58.478  25.036  1.00 32.39      A  C
ATOM   1003  CG  ASN A 701      66.303  57.557  23.843  1.00 44.35      A  C
ATOM   1004  OD1 ASN A 701      65.315  57.517  23.094  1.00 40.67      A  O
ATOM   1005  ND2 ASN A 701      67.394  56.817  23.639  1.00 42.83      A  N
ATOM   1006  C   ASN A 701      65.466  60.725  25.746  1.00 30.84      A  C
```

FIGURE 1A-19

| ATOM | 1007 | O   | ASN | A | 701 | 64.246 | 60.853 | 25.792 | 1.00 | 34.70 | A | O |
|------|------|-----|-----|---|-----|--------|--------|--------|------|-------|---|---|
| ATOM | 1008 | N   | TYR | A | 702 | 66.279 | 61.294 | 26.624 | 1.00 | 34.94 | A | N |
| ATOM | 1009 | CA  | TYR | A | 702 | 65.765 | 62.081 | 27.741 | 1.00 | 35.56 | A | C |
| ATOM | 1010 | CB  | TYR | A | 702 | 66.921 | 62.570 | 28.619 | 1.00 | 30.10 | A | C |
| ATOM | 1011 | CG  | TYR | A | 702 | 66.502 | 63.396 | 29.813 | 1.00 | 33.06 | A | C |
| ATOM | 1012 | CD1 | TYR | A | 702 | 66.209 | 62.794 | 31.040 | 1.00 | 33.71 | A | C |
| ATOM | 1013 | CE1 | TYR | A | 702 | 65.857 | 63.560 | 32.155 | 1.00 | 39.15 | A | C |
| ATOM | 1014 | CD2 | TYR | A | 702 | 66.426 | 64.784 | 29.724 | 1.00 | 33.38 | A | C |
| ATOM | 1015 | CE2 | TYR | A | 702 | 66.074 | 65.560 | 30.823 | 1.00 | 44.97 | A | C |
| ATOM | 1016 | CZ  | TYR | A | 702 | 65.794 | 64.943 | 32.038 | 1.00 | 39.00 | A | C |
| ATOM | 1017 | OH  | TYR | A | 702 | 65.489 | 65.720 | 33.130 | 1.00 | 46.57 | A | O |
| ATOM | 1018 | C   | TYR | A | 702 | 65.009 | 63.280 | 27.170 | 1.00 | 39.06 | A | C |
| ATOM | 1019 | O   | TYR | A | 702 | 63.894 | 63.597 | 27.590 | 1.00 | 38.30 | A | O |
| ATOM | 1020 | N   | LEU | A | 703 | 65.636 | 63.948 | 26.212 | 1.00 | 36.63 | A | N |
| ATOM | 1021 | CA  | LEU | A | 703 | 65.027 | 65.102 | 25.583 | 1.00 | 37.77 | A | C |
| ATOM | 1022 | CB  | LEU | A | 703 | 66.007 | 65.745 | 24.600 | 1.00 | 43.10 | A | C |
| ATOM | 1023 | CG  | LEU | A | 703 | 67.249 | 66.444 | 25.163 | 1.00 | 33.24 | A | C |
| ATOM | 1024 | CD1 | LEU | A | 703 | 68.195 | 66.750 | 24.013 | 1.00 | 45.83 | A | C |
| ATOM | 1025 | CD2 | LEU | A | 703 | 66.857 | 67.727 | 25.881 | 1.00 | 30.54 | A | C |
| ATOM | 1026 | C   | LEU | A | 703 | 63.741 | 64.722 | 24.853 | 1.00 | 31.26 | A | C |
| ATOM | 1027 | O   | LEU | A | 703 | 62.717 | 65.365 | 25.031 | 1.00 | 33.65 | A | O |
| ATOM | 1028 | N   | ARG | A | 704 | 63.789 | 63.662 | 24.054 | 1.00 | 29.67 | A | N |
| ATOM | 1029 | CA  | ARG | A | 704 | 62.611 | 63.247 | 23.303 | 1.00 | 32.79 | A | C |
| ATOM | 1030 | CB  | ARG | A | 704 | 62.970 | 62.121 | 22.327 | 1.00 | 32.73 | A | C |
| ATOM | 1031 | CG  | ARG | A | 704 | 64.309 | 62.390 | 21.659 | 1.00 | 38.72 | A | C |
| ATOM | 1032 | CD  | ARG | A | 704 | 64.346 | 62.312 | 20.177 | 1.00 | 41.92 | A | C |
| ATOM | 1033 | NE  | ARG | A | 704 | 64.871 | 61.036 | 19.752 | 1.00 | 36.17 | A | N |
| ATOM | 1034 | CZ  | ARG | A | 704 | 65.515 | 60.812 | 18.609 | 1.00 | 34.17 | A | C |
| ATOM | 1035 | NH1 | ARG | A | 704 | 65.758 | 61.784 | 17.736 | 1.00 | 36.29 | A | N |
| ATOM | 1036 | NH2 | ARG | A | 704 | 65.858 | 59.570 | 18.305 | 1.00 | 32.14 | A | N |
| ATOM | 1037 | C   | ARG | A | 704 | 61.481 | 62.824 | 24.229 | 1.00 | 39.84 | A | C |
| ATOM | 1038 | O   | ARG | A | 704 | 60.329 | 63.125 | 23.951 | 1.00 | 36.90 | A | O |
| ATOM | 1039 | N   | SER | A | 705 | 61.815 | 62.144 | 25.327 | 1.00 | 41.33 | A | N |
| ATOM | 1040 | CA  | SER | A | 705 | 60.817 | 61.691 | 26.295 | 1.00 | 42.80 | A | C |
| ATOM | 1041 | CB  | SER | A | 705 | 61.453 | 60.785 | 27.365 | 1.00 | 36.27 | A | C |
| ATOM | 1042 | OG  | SER | A | 705 | 62.136 | 61.564 | 28.334 | 1.00 | 41.54 | A | O |
| ATOM | 1043 | C   | SER | A | 705 | 60.150 | 62.877 | 26.997 | 1.00 | 44.70 | A | C |
| ATOM | 1044 | O   | SER | A | 705 | 59.142 | 62.702 | 27.672 | 1.00 | 48.14 | A | O |
| ATOM | 1045 | N   | LYS | A | 706 | 60.704 | 64.078 | 26.843 | 1.00 | 40.87 | A | N |
| ATOM | 1046 | CA  | LYS | A | 706 | 60.112 | 65.244 | 27.485 | 1.00 | 40.83 | A | C |
| ATOM | 1047 | CB  | LYS | A | 706 | 61.134 | 65.888 | 28.425 | 1.00 | 43.37 | A | C |
| ATOM | 1048 | CG  | LYS | A | 706 | 61.525 | 64.934 | 29.540 | 1.00 | 56.87 | A | C |
| ATOM | 1049 | CD  | LYS | A | 706 | 62.139 | 65.630 | 30.725 | 1.00 | 58.24 | A | C |
| ATOM | 1050 | CE  | LYS | A | 706 | 62.360 | 64.628 | 31.846 | 1.00 | 53.74 | A | C |
| ATOM | 1051 | NZ  | LYS | A | 706 | 61.089 | 63.957 | 32.239 | 1.00 | 51.00 | A | N |
| ATOM | 1052 | C   | LYS | A | 706 | 59.516 | 66.298 | 26.545 | 1.00 | 45.71 | A | C |
| ATOM | 1053 | O   | LYS | A | 706 | 59.257 | 67.434 | 26.955 | 1.00 | 38.26 | A | O |
| ATOM | 1054 | N   | ARG | A | 707 | 59.279 | 65.928 | 25.291 | 1.00 | 47.05 | A | N |
| ATOM | 1055 | CA  | ARG | A | 707 | 58.703 | 66.879 | 24.338 | 1.00 | 50.72 | A | C |
| ATOM | 1056 | CB  | ARG | A | 707 | 58.630 | 66.266 | 22.937 | 1.00 | 45.57 | A | C |
| ATOM | 1057 | CG  | ARG | A | 707 | 59.943 | 66.254 | 22.215 | 1.00 | 36.56 | A | C |
| ATOM | 1058 | CD  | ARG | A | 707 | 59.867 | 65.460 | 20.931 | 1.00 | 34.09 | A | C |
| ATOM | 1059 | NE  | ARG | A | 707 | 61.185 | 65.464 | 20.314 | 1.00 | 32.26 | A | N |
| ATOM | 1060 | CZ  | ARG | A | 707 | 61.451 | 65.054 | 19.080 | 1.00 | 38.18 | A | C |
| ATOM | 1061 | NH1 | ARG | A | 707 | 62.698 | 65.108 | 18.629 | 1.00 | 33.62 | A | N |
| ATOM | 1062 | NH2 | ARG | A | 707 | 60.481 | 64.589 | 18.301 | 1.00 | 37.91 | A | N |

FIGURE 1A-20

```
ATOM  1063  C    ARG A 707    57.303  67.317  24.756  1.00 48.72    A  C
ATOM  1064  O    ARG A 707    56.897  68.444  24.506  1.00 52.49    A  O
ATOM  1065  N    GLU A 708    56.574  66.416  25.398  1.00 52.77    A  N
ATOM  1066  CA   GLU A 708    55.215  66.704  25.831  1.00 59.77    A  C
ATOM  1067  CB   GLU A 708    54.379  65.430  25.708  1.00 58.81    A  C
ATOM  1068  CG   GLU A 708    52.973  65.662  25.253  1.00 73.75    A  C
ATOM  1069  CD   GLU A 708    52.345  64.405  24.724  1.00 78.91    A  C
ATOM  1070  OE1  GLU A 708    52.276  63.415  25.486  1.00 80.14    A  O
ATOM  1071  OE2  GLU A 708    51.926  64.407  23.546  1.00 84.17    A  O
ATOM  1072  C    GLU A 708    55.181  67.222  27.266  1.00 61.99    A  C
ATOM  1073  O    GLU A 708    54.112  67.396  27.846  1.00 66.97    A  O
ATOM  1074  N    LYS A 709    56.354  67.474  27.835  1.00 63.27    A  N
ATOM  1075  CA   LYS A 709    56.438  67.951  29.209  1.00 65.26    A  C
ATOM  1076  CB   LYS A 709    56.732  66.774  30.149  1.00 66.61    A  C
ATOM  1077  CG   LYS A 709    55.568  65.787  30.237  1.00 78.03    A  C
ATOM  1078  CD   LYS A 709    54.293  66.509  30.690  1.00 86.98    A  C
ATOM  1079  CE   LYS A 709    53.019  65.843  30.172  1.00 89.08    A  C
ATOM  1080  NZ   LYS A 709    52.796  64.485  30.737  1.00 89.88    A  N
ATOM  1081  C    LYS A 709    57.461  69.057  29.406  1.00 64.87    A  C
ATOM  1082  O    LYS A 709    58.284  69.009  30.323  1.00 69.70    A  O
ATOM  1083  N    PHE A 710    57.399  70.049  28.527  1.00 56.84    A  N
ATOM  1084  CA   PHE A 710    58.280  71.203  28.582  1.00 60.45    A  C
ATOM  1085  CB   PHE A 710    58.953  71.439  27.229  1.00 51.04    A  C
ATOM  1086  CG   PHE A 710    59.935  72.577  27.235  1.00 47.85    A  C
ATOM  1087  CD1  PHE A 710    61.265  72.367  27.598  1.00 40.02    A  C
ATOM  1088  CD2  PHE A 710    59.530  73.862  26.886  1.00 40.95    A  C
ATOM  1089  CE1  PHE A 710    62.182  73.424  27.611  1.00 49.94    A  C
ATOM  1090  CE2  PHE A 710    60.435  74.927  26.896  1.00 48.27    A  C
ATOM  1091  CZ   PHE A 710    61.764  74.712  27.258  1.00 43.83    A  C
ATOM  1092  C    PHE A 710    57.391  72.392  28.920  1.00 63.73    A  C
ATOM  1093  O    PHE A 710    56.303  72.540  28.357  1.00 60.41    A  O
ATOM  1104  N    LEU A 783    60.763  69.734  32.298  1.00 52.05    A  N
ATOM  1105  CA   LEU A 783    61.973  70.294  31.707  1.00 43.33    A  C
ATOM  1106  CB   LEU A 783    62.377  69.461  30.491  1.00 49.08    A  C
ATOM  1107  CG   LEU A 783    63.755  69.735  29.893  1.00 56.97    A  C
ATOM  1108  CD1  LEU A 783    64.845  69.356  30.897  1.00 59.28    A  C
ATOM  1109  CD2  LEU A 783    63.908  68.927  28.618  1.00 58.05    A  C
ATOM  1110  C    LEU A 783    61.750  71.745  31.291  1.00 43.29    A  C
ATOM  1111  O    LEU A 783    60.749  72.065  30.663  1.00 43.96    A  O
ATOM  1112  N    THR A 784    62.697  72.617  31.631  1.00 42.77    A  N
ATOM  1113  CA   THR A 784    62.607  74.041  31.297  1.00 39.31    A  C
ATOM  1114  CB   THR A 784    62.708  74.919  32.553  1.00 42.14    A  C
ATOM  1115  OG1  THR A 784    63.996  74.713  33.159  1.00 44.64    A  O
ATOM  1116  CG2  THR A 784    61.600  74.564  33.561  1.00 47.67    A  C
ATOM  1117  C    THR A 784    63.750  74.503  30.394  1.00 41.01    A  C
ATOM  1118  O    THR A 784    64.707  73.771  30.159  1.00 44.85    A  O
ATOM  1119  N    PHE A 785    63.654  75.748  29.945  1.00 36.93    A  N
ATOM  1120  CA   PHE A 785    64.660  76.359  29.092  1.00 43.65    A  C
ATOM  1121  CB   PHE A 785    64.187  77.735  28.638  1.00 27.20    A  C
ATOM  1122  CG   PHE A 785    65.256  78.545  27.960  1.00 38.98    A  C
ATOM  1123  CD1  PHE A 785    65.581  78.318  26.626  1.00 34.67    A  C
ATOM  1124  CD2  PHE A 785    65.976  79.496  28.672  1.00 36.66    A  C
ATOM  1125  CE1  PHE A 785    66.608  79.024  26.009  1.00 33.84    A  C
ATOM  1126  CE2  PHE A 785    67.008  80.209  28.070  1.00 38.30    A  C
ATOM  1127  CZ   PHE A 785    67.328  79.973  26.732  1.00 49.11    A  C
ATOM  1128  C    PHE A 785    65.966  76.504  29.878  1.00 49.67    A  C
```

FIGURE 1A-21

```
ATOM   1129  O    PHE A 785      67.067  76.378  29.330  1.00 45.33      A    O
ATOM   1130  N    GLU A 786      65.834  76.796  31.164  1.00 42.89      A    N
ATOM   1131  CA   GLU A 786      66.995  76.945  32.032  1.00 41.29      A    C
ATOM   1132  CB   GLU A 786      66.547  77.394  33.430  1.00 48.92      A    C
ATOM   1133  CG   GLU A 786      66.011  78.840  33.499  1.00 62.18      A    C
ATOM   1134  CD   GLU A 786      64.812  79.129  32.572  1.00 62.99      A    C
ATOM   1135  OE1  GLU A 786      63.821  78.363  32.573  1.00 54.09      A    O
ATOM   1136  OE2  GLU A 786      64.859  80.149  31.849  1.00 66.85      A    O
ATOM   1137  C    GLU A 786      67.733  75.601  32.097  1.00 27.41      A    C
ATOM   1138  O    GLU A 786      68.954  75.561  32.092  1.00 35.10      A    O
ATOM   1139  N    ASP A 787      66.987  74.502  32.169  1.00 29.15      A    N
ATOM   1140  CA   ASP A 787      67.605  73.174  32.174  1.00 33.03      A    C
ATOM   1141  CB   ASP A 787      66.544  72.083  32.253  1.00 31.43      A    C
ATOM   1142  CG   ASP A 787      65.786  72.090  33.566  1.00 49.43      A    C
ATOM   1143  OD1  ASP A 787      64.653  71.566  33.593  1.00 44.17      A    O
ATOM   1144  OD2  ASP A 787      66.325  72.605  34.565  1.00 41.96      A    O
ATOM   1145  C    ASP A 787      68.381  72.982  30.859  1.00 41.68      A    C
ATOM   1146  O    ASP A 787      69.501  72.468  30.851  1.00 40.18      A    O
ATOM   1147  N    LEU A 788      67.771  73.387  29.748  1.00 35.08      A    N
ATOM   1148  CA   LEU A 788      68.405  73.251  28.437  1.00 41.52      A    C
ATOM   1149  CB   LEU A 788      67.490  73.831  27.355  1.00 30.36      A    C
ATOM   1150  CG   LEU A 788      66.624  72.910  26.494  1.00 47.11      A    C
ATOM   1151  CD1  LEU A 788      66.164  71.683  27.240  1.00 33.29      A    C
ATOM   1152  CD2  LEU A 788      65.467  73.724  25.966  1.00 37.55      A    C
ATOM   1153  C    LEU A 788      69.759  73.962  28.424  1.00 36.33      A    C
ATOM   1154  O    LEU A 788      70.769  73.380  28.034  1.00 32.18      A    O
ATOM   1155  N    LEU A 789      69.765  75.221  28.859  1.00 36.58      A    N
ATOM   1156  CA   LEU A 789      70.980  76.030  28.920  1.00 37.98      A    C
ATOM   1157  CB   LEU A 789      70.635  77.425  29.447  1.00 48.62      A    C
ATOM   1158  CG   LEU A 789      71.542  78.587  29.052  1.00 56.54      A    C
ATOM   1159  CD1  LEU A 789      72.961  78.331  29.524  1.00 65.84      A    C
ATOM   1160  CD2  LEU A 789      71.521  78.745  27.544  1.00 67.11      A    C
ATOM   1161  C    LEU A 789      72.014  75.357  29.839  1.00 40.45      A    C
ATOM   1162  O    LEU A 789      73.218  75.346  29.546  1.00 37.47      A    O
ATOM   1163  N    CYS A 790      71.531  74.772  30.936  1.00 39.90      A    N
ATOM   1164  CA   CYS A 790      72.402  74.088  31.891  1.00 44.05      A    C
ATOM   1165  CB   CYS A 790      71.629  73.692  33.150  1.00 39.06      A    C
ATOM   1166  SG   CYS A 790      72.741  73.146  34.480  1.00 53.93      A    S
ATOM   1167  C    CYS A 790      73.048  72.832  31.281  1.00 34.74      A    C
ATOM   1168  O    CYS A 790      74.215  72.544  31.540  1.00 30.49      A    O
ATOM   1169  N    PHE A 791      72.280  72.075  30.499  1.00 34.79      A    N
ATOM   1170  CA   PHE A 791      72.828  70.893  29.837  1.00 35.07      A    C
ATOM   1171  CB   PHE A 791      71.745  70.194  29.010  1.00 34.81      A    C
ATOM   1172  CG   PHE A 791      70.727  69.447  29.842  1.00 37.83      A    C
ATOM   1173  CD1  PHE A 791      69.429  69.252  29.371  1.00 37.26      A    C
ATOM   1174  CD2  PHE A 791      71.065  68.940  31.091  1.00 36.57      A    C
ATOM   1175  CE1  PHE A 791      68.481  68.563  30.135  1.00 35.45      A    C
ATOM   1176  CE2  PHE A 791      70.126  68.247  31.863  1.00 37.44      A    C
ATOM   1177  CZ   PHE A 791      68.828  68.061  31.379  1.00 42.31      A    C
ATOM   1178  C    PHE A 791      73.953  71.359  28.911  1.00 32.40      A    C
ATOM   1179  O    PHE A 791      75.062  70.801  28.904  1.00 33.48      A    O
ATOM   1180  N    ALA A 792      73.666  72.424  28.167  1.00 30.28      A    N
ATOM   1181  CA   ALA A 792      74.607  72.972  27.210  1.00 31.09      A    C
ATOM   1182  CB   ALA A 792      73.962  74.130  26.474  1.00 27.22      A    C
ATOM   1183  C    ALA A 792      75.906  73.417  27.871  1.00 32.64      A    C
ATOM   1184  O    ALA A 792      76.997  73.134  27.371  1.00 33.07      A    O
```

FIGURE 1A-22

```
ATOM   1185  N    TYR A 793      75.769  74.137  28.980  1.00 38.88      A  N
ATOM   1186  CA   TYR A 793      76.901  74.652  29.743  1.00 27.39      A  C
ATOM   1187  CB   TYR A 793      76.374  75.506  30.907  1.00 37.33      A  C
ATOM   1188  CG   TYR A 793      77.441  75.993  31.859  1.00 42.49      A  C
ATOM   1189  CD1  TYR A 793      78.420  76.895  31.440  1.00 46.49      A  C
ATOM   1190  CE1  TYR A 793      79.400  77.355  32.312  1.00 52.96      A  C
ATOM   1191  CD2  TYR A 793      77.467  75.557  33.182  1.00 48.58      A  C
ATOM   1192  CE2  TYR A 793      78.445  76.015  34.069  1.00 55.09      A  C
ATOM   1193  CZ   TYR A 793      79.406  76.912  33.625  1.00 57.17      A  C
ATOM   1194  OH   TYR A 793      80.374  77.363  34.489  1.00 65.06      A  O
ATOM   1195  C    TYR A 793      77.735  73.484  30.285  1.00 18.76      A  C
ATOM   1196  O    TYR A 793      78.973  73.503  30.230  1.00 28.67      A  O
ATOM   1197  N    GLN A 794      77.050  72.475  30.816  1.00 23.10      A  N
ATOM   1198  CA   GLN A 794      77.740  71.307  31.356  1.00 30.66      A  C
ATOM   1199  CB   GLN A 794      76.739  70.373  32.025  1.00 29.05      A  C
ATOM   1200  CG   GLN A 794      76.262  70.868  33.399  1.00 30.82      A  C
ATOM   1201  CD   GLN A 794      75.281  69.906  34.007  1.00 19.50      A  C
ATOM   1202  OE1  GLN A 794      75.646  68.832  34.491  1.00 36.24      A  O
ATOM   1203  NE2  GLN A 794      74.002  70.256  33.931  1.00 32.39      A  N
ATOM   1204  C    GLN A 794      78.552  70.521  30.311  1.00 38.98      A  C
ATOM   1205  O    GLN A 794      79.664  70.042  30.595  1.00 32.26      A  O
ATOM   1206  N    VAL A 795      78.001  70.374  29.112  1.00 32.02      A  N
ATOM   1207  CA   VAL A 795      78.712  69.638  28.070  1.00 26.97      A  C
ATOM   1208  CB   VAL A 795      77.777  69.341  26.850  1.00 28.07      A  C
ATOM   1209  CG1  VAL A 795      78.552  68.685  25.699  1.00 19.30      A  C
ATOM   1210  CG2  VAL A 795      76.693  68.392  27.292  1.00 20.08      A  C
ATOM   1211  C    VAL A 795      79.934  70.450  27.665  1.00 18.95      A  C
ATOM   1212  O    VAL A 795      80.994  69.882  27.433  1.00 34.05      A  O
ATOM   1213  N    ALA A 796      79.801  71.780  27.622  1.00 22.82      A  N
ATOM   1214  CA   ALA A 796      80.938  72.621  27.255  1.00 27.91      A  C
ATOM   1215  CB   ALA A 796      80.512  74.086  27.143  1.00 25.95      A  C
ATOM   1216  C    ALA A 796      82.059  72.460  28.296  1.00 35.38      A  C
ATOM   1217  O    ALA A 796      83.253  72.392  27.955  1.00 30.84      A  O
ATOM   1218  N    LYS A 797      81.668  72.390  29.562  1.00 34.10      A  N
ATOM   1219  CA   LYS A 797      82.623  72.216  30.652  1.00 38.88      A  C
ATOM   1220  CB   LYS A 797      81.905  72.344  32.002  1.00 45.55      A  C
ATOM   1221  CG   LYS A 797      82.830  72.317  33.202  1.00 64.82      A  C
ATOM   1222  CD   LYS A 797      83.888  73.432  33.152  1.00 77.92      A  C
ATOM   1223  CE   LYS A 797      83.305  74.828  33.386  1.00 84.97      A  C
ATOM   1224  NZ   LYS A 797      84.370  75.892  33.438  1.00 70.10      A  N
ATOM   1225  C    LYS A 797      83.310  70.844  30.536  1.00 27.01      A  C
ATOM   1226  O    LYS A 797      84.535  70.727  30.698  1.00 30.98      A  O
ATOM   1227  N    GLY A 798      82.532  69.805  30.262  1.00 31.17      A  N
ATOM   1228  CA   GLY A 798      83.135  68.494  30.097  1.00 28.24      A  C
ATOM   1229  C    GLY A 798      84.130  68.513  28.931  1.00 30.21      A  C
ATOM   1230  O    GLY A 798      85.236  67.968  29.028  1.00 29.62      A  O
ATOM   1231  N    MET A 799      83.764  69.159  27.830  1.00 26.76      A  N
ATOM   1232  CA   MET A 799      84.667  69.217  26.668  1.00 28.15      A  C
ATOM   1233  CB   MET A 799      83.928  69.768  25.441  1.00 28.69      A  C
ATOM   1234  CG   MET A 799      82.896  68.800  24.853  1.00 20.11      A  C
ATOM   1235  SD   MET A 799      83.592  67.132  24.513  1.00 29.35      A  S
ATOM   1236  CE   MET A 799      85.034  67.527  23.473  1.00 28.29      A  C
ATOM   1237  C    MET A 799      85.910  70.069  26.968  1.00 29.07      A  C
ATOM   1238  O    MET A 799      86.995  69.836  26.430  1.00 31.45      A  O
ATOM   1239  N    GLU A 800      85.746  71.059  27.835  1.00 32.52      A  N
ATOM   1240  CA   GLU A 800      86.859  71.918  28.226  1.00 31.81      A  C
```

FIGURE 1A-23

```
ATOM   1241  CB   GLU A 800      86.333  73.064  29.095  1.00 37.15      A  C
ATOM   1242  CG   GLU A 800      87.392  74.014  29.626  1.00 41.77      A  C
ATOM   1243  CD   GLU A 800      86.766  75.131  30.445  1.00 53.23      A  C
ATOM   1244  OE1  GLU A 800      85.907  74.824  31.305  1.00 50.33      A  O
ATOM   1245  OE2  GLU A 800      87.129  76.304  30.231  1.00 43.76      A  O
ATOM   1246  C    GLU A 800      87.857  71.046  28.998  1.00 27.94      A  C
ATOM   1247  O    GLU A 800      89.075  71.154  28.812  1.00 30.49      A  O
ATOM   1248  N    PHE A 801      87.334  70.158  29.841  1.00 27.47      A  N
ATOM   1249  CA   PHE A 801      88.187  69.234  30.597  1.00 30.57      A  C
ATOM   1250  CB   PHE A 801      87.332  68.388  31.566  1.00 24.82      A  C
ATOM   1251  CG   PHE A 801      88.096  67.304  32.278  1.00 33.77      A  C
ATOM   1252  CD1  PHE A 801      87.940  65.961  31.907  1.00 30.78      A  C
ATOM   1253  CD2  PHE A 801      88.971  67.619  33.323  1.00 34.58      A  C
ATOM   1254  CE1  PHE A 801      88.650  64.938  32.569  1.00 34.99      A  C
ATOM   1255  CE2  PHE A 801      89.686  66.615  33.998  1.00 26.84      A  C
ATOM   1256  CZ   PHE A 801      89.525  65.265  33.619  1.00 30.92      A  C
ATOM   1257  C    PHE A 801      88.939  68.332  29.614  1.00 35.75      A  C
ATOM   1258  O    PHE A 801      90.161  68.152  29.724  1.00 33.51      A  O
ATOM   1259  N    LEU A 802      88.216  67.771  28.642  1.00 33.96      A  N
ATOM   1260  CA   LEU A 802      88.853  66.903  27.652  1.00 31.56      A  C
ATOM   1261  CB   LEU A 802      87.808  66.302  26.704  1.00 31.61      A  C
ATOM   1262  CG   LEU A 802      86.811  65.364  27.407  1.00 35.50      A  C
ATOM   1263  CD1  LEU A 802      85.866  64.724  26.389  1.00 32.60      A  C
ATOM   1264  CD2  LEU A 802      87.580  64.287  28.175  1.00 30.75      A  C
ATOM   1265  C    LEU A 802      89.946  67.634  26.859  1.00 24.39      A  C
ATOM   1266  O    LEU A 802      91.021  67.080  26.617  1.00 26.18      A  O
ATOM   1267  N    GLU A 803      89.683  68.875  26.462  1.00 27.03      A  N
ATOM   1268  CA   GLU A 803      90.688  69.643  25.744  1.00 36.31      A  C
ATOM   1269  CB   GLU A 803      90.167  71.034  25.388  1.00 30.66      A  C
ATOM   1270  CG   GLU A 803      91.258  71.909  24.772  1.00 34.54      A  C
ATOM   1271  CD   GLU A 803      90.738  73.252  24.325  1.00 40.43      A  C
ATOM   1272  OE1  GLU A 803      89.768  73.733  24.941  1.00 56.56      A  O
ATOM   1273  OE2  GLU A 803      91.306  73.833  23.373  1.00 51.14      A  O
ATOM   1274  C    GLU A 803      91.945  69.806  26.608  1.00 42.60      A  C
ATOM   1275  O    GLU A 803      93.071  69.675  26.121  1.00 35.21      A  O
ATOM   1276  N    PHE A 804      91.732  70.103  27.890  1.00 42.72      A  N
ATOM   1277  CA   PHE A 804      92.824  70.286  28.833  1.00 39.97      A  C
ATOM   1278  CB   PHE A 804      92.279  70.700  30.203  1.00 51.70      A  C
ATOM   1279  CG   PHE A 804      93.329  70.766  31.280  1.00 55.31      A  C
ATOM   1280  CD1  PHE A 804      94.413  71.633  31.164  1.00 54.28      A  C
ATOM   1281  CD2  PHE A 804      93.231  69.965  32.414  1.00 51.55      A  C
ATOM   1282  CE1  PHE A 804      95.381  71.702  32.161  1.00 58.51      A  C
ATOM   1283  CE2  PHE A 804      94.195  70.026  33.416  1.00 55.65      A  C
ATOM   1284  CZ   PHE A 804      95.271  70.896  33.290  1.00 56.65      A  C
ATOM   1285  C    PHE A 804      93.646  69.004  28.972  1.00 37.06      A  C
ATOM   1286  O    PHE A 804      94.869  69.058  29.065  1.00 33.12      A  O
ATOM   1287  N    LYS A 805      92.973  67.858  28.988  1.00 28.01      A  N
ATOM   1288  CA   LYS A 805      93.655  66.573  29.098  1.00 26.94      A  C
ATOM   1289  CB   LYS A 805      92.738  65.546  29.763  1.00 29.49      A  C
ATOM   1290  CG   LYS A 805      92.420  65.859  31.230  1.00 39.73      A  C
ATOM   1291  CD   LYS A 805      93.709  66.041  32.038  1.00 42.86      A  C
ATOM   1292  CE   LYS A 805      93.451  66.416  33.491  1.00 51.33      A  C
ATOM   1293  NZ   LYS A 805      93.350  65.230  34.388  1.00 52.01      A  N
ATOM   1294  C    LYS A 805      94.143  66.034  27.748  1.00 30.74      A  C
ATOM   1295  O    LYS A 805      94.476  64.860  27.632  1.00 25.86      A  O
ATOM   1296  N    SER A 806      94.171  66.894  26.733  1.00 30.61      A  N
```

FIGURE 1A-24

```
ATOM   1297  CA   SER A 806      94.629  66.526  25.391  1.00 34.95      A  C
ATOM   1298  CB   SER A 806      96.135  66.249  25.422  1.00 38.77      A  C
ATOM   1299  OG   SER A 806      96.671  66.238  24.109  1.00 40.79      A  O
ATOM   1300  C    SER A 806      93.885  65.349  24.726  1.00 23.27      A  C
ATOM   1301  O    SER A 806      94.481  64.483  24.080  1.00 30.69      A  O
ATOM   1302  N    CYS A 807      92.568  65.350  24.868  1.00 27.77      A  N
ATOM   1303  CA   CYS A 807      91.716  64.324  24.284  1.00 33.33      A  C
ATOM   1304  CB   CYS A 807      90.904  63.606  25.364  1.00 30.06      A  C
ATOM   1305  SG   CYS A 807      91.919  62.711  26.510  1.00 37.88      A  S
ATOM   1306  C    CYS A 807      90.732  64.926  23.317  1.00 28.37      A  C
ATOM   1307  O    CYS A 807      90.481  66.117  23.346  1.00 31.30      A  O
ATOM   1308  N    VAL A 808      90.195  64.092  22.435  1.00 27.15      A  N
ATOM   1309  CA   VAL A 808      89.165  64.549  21.510  1.00 26.37      A  C
ATOM   1310  CB   VAL A 808      89.658  64.661  20.049  1.00 30.70      A  C
ATOM   1311  CG1  VAL A 808      90.691  65.777  19.921  1.00 24.77      A  C
ATOM   1312  CG2  VAL A 808      90.206  63.311  19.587  1.00 30.86      A  C
ATOM   1313  C    VAL A 808      88.095  63.473  21.548  1.00 24.42      A  C
ATOM   1314  O    VAL A 808      88.369  62.333  21.949  1.00 33.70      A  O
ATOM   1315  N    HIS A 809      86.878  63.840  21.155  1.00 25.97      A  N
ATOM   1316  CA   HIS A 809      85.785  62.877  21.063  1.00 24.72      A  C
ATOM   1317  CB   HIS A 809      84.555  63.337  21.865  1.00 23.67      A  C
ATOM   1318  CG   HIS A 809      83.615  62.220  22.201  1.00 26.04      A  C
ATOM   1319  CD2  HIS A 809      82.948  61.926  23.344  1.00 24.93      A  C
ATOM   1320  ND1  HIS A 809      83.329  61.201  21.318  1.00 20.09      A  N
ATOM   1321  CE1  HIS A 809      82.534  60.322  21.904  1.00 31.71      A  C
ATOM   1322  NE2  HIS A 809      82.291  60.738  23.135  1.00 28.91      A  N
ATOM   1323  C    HIS A 809      85.428  62.820  19.567  1.00 24.61      A  C
ATOM   1324  O    HIS A 809      85.010  63.829  18.974  1.00 22.91      A  O
ATOM   1325  N    ARG A 810      85.590  61.654  18.960  1.00 24.30      A  N
ATOM   1326  CA   ARG A 810      85.302  61.513  17.535  1.00 34.49      A  C
ATOM   1327  CB   ARG A 810      86.179  60.409  16.931  1.00 27.22      A  C
ATOM   1328  CG   ARG A 810      87.689  60.675  17.051  1.00 35.93      A  C
ATOM   1329  CD   ARG A 810      88.514  59.663  16.244  1.00 37.88      A  C
ATOM   1330  NE   ARG A 810      88.295  58.282  16.671  1.00 55.84      A  N
ATOM   1331  CZ   ARG A 810      89.150  57.284  16.448  1.00 70.03      A  C
ATOM   1332  NH1  ARG A 810      88.870  56.051  16.868  1.00 61.05      A  N
ATOM   1333  NH2  ARG A 810      90.295  57.521  15.814  1.00 64.49      A  N
ATOM   1334  C    ARG A 810      83.824  61.225  17.250  1.00 35.04      A  C
ATOM   1335  O    ARG A 810      83.429  61.060  16.102  1.00 32.88      A  O
ATOM   1336  N    ASP A 811      83.013  61.170  18.302  1.00 27.66      A  N
ATOM   1337  CA   ASP A 811      81.586  60.917  18.140  1.00 18.35      A  C
ATOM   1338  CB   ASP A 811      81.305  59.403  18.252  1.00 19.79      A  C
ATOM   1339  CG   ASP A 811      79.897  59.005  17.757  1.00 18.80      A  C
ATOM   1340  OD1  ASP A 811      79.529  57.826  17.969  1.00 20.03      A  O
ATOM   1341  OD2  ASP A 811      79.177  59.850  17.159  1.00 22.07      A  O
ATOM   1342  C    ASP A 811      80.790  61.698  19.178  1.00 20.66      A  C
ATOM   1343  O    ASP A 811      79.957  61.147  19.898  1.00 24.82      A  O
ATOM   1344  N    LEU A 812      81.070  62.991  19.273  1.00 21.58      A  N
ATOM   1345  CA   LEU A 812      80.366  63.836  20.219  1.00 19.92      A  C
ATOM   1346  CB   LEU A 812      81.063  65.195  20.346  1.00 18.02      A  C
ATOM   1347  CG   LEU A 812      80.311  66.150  21.288  1.00 23.99      A  C
ATOM   1348  CD1  LEU A 812      80.178  65.542  22.680  1.00 28.58      A  C
ATOM   1349  CD2  LEU A 812      81.048  67.486  21.354  1.00 19.30      A  C
ATOM   1350  C    LEU A 812      78.946  64.046  19.672  1.00 32.84      A  C
ATOM   1351  O    LEU A 812      78.792  64.483  18.536  1.00 25.79      A  O
ATOM   1352  N    ALA A 813      77.930  63.711  20.469  1.00 19.86      A  N
```

FIGURE 1A-25

```
ATOM 1353  CA   ALA A 813      76.503  63.859  20.085  1.00 21.67      A C
ATOM 1354  CB   ALA A 813      76.096  62.819  18.963  1.00 15.56      A C
ATOM 1355  C    ALA A 813      75.657  63.622  21.341  1.00 26.37      A C
ATOM 1356  O    ALA A 813      76.139  63.056  22.329  1.00 24.90      A O
ATOM 1357  N    ALA A 814      74.398  64.046  21.297  1.00 23.92      A N
ATOM 1358  CA   ALA A 814      73.517  63.898  22.452  1.00 28.31      A C
ATOM 1359  CB   ALA A 814      72.149  64.551  22.165  1.00 28.28      A C
ATOM 1360  C    ALA A 814      73.348  62.445  22.882  1.00 32.87      A C
ATOM 1361  O    ALA A 814      73.100  62.173  24.053  1.00 26.89      A O
ATOM 1362  N    ARG A 815      73.498  61.506  21.950  1.00 21.80      A N
ATOM 1363  CA   ARG A 815      73.365  60.085  22.304  1.00 23.55      A C
ATOM 1364  CB   ARG A 815      73.228  59.214  21.036  1.00 25.75      A C
ATOM 1365  CG   ARG A 815      74.347  59.439  20.004  1.00 23.23      A C
ATOM 1366  CD   ARG A 815      74.193  58.593  18.700  1.00 25.96      A C
ATOM 1367  NE   ARG A 815      75.332  58.889  17.841  1.00 21.77      A N
ATOM 1368  CZ   ARG A 815      75.384  59.896  16.977  1.00 28.37      A C
ATOM 1369  NH1  ARG A 815      76.497  60.106  16.273  1.00 26.55      A N
ATOM 1370  NH2  ARG A 815      74.306  60.649  16.763  1.00 22.70      A N
ATOM 1371  C    ARG A 815      74.558  59.604  23.168  1.00 26.22      A C
ATOM 1372  O    ARG A 815      74.468  58.556  23.808  1.00 28.95      A O
ATOM 1373  N    ASN A 816      75.656  60.369  23.186  1.00 28.33      A N
ATOM 1374  CA   ASN A 816      76.845  60.013  23.985  1.00 28.70      A C
ATOM 1375  CB   ASN A 816      78.124  60.068  23.141  1.00 18.69      A C
ATOM 1376  CG   ASN A 816      78.343  58.820  22.323  1.00 31.48      A C
ATOM 1377  OD1  ASN A 816      78.907  58.867  21.225  1.00 42.70      A O
ATOM 1378  ND2  ASN A 816      77.912  57.693  22.850  1.00 21.36      A N
ATOM 1379  C    ASN A 816      77.022  60.925  25.208  1.00 30.37      A C
ATOM 1380  O    ASN A 816      78.139  61.128  25.701  1.00 29.65      A O
ATOM 1381  N    VAL A 817      75.918  61.505  25.668  1.00 29.94      A N
ATOM 1382  CA   VAL A 817      75.919  62.341  26.858  1.00 32.30      A C
ATOM 1383  CB   VAL A 817      75.506  63.807  26.544  1.00 25.91      A C
ATOM 1384  CG1  VAL A 817      75.376  64.606  27.857  1.00 27.91      A C
ATOM 1385  CG2  VAL A 817      76.548  64.471  25.642  1.00 24.82      A C
ATOM 1386  C    VAL A 817      74.860  61.675  27.739  1.00 37.46      A C
ATOM 1387  O    VAL A 817      73.758  61.403  27.262  1.00 35.01      A O
ATOM 1388  N    LEU A 818      75.192  61.370  28.992  1.00 34.17      A N
ATOM 1389  CA   LEU A 818      74.223  60.713  29.891  1.00 31.26      A C
ATOM 1390  CB   LEU A 818      74.798  59.408  30.469  1.00 24.72      A C
ATOM 1391  CG   LEU A 818      75.333  58.333  29.501  1.00 30.63      A C
ATOM 1392  CD1  LEU A 818      75.569  57.029  30.272  1.00 29.48      A C
ATOM 1393  CD2  LEU A 818      74.356  58.081  28.359  1.00 30.42      A C
ATOM 1394  C    LEU A 818      73.736  61.627  31.028  1.00 27.84      A C
ATOM 1395  O    LEU A 818      74.451  62.525  31.472  1.00 36.46      A O
ATOM 1396  N    VAL A 819      72.507  61.384  31.487  1.00 35.55      A N
ATOM 1397  CA   VAL A 819      71.881  62.200  32.525  1.00 37.56      A C
ATOM 1398  CB   VAL A 819      70.462  62.630  32.070  1.00 38.32      A C
ATOM 1399  CG1  VAL A 819      69.893  63.656  33.026  1.00 40.01      A C
ATOM 1400  CG2  VAL A 819      70.518  63.185  30.634  1.00 35.86      A C
ATOM 1401  C    VAL A 819      71.760  61.484  33.874  1.00 30.84      A C
ATOM 1402  O    VAL A 819      71.346  60.341  33.918  1.00 24.97      A O
ATOM 1403  N    THR A 820      72.156  62.152  34.951  1.00 37.74      A N
ATOM 1404  CA   THR A 820      72.050  61.586  36.303  1.00 46.56      A C
ATOM 1405  CB   THR A 820      73.423  61.413  37.029  1.00 51.43      A C
ATOM 1406  OG1  THR A 820      74.275  62.536  36.768  1.00 48.12      A O
ATOM 1407  CG2  THR A 820      74.091  60.160  36.587  1.00 59.89      A C
ATOM 1408  C    THR A 820      71.165  62.460  37.183  1.00 47.62      A C
```

FIGURE 1A-26

```
ATOM   1409  O    THR A 820      70.596  63.442  36.709  1.00 36.00      A  O
ATOM   1410  N    HIS A 821      71.102  62.128  38.474  1.00 48.67      A  N
ATOM   1411  CA   HIS A 821      70.223  62.800  39.431  1.00 43.14      A  C
ATOM   1412  CB   HIS A 821      70.611  62.373  40.854  1.00 41.16      A  C
ATOM   1413  CG   HIS A 821      70.292  60.940  41.127  1.00 35.55      A  C
ATOM   1414  CD2  HIS A 821      69.100  60.299  41.213  1.00 38.67      A  C
ATOM   1415  ND1  HIS A 821      71.258  59.957  41.165  1.00 43.45      A  N
ATOM   1416  CE1  HIS A 821      70.677  58.772  41.255  1.00 45.66      A  C
ATOM   1417  NE2  HIS A 821      69.367  58.951  41.283  1.00 41.92      A  N
ATOM   1418  C    HIS A 821      69.861  64.285  39.426  1.00 46.64      A  C
ATOM   1419  O    HIS A 821      68.695  64.621  39.210  1.00 64.64      A  O
ATOM   1420  N    GLY A 822      70.794  65.191  39.658  1.00 44.59      A  N
ATOM   1421  CA   GLY A 822      70.365  66.582  39.702  1.00 35.60      A  C
ATOM   1422  C    GLY A 822      70.359  67.305  38.371  1.00 43.41      A  C
ATOM   1423  O    GLY A 822      70.762  68.472  38.301  1.00 41.03      A  O
ATOM   1424  N    LYS A 823      69.891  66.640  37.316  1.00 43.87      A  N
ATOM   1425  CA   LYS A 823      69.892  67.269  35.997  1.00 53.19      A  C
ATOM   1426  CB   LYS A 823      69.249  68.665  36.072  1.00 56.09      A  C
ATOM   1427  CG   LYS A 823      68.026  68.887  35.198  1.00 59.24      A  C
ATOM   1428  CD   LYS A 823      66.845  68.061  35.650  1.00 53.82      A  C
ATOM   1429  CE   LYS A 823      65.572  68.554  34.987  1.00 61.09      A  C
ATOM   1430  NZ   LYS A 823      64.361  67.839  35.483  1.00 63.41      A  N
ATOM   1431  C    LYS A 823      71.359  67.421  35.552  1.00 46.64      A  C
ATOM   1432  O    LYS A 823      71.681  68.288  34.744  1.00 44.14      A  O
ATOM   1433  N    VAL A 824      72.249  66.604  36.112  1.00 42.54      A  N
ATOM   1434  CA   VAL A 824      73.667  66.669  35.748  1.00 41.12      A  C
ATOM   1435  CB   VAL A 824      74.586  66.273  36.942  1.00 40.96      A  C
ATOM   1436  CG1  VAL A 824      76.050  66.216  36.485  1.00 40.81      A  C
ATOM   1437  CG2  VAL A 824      74.439  67.286  38.074  1.00 40.57      A  C
ATOM   1438  C    VAL A 824      73.936  65.715  34.581  1.00 32.29      A  C
ATOM   1439  O    VAL A 824      73.474  64.567  34.582  1.00 33.32      A  O
ATOM   1440  N    VAL A 825      74.661  66.193  33.577  1.00 32.40      A  N
ATOM   1441  CA   VAL A 825      74.972  65.338  32.433  1.00 32.94      A  C
ATOM   1442  CB   VAL A 825      74.498  65.968  31.119  1.00 27.07      A  C
ATOM   1443  CG1  VAL A 825      72.963  66.096  31.142  1.00 30.78      A  C
ATOM   1444  CG2  VAL A 825      75.137  67.308  30.931  1.00 22.25      A  C
ATOM   1445  C    VAL A 825      76.473  65.072  32.365  1.00 34.64      A  C
ATOM   1446  O    VAL A 825      77.287  65.889  32.809  1.00 30.10      A  O
ATOM   1447  N    LYS A 826      76.816  63.922  31.800  1.00 29.65      A  N
ATOM   1448  CA   LYS A 826      78.198  63.466  31.696  1.00 30.34      A  C
ATOM   1449  CB   LYS A 826      78.443  62.346  32.719  1.00 26.65      A  C
ATOM   1450  CG   LYS A 826      78.381  62.800  34.208  1.00 31.34      A  C
ATOM   1451  CD   LYS A 826      78.339  61.582  35.149  1.00 36.38      A  C
ATOM   1452  CE   LYS A 826      78.669  61.977  36.604  1.00 35.82      A  C
ATOM   1453  NZ   LYS A 826      80.046  62.578  36.718  1.00 33.46      A  N
ATOM   1454  C    LYS A 826      78.495  62.918  30.301  1.00 33.42      A  C
ATOM   1455  O    LYS A 826      77.748  62.088  29.779  1.00 25.81      A  O
ATOM   1456  N    ILE A 827      79.606  63.366  29.730  1.00 35.53      A  N
ATOM   1457  CA   ILE A 827      80.028  62.921  28.418  1.00 29.54      A  C
ATOM   1458  CB   ILE A 827      81.049  63.901  27.831  1.00 25.09      A  C
ATOM   1459  CG2  ILE A 827      81.470  63.455  26.436  1.00 30.54      A  C
ATOM   1460  CG1  ILE A 827      80.475  65.323  27.844  1.00 27.56      A  C
ATOM   1461  CD1  ILE A 827      81.469  66.387  27.327  1.00 25.13      A  C
ATOM   1462  C    ILE A 827      80.687  61.547  28.523  1.00 31.63      A  C
ATOM   1463  O    ILE A 827      81.427  61.276  29.465  1.00 26.88      A  O
ATOM   1464  N    CYS A 828      80.411  60.673  27.565  1.00 25.22      A  N
```

FIGURE 1A-27

```
ATOM   1465  CA   CYS A 828      81.046  59.351  27.522  1.00 30.92      A  C
ATOM   1466  CB   CYS A 828      80.291  58.342  28.378  1.00 31.66      A  C
ATOM   1467  SG   CYS A 828      78.678  57.886  27.654  1.00 37.05      A  S
ATOM   1468  C    CYS A 828      81.028  58.837  26.089  1.00 31.79      A  C
ATOM   1469  O    CYS A 828      80.724  59.578  25.158  1.00 30.29      A  O
ATOM   1470  N    ASP A 829      81.385  57.567  25.936  1.00 33.60      A  N
ATOM   1471  CA   ASP A 829      81.294  56.886  24.660  1.00 33.35      A  C
ATOM   1472  CB   ASP A 829      82.641  56.411  24.108  1.00 39.34      A  C
ATOM   1473  CG   ASP A 829      82.493  55.758  22.720  1.00 39.48      A  C
ATOM   1474  OD1  ASP A 829      82.957  56.348  21.724  1.00 51.36      A  O
ATOM   1475  OD2  ASP A 829      81.896  54.666  22.620  1.00 35.76      A  O
ATOM   1476  C    ASP A 829      80.461  55.675  25.038  1.00 31.88      A  C
ATOM   1477  O    ASP A 829      80.936  54.767  25.727  1.00 31.56      A  O
ATOM   1478  N    PHE A 830      79.208  55.681  24.603  1.00 29.98      A  N
ATOM   1479  CA   PHE A 830      78.273  54.606  24.891  1.00 32.66      A  C
ATOM   1480  CB   PHE A 830      76.925  55.196  25.311  1.00 40.58      A  C
ATOM   1481  CG   PHE A 830      76.332  54.548  26.524  1.00 46.50      A  C
ATOM   1482  CD1  PHE A 830      77.104  54.354  27.669  1.00 43.87      A  C
ATOM   1483  CD2  PHE A 830      74.987  54.179  26.546  1.00 53.85      A  C
ATOM   1484  CE1  PHE A 830      76.546  53.803  28.821  1.00 51.79      A  C
ATOM   1485  CE2  PHE A 830      74.415  53.628  27.694  1.00 48.58      A  C
ATOM   1486  CZ   PHE A 830      75.196  53.439  28.835  1.00 58.55      A  C
ATOM   1487  C    PHE A 830      78.076  53.729  23.668  1.00 40.09      A  C
ATOM   1488  O    PHE A 830      77.053  53.036  23.545  1.00 36.05      A  O
ATOM   1489  N    GLY A 831      79.045  53.788  22.759  1.00 31.84      A  N
ATOM   1490  CA   GLY A 831      78.976  52.983  21.561  1.00 34.31      A  C
ATOM   1491  C    GLY A 831      78.792  51.498  21.832  1.00 43.10      A  C
ATOM   1492  O    GLY A 831      78.088  50.811  21.091  1.00 39.28      A  O
ATOM   1493  N    LEU A 832      79.408  50.980  22.888  1.00 37.26      A  N
ATOM   1494  CA   LEU A 832      79.281  49.549  23.175  1.00 39.72      A  C
ATOM   1495  CB   LEU A 832      80.199  49.152  24.344  1.00 30.69      A  C
ATOM   1496  CG   LEU A 832      80.448  47.662  24.587  1.00 41.59      A  C
ATOM   1497  CD1  LEU A 832      81.249  47.090  23.408  1.00 34.03      A  C
ATOM   1498  CD2  LEU A 832      81.232  47.465  25.910  1.00 42.74      A  C
ATOM   1499  C    LEU A 832      77.834  49.179  23.512  1.00 32.53      A  C
ATOM   1500  O    LEU A 832      77.414  48.035  23.320  1.00 37.50      A  O
ATOM   1501  N    ALA A 833      77.079  50.149  24.019  1.00 32.42      A  N
ATOM   1502  CA   ALA A 833      75.696  49.909  24.404  1.00 41.83      A  C
ATOM   1503  CB   ALA A 833      75.317  50.789  25.609  1.00 38.69      A  C
ATOM   1504  C    ALA A 833      74.690  50.128  23.274  1.00 47.86      A  C
ATOM   1505  O    ALA A 833      73.507  50.371  23.536  1.00 43.18      A  O
ATOM   1506  N    ARG A 834      75.144  50.079  22.026  1.00 44.80      A  N
ATOM   1507  CA   ARG A 834      74.199  50.225  20.935  1.00 45.98      A  C
ATOM   1508  CB   ARG A 834      73.862  51.696  20.687  1.00 49.29      A  C
ATOM   1509  CG   ARG A 834      75.009  52.539  20.251  1.00 44.92      A  C
ATOM   1510  CD   ARG A 834      74.601  53.993  20.026  1.00 52.74      A  C
ATOM   1511  NE   ARG A 834      75.824  54.735  19.779  1.00 58.68      A  N
ATOM   1512  CZ   ARG A 834      76.321  55.675  20.573  1.00 52.97      A  C
ATOM   1513  NH1  ARG A 834      75.693  56.050  21.688  1.00 34.52      A  N
ATOM   1514  NH2  ARG A 834      77.507  56.175  20.281  1.00 42.43      A  N
ATOM   1515  C    ARG A 834      74.643  49.556  19.653  1.00 43.20      A  C
ATOM   1516  O    ARG A 834      75.834  49.421  19.370  1.00 44.04      A  O
ATOM   1517  N    ASP A 835      73.658  49.105  18.887  1.00 49.52      A  N
ATOM   1518  CA   ASP A 835      73.916  48.444  17.622  1.00 46.71      A  C
ATOM   1519  CB   ASP A 835      72.781  47.477  17.306  1.00 58.15      A  C
ATOM   1520  CG   ASP A 835      73.067  46.638  16.087  1.00 55.74      A  C
```

FIGURE 1A-28

```
ATOM   1521  OD1 ASP A 835      72.695  47.052  14.971  1.00 62.21      A    O
ATOM   1522  OD2 ASP A 835      73.685  45.567  16.246  1.00 63.53      A    O
ATOM   1523  C   ASP A 835      74.018  49.508  16.545  1.00 44.39      A    C
ATOM   1524  O   ASP A 835      73.009  50.069  16.113  1.00 41.90      A    O
ATOM   1525  N   ILE A 836      75.240  49.802  16.123  1.00 43.94      A    N
ATOM   1526  CA  ILE A 836      75.446  50.822  15.109  1.00 58.16      A    C
ATOM   1527  CB  ILE A 836      76.966  51.049  14.841  1.00 63.54      A    C
ATOM   1528  CG2 ILE A 836      77.652  51.542  16.128  1.00 55.72      A    C
ATOM   1529  CG1 ILE A 836      77.629  49.753  14.365  1.00 74.94      A    C
ATOM   1530  CD1 ILE A 836      77.400  49.419  12.891  1.00 83.58      A    C
ATOM   1531  C   ILE A 836      74.713  50.487  13.811  1.00 57.31      A    C
ATOM   1532  O   ILE A 836      74.260  51.386  13.112  1.00 60.41      A    O
ATOM   1533  N   MET A 837      74.577  49.196  13.511  1.00 57.23      A    N
ATOM   1534  CA  MET A 837      73.894  48.749  12.297  1.00 57.86      A    C
ATOM   1535  CB  MET A 837      73.987  47.225  12.165  1.00 66.40      A    C
ATOM   1536  CG  MET A 837      73.866  46.708  10.737  1.00 74.26      A    C
ATOM   1537  SD  MET A 837      75.439  46.776   9.837  1.00 91.89      A    S
ATOM   1538  CE  MET A 837      75.730  48.593   9.719  1.00 74.42      A    C
ATOM   1539  C   MET A 837      72.421  49.168  12.303  1.00 58.57      A    C
ATOM   1540  O   MET A 837      71.851  49.483  11.266  1.00 54.97      A    O
ATOM   1541  N   SER A 838      71.800  49.162  13.476  1.00 54.44      A    N
ATOM   1542  CA  SER A 838      70.409  49.561  13.570  1.00 52.49      A    C
ATOM   1543  CB  SER A 838      69.714  48.808  14.704  1.00 59.76      A    C
ATOM   1544  OG  SER A 838      70.090  49.335  15.962  1.00 77.03      A    O
ATOM   1545  C   SER A 838      70.270  51.072  13.801  1.00 54.08      A    C
ATOM   1546  O   SER A 838      69.163  51.566  14.023  1.00 49.78      A    O
ATOM   1547  N   ASP A 839      71.377  51.814  13.748  1.00 43.27      A    N
ATOM   1548  CA  ASP A 839      71.296  53.264  13.966  1.00 39.84      A    C
ATOM   1549  CB  ASP A 839      72.244  53.666  15.109  1.00 36.49      A    C
ATOM   1550  CG  ASP A 839      72.063  55.103  15.546  1.00 39.83      A    C
ATOM   1551  OD1 ASP A 839      72.320  55.400  16.737  1.00 53.20      A    O
ATOM   1552  OD2 ASP A 839      71.676  55.937  14.706  1.00 44.41      A    O
ATOM   1553  C   ASP A 839      71.634  53.995  12.663  1.00 29.96      A    C
ATOM   1554  O   ASP A 839      72.781  54.022  12.234  1.00 38.75      A    O
ATOM   1555  N   SER A 840      70.620  54.574  12.025  1.00 39.27      A    N
ATOM   1556  CA  SER A 840      70.811  55.276  10.755  1.00 41.65      A    C
ATOM   1557  CB  SER A 840      69.451  55.546  10.089  1.00 48.42      A    C
ATOM   1558  OG  SER A 840      68.577  56.290  10.932  1.00 50.43      A    O
ATOM   1559  C   SER A 840      71.620  56.580  10.819  1.00 43.21      A    C
ATOM   1560  O   SER A 840      71.845  57.224   9.795  1.00 43.42      A    O
ATOM   1561  N   ASN A 841      72.067  56.968  12.007  1.00 39.54      A    N
ATOM   1562  CA  ASN A 841      72.868  58.188  12.127  1.00 35.88      A    C
ATOM   1563  CB  ASN A 841      72.730  58.757  13.543  1.00 38.71      A    C
ATOM   1564  CG  ASN A 841      71.318  59.272  13.821  1.00 37.16      A    C
ATOM   1565  OD1 ASN A 841      70.828  60.161  13.123  1.00 52.04      A    O
ATOM   1566  ND2 ASN A 841      70.662  58.714  14.827  1.00 33.23      A    N
ATOM   1567  C   ASN A 841      74.330  57.883  11.765  1.00 34.74      A    C
ATOM   1568  O   ASN A 841      75.178  58.785  11.622  1.00 31.46      A    O
ATOM   1569  N   TYR A 842      74.621  56.597  11.606  1.00 26.60      A    N
ATOM   1570  CA  TYR A 842      75.955  56.190  11.222  1.00 33.38      A    C
ATOM   1571  CB  TYR A 842      76.472  55.119  12.178  1.00 26.59      A    C
ATOM   1572  CG  TYR A 842      76.724  55.619  13.591  1.00 31.09      A    C
ATOM   1573  CD1 TYR A 842      77.986  56.076  13.980  1.00 27.52      A    C
ATOM   1574  CE1 TYR A 842      78.219  56.529  15.285  1.00 28.06      A    C
ATOM   1575  CD2 TYR A 842      75.696  55.630  14.537  1.00 24.88      A    C
ATOM   1576  CE2 TYR A 842      75.909  56.080  15.829  1.00 31.76      A    C
```

FIGURE 1A-29

```
ATOM  1577  CZ   TYR A 842      77.171  56.527  16.198  1.00 25.62      A  C
ATOM  1578  OH   TYR A 842      77.357  56.965  17.472  1.00 31.07      A  O
ATOM  1579  C    TYR A 842      75.926  55.653   9.790  1.00 35.07      A  C
ATOM  1580  O    TYR A 842      75.187  54.726   9.476  1.00 37.52      A  O
ATOM  1581  N    VAL A 843      76.736  56.232   8.921  1.00 35.13      A  N
ATOM  1582  CA   VAL A 843      76.776  55.791   7.540  1.00 39.14      A  C
ATOM  1583  CB   VAL A 843      76.948  56.994   6.592  1.00 36.92      A  C
ATOM  1584  CG1  VAL A 843      76.831  56.548   5.160  1.00 46.02      A  C
ATOM  1585  CG2  VAL A 843      75.888  58.040   6.902  1.00 39.94      A  C
ATOM  1586  C    VAL A 843      77.922  54.817   7.335  1.00 33.67      A  C
ATOM  1587  O    VAL A 843      79.046  55.107   7.739  1.00 31.31      A  O
ATOM  1588  N    VAL A 844      77.628  53.671   6.712  1.00 33.93      A  N
ATOM  1589  CA   VAL A 844      78.627  52.628   6.433  1.00 38.28      A  C
ATOM  1590  CB   VAL A 844      77.933  51.286   6.046  1.00 41.20      A  C
ATOM  1591  CG1  VAL A 844      78.959  50.270   5.548  1.00 33.69      A  C
ATOM  1592  CG2  VAL A 844      77.189  50.721   7.247  1.00 36.39      A  C
ATOM  1593  C    VAL A 844      79.601  53.009   5.318  1.00 37.89      A  C
ATOM  1594  O    VAL A 844      79.182  53.442   4.263  1.00 39.57      A  O
ATOM  1595  N    ARG A 845      80.899  52.839   5.562  1.00 36.08      A  N
ATOM  1596  CA   ARG A 845      81.938  53.166   4.578  1.00 44.80      A  C
ATOM  1597  CB   ARG A 845      82.393  54.624   4.749  1.00 54.46      A  C
ATOM  1598  CG   ARG A 845      82.812  55.331   3.469  1.00 60.56      A  C
ATOM  1599  CD   ARG A 845      83.876  54.573   2.675  1.00 76.55      A  C
ATOM  1600  NE   ARG A 845      84.188  55.265   1.420  1.00 85.97      A  N
ATOM  1601  CZ   ARG A 845      85.055  54.836   0.503  1.00 87.18      A  C
ATOM  1602  NH1  ARG A 845      85.722  53.701   0.682  1.00 83.82      A  N
ATOM  1603  NH2  ARG A 845      85.250  55.547  -0.601  1.00 79.62      A  N
ATOM  1604  C    ARG A 845      83.127  52.238   4.829  1.00 45.78      A  C
ATOM  1605  O    ARG A 845      83.992  52.538   5.651  1.00 48.96      A  O
ATOM  1606  N    GLY A 846      83.174  51.109   4.133  1.00 44.75      A  N
ATOM  1607  CA   GLY A 846      84.273  50.191   4.360  1.00 48.39      A  C
ATOM  1608  C    GLY A 846      84.279  49.775   5.822  1.00 50.55      A  C
ATOM  1609  O    GLY A 846      83.266  49.297   6.335  1.00 50.82      A  O
ATOM  1610  N    ASN A 847      85.404  49.965   6.506  1.00 51.90      A  N
ATOM  1611  CA   ASN A 847      85.492  49.579   7.913  1.00 59.11      A  C
ATOM  1612  CB   ASN A 847      86.914  49.125   8.262  1.00 66.58      A  C
ATOM  1613  CG   ASN A 847      87.156  47.665   7.916  1.00 78.75      A  C
ATOM  1614  OD1  ASN A 847      88.262  47.147   8.083  1.00 92.70      A  O
ATOM  1615  ND2  ASN A 847      86.117  46.992   7.438  1.00 80.21      A  N
ATOM  1616  C    ASN A 847      85.062  50.685   8.861  1.00 54.71      A  C
ATOM  1617  O    ASN A 847      85.229  50.570  10.077  1.00 54.47      A  O
ATOM  1618  N    ALA A 848      84.490  51.750   8.311  1.00 45.22      A  N
ATOM  1619  CA   ALA A 848      84.056  52.847   9.151  1.00 39.04      A  C
ATOM  1620  CB   ALA A 848      84.691  54.138   8.670  1.00 36.83      A  C
ATOM  1621  C    ALA A 848      82.534  52.988   9.241  1.00 39.62      A  C
ATOM  1622  O    ALA A 848      81.796  52.588   8.342  1.00 40.31      A  O
ATOM  1623  N    ARG A 849      82.080  53.521  10.369  1.00 35.92      A  N
ATOM  1624  CA   ARG A 849      80.658  53.759  10.628  1.00 36.87      A  C
ATOM  1625  CB   ARG A 849      80.162  52.837  11.725  1.00 39.24      A  C
ATOM  1626  CG   ARG A 849      80.483  51.375  11.465  1.00 41.59      A  C
ATOM  1627  CD   ARG A 849      79.661  50.799  10.325  1.00 42.37      A  C
ATOM  1628  NE   ARG A 849      79.941  49.374  10.194  1.00 42.67      A  N
ATOM  1629  CZ   ARG A 849      80.925  48.860   9.464  1.00 46.19      A  C
ATOM  1630  NH1  ARG A 849      81.733  49.651   8.764  1.00 36.05      A  N
ATOM  1631  NH2  ARG A 849      81.123  47.550   9.466  1.00 46.37      A  N
ATOM  1632  C    ARG A 849      80.684  55.194  11.105  1.00 40.38      A  C
```

FIGURE 1A-30

| ATOM | 1633 | O   | ARG | A | 849 | 80.959 | 55.465 | 12.270 | 1.00 | 36.13 | A | O |
|------|------|-----|-----|---|-----|--------|--------|--------|------|-------|---|---|
| ATOM | 1634 | N   | LEU | A | 850 | 80.402 | 56.104 | 10.179 | 1.00 | 31.03 | A | N |
| ATOM | 1635 | CA  | LEU | A | 850 | 80.484 | 57.531 | 10.433 | 1.00 | 27.76 | A | C |
| ATOM | 1636 | CB  | LEU | A | 850 | 81.168 | 58.188 | 9.234  | 1.00 | 34.00 | A | C |
| ATOM | 1637 | CG  | LEU | A | 850 | 82.497 | 57.550 | 8.800  | 1.00 | 46.47 | A | C |
| ATOM | 1638 | CD1 | LEU | A | 850 | 82.868 | 58.013 | 7.402  | 1.00 | 46.56 | A | C |
| ATOM | 1639 | CD2 | LEU | A | 850 | 83.580 | 57.914 | 9.792  | 1.00 | 39.86 | A | C |
| ATOM | 1640 | C   | LEU | A | 850 | 79.209 | 58.313 | 10.754 | 1.00 | 32.07 | A | C |
| ATOM | 1641 | O   | LEU | A | 850 | 78.211 | 58.220 | 10.054 | 1.00 | 31.13 | A | O |
| ATOM | 1642 | N   | PRO | A | 851 | 79.250 | 59.111 | 11.830 | 1.00 | 31.83 | A | N |
| ATOM | 1643 | CD  | PRO | A | 851 | 80.396 | 59.184 | 12.763 | 1.00 | 25.33 | A | C |
| ATOM | 1644 | CA  | PRO | A | 851 | 78.132 | 59.949 | 12.280 | 1.00 | 28.95 | A | C |
| ATOM | 1645 | CB  | PRO | A | 851 | 78.461 | 60.194 | 13.755 | 1.00 | 27.89 | A | C |
| ATOM | 1646 | CG  | PRO | A | 851 | 79.952 | 60.266 | 13.758 | 1.00 | 28.93 | A | C |
| ATOM | 1647 | C   | PRO | A | 851 | 78.196 | 61.224 | 11.422 | 1.00 | 25.13 | A | C |
| ATOM | 1648 | O   | PRO | A | 851 | 78.401 | 62.340 | 11.916 | 1.00 | 20.72 | A | O |
| ATOM | 1649 | N   | VAL | A | 852 | 78.015 | 61.038 | 10.121 | 1.00 | 25.66 | A | N |
| ATOM | 1650 | CA  | VAL | A | 852 | 78.124 | 62.130 | 9.157  | 1.00 | 22.12 | A | C |
| ATOM | 1651 | CB  | VAL | A | 852 | 77.649 | 61.657 | 7.758  | 1.00 | 29.72 | A | C |
| ATOM | 1652 | CG1 | VAL | A | 852 | 77.629 | 62.816 | 6.798  | 1.00 | 31.03 | A | C |
| ATOM | 1653 | CG2 | VAL | A | 852 | 78.620 | 60.570 | 7.242  | 1.00 | 23.95 | A | C |
| ATOM | 1654 | C   | VAL | A | 852 | 77.479 | 63.474 | 9.485  | 1.00 | 15.96 | A | C |
| ATOM | 1655 | O   | VAL | A | 852 | 78.120 | 64.516 | 9.311  | 1.00 | 19.88 | A | O |
| ATOM | 1656 | N   | LYS | A | 853 | 76.229 | 63.464 | 9.973  | 1.00 | 18.43 | A | N |
| ATOM | 1657 | CA  | LYS | A | 853 | 75.578 | 64.730 | 10.279 | 1.00 | 14.79 | A | C |
| ATOM | 1658 | CB  | LYS | A | 853 | 74.071 | 64.510 | 10.473 | 1.00 | 22.21 | A | C |
| ATOM | 1659 | CG  | LYS | A | 853 | 73.354 | 64.262 | 9.141  | 1.00 | 21.46 | A | C |
| ATOM | 1660 | CD  | LYS | A | 853 | 71.836 | 64.204 | 9.334  | 1.00 | 23.33 | A | C |
| ATOM | 1661 | CE  | LYS | A | 853 | 71.085 | 64.117 | 8.001  | 1.00 | 20.42 | A | C |
| ATOM | 1662 | NZ  | LYS | A | 853 | 69.594 | 64.135 | 8.240  | 1.00 | 21.53 | A | N |
| ATOM | 1663 | C   | LYS | A | 853 | 76.184 | 65.502 | 11.471 | 1.00 | 22.36 | A | C |
| ATOM | 1664 | O   | LYS | A | 853 | 75.876 | 66.670 | 11.675 | 1.00 | 21.12 | A | O |
| ATOM | 1665 | N   | TRP | A | 854 | 77.049 | 64.850 | 12.243 | 1.00 | 19.97 | A | N |
| ATOM | 1666 | CA  | TRP | A | 854 | 77.711 | 65.506 | 13.374 | 1.00 | 23.68 | A | C |
| ATOM | 1667 | CB  | TRP | A | 854 | 77.730 | 64.563 | 14.582 | 1.00 | 21.53 | A | C |
| ATOM | 1668 | CG  | TRP | A | 854 | 76.400 | 64.507 | 15.315 | 1.00 | 22.73 | A | C |
| ATOM | 1669 | CD2 | TRP | A | 854 | 75.231 | 63.775 | 14.919 | 1.00 | 22.00 | A | C |
| ATOM | 1670 | CE2 | TRP | A | 854 | 74.214 | 64.063 | 15.863 | 1.00 | 22.04 | A | C |
| ATOM | 1671 | CE3 | TRP | A | 854 | 74.944 | 62.909 | 13.858 | 1.00 | 20.00 | A | C |
| ATOM | 1672 | CD1 | TRP | A | 854 | 76.060 | 65.189 | 16.449 | 1.00 | 24.79 | A | C |
| ATOM | 1673 | NE1 | TRP | A | 854 | 74.743 | 64.928 | 16.786 | 1.00 | 23.65 | A | N |
| ATOM | 1674 | CZ2 | TRP | A | 854 | 72.927 | 63.514 | 15.776 | 1.00 | 20.54 | A | C |
| ATOM | 1675 | CZ3 | TRP | A | 854 | 73.651 | 62.358 | 13.769 | 1.00 | 21.48 | A | C |
| ATOM | 1676 | CH2 | TRP | A | 854 | 72.665 | 62.666 | 14.723 | 1.00 | 24.05 | A | C |
| ATOM | 1677 | C   | TRP | A | 854 | 79.153 | 65.927 | 13.045 | 1.00 | 28.27 | A | C |
| ATOM | 1678 | O   | TRP | A | 854 | 79.784 | 66.689 | 13.788 | 1.00 | 23.64 | A | O |
| ATOM | 1679 | N   | MET | A | 855 | 79.652 | 65.468 | 11.907 | 1.00 | 21.55 | A | N |
| ATOM | 1680 | CA  | MET | A | 855 | 81.048 | 65.731 | 11.507 | 1.00 | 19.24 | A | C |
| ATOM | 1681 | CB  | MET | A | 855 | 81.508 | 64.604 | 10.571 | 1.00 | 20.61 | A | C |
| ATOM | 1682 | CG  | MET | A | 855 | 81.558 | 63.240 | 11.280 | 1.00 | 23.67 | A | C |
| ATOM | 1683 | SD  | MET | A | 855 | 81.723 | 61.834 | 10.161 | 1.00 | 28.09 | A | S |
| ATOM | 1684 | CE  | MET | A | 855 | 83.390 | 62.106 | 9.462  | 1.00 | 27.72 | A | C |
| ATOM | 1685 | C   | MET | A | 855 | 81.468 | 67.068 | 10.898 | 1.00 | 29.16 | A | C |
| ATOM | 1686 | O   | MET | A | 855 | 80.841 | 67.591 | 9.969  | 1.00 | 28.40 | A | O |
| ATOM | 1687 | N   | ALA | A | 856 | 82.576 | 67.601 | 11.414 | 1.00 | 23.21 | A | N |
| ATOM | 1688 | CA  | ALA | A | 856 | 83.128 | 68.844 | 10.899 | 1.00 | 24.68 | A | C |

FIGURE 1A-31

```
ATOM   1689  CB   ALA A 856      84.338  69.298  11.735  1.00 24.66      A    C
ATOM   1690  C    ALA A 856      83.579  68.533   9.477  1.00 20.75      A    C
ATOM   1691  O    ALA A 856      83.885  67.387   9.143  1.00 19.20      A    O
ATOM   1692  N    PRO A 857      83.635  69.554   8.620  1.00 24.01      A    N
ATOM   1693  CD   PRO A 857      83.298  70.958   8.897  1.00 21.23      A    C
ATOM   1694  CA   PRO A 857      84.061  69.365   7.226  1.00 25.80      A    C
ATOM   1695  CB   PRO A 857      84.097  70.790   6.670  1.00 27.31      A    C
ATOM   1696  CG   PRO A 857      83.131  71.532   7.503  1.00 34.21      A    C
ATOM   1697  C    PRO A 857      85.443  68.704   7.132  1.00 29.61      A    C
ATOM   1698  O    PRO A 857      85.643  67.805   6.303  1.00 28.12      A    O
ATOM   1699  N    GLU A 858      86.399  69.147   7.963  1.00 25.86      A    N
ATOM   1700  CA   GLU A 858      87.743  68.554   7.912  1.00 25.02      A    C
ATOM   1701  CB   GLU A 858      88.747  69.335   8.783  1.00 35.35      A    C
ATOM   1702  CG   GLU A 858      88.555  69.288  10.303  1.00 29.00      A    C
ATOM   1703  CD   GLU A 858      87.588  70.324  10.814  1.00 34.70      A    C
ATOM   1704  OE1  GLU A 858      87.614  70.607  12.039  1.00 29.84      A    O
ATOM   1705  OE2  GLU A 858      86.792  70.852   9.997  1.00 29.59      A    O
ATOM   1706  C    GLU A 858      87.726  67.060   8.293  1.00 32.17      A    C
ATOM   1707  O    GLU A 858      88.580  66.286   7.854  1.00 28.08      A    O
ATOM   1708  N    SER A 859      86.742  66.642   9.087  1.00 23.49      A    N
ATOM   1709  CA   SER A 859      86.635  65.221   9.441  1.00 23.76      A    C
ATOM   1710  CB   SER A 859      85.754  65.035  10.695  1.00 27.68      A    C
ATOM   1711  OG   SER A 859      86.186  65.848  11.779  1.00 28.41      A    O
ATOM   1712  C    SER A 859      85.986  64.481   8.254  1.00 27.03      A    C
ATOM   1713  O    SER A 859      86.372  63.365   7.909  1.00 28.11      A    O
ATOM   1714  N    LEU A 860      84.971  65.096   7.654  1.00 27.75      A    N
ATOM   1715  CA   LEU A 860      84.277  64.491   6.517  1.00 35.97      A    C
ATOM   1716  CB   LEU A 860      83.116  65.376   6.061  1.00 30.04      A    C
ATOM   1717  CG   LEU A 860      81.803  65.428   6.820  1.00 35.49      A    C
ATOM   1718  CD1  LEU A 860      80.906  66.505   6.175  1.00 36.33      A    C
ATOM   1719  CD2  LEU A 860      81.151  64.045   6.773  1.00 35.38      A    C
ATOM   1720  C    LEU A 860      85.199  64.310   5.303  1.00 29.36      A    C
ATOM   1721  O    LEU A 860      85.263  63.240   4.703  1.00 33.42      A    O
ATOM   1722  N    PHE A 861      85.914  65.372   4.965  1.00 29.96      A    N
ATOM   1723  CA   PHE A 861      86.769  65.371   3.782  1.00 38.84      A    C
ATOM   1724  CB   PHE A 861      86.635  66.731   3.104  1.00 29.64      A    C
ATOM   1725  CG   PHE A 861      85.207  67.161   2.920  1.00 30.92      A    C
ATOM   1726  CD1  PHE A 861      84.751  68.360   3.448  1.00 29.49      A    C
ATOM   1727  CD2  PHE A 861      84.307  66.337   2.255  1.00 34.82      A    C
ATOM   1728  CE1  PHE A 861      83.420  68.735   3.323  1.00 37.84      A    C
ATOM   1729  CE2  PHE A 861      82.963  66.705   2.125  1.00 40.48      A    C
ATOM   1730  CZ   PHE A 861      82.524  67.905   2.662  1.00 36.53      A    C
ATOM   1731  C    PHE A 861      88.243  65.032   3.946  1.00 46.78      A    C
ATOM   1732  O    PHE A 861      88.913  64.772   2.956  1.00 44.27      A    O
ATOM   1733  N    GLU A 862      88.756  65.036   5.175  1.00 43.95      A    N
ATOM   1734  CA   GLU A 862      90.169  64.739   5.384  1.00 35.08      A    C
ATOM   1735  CB   GLU A 862      90.902  66.035   5.692  1.00 43.26      A    C
ATOM   1736  CG   GLU A 862      90.748  67.070   4.600  1.00 54.13      A    C
ATOM   1737  CD   GLU A 862      90.546  68.467   5.154  1.00 68.44      A    C
ATOM   1738  OE1  GLU A 862      91.498  69.019   5.751  1.00 72.44      A    O
ATOM   1739  OE2  GLU A 862      89.426  69.009   5.000  1.00 70.92      A    O
ATOM   1740  C    GLU A 862      90.451  63.708   6.480  1.00 39.32      A    C
ATOM   1741  O    GLU A 862      91.598  63.363   6.723  1.00 36.58      A    O
ATOM   1742  N    GLY A 863      89.412  63.211   7.146  1.00 31.66      A    N
ATOM   1743  CA   GLY A 863      89.640  62.243   8.203  1.00 33.35      A    C
ATOM   1744  C    GLY A 863      90.375  62.859   9.392  1.00 28.22      A    C
```

FIGURE 1A-32

```
ATOM   1745  O    GLY A 863      90.974  62.150  10.185  1.00 40.49      A  O
ATOM   1746  N    ILE A 864      90.311  64.184   9.510  1.00 29.05      A  N
ATOM   1747  CA   ILE A 864      90.948  64.957  10.589  1.00 35.86      A  C
ATOM   1748  CB   ILE A 864      91.357  66.368  10.038  1.00 40.64      A  C
ATOM   1749  CG2  ILE A 864      91.719  67.325  11.160  1.00 45.41      A  C
ATOM   1750  CG1  ILE A 864      92.545  66.233   9.082  1.00 56.84      A  C
ATOM   1751  CD1  ILE A 864      92.887  67.538   8.351  1.00 61.68      A  C
ATOM   1752  C    ILE A 864      89.980  65.149  11.776  1.00 42.22      A  C
ATOM   1753  O    ILE A 864      88.807  65.496  11.571  1.00 32.77      A  O
ATOM   1754  N    TYR A 865      90.466  64.924  13.002  1.00 34.46      A  N
ATOM   1755  CA   TYR A 865      89.655  65.108  14.221  1.00 30.04      A  C
ATOM   1756  CB   TYR A 865      89.196  63.781  14.832  1.00 32.17      A  C
ATOM   1757  CG   TYR A 865      88.244  62.981  13.995  1.00 32.72      A  C
ATOM   1758  CD1  TYR A 865      88.722  62.047  13.076  1.00 34.65      A  C
ATOM   1759  CE1  TYR A 865      87.851  61.315  12.274  1.00 38.53      A  C
ATOM   1760  CD2  TYR A 865      86.854  63.171  14.100  1.00 30.12      A  C
ATOM   1761  CE2  TYR A 865      85.965  62.438  13.296  1.00 35.67      A  C
ATOM   1762  CZ   TYR A 865      86.476  61.514  12.388  1.00 39.91      A  C
ATOM   1763  OH   TYR A 865      85.630  60.780  11.592  1.00 45.26      A  O
ATOM   1764  C    TYR A 865      90.439  65.833  15.307  1.00 31.35      A  C
ATOM   1765  O    TYR A 865      91.304  65.240  15.951  1.00 28.87      A  O
ATOM   1766  N    THR A 866      90.114  67.100  15.530  1.00 27.18      A  N
ATOM   1767  CA   THR A 866      90.784  67.887  16.551  1.00 30.41      A  C
ATOM   1768  CB   THR A 866      91.478  69.121  15.931  1.00 23.79      A  C
ATOM   1769  OG1  THR A 866      90.471  70.014  15.461  1.00 32.22      A  O
ATOM   1770  CG2  THR A 866      92.392  68.717  14.735  1.00 30.47      A  C
ATOM   1771  C    THR A 866      89.749  68.380  17.558  1.00 29.39      A  C
ATOM   1772  O    THR A 866      88.544  68.107  17.427  1.00 28.48      A  O
ATOM   1773  N    ILE A 867      90.205  69.108  18.568  1.00 28.09      A  N
ATOM   1774  CA   ILE A 867      89.277  69.640  19.543  1.00 29.64      A  C
ATOM   1775  CB   ILE A 867      90.019  70.309  20.745  1.00 31.25      A  C
ATOM   1776  CG2  ILE A 867      90.667  71.610  20.320  1.00 28.11      A  C
ATOM   1777  CG1  ILE A 867      89.029  70.563  21.886  1.00 28.92      A  C
ATOM   1778  CD1  ILE A 867      88.484  69.240  22.525  1.00 29.71      A  C
ATOM   1779  C    ILE A 867      88.363  70.654  18.818  1.00 30.42      A  C
ATOM   1780  O    ILE A 867      87.195  70.831  19.185  1.00 31.23      A  O
ATOM   1781  N    LYS A 868      88.885  71.295  17.774  1.00 27.55      A  N
ATOM   1782  CA   LYS A 868      88.085  72.265  17.007  1.00 27.38      A  C
ATOM   1783  CB   LYS A 868      88.965  73.045  16.025  1.00 39.18      A  C
ATOM   1784  CG   LYS A 868      89.982  73.997  16.665  1.00 48.36      A  C
ATOM   1785  CD   LYS A 868      90.902  74.588  15.585  1.00 59.83      A  C
ATOM   1786  CE   LYS A 868      91.865  75.623  16.134  1.00 68.20      A  C
ATOM   1787  NZ   LYS A 868      91.144  76.804  16.691  1.00 80.94      A  N
ATOM   1788  C    LYS A 868      86.975  71.543  16.222  1.00 23.44      A  C
ATOM   1789  O    LYS A 868      85.898  72.100  15.990  1.00 29.16      A  O
ATOM   1790  N    SER A 869      87.250  70.318  15.781  1.00 21.66      A  N
ATOM   1791  CA   SER A 869      86.221  69.552  15.072  1.00 24.34      A  C
ATOM   1792  CB   SER A 869      86.802  68.218  14.589  1.00 21.56      A  C
ATOM   1793  OG   SER A 869      87.937  68.440  13.772  1.00 34.18      A  O
ATOM   1794  C    SER A 869      85.110  69.303  16.112  1.00 29.43      A  C
ATOM   1795  O    SER A 869      83.919  69.303  15.788  1.00 25.33      A  O
ATOM   1796  N    ASP A 870      85.512  69.092  17.365  1.00 22.15      A  N
ATOM   1797  CA   ASP A 870      84.543  68.864  18.423  1.00 26.76      A  C
ATOM   1798  CB   ASP A 870      85.216  68.411  19.720  1.00 28.05      A  C
ATOM   1799  CG   ASP A 870      85.424  66.907  19.765  1.00 27.15      A  C
ATOM   1800  OD1  ASP A 870      84.493  66.158  19.378  1.00 29.32      A  O
```

FIGURE 1A-33

```
ATOM   1801  OD2 ASP A 870      86.502  66.470  20.203  1.00 27.89      A  O
ATOM   1802  C   ASP A 870      83.690  70.097  18.689  1.00 19.48      A  C
ATOM   1803  O   ASP A 870      82.548  69.976  19.125  1.00 30.85      A  O
ATOM   1804  N   VAL A 871      84.230  71.280  18.428  1.00 24.09      A  N
ATOM   1805  CA  VAL A 871      83.438  72.480  18.613  1.00 23.70      A  C
ATOM   1806  CB  VAL A 871      84.297  73.770  18.454  1.00 33.06      A  C
ATOM   1807  CG1 VAL A 871      83.395  75.004  18.437  1.00 30.17      A  C
ATOM   1808  CG2 VAL A 871      85.280  73.880  19.633  1.00 31.93      A  C
ATOM   1809  C   VAL A 871      82.304  72.453  17.578  1.00 27.54      A  C
ATOM   1810  O   VAL A 871      81.171  72.847  17.866  1.00 25.31      A  O
ATOM   1811  N   TRP A 872      82.605  71.971  16.379  1.00 28.86      A  N
ATOM   1812  CA  TRP A 872      81.586  71.866  15.341  1.00 27.21      A  C
ATOM   1813  CB  TRP A 872      82.211  71.389  14.032  1.00 26.36      A  C
ATOM   1814  CG  TRP A 872      81.192  71.129  12.941  1.00 28.70      A  C
ATOM   1815  CD2 TRP A 872      81.003  71.891  11.744  1.00 25.77      A  C
ATOM   1816  CE2 TRP A 872      79.963  71.267  11.011  1.00 29.15      A  C
ATOM   1817  CE3 TRP A 872      81.612  73.043  11.213  1.00 23.49      A  C
ATOM   1818  CD1 TRP A 872      80.285  70.109  12.891  1.00 25.08      A  C
ATOM   1819  NE1 TRP A 872      79.543  70.184  11.737  1.00 25.31      A  N
ATOM   1820  CZ2 TRP A 872      79.516  71.755   9.775  1.00 29.06      A  C
ATOM   1821  CZ3 TRP A 872      81.167  73.529   9.984  1.00 33.04      A  C
ATOM   1822  CH2 TRP A 872      80.127  72.882   9.279  1.00 32.08      A  C
ATOM   1823  C   TRP A 872      80.511  70.859  15.801  1.00 20.40      A  C
ATOM   1824  O   TRP A 872      79.307  71.162  15.822  1.00 24.01      A  O
ATOM   1825  N   SER A 873      80.947  69.662  16.181  1.00 21.39      A  N
ATOM   1826  CA  SER A 873      80.000  68.656  16.639  1.00 24.34      A  C
ATOM   1827  CB  SER A 873      80.751  67.379  17.023  1.00 23.74      A  C
ATOM   1828  OG  SER A 873      81.368  66.804  15.890  1.00 45.84      A  O
ATOM   1829  C   SER A 873      79.203  69.203  17.840  1.00 27.38      A  C
ATOM   1830  O   SER A 873      77.998  68.970  17.974  1.00 22.82      A  O
ATOM   1831  N   TYR A 874      79.875  69.940  18.713  1.00 23.58      A  N
ATOM   1832  CA  TYR A 874      79.190  70.516  19.867  1.00 24.16      A  C
ATOM   1833  CB  TYR A 874      80.177  71.309  20.726  1.00 23.96      A  C
ATOM   1834  CG  TYR A 874      79.522  72.019  21.881  1.00 24.05      A  C
ATOM   1835  CD1 TYR A 874      79.100  71.317  22.997  1.00 26.60      A  C
ATOM   1836  CE1 TYR A 874      78.475  71.968  24.061  1.00 35.20      A  C
ATOM   1837  CD2 TYR A 874      79.307  73.395  21.842  1.00 26.79      A  C
ATOM   1838  CE2 TYR A 874      78.681  74.054  22.892  1.00 33.37      A  C
ATOM   1839  CZ  TYR A 874      78.268  73.336  23.997  1.00 30.60      A  C
ATOM   1840  OH  TYR A 874      77.633  73.979  25.038  1.00 37.86      A  O
ATOM   1841  C   TYR A 874      78.048  71.445  19.392  1.00 27.70      A  C
ATOM   1842  O   TYR A 874      76.982  71.511  20.008  1.00 26.54      A  O
ATOM   1843  N   GLY A 875      78.281  72.175  18.308  1.00 24.67      A  N
ATOM   1844  CA  GLY A 875      77.234  73.039  17.792  1.00 22.15      A  C
ATOM   1845  C   GLY A 875      76.037  72.204  17.337  1.00 21.26      A  C
ATOM   1846  O   GLY A 875      74.873  72.608  17.515  1.00 28.89      A  O
ATOM   1847  N   ILE A 876      76.309  71.038  16.743  1.00 22.43      A  N
ATOM   1848  CA  ILE A 876      75.221  70.167  16.307  1.00 21.44      A  C
ATOM   1849  CB  ILE A 876      75.751  68.955  15.469  1.00 21.86      A  C
ATOM   1850  CG2 ILE A 876      74.568  68.042  15.049  1.00 18.60      A  C
ATOM   1851  CG1 ILE A 876      76.545  69.456  14.244  1.00 28.14      A  C
ATOM   1852  CD1 ILE A 876      75.737  70.256  13.162  1.00 17.73      A  C
ATOM   1853  C   ILE A 876      74.491  69.666  17.573  1.00 24.59      A  C
ATOM   1854  O   ILE A 876      73.250  69.617  17.624  1.00 20.94      A  O
ATOM   1855  N   LEU A 877      75.251  69.319  18.606  1.00 21.17      A  N
ATOM   1856  CA  LEU A 877      74.646  68.840  19.853  1.00 24.03      A  C
```

FIGURE 1A-34

```
ATOM  1857  CB   LEU A 877      75.751  68.368  20.823  1.00 24.36      A C
ATOM  1858  CG   LEU A 877      75.369  67.594  22.099  1.00 25.33      A C
ATOM  1859  CD1  LEU A 877      76.578  66.832  22.653  1.00 24.49      A C
ATOM  1860  CD2  LEU A 877      74.834  68.560  23.140  1.00 27.06      A C
ATOM  1861  C    LEU A 877      73.768  69.952  20.493  1.00 18.08      A C
ATOM  1862  O    LEU A 877      72.717  69.667  21.101  1.00 25.33      A O
ATOM  1863  N    LEU A 878      74.198  71.208  20.334  1.00 21.45      A N
ATOM  1864  CA   LEU A 878      73.438  72.342  20.857  1.00 25.98      A C
ATOM  1865  CB   LEU A 878      74.191  73.661  20.608  1.00 23.00      A C
ATOM  1866  CG   LEU A 878      75.224  74.179  21.608  1.00 37.91      A C
ATOM  1867  CD1  LEU A 878      75.619  75.598  21.210  1.00 34.99      A C
ATOM  1868  CD2  LEU A 878      74.622  74.194  23.007  1.00 40.61      A C
ATOM  1869  C    LEU A 878      72.078  72.370  20.129  1.00 36.02      A C
ATOM  1870  O    LEU A 878      71.016  72.561  20.746  1.00 29.27      A O
ATOM  1871  N    TRP A 879      72.118  72.172  18.815  1.00 25.31      A N
ATOM  1872  CA   TRP A 879      70.890  72.151  18.026  1.00 30.32      A C
ATOM  1873  CB   TRP A 879      71.216  71.990  16.537  1.00 29.04      A C
ATOM  1874  CG   TRP A 879      70.054  72.332  15.636  1.00 22.79      A C
ATOM  1875  CD2  TRP A 879      69.038  71.438  15.185  1.00 20.14      A C
ATOM  1876  CE2  TRP A 879      68.163  72.179  14.349  1.00 25.41      A C
ATOM  1877  CE3  TRP A 879      68.779  70.074  15.399  1.00 19.87      A C
ATOM  1878  CD1  TRP A 879      69.766  73.553  15.083  1.00 26.25      A C
ATOM  1879  NE1  TRP A 879      68.631  73.466  14.302  1.00 28.09      A N
ATOM  1880  CZ2  TRP A 879      67.047  71.597  13.729  1.00 26.82      A C
ATOM  1881  CZ3  TRP A 879      67.683  69.502  14.781  1.00 23.05      A C
ATOM  1882  CH2  TRP A 879      66.829  70.255  13.956  1.00 19.35      A C
ATOM  1883  C    TRP A 879      70.012  70.975  18.533  1.00 16.87      A C
ATOM  1884  O    TRP A 879      68.800  71.106  18.679  1.00 28.08      A O
ATOM  1885  N    GLU A 880      70.626  69.829  18.811  1.00 22.32      A N
ATOM  1886  CA   GLU A 880      69.849  68.718  19.348  1.00 23.23      A C
ATOM  1887  CB   GLU A 880      70.751  67.524  19.635  1.00 28.40      A C
ATOM  1888  CG   GLU A 880      71.273  66.800  18.418  1.00 22.68      A C
ATOM  1889  CD   GLU A 880      72.043  65.583  18.829  1.00 20.77      A C
ATOM  1890  OE1  GLU A 880      73.267  65.705  19.100  1.00 20.80      A O
ATOM  1891  OE2  GLU A 880      71.424  64.500  18.901  1.00 20.93      A O
ATOM  1892  C    GLU A 880      69.151  69.134  20.667  1.00 27.22      A C
ATOM  1893  O    GLU A 880      67.974  68.847  20.887  1.00 24.55      A O
ATOM  1894  N    ILE A 881      69.890  69.788  21.554  1.00 25.09      A N
ATOM  1895  CA   ILE A 881      69.309  70.226  22.824  1.00 33.41      A C
ATOM  1896  CB   ILE A 881      70.398  70.899  23.741  1.00 28.94      A C
ATOM  1897  CG2  ILE A 881      69.716  71.649  24.928  1.00 29.58      A C
ATOM  1898  CG1  ILE A 881      71.405  69.830  24.220  1.00 29.80      A C
ATOM  1899  CD1  ILE A 881      72.639  70.387  24.967  1.00 28.21      A C
ATOM  1900  C    ILE A 881      68.139  71.222  22.619  1.00 28.75      A C
ATOM  1901  O    ILE A 881      67.041  71.029  23.146  1.00 31.32      A O
ATOM  1902  N    PHE A 882      68.364  72.270  21.837  1.00 30.26      A N
ATOM  1903  CA   PHE A 882      67.326  73.257  21.658  1.00 29.25      A C
ATOM  1904  CB   PHE A 882      67.969  74.626  21.436  1.00 26.57      A C
ATOM  1905  CG   PHE A 882      68.727  75.112  22.637  1.00 34.87      A C
ATOM  1906  CD1  PHE A 882      70.098  74.850  22.775  1.00 27.99      A C
ATOM  1907  CD2  PHE A 882      68.062  75.764  23.669  1.00 31.86      A C
ATOM  1908  CE1  PHE A 882      70.790  75.231  23.929  1.00 41.48      A C
ATOM  1909  CE2  PHE A 882      68.739  76.149  24.828  1.00 36.30      A C
ATOM  1910  CZ   PHE A 882      70.108  75.881  24.960  1.00 37.48      A C
ATOM  1911  C    PHE A 882      66.208  72.962  20.651  1.00 31.70      A C
ATOM  1912  O    PHE A 882      65.422  73.846  20.309  1.00 25.27      A O
```

FIGURE 1A-35

```
ATOM   1913  N    SER A 883      66.124  71.704  20.226  1.00 29.58      A  N
ATOM   1914  CA   SER A 883      65.064  71.251  19.323  1.00 35.05      A  C
ATOM   1915  CB   SER A 883      65.643  70.732  18.001  1.00 26.69      A  C
ATOM   1916  OG   SER A 883      66.254  69.458  18.187  1.00 25.21      A  O
ATOM   1917  C    SER A 883      64.415  70.080  20.054  1.00 37.08      A  C
ATOM   1918  O    SER A 883      63.482  69.450  19.556  1.00 28.25      A  O
ATOM   1919  N    LEU A 884      64.924  69.800  21.252  1.00 27.50      A  N
ATOM   1920  CA   LEU A 884      64.473  68.664  22.048  1.00 23.65      A  C
ATOM   1921  CB   LEU A 884      63.011  68.779  22.511  1.00 25.91      A  C
ATOM   1922  CG   LEU A 884      62.661  69.912  23.494  1.00 37.65      A  C
ATOM   1923  CD1  LEU A 884      61.289  69.640  24.124  1.00 30.06      A  C
ATOM   1924  CD2  LEU A 884      63.696  69.998  24.594  1.00 30.97      A  C
ATOM   1925  C    LEU A 884      64.679  67.323  21.338  1.00 27.89      A  C
ATOM   1926  O    LEU A 884      63.804  66.447  21.329  1.00 26.91      A  O
ATOM   1927  N    GLY A 885      65.854  67.161  20.733  1.00 23.64      A  N
ATOM   1928  CA   GLY A 885      66.162  65.870  20.156  1.00 22.31      A  C
ATOM   1929  C    GLY A 885      65.803  65.532  18.731  1.00 26.28      A  C
ATOM   1930  O    GLY A 885      65.656  64.350  18.399  1.00 28.49      A  O
ATOM   1931  N    VAL A 886      65.680  66.545  17.884  1.00 24.04      A  N
ATOM   1932  CA   VAL A 886      65.367  66.282  16.494  1.00 25.86      A  C
ATOM   1933  CB   VAL A 886      64.753  67.537  15.799  1.00 30.42      A  C
ATOM   1934  CG1  VAL A 886      64.527  67.249  14.293  1.00 22.68      A  C
ATOM   1935  CG2  VAL A 886      63.421  67.934  16.501  1.00 24.27      A  C
ATOM   1936  C    VAL A 886      66.661  65.891  15.770  1.00 26.42      A  C
ATOM   1937  O    VAL A 886      67.746  66.395  16.089  1.00 22.30      A  O
ATOM   1938  N    ASN A 887      66.544  64.976  14.818  1.00 24.83      A  N
ATOM   1939  CA   ASN A 887      67.685  64.575  14.000  1.00 29.17      A  C
ATOM   1940  CB   ASN A 887      67.221  63.548  12.946  1.00 32.22      A  C
ATOM   1941  CG   ASN A 887      68.375  62.926  12.169  1.00 45.13      A  C
ATOM   1942  OD1  ASN A 887      69.244  62.269  12.747  1.00 45.64      A  O
ATOM   1943  ND2  ASN A 887      68.381  63.121  10.848  1.00 38.84      A  N
ATOM   1944  C    ASN A 887      68.197  65.847  13.288  1.00 19.41      A  C
ATOM   1945  O    ASN A 887      67.399  66.639  12.793  1.00 27.03      A  O
ATOM   1946  N    PRO A 888      69.533  66.071  13.253  1.00 24.85      A  N
ATOM   1947  CD   PRO A 888      70.580  65.267  13.911  1.00 26.34      A  C
ATOM   1948  CA   PRO A 888      70.118  67.249  12.587  1.00 26.01      A  C
ATOM   1949  CB   PRO A 888      71.634  67.045  12.777  1.00 21.41      A  C
ATOM   1950  CG   PRO A 888      71.715  66.257  14.043  1.00 31.89      A  C
ATOM   1951  C    PRO A 888      69.737  67.242  11.085  1.00 22.57      A  C
ATOM   1952  O    PRO A 888      69.540  66.171  10.513  1.00 20.47      A  O
ATOM   1953  N    TYR A 889      69.666  68.418  10.463  1.00 18.75      A  N
ATOM   1954  CA   TYR A 889      69.307  68.535   9.041  1.00 25.71      A  C
ATOM   1955  CB   TYR A 889      70.507  68.127   8.169  1.00 21.20      A  C
ATOM   1956  CG   TYR A 889      71.825  68.781   8.569  1.00 21.25      A  C
ATOM   1957  CD1  TYR A 889      72.706  68.146   9.465  1.00 22.87      A  C
ATOM   1958  CE1  TYR A 889      73.934  68.726   9.809  1.00 18.61      A  C
ATOM   1959  CD2  TYR A 889      72.208  70.016   8.035  1.00 22.33      A  C
ATOM   1960  CE2  TYR A 889      73.449  70.604   8.374  1.00 23.38      A  C
ATOM   1961  CZ   TYR A 889      74.296  69.959   9.253  1.00 24.52      A  C
ATOM   1962  OH   TYR A 889      75.508  70.533   9.574  1.00 27.12      A  O
ATOM   1963  C    TYR A 889      68.096  67.623   8.766  1.00 24.34      A  C
ATOM   1964  O    TYR A 889      68.120  66.761   7.868  1.00 23.59      A  O
ATOM   1965  N    PRO A 890      67.008  67.814   9.542  1.00 23.16      A  N
ATOM   1966  CD   PRO A 890      66.803  68.958  10.454  1.00 25.47      A  C
ATOM   1967  CA   PRO A 890      65.790  67.010   9.416  1.00 20.70      A  C
ATOM   1968  CB   PRO A 890      64.832  67.649  10.437  1.00 17.69      A  C
```

FIGURE 1A-36

```
ATOM   1969  CG   PRO A 890      65.304  69.091  10.500  1.00 23.89      A  C
ATOM   1970  C    PRO A 890      65.227  66.957   8.007  1.00 27.65      A  C
ATOM   1971  O    PRO A 890      65.036  67.992   7.367  1.00 23.33      A  O
ATOM   1972  N    GLY A 891      65.000  65.737   7.527  1.00 23.91      A  N
ATOM   1973  CA   GLY A 891      64.447  65.557   6.196  1.00 30.05      A  C
ATOM   1974  C    GLY A 891      65.497  65.504   5.100  1.00 32.95      A  C
ATOM   1975  O    GLY A 891      65.186  65.159   3.965  1.00 34.28      A  O
ATOM   1976  N    ILE A 892      66.741  65.850   5.419  1.00 27.81      A  N
ATOM   1977  CA   ILE A 892      67.797  65.823   4.413  1.00 21.81      A  C
ATOM   1978  CB   ILE A 892      68.768  67.004   4.613  1.00 20.38      A  C
ATOM   1979  CG2  ILE A 892      69.915  66.962   3.569  1.00 22.73      A  C
ATOM   1980  CG1  ILE A 892      67.992  68.319   4.510  1.00 22.65      A  C
ATOM   1981  CD1  ILE A 892      68.856  69.559   4.769  1.00 25.84      A  C
ATOM   1982  C    ILE A 892      68.539  64.497   4.514  1.00 27.24      A  C
ATOM   1983  O    ILE A 892      69.102  64.167   5.558  1.00 28.45      A  O
ATOM   1984  N    PRO A 893      68.558  63.718   3.422  1.00 25.37      A  N
ATOM   1985  CD   PRO A 893      67.850  63.921   2.136  1.00 36.37      A  C
ATOM   1986  CA   PRO A 893      69.246  62.421   3.444  1.00 22.06      A  C
ATOM   1987  CB   PRO A 893      68.649  61.689   2.238  1.00 25.09      A  C
ATOM   1988  CG   PRO A 893      68.436  62.824   1.248  1.00 27.00      A  C
ATOM   1989  C    PRO A 893      70.761  62.545   3.332  1.00 25.30      A  C
ATOM   1990  O    PRO A 893      71.284  63.575   2.902  1.00 19.86      A  O
ATOM   1991  N    VAL A 894      71.463  61.493   3.742  1.00 21.26      A  N
ATOM   1992  CA   VAL A 894      72.914  61.487   3.604  1.00 26.11      A  C
ATOM   1993  CB   VAL A 894      73.607  60.684   4.731  1.00 25.42      A  C
ATOM   1994  CG1  VAL A 894      75.124  60.729   4.531  1.00 23.77      A  C
ATOM   1995  CG2  VAL A 894      73.228  61.268   6.087  1.00 27.16      A  C
ATOM   1996  C    VAL A 894      73.239  60.843   2.250  1.00 25.07      A  C
ATOM   1997  O    VAL A 894      72.999  59.658   2.044  1.00 25.02      A  O
ATOM   1998  N    ASP A 895      73.757  61.651   1.330  1.00 27.26      A  N
ATOM   1999  CA   ASP A 895      74.135  61.213  -0.014  1.00 31.10      A  C
ATOM   2000  CB   ASP A 895      72.898  61.138  -0.937  1.00 23.41      A  C
ATOM   2001  CG   ASP A 895      72.099  62.468  -1.025  1.00 25.35      A  C
ATOM   2002  OD1  ASP A 895      72.619  63.560  -0.660  1.00 25.98      A  O
ATOM   2003  OD2  ASP A 895      70.922  62.409  -1.486  1.00 28.29      A  O
ATOM   2004  C    ASP A 895      75.169  62.224  -0.529  1.00 33.07      A  C
ATOM   2005  O    ASP A 895      75.597  63.090   0.236  1.00 29.37      A  O
ATOM   2006  N    ALA A 896      75.580  62.128  -1.794  1.00 30.31      A  N
ATOM   2007  CA   ALA A 896      76.578  63.071  -2.340  1.00 27.93      A  C
ATOM   2008  CB   ALA A 896      76.869  62.777  -3.837  1.00 24.53      A  C
ATOM   2009  C    ALA A 896      76.139  64.533  -2.175  1.00 20.55      A  C
ATOM   2010  O    ALA A 896      76.974  65.404  -1.955  1.00 26.11      A  O
ATOM   2011  N    ASN A 897      74.836  64.805  -2.292  1.00 18.45      A  N
ATOM   2012  CA   ASN A 897      74.352  66.185  -2.112  1.00 19.04      A  C
ATOM   2013  CB   ASN A 897      72.865  66.300  -2.496  1.00 20.38      A  C
ATOM   2014  CG   ASN A 897      72.648  66.199  -4.002  1.00 29.50      A  C
ATOM   2015  OD1  ASN A 897      73.551  66.474  -4.773  1.00 24.88      A  O
ATOM   2016  ND2  ASN A 897      71.455  65.821  -4.416  1.00 18.50      A  N
ATOM   2017  C    ASN A 897      74.531  66.691  -0.665  1.00 23.49      A  C
ATOM   2018  O    ASN A 897      74.645  67.894  -0.436  1.00 25.13      A  O
ATOM   2019  N    PHE A 898      74.522  65.791   0.314  1.00 27.16      A  N
ATOM   2020  CA   PHE A 898      74.700  66.237   1.693  1.00 22.66      A  C
ATOM   2021  CB   PHE A 898      74.462  65.108   2.701  1.00 24.49      A  C
ATOM   2022  CG   PHE A 898      74.727  65.528   4.116  1.00 24.86      A  C
ATOM   2023  CD1  PHE A 898      75.979  65.320   4.690  1.00 26.32      A  C
ATOM   2024  CD2  PHE A 898      73.778  66.273   4.820  1.00 24.30      A  C
```

FIGURE 1A-37

```
ATOM   2025  CE1  PHE A 898      76.288  65.863   5.941  1.00 33.49      A  C
ATOM   2026  CE2  PHE A 898      74.077  66.821   6.066  1.00 27.99      A  C
ATOM   2027  CZ   PHE A 898      75.345  66.615   6.626  1.00 20.22      A  C
ATOM   2028  C    PHE A 898      76.131  66.768   1.858  1.00 21.36      A  C
ATOM   2029  O    PHE A 898      76.346  67.833   2.453  1.00 22.32      A  O
ATOM   2030  N    TYR A 899      77.101  66.027   1.313  1.00 25.68      A  N
ATOM   2031  CA   TYR A 899      78.493  66.458   1.402  1.00 31.27      A  C
ATOM   2032  CB   TYR A 899      79.437  65.414   0.798  1.00 35.72      A  C
ATOM   2033  CG   TYR A 899      79.474  64.135   1.599  1.00 46.03      A  C
ATOM   2034  CD1  TYR A 899      78.488  63.169   1.439  1.00 56.64      A  C
ATOM   2035  CE1  TYR A 899      78.481  62.010   2.198  1.00 52.46      A  C
ATOM   2036  CD2  TYR A 899      80.467  63.906   2.551  1.00 53.32      A  C
ATOM   2037  CE2  TYR A 899      80.466  62.742   3.324  1.00 57.81      A  C
ATOM   2038  CZ   TYR A 899      79.465  61.802   3.132  1.00 55.17      A  C
ATOM   2039  OH   TYR A 899      79.443  60.636   3.850  1.00 64.63      A  O
ATOM   2040  C    TYR A 899      78.686  67.800   0.713  1.00 34.70      A  C
ATOM   2041  O    TYR A 899      79.382  68.673   1.240  1.00 24.73      A  O
ATOM   2042  N    LYS A 900      78.060  67.975  -0.454  1.00 24.76      A  N
ATOM   2043  CA   LYS A 900      78.179  69.243  -1.175  1.00 22.75      A  C
ATOM   2044  CB   LYS A 900      77.512  69.139  -2.557  1.00 28.16      A  C
ATOM   2045  CG   LYS A 900      78.305  68.310  -3.565  1.00 37.25      A  C
ATOM   2046  CD   LYS A 900      77.544  68.095  -4.880  1.00 46.61      A  C
ATOM   2047  CE   LYS A 900      77.137  69.406  -5.561  1.00 32.60      A  C
ATOM   2048  NZ   LYS A 900      76.505  69.093  -6.879  1.00 38.79      A  N
ATOM   2049  C    LYS A 900      77.567  70.399  -0.377  1.00 21.79      A  C
ATOM   2050  O    LYS A 900      78.105  71.502  -0.370  1.00 28.31      A  O
ATOM   2051  N    LEU A 901      76.443  70.141   0.285  1.00 24.60      A  N
ATOM   2052  CA   LEU A 901      75.781  71.153   1.111  1.00 29.33      A  C
ATOM   2053  CB   LEU A 901      74.581  70.556   1.865  1.00 30.27      A  C
ATOM   2054  CG   LEU A 901      73.242  70.277   1.197  1.00 49.63      A  C
ATOM   2055  CD1  LEU A 901      72.241  69.854   2.274  1.00 40.30      A  C
ATOM   2056  CD2  LEU A 901      72.747  71.534   0.477  1.00 53.28      A  C
ATOM   2057  C    LEU A 901      76.762  71.679   2.170  1.00 22.72      A  C
ATOM   2058  O    LEU A 901      76.930  72.888   2.335  1.00 27.81      A  O
ATOM   2059  N    ILE A 902      77.349  70.753   2.926  1.00 27.82      A  N
ATOM   2060  CA   ILE A 902      78.304  71.112   3.969  1.00 26.95      A  C
ATOM   2061  CB   ILE A 902      78.871  69.857   4.679  1.00 24.42      A  C
ATOM   2062  CG2  ILE A 902      79.861  70.274   5.737  1.00 25.25      A  C
ATOM   2063  CG1  ILE A 902      77.728  69.080   5.337  1.00 23.50      A  C
ATOM   2064  CD1  ILE A 902      76.995  69.873   6.442  1.00 27.38      A  C
ATOM   2065  C    ILE A 902      79.460  71.898   3.350  1.00 29.55      A  C
ATOM   2066  O    ILE A 902      79.785  72.982   3.804  1.00 25.36      A  O
ATOM   2067  N    GLN A 903      80.063  71.350   2.302  1.00 32.67      A  N
ATOM   2068  CA   GLN A 903      81.170  72.026   1.623  1.00 31.83      A  C
ATOM   2069  CB   GLN A 903      81.561  71.249   0.367  1.00 35.18      A  C
ATOM   2070  CG   GLN A 903      82.565  71.960  -0.513  1.00 49.47      A  C
ATOM   2071  CD   GLN A 903      83.948  72.052   0.128  1.00 63.68      A  C
ATOM   2072  OE1  GLN A 903      84.723  72.967  -0.166  1.00 62.60      A  O
ATOM   2073  NE2  GLN A 903      84.265  71.096   0.996  1.00 58.43      A  N
ATOM   2074  C    GLN A 903      80.814  73.466   1.231  1.00 29.31      A  C
ATOM   2075  O    GLN A 903      81.658  74.360   1.289  1.00 34.99      A  O
ATOM   2076  N    ASN A 904      79.562  73.691   0.832  1.00 28.88      A  N
ATOM   2077  CA   ASN A 904      79.127  75.023   0.421  1.00 28.87      A  C
ATOM   2078  CB   ASN A 904      77.928  74.920  -0.517  1.00 31.76      A  C
ATOM   2079  CG   ASN A 904      78.306  74.404  -1.890  1.00 40.35      A  C
ATOM   2080  OD1  ASN A 904      77.728  73.442  -2.376  1.00 44.43      A  O
```

FIGURE 1A-38

```
ATOM   2081  ND2 ASN A 904      79.276  75.053  -2.526  1.00 34.88      A N
ATOM   2082  C   ASN A 904      78.780  75.964   1.571  1.00 30.49      A C
ATOM   2083  O   ASN A 904      78.469  77.109   1.335  1.00 29.38      A O
ATOM   2084  N   GLY A 905      78.782  75.482   2.807  1.00 29.66      A N
ATOM   2085  CA  GLY A 905      78.489  76.383   3.919  1.00 27.05      A C
ATOM   2086  C   GLY A 905      77.075  76.351   4.459  1.00 27.49      A C
ATOM   2087  O   GLY A 905      76.696  77.181   5.281  1.00 27.57      A O
ATOM   2088  N   PHE A 906      76.291  75.384   4.001  1.00 23.53      A N
ATOM   2089  CA  PHE A 906      74.908  75.219   4.476  1.00 29.09      A C
ATOM   2090  CB  PHE A 906      74.285  73.992   3.786  1.00 24.65      A C
ATOM   2091  CG  PHE A 906      72.806  73.819   4.036  1.00 30.84      A C
ATOM   2092  CD1 PHE A 906      71.880  74.273   3.114  1.00 30.82      A C
ATOM   2093  CD2 PHE A 906      72.348  73.152   5.173  1.00 28.48      A C
ATOM   2094  CE1 PHE A 906      70.512  74.063   3.309  1.00 32.41      A C
ATOM   2095  CE2 PHE A 906      70.987  72.940   5.372  1.00 32.43      A C
ATOM   2096  CZ  PHE A 906      70.071  73.396   4.437  1.00 29.36      A C
ATOM   2097  C   PHE A 906      74.912  75.001   6.002  1.00 33.07      A C
ATOM   2098  O   PHE A 906      75.723  74.230   6.517  1.00 31.41      A O
ATOM   2099  N   LYS A 907      74.007  75.686   6.703  1.00 31.29      A N
ATOM   2100  CA  LYS A 907      73.858  75.581   8.157  1.00 34.28      A C
ATOM   2101  CB  LYS A 907      74.423  76.814   8.869  1.00 28.65      A C
ATOM   2102  CG  LYS A 907      75.943  76.948   8.843  1.00 30.44      A C
ATOM   2103  CD  LYS A 907      76.350  78.282   9.467  1.00 36.22      A C
ATOM   2104  CE  LYS A 907      77.790  78.641   9.159  1.00 41.15      A C
ATOM   2105  NZ  LYS A 907      77.994  78.800   7.687  1.00 58.93      A N
ATOM   2106  C   LYS A 907      72.381  75.463   8.529  1.00 32.83      A C
ATOM   2107  O   LYS A 907      71.499  75.970   7.828  1.00 29.75      A O
ATOM   2108  N   MET A 908      72.112  74.800   9.644  1.00 31.57      A N
ATOM   2109  CA  MET A 908      70.740  74.636  10.085  1.00 27.84      A C
ATOM   2110  CB  MET A 908      70.647  73.614  11.224  1.00 26.24      A C
ATOM   2111  CG  MET A 908      70.849  72.152  10.795  1.00 24.69      A C
ATOM   2112  SD  MET A 908      70.479  71.005  12.127  1.00 25.81      A S
ATOM   2113  CE  MET A 908      72.092  70.931  13.010  1.00 14.17      A C
ATOM   2114  C   MET A 908      70.172  75.950  10.579  1.00 28.41      A C
ATOM   2115  O   MET A 908      70.919  76.841  10.998  1.00 27.04      A O
ATOM   2116  N   ASP A 909      68.842  76.034  10.541  1.00 27.28      A N
ATOM   2117  CA  ASP A 909      68.089  77.178  11.034  1.00 34.02      A C
ATOM   2118  CB  ASP A 909      66.650  77.124  10.529  1.00 35.56      A C
ATOM   2119  CG  ASP A 909      66.549  77.319   9.040  1.00 39.92      A C
ATOM   2120  OD1 ASP A 909      65.662  76.690   8.428  1.00 49.21      A O
ATOM   2121  OD2 ASP A 909      67.351  78.105   8.492  1.00 36.71      A O
ATOM   2122  C   ASP A 909      68.035  77.124  12.556  1.00 33.08      A C
ATOM   2123  O   ASP A 909      68.305  76.084  13.173  1.00 27.48      A O
ATOM   2124  N   GLN A 910      67.655  78.245  13.156  1.00 35.25      A N
ATOM   2125  CA  GLN A 910      67.530  78.336  14.606  1.00 27.39      A C
ATOM   2126  CB  GLN A 910      67.211  79.785  14.994  1.00 31.14      A C
ATOM   2127  CG  GLN A 910      66.867  79.994  16.468  1.00 38.19      A C
ATOM   2128  CD  GLN A 910      66.651  81.474  16.819  1.00 39.30      A C
ATOM   2129  OE1 GLN A 910      66.023  81.792  17.825  1.00 44.51      A O
ATOM   2130  NE2 GLN A 910      67.191  82.371  15.999  1.00 39.08      A N
ATOM   2131  C   GLN A 910      66.416  77.400  15.085  1.00 29.34      A C
ATOM   2132  O   GLN A 910      65.278  77.500  14.635  1.00 32.68      A O
ATOM   2133  N   PRO A 911      66.734  76.454  15.987  1.00 28.80      A N
ATOM   2134  CD  PRO A 911      68.033  76.165  16.625  1.00 31.10      A C
ATOM   2135  CA  PRO A 911      65.683  75.551  16.464  1.00 25.54      A C
ATOM   2136  CB  PRO A 911      66.468  74.455  17.180  1.00 28.54      A C
```

FIGURE 1A-39

| | | | | | | | | | | |
|---|---|---|---|---|---|---|---|---|---|---|
| ATOM | 2137 | CG | PRO | A | 911 | 67.659 | 75.206 | 17.727 | 1.00 26.37 | A C |
| ATOM | 2138 | C | PRO | A | 911 | 64.712 | 76.318 | 17.376 | 1.00 31.06 | A C |
| ATOM | 2139 | O | PRO | A | 911 | 65.057 | 77.385 | 17.905 | 1.00 30.40 | A O |
| ATOM | 2140 | N | PHE | A | 912 | 63.510 | 75.776 | 17.556 | 1.00 28.38 | A N |
| ATOM | 2141 | CA | PHE | A | 912 | 62.470 | 76.437 | 18.339 | 1.00 34.79 | A C |
| ATOM | 2142 | CB | PHE | A | 912 | 61.241 | 75.526 | 18.452 | 1.00 35.20 | A C |
| ATOM | 2143 | CG | PHE | A | 912 | 60.047 | 76.197 | 19.084 | 1.00 48.10 | A C |
| ATOM | 2144 | CD1 | PHE | A | 912 | 59.320 | 77.162 | 18.382 | 1.00 41.80 | A C |
| ATOM | 2145 | CD2 | PHE | A | 912 | 59.678 | 75.901 | 20.403 | 1.00 45.27 | A C |
| ATOM | 2146 | CE1 | PHE | A | 912 | 58.237 | 77.834 | 18.985 | 1.00 48.49 | A C |
| ATOM | 2147 | CE2 | PHE | A | 912 | 58.597 | 76.563 | 21.022 | 1.00 47.03 | A C |
| ATOM | 2148 | CZ | PHE | A | 912 | 57.876 | 77.533 | 20.310 | 1.00 49.43 | A C |
| ATOM | 2149 | C | PHE | A | 912 | 62.854 | 76.942 | 19.741 | 1.00 43.32 | A C |
| ATOM | 2150 | O | PHE | A | 912 | 62.626 | 78.109 | 20.065 | 1.00 39.88 | A O |
| ATOM | 2151 | N | TYR | A | 913 | 63.436 | 76.086 | 20.574 | 1.00 37.92 | A N |
| ATOM | 2152 | CA | TYR | A | 913 | 63.783 | 76.512 | 21.926 | 1.00 34.44 | A C |
| ATOM | 2153 | CB | TYR | A | 913 | 63.859 | 75.299 | 22.836 | 1.00 25.54 | A C |
| ATOM | 2154 | CG | TYR | A | 913 | 62.581 | 74.504 | 22.797 | 1.00 30.88 | A C |
| ATOM | 2155 | CD1 | TYR | A | 913 | 62.434 | 73.418 | 21.939 | 1.00 31.68 | A C |
| ATOM | 2156 | CE1 | TYR | A | 913 | 61.224 | 72.711 | 21.865 | 1.00 29.09 | A C |
| ATOM | 2157 | CD2 | TYR | A | 913 | 61.490 | 74.873 | 23.588 | 1.00 37.57 | A C |
| ATOM | 2158 | CE2 | TYR | A | 913 | 60.285 | 74.180 | 23.523 | 1.00 33.58 | A C |
| ATOM | 2159 | CZ | TYR | A | 913 | 60.156 | 73.106 | 22.666 | 1.00 39.62 | A C |
| ATOM | 2160 | OH | TYR | A | 913 | 58.953 | 72.438 | 22.605 | 1.00 34.38 | A O |
| ATOM | 2161 | C | TYR | A | 913 | 65.025 | 77.368 | 22.093 | 1.00 33.44 | A C |
| ATOM | 2162 | O | TYR | A | 913 | 65.326 | 77.802 | 23.198 | 1.00 39.89 | A O |
| ATOM | 2163 | N | ALA | A | 914 | 65.758 | 77.620 | 21.015 | 1.00 33.79 | A N |
| ATOM | 2164 | CA | ALA | A | 914 | 66.940 | 78.454 | 21.154 | 1.00 33.55 | A C |
| ATOM | 2165 | CB | ALA | A | 914 | 67.947 | 78.134 | 20.070 | 1.00 32.85 | A C |
| ATOM | 2166 | C | ALA | A | 914 | 66.557 | 79.931 | 21.077 | 1.00 42.71 | A C |
| ATOM | 2167 | O | ALA | A | 914 | 65.547 | 80.298 | 20.482 | 1.00 43.08 | A O |
| ATOM | 2168 | N | THR | A | 915 | 67.371 | 80.772 | 21.697 | 1.00 37.72 | A N |
| ATOM | 2169 | CA | THR | A | 915 | 67.154 | 82.210 | 21.675 | 1.00 41.95 | A C |
| ATOM | 2170 | CB | THR | A | 915 | 67.613 | 82.872 | 23.006 | 1.00 39.56 | A C |
| ATOM | 2171 | OG1 | THR | A | 915 | 68.951 | 82.453 | 23.298 | 1.00 39.24 | A O |
| ATOM | 2172 | CG2 | THR | A | 915 | 66.703 | 82.458 | 24.162 | 1.00 30.17 | A C |
| ATOM | 2173 | C | THR | A | 915 | 68.092 | 82.596 | 20.558 | 1.00 43.78 | A C |
| ATOM | 2174 | O | THR | A | 915 | 68.870 | 81.751 | 20.101 | 1.00 42.43 | A O |
| ATOM | 2175 | N | GLU | A | 916 | 68.035 | 83.846 | 20.111 | 1.00 43.13 | A N |
| ATOM | 2176 | CA | GLU | A | 916 | 68.912 | 84.277 | 19.034 | 1.00 43.91 | A C |
| ATOM | 2177 | CB | GLU | A | 916 | 68.527 | 85.671 | 18.549 | 1.00 52.02 | A C |
| ATOM | 2178 | CG | GLU | A | 916 | 69.257 | 86.073 | 17.282 | 1.00 69.47 | A C |
| ATOM | 2179 | CD | GLU | A | 916 | 69.386 | 87.572 | 17.125 | 1.00 79.04 | A C |
| ATOM | 2180 | OE1 | GLU | A | 916 | 69.911 | 88.018 | 16.079 | 1.00 83.99 | A O |
| ATOM | 2181 | OE2 | GLU | A | 916 | 68.970 | 88.304 | 18.050 | 1.00 80.31 | A O |
| ATOM | 2182 | C | GLU | A | 916 | 70.386 | 84.281 | 19.452 | 1.00 47.14 | A C |
| ATOM | 2183 | O | GLU | A | 916 | 71.261 | 84.045 | 18.621 | 1.00 46.68 | A O |
| ATOM | 2184 | N | GLU | A | 917 | 70.662 | 84.559 | 20.727 | 1.00 41.41 | A N |
| ATOM | 2185 | CA | GLU | A | 917 | 72.050 | 84.586 | 21.219 | 1.00 45.27 | A C |
| ATOM | 2186 | CB | GLU | A | 917 | 72.126 | 85.104 | 22.666 | 1.00 46.81 | A C |
| ATOM | 2187 | CG | GLU | A | 917 | 71.342 | 86.384 | 22.942 | 1.00 58.36 | A C |
| ATOM | 2188 | CD | GLU | A | 917 | 69.841 | 86.131 | 23.065 | 1.00 73.36 | A C |
| ATOM | 2189 | OE1 | GLU | A | 917 | 69.087 | 86.470 | 22.121 | 1.00 65.38 | A O |
| ATOM | 2190 | OE2 | GLU | A | 917 | 69.419 | 85.580 | 24.112 | 1.00 79.68 | A O |
| ATOM | 2191 | C | GLU | A | 917 | 72.647 | 83.176 | 21.156 | 1.00 33.48 | A C |
| ATOM | 2192 | O | GLU | A | 917 | 73.789 | 82.994 | 20.733 | 1.00 40.49 | A O |

FIGURE 1A-40

```
ATOM   2193  N   ILE A 918      71.872  82.188  21.592  1.00 36.06      A N
ATOM   2194  CA  ILE A 918      72.322  80.803  21.535  1.00 40.18      A C
ATOM   2195  CB  ILE A 918      71.295  79.861  22.182  1.00 38.47      A C
ATOM   2196  CG2 ILE A 918      71.581  78.414  21.792  1.00 31.19      A C
ATOM   2197  CG1 ILE A 918      71.357  80.021  23.711  1.00 41.68      A C
ATOM   2198  CD1 ILE A 918      70.344  79.195  24.454  1.00 47.45      A C
ATOM   2199  C   ILE A 918      72.561  80.399  20.072  1.00 45.43      A C
ATOM   2200  O   ILE A 918      73.567  79.762  19.760  1.00 48.76      A O
ATOM   2201  N   TYR A 919      71.661  80.803  19.176  1.00 41.55      A N
ATOM   2202  CA  TYR A 919      71.808  80.464  17.762  1.00 38.07      A C
ATOM   2203  CB  TYR A 919      70.579  80.903  16.958  1.00 35.71      A C
ATOM   2204  CG  TYR A 919      70.663  80.500  15.507  1.00 34.75      A C
ATOM   2205  CD1 TYR A 919      70.879  79.164  15.148  1.00 31.63      A C
ATOM   2206  CE1 TYR A 919      70.973  78.781  13.817  1.00 33.76      A C
ATOM   2207  CD2 TYR A 919      70.541  81.444  14.491  1.00 35.97      A C
ATOM   2208  CE2 TYR A 919      70.633  81.071  13.148  1.00 38.32      A C
ATOM   2209  CZ  TYR A 919      70.850  79.731  12.823  1.00 37.78      A C
ATOM   2210  OH  TYR A 919      70.944  79.346  11.507  1.00 36.76      A O
ATOM   2211  C   TYR A 919      73.054  81.085  17.156  1.00 36.79      A C
ATOM   2212  O   TYR A 919      73.676  80.507  16.261  1.00 38.14      A O
ATOM   2213  N   ILE A 920      73.418  82.272  17.631  1.00 41.15      A N
ATOM   2214  CA  ILE A 920      74.620  82.938  17.130  1.00 39.43      A C
ATOM   2215  CB  ILE A 920      74.746  84.379  17.703  1.00 49.25      A C
ATOM   2216  CG2 ILE A 920      76.143  84.930  17.444  1.00 39.69      A C
ATOM   2217  CG1 ILE A 920      73.690  85.289  17.064  1.00 52.36      A C
ATOM   2218  CD1 ILE A 920      73.615  86.684  17.694  1.00 45.94      A C
ATOM   2219  C   ILE A 920      75.845  82.111  17.544  1.00 37.36      A C
ATOM   2220  O   ILE A 920      76.832  82.026  16.819  1.00 39.26      A O
ATOM   2221  N   ILE A 921      75.766  81.504  18.719  1.00 36.25      A N
ATOM   2222  CA  ILE A 921      76.844  80.666  19.219  1.00 40.37      A C
ATOM   2223  CB  ILE A 921      76.600  80.311  20.708  1.00 40.80      A C
ATOM   2224  CG2 ILE A 921      77.451  79.123  21.121  1.00 34.51      A C
ATOM   2225  CG1 ILE A 921      76.899  81.537  21.579  1.00 37.03      A C
ATOM   2226  CD1 ILE A 921      76.492  81.359  23.036  1.00 55.72      A C
ATOM   2227  C   ILE A 921      76.910  79.400  18.354  1.00 35.36      A C
ATOM   2228  O   ILE A 921      77.989  78.984  17.929  1.00 37.55      A O
ATOM   2229  N   MET A 922      75.751  78.807  18.081  1.00 33.76      A N
ATOM   2230  CA  MET A 922      75.685  77.616  17.233  1.00 35.92      A C
ATOM   2231  CB  MET A 922      74.236  77.223  16.936  1.00 35.18      A C
ATOM   2232  CG  MET A 922      73.490  76.543  18.036  1.00 40.08      A C
ATOM   2233  SD  MET A 922      71.865  76.044  17.411  1.00 40.93      A S
ATOM   2234  CE  MET A 922      71.012  75.827  18.953  1.00 42.86      A C
ATOM   2235  C   MET A 922      76.352  77.867  15.889  1.00 31.02      A C
ATOM   2236  O   MET A 922      77.159  77.061  15.436  1.00 33.94      A O
ATOM   2237  N   GLN A 923      75.967  78.975  15.245  1.00 34.07      A N
ATOM   2238  CA  GLN A 923      76.490  79.349  13.940  1.00 30.72      A C
ATOM   2239  CB  GLN A 923      75.853  80.662  13.454  1.00 37.12      A C
ATOM   2240  CG  GLN A 923      74.407  80.535  12.974  1.00 42.22      A C
ATOM   2241  CD  GLN A 923      73.795  81.888  12.595  1.00 56.46      A C
ATOM   2242  OE1 GLN A 923      73.666  82.786  13.433  1.00 52.35      A O
ATOM   2243  NE2 GLN A 923      73.420  82.034  11.333  1.00 48.89      A N
ATOM   2244  C   GLN A 923      78.006  79.504  13.916  1.00 31.46      A C
ATOM   2245  O   GLN A 923      78.641  79.152  12.937  1.00 29.99      A O
ATOM   2246  N   SER A 924      78.579  80.059  14.979  1.00 31.87      A N
ATOM   2247  CA  SER A 924      80.024  80.247  15.032  1.00 31.47      A C
ATOM   2248  CB  SER A 924      80.408  81.163  16.207  1.00 38.21      A C
```

FIGURE 1A-41

```
ATOM   2249  OG   SER A 924      80.049  80.583  17.450  1.00 47.25      A    O
ATOM   2250  C    SER A 924      80.701  78.884  15.182  1.00 26.79      A    C
ATOM   2251  O    SER A 924      81.827  78.689  14.728  1.00 30.24      A    O
ATOM   2252  N    CYS A 925      80.010  77.934  15.815  1.00 25.59      A    N
ATOM   2253  CA   CYS A 925      80.592  76.602  15.957  1.00 28.34      A    C
ATOM   2254  CB   CYS A 925      79.730  75.719  16.864  1.00 31.37      A    C
ATOM   2255  SG   CYS A 925      79.788  76.126  18.643  1.00 33.43      A    S
ATOM   2256  C    CYS A 925      80.699  75.955  14.584  1.00 31.80      A    C
ATOM   2257  O    CYS A 925      81.521  75.062  14.375  1.00 26.21      A    O
ATOM   2258  N    TRP A 926      79.876  76.424  13.643  1.00 30.88      A    N
ATOM   2259  CA   TRP A 926      79.852  75.854  12.297  1.00 33.46      A    C
ATOM   2260  CB   TRP A 926      78.388  75.664  11.829  1.00 25.22      A    C
ATOM   2261  CG   TRP A 926      77.543  74.793  12.784  1.00 22.83      A    C
ATOM   2262  CD2  TRP A 926      76.136  74.930  13.061  1.00 23.07      A    C
ATOM   2263  CE2  TRP A 926      75.788  73.925  13.987  1.00 24.03      A    C
ATOM   2264  CE3  TRP A 926      75.138  75.809  12.610  1.00 30.17      A    C
ATOM   2265  CD1  TRP A 926      77.976  73.730  13.541  1.00 23.38      A    C
ATOM   2266  NE1  TRP A 926      76.925  73.206  14.273  1.00 22.81      A    N
ATOM   2267  CZ2  TRP A 926      74.487  73.773  14.469  1.00 22.27      A    C
ATOM   2268  CZ3  TRP A 926      73.841  75.654  13.093  1.00 23.49      A    C
ATOM   2269  CH2  TRP A 926      73.533  74.644  14.010  1.00 26.69      A    C
ATOM   2270  C    TRP A 926      80.653  76.651  11.266  1.00 33.51      A    C
ATOM   2271  O    TRP A 926      80.376  76.606  10.067  1.00 35.07      A    O
ATOM   2272  N    ALA A 927      81.657  77.383  11.731  1.00 35.20      A    N
ATOM   2273  CA   ALA A 927      82.492  78.145  10.815  1.00 32.44      A    C
ATOM   2274  CB   ALA A 927      83.473  79.038  11.593  1.00 30.72      A    C
ATOM   2275  C    ALA A 927      83.227  77.072  10.035  1.00 36.38      A    C
ATOM   2276  O    ALA A 927      83.733  76.115  10.621  1.00 29.85      A    O
ATOM   2277  N    PHE A 928      83.271  77.210   8.714  1.00 33.16      A    N
ATOM   2278  CA   PHE A 928      83.930  76.202   7.892  1.00 32.30      A    C
ATOM   2279  CB   PHE A 928      83.820  76.570   6.405  1.00 28.44      A    C
ATOM   2280  CG   PHE A 928      84.149  75.431   5.485  1.00 34.72      A    C
ATOM   2281  CD1  PHE A 928      83.186  74.479   5.163  1.00 34.80      A    C
ATOM   2282  CD2  PHE A 928      85.438  75.271   4.991  1.00 37.18      A    C
ATOM   2283  CE1  PHE A 928      83.507  73.381   4.365  1.00 38.58      A    C
ATOM   2284  CE2  PHE A 928      85.768  74.174   4.191  1.00 35.33      A    C
ATOM   2285  CZ   PHE A 928      84.801  73.230   3.881  1.00 32.57      A    C
ATOM   2286  C    PHE A 928      85.405  76.076   8.294  1.00 37.00      A    C
ATOM   2287  O    PHE A 928      85.945  74.970   8.448  1.00 32.54      A    O
ATOM   2288  N    ASP A 929      86.038  77.234   8.453  1.00 33.68      A    N
ATOM   2289  CA   ASP A 929      87.443  77.361   8.839  1.00 38.69      A    C
ATOM   2290  CB   ASP A 929      87.886  78.797   8.536  1.00 38.64      A    C
ATOM   2291  CG   ASP A 929      89.351  79.053   8.832  1.00 46.76      A    C
ATOM   2292  OD1  ASP A 929      89.838  80.115   8.385  1.00 48.27      A    O
ATOM   2293  OD2  ASP A 929      90.009  78.226   9.502  1.00 41.95      A    O
ATOM   2294  C    ASP A 929      87.515  77.071  10.334  1.00 31.10      A    C
ATOM   2295  O    ASP A 929      86.965  77.824  11.133  1.00 32.25      A    O
ATOM   2296  N    SER A 930      88.187  75.992  10.718  1.00 34.66      A    N
ATOM   2297  CA   SER A 930      88.263  75.631  12.138  1.00 39.29      A    C
ATOM   2298  CB   SER A 930      89.085  74.351  12.325  1.00 31.30      A    C
ATOM   2299  OG   SER A 930      90.439  74.544  11.957  1.00 37.65      A    O
ATOM   2300  C    SER A 930      88.809  76.727  13.057  1.00 41.98      A    C
ATOM   2301  O    SER A 930      88.396  76.823  14.214  1.00 35.59      A    O
ATOM   2302  N    ARG A 931      89.730  77.546  12.543  1.00 42.29      A    N
ATOM   2303  CA   ARG A 931      90.325  78.640  13.325  1.00 39.99      A    C
ATOM   2304  CB   ARG A 931      91.389  79.391  12.512  1.00 46.23      A    C
```

FIGURE 1A-42

```
ATOM   2305  CG   ARG A  931      92.647  78.614  12.185  1.00 47.81      A    C
ATOM   2306  CD   ARG A  931      92.420  77.618  11.066  1.00 73.98      A    C
ATOM   2307  NE   ARG A  931      93.673  77.026  10.597  1.00 87.97      A    N
ATOM   2308  CZ   ARG A  931      94.484  76.280  11.345  1.00 92.77      A    C
ATOM   2309  NH1  ARG A  931      94.180  76.024  12.613  1.00 96.94      A    N
ATOM   2310  NH2  ARG A  931      95.603  75.791  10.824  1.00 85.81      A    N
ATOM   2311  C    ARG A  931      89.284  79.657  13.770  1.00 41.62      A    C
ATOM   2312  O    ARG A  931      89.429  80.282  14.812  1.00 43.79      A    O
ATOM   2313  N    LYS A  932      88.232  79.823  12.975  1.00 42.96      A    N
ATOM   2314  CA   LYS A  932      87.194  80.796  13.293  1.00 36.50      A    C
ATOM   2315  CB   LYS A  932      86.458  81.211  12.017  1.00 46.92      A    C
ATOM   2316  CG   LYS A  932      87.364  81.824  10.949  1.00 48.43      A    C
ATOM   2317  CD   LYS A  932      86.562  82.237   9.724  1.00 63.51      A    C
ATOM   2318  CE   LYS A  932      87.457  82.868   8.668  1.00 75.19      A    C
ATOM   2319  NZ   LYS A  932      88.218  84.034   9.214  1.00 82.48      A    N
ATOM   2320  C    LYS A  932      86.180  80.362  14.333  1.00 34.91      A    C
ATOM   2321  O    LYS A  932      85.417  81.183  14.819  1.00 40.88      A    O
ATOM   2322  N    ARG A  933      86.159  79.077  14.674  1.00 32.86      A    N
ATOM   2323  CA   ARG A  933      85.215  78.576  15.667  1.00 37.09      A    C
ATOM   2324  CB   ARG A  933      85.126  77.042  15.610  1.00 33.08      A    C
ATOM   2325  CG   ARG A  933      84.797  76.495  14.221  1.00 31.62      A    C
ATOM   2326  CD   ARG A  933      84.907  74.971  14.122  1.00 37.77      A    C
ATOM   2327  NE   ARG A  933      84.927  74.605  12.716  1.00 28.41      A    N
ATOM   2328  CZ   ARG A  933      85.432  73.489  12.209  1.00 31.12      A    C
ATOM   2329  NH1  ARG A  933      85.974  72.560  12.989  1.00 30.45      A    N
ATOM   2330  NH2  ARG A  933      85.451  73.341  10.894  1.00 28.26      A    N
ATOM   2331  C    ARG A  933      85.678  78.972  17.048  1.00 37.84      A    C
ATOM   2332  O    ARG A  933      86.864  79.162  17.278  1.00 34.22      A    O
ATOM   2333  N    PRO A  934      84.742  79.112  17.990  1.00 37.96      A    N
ATOM   2334  CD   PRO A  934      83.273  79.149  17.872  1.00 33.68      A    C
ATOM   2335  CA   PRO A  934      85.177  79.479  19.334  1.00 38.11      A    C
ATOM   2336  CB   PRO A  934      83.881  79.905  20.011  1.00 36.78      A    C
ATOM   2337  CG   PRO A  934      82.836  79.055  19.307  1.00 36.27      A    C
ATOM   2338  C    PRO A  934      85.827  78.283  20.033  1.00 43.86      A    C
ATOM   2339  O    PRO A  934      85.776  77.142  19.559  1.00 35.18      A    O
ATOM   2340  N    SER A  935      86.440  78.557  21.171  1.00 40.28      A    N
ATOM   2341  CA   SER A  935      87.095  77.525  21.949  1.00 37.76      A    C
ATOM   2342  CB   SER A  935      88.343  78.110  22.628  1.00 40.88      A    C
ATOM   2343  OG   SER A  935      87.958  79.053  23.624  1.00 38.91      A    O
ATOM   2344  C    SER A  935      86.111  77.067  23.021  1.00 29.10      A    C
ATOM   2345  O    SER A  935      85.142  77.768  23.337  1.00 34.08      A    O
ATOM   2346  N    PHE A  936      86.370  75.908  23.611  1.00 29.14      A    N
ATOM   2347  CA   PHE A  936      85.490  75.440  24.654  1.00 36.41      A    C
ATOM   2348  CB   PHE A  936      85.810  73.986  24.999  1.00 34.33      A    C
ATOM   2349  CG   PHE A  936      85.186  73.018  24.037  1.00 31.69      A    C
ATOM   2350  CD1  PHE A  936      83.796  72.994  23.880  1.00 32.90      A    C
ATOM   2351  CD2  PHE A  936      85.973  72.182  23.248  1.00 31.35      A    C
ATOM   2352  CE1  PHE A  936      83.180  72.146  22.937  1.00 36.38      A    C
ATOM   2353  CE2  PHE A  936      85.385  71.325  22.299  1.00 32.25      A    C
ATOM   2354  CZ   PHE A  936      83.977  71.309  22.144  1.00 29.01      A    C
ATOM   2355  C    PHE A  936      85.538  76.372  25.863  1.00 38.79      A    C
ATOM   2356  O    PHE A  936      84.497  76.713  26.424  1.00 38.62      A    O
ATOM   2357  N    PRO A  937      86.741  76.802  26.283  1.00 46.38      A    N
ATOM   2358  CD   PRO A  937      88.123  76.431  25.926  1.00 44.38      A    C
ATOM   2359  CA   PRO A  937      86.704  77.711  27.436  1.00 44.69      A    C
ATOM   2360  CB   PRO A  937      88.188  77.994  27.721  1.00 40.45      A    C
```

FIGURE 1A-43

```
ATOM   2361  CG   PRO A 937      88.901  77.606  26.453  1.00 54.96      A  C
ATOM   2362  C    PRO A 937      85.884  78.952  27.040  1.00 43.70      A  C
ATOM   2363  O    PRO A 937      85.185  79.523  27.871  1.00 47.91      A  O
ATOM   2364  N    ASN A 938      85.950  79.347  25.765  1.00 45.95      A  N
ATOM   2365  CA   ASN A 938      85.147  80.484  25.288  1.00 52.41      A  C
ATOM   2366  CB   ASN A 938      85.315  80.740  23.778  1.00 54.07      A  C
ATOM   2367  CG   ASN A 938      86.609  81.441  23.419  1.00 63.11      A  C
ATOM   2368  OD1  ASN A 938      87.188  82.188  24.221  1.00 52.14      A  O
ATOM   2369  ND2  ASN A 938      87.057  81.227  22.177  1.00 48.88      A  N
ATOM   2370  C    ASN A 938      83.671  80.133  25.489  1.00 53.45      A  C
ATOM   2371  O    ASN A 938      82.920  80.880  26.111  1.00 58.29      A  O
ATOM   2372  N    LEU A 939      83.266  78.986  24.942  1.00 44.98      A  N
ATOM   2373  CA   LEU A 939      81.882  78.547  25.029  1.00 41.00      A  C
ATOM   2374  CB   LEU A 939      81.709  77.209  24.300  1.00 37.01      A  C
ATOM   2375  CG   LEU A 939      81.933  77.296  22.789  1.00 41.91      A  C
ATOM   2376  CD1  LEU A 939      82.108  75.905  22.194  1.00 38.37      A  C
ATOM   2377  CD2  LEU A 939      80.767  78.031  22.150  1.00 41.83      A  C
ATOM   2378  C    LEU A 939      81.393  78.426  26.462  1.00 41.66      A  C
ATOM   2379  O    LEU A 939      80.244  78.761  26.767  1.00 36.00      A  O
ATOM   2380  N    THR A 940      82.250  77.936  27.348  1.00 34.63      A  N
ATOM   2381  CA   THR A 940      81.840  77.781  28.741  1.00 45.09      A  C
ATOM   2382  CB   THR A 940      82.935  77.058  29.548  1.00 42.40      A  C
ATOM   2383  OG1  THR A 940      83.140  75.752  28.982  1.00 50.63      A  O
ATOM   2384  CG2  THR A 940      82.518  76.889  30.990  1.00 50.57      A  C
ATOM   2385  C    THR A 940      81.485  79.137  29.384  1.00 49.63      A  C
ATOM   2386  O    THR A 940      80.605  79.210  30.248  1.00 51.44      A  O
ATOM   2387  N    SER A 941      82.153  80.207  28.951  1.00 47.57      A  N
ATOM   2388  CA   SER A 941      81.870  81.540  29.482  1.00 56.41      A  C
ATOM   2389  CB   SER A 941      83.010  82.501  29.157  1.00 56.43      A  C
ATOM   2390  OG   SER A 941      84.177  82.132  29.866  1.00 72.87      A  O
ATOM   2391  C    SER A 941      80.569  82.079  28.903  1.00 56.70      A  C
ATOM   2392  O    SER A 941      79.674  82.488  29.644  1.00 60.82      A  O
ATOM   2393  N    PHE A 942      80.473  82.086  27.576  1.00 55.02      A  N
ATOM   2394  CA   PHE A 942      79.269  82.555  26.902  1.00 54.59      A  C
ATOM   2395  CB   PHE A 942      79.292  82.167  25.415  1.00 63.63      A  C
ATOM   2396  CG   PHE A 942      80.492  82.681  24.649  1.00 72.67      A  C
ATOM   2397  CD1  PHE A 942      80.781  82.175  23.379  1.00 73.97      A  C
ATOM   2398  CD2  PHE A 942      81.318  83.675  25.174  1.00 77.86      A  C
ATOM   2399  CE1  PHE A 942      81.874  82.648  22.640  1.00 71.77      A  C
ATOM   2400  CE2  PHE A 942      82.416  84.156  24.440  1.00 77.04      A  C
ATOM   2401  CZ   PHE A 942      82.690  83.639  23.170  1.00 72.95      A  C
ATOM   2402  C    PHE A 942      78.054  81.893  27.560  1.00 57.01      A  C
ATOM   2403  O    PHE A 942      77.124  82.566  28.000  1.00 61.68      A  O
ATOM   2404  N    LEU A 943      78.077  80.566  27.641  1.00 54.34      A  N
ATOM   2405  CA   LEU A 943      76.965  79.827  28.221  1.00 52.59      A  C
ATOM   2406  CB   LEU A 943      77.130  78.330  27.954  1.00 51.40      A  C
ATOM   2407  CG   LEU A 943      77.108  77.998  26.457  1.00 48.84      A  C
ATOM   2408  CD1  LEU A 943      77.273  76.519  26.266  1.00 39.87      A  C
ATOM   2409  CD2  LEU A 943      75.801  78.467  25.844  1.00 47.50      A  C
ATOM   2410  C    LEU A 943      76.792  80.082  29.708  1.00 57.33      A  C
ATOM   2411  O    LEU A 943      75.667  80.253  30.178  1.00 48.40      A  O
ATOM   2412  N    GLY A 944      77.900  80.096  30.447  1.00 59.64      A  N
ATOM   2413  CA   GLY A 944      77.818  80.352  31.874  1.00 56.70      A  C
ATOM   2414  C    GLY A 944      77.084  81.667  32.052  1.00 62.54      A  C
ATOM   2415  O    GLY A 944      76.230  81.811  32.928  1.00 65.98      A  O
ATOM   2416  N    CYS A 945      77.409  82.629  31.195  1.00 65.46      A  N
```

FIGURE 1A-44

```
ATOM   2417  CA   CYS A 945      76.766  83.936  31.240  1.00 71.45      A    C
ATOM   2418  CB   CYS A 945      77.487  84.914  30.306  1.00 71.39      A    C
ATOM   2419  SG   CYS A 945      79.134  85.413  30.908  1.00 77.45      A    S
ATOM   2420  C    CYS A 945      75.289  83.826  30.864  1.00 72.69      A    C
ATOM   2421  O    CYS A 945      74.422  84.241  31.631  1.00 76.19      A    O
ATOM   2422  N    GLN A 946      74.999  83.268  29.690  1.00 71.07      A    N
ATOM   2423  CA   GLN A 946      73.611  83.106  29.264  1.00 66.73      A    C
ATOM   2424  CB   GLN A 946      73.510  82.167  28.055  1.00 63.81      A    C
ATOM   2425  CG   GLN A 946      73.625  82.834  26.687  1.00 65.67      A    C
ATOM   2426  CD   GLN A 946      72.485  83.803  26.400  1.00 66.21      A    C
ATOM   2427  OE1  GLN A 946      72.665  85.020  26.448  1.00 61.19      A    O
ATOM   2428  NE2  GLN A 946      71.300  83.264  26.107  1.00 68.76      A    N
ATOM   2429  C    GLN A 946      72.810  82.523  30.423  1.00 63.35      A    C
ATOM   2430  O    GLN A 946      71.641  82.856  30.607  1.00 63.97      A    O
ATOM   2431  N    LEU A 947      73.447  81.649  31.197  1.00 62.07      A    N
ATOM   2432  CA   LEU A 947      72.797  81.022  32.343  1.00 69.95      A    C
ATOM   2433  CB   LEU A 947      73.663  79.888  32.912  1.00 63.45      A    C
ATOM   2434  CG   LEU A 947      73.146  78.448  32.818  1.00 60.05      A    C
ATOM   2435  CD1  LEU A 947      74.157  77.513  33.462  1.00 58.70      A    C
ATOM   2436  CD2  LEU A 947      71.786  78.313  33.497  1.00 48.98      A    C
ATOM   2437  C    LEU A 947      72.570  82.070  33.421  1.00 73.31      A    C
ATOM   2438  O    LEU A 947      73.280  82.012  34.445  1.00 76.89      A    O
ATOM   2439  OXT  LEU A 947      71.700  82.943  33.223  1.00 78.65      A    O
TER    2440       LEU A 947                                              A
ATOM   2441  P    PO4 B 300      89.395  39.990  39.032  1.00 43.76      C    P
ATOM   2442  O1   PO4 B 300      90.643  40.733  39.360  1.00 43.68      C    O
ATOM   2443  O2   PO4 B 300      88.218  40.838  39.360  1.00 39.00      C    O
ATOM   2444  O3   PO4 B 300      89.377  39.650  37.587  1.00 44.11      C    O
ATOM   2445  O4   PO4 B 300      89.347  38.741  39.826  1.00 40.74      C    O
TER    2446       PO4 B 300                                              C
ATOM   2447  C1   CAP C 400      99.914  60.317  29.193  1.00 53.31      ACAP C
ATOM   2448  C2   CAP C 400      99.954  59.029  28.369  1.00 55.34      ACAP C
ATOM   2449  C3   CAP C 400     101.125  58.906  27.359  1.00 50.91      ACAP C
ATOM   2450  C4   CAP C 400     101.759  60.139  26.643  1.00 53.92      ACAP C
ATOM   2451  C5   CAP C 400     101.058  61.434  27.025  1.00 54.35      ACAP C
ATOM   2452  C6   CAP C 400     100.298  61.564  28.380  1.00 57.16      ACAP N
ATOM   2453  N1   CAP C 400     101.921  59.954  25.147  1.00 50.44      ACAP N
ATOM   2454  C7   CAP C 400     103.250  59.940  24.447  1.00 41.49      ACAP C
ATOM   2455  C8   CAP C 400     103.214  59.535  22.934  1.00 33.65      ACAP C
ATOM   2456  S1   CAP C 400     103.202  57.729  22.681  1.00 34.54      ACAP S
ATOM   2457  O1   CAP C 400     104.253  57.122  23.467  1.00 37.44      ACAP O
ATOM   2458  O2   CAP C 400     101.884  57.266  23.117  1.00 39.81      ACAP O
ATOM   2459  O3   CAP C 400     103.438  57.267  21.153  1.00 34.13      ACAP O
TER    2460       CAP C 400                                              ACAP
ATOM   2461  OH2  TIP D   1      79.021  62.337  16.446  1.00 23.77      D    O
ATOM   2462  OH2  TIP D   2      72.604  62.185  19.357  1.00 20.37      D    O
ATOM   2463  OH2  TIP D   3      78.400  67.184   8.690  1.00 20.55      D    O
ATOM   2464  OH2  TIP D   4      95.924  47.609  25.919  1.00 31.71      D    O
ATOM   2465  OH2  TIP D   5      74.585  61.100  10.353  1.00 24.59      D    O
ATOM   2466  OH2  TIP D   6      66.150  70.684   7.059  1.00 26.22      D    O
ATOM   2467  OH2  TIP D   7      74.217  73.183  10.870  1.00 21.49      D    O
ATOM   2468  OH2  TIP D   8      71.557  60.422  17.391  1.00 23.58      D    O
ATOM   2469  OH2  TIP D   9      71.332  65.343   0.727  1.00 26.30      D    O
ATOM   2470  OH2  TIP D  10      83.877  65.941  13.458  1.00 27.05      D    O
ATOM   2471  OH2  TIP D  11      66.013  63.401   9.061  1.00 34.74      D    O
ATOM   2472  OH2  TIP D  12      78.599  73.961   6.207  1.00 28.64      D    O
```

FIGURE 1A-45

```
ATOM   2473  OH2 TIP D  13      77.171  68.824  10.507  1.00 24.81      D   O
ATOM   2474  OH2 TIP D  14      80.089  56.184  20.241  1.00 33.39      D   O
ATOM   2475  OH2 TIP D  15     103.643  45.485  27.690  1.00 30.52      D   O
ATOM   2476  OH2 TIP D  16      81.592  52.239  24.368  1.00 39.77      D   O
ATOM   2477  OH2 TIP D  17      99.730  45.736  34.682  1.00 31.23      D   O
ATOM   2478  OH2 TIP D  18      83.492  56.874  28.086  1.00 30.38      D   O
ATOM   2479  OH2 TIP D  19      99.402  51.078  42.024  1.00 26.72      D   O
ATOM   2480  OH2 TIP D  20      74.937  53.269   5.780  1.00 29.20      D   O
ATOM   2481  OH2 TIP D  21      67.440  58.797  28.521  1.00 33.41      D   O
ATOM   2482  OH2 TIP D  22      62.642  68.923   6.292  1.00 34.34      D   O
ATOM   2483  OH2 TIP D  23      95.179  43.152  33.752  1.00 33.86      D   O
ATOM   2484  OH2 TIP D  24      66.821  63.358  40.562  1.00 43.17      D   O
ATOM   2485  OH2 TIP D  25      83.355  58.664  29.776  1.00 27.63      D   O
ATOM   2486  OH2 TIP D  26      93.650  57.222  23.244  1.00 36.19      D   O
ATOM   2487  OH2 TIP D  28      87.163  60.681  33.726  1.00 32.51      D   O
ATOM   2488  OH2 TIP D  29      69.457  60.278  -1.889  1.00 34.30      D   O
ATOM   2489  OH2 TIP D  30      88.871  77.923  16.538  1.00 41.13      D   O
ATOM   2490  OH2 TIP D  31      92.971  68.351  19.254  1.00 34.45      D   O
ATOM   2491  OH2 TIP D  32      96.540  52.139  34.020  1.00 31.68      D   O
ATOM   2492  OH2 TIP D  33      67.139  73.630  10.187  1.00 41.17      D   O
ATOM   2493  OH2 TIP D  34      69.701  61.444   8.528  1.00 42.77      D   O
ATOM   2494  OH2 TIP D  35      67.159  80.595  11.503  1.00 44.26      D   O
ATOM   2495  OH2 TIP D  36     105.115  48.568  29.009  1.00 32.95      D   O
ATOM   2496  OH2 TIP D  37      69.208  64.246  17.221  1.00 28.09      D   O
ATOM   2497  OH2 TIP D  38      78.478  46.794  21.165  1.00 45.55      D   O
ATOM   2498  OH2 TIP D  39      93.658  66.035  17.251  1.00 31.58      D   O
ATOM   2499  OH2 TIP D  40      90.133  71.061  13.089  1.00 31.24      D   O
ATOM   2500  OH2 TIP D  41      92.092  80.189  16.315  1.00 55.89      D   O
ATOM   2501  OH2 TIP D  42      69.574  61.959  15.844  1.00 31.34      D   O
ATOM   2502  OH2 TIP D  43      85.655  55.827  26.768  1.00 33.77      D   O
ATOM   2503  OH2 TIP D  44      82.527  64.402  17.208  1.00 31.53      D   O
ATOM   2504  OH2 TIP D  45      95.843  55.544  37.305  1.00 43.63      D   O
ATOM   2505  OH2 TIP D  46      91.224  58.762  35.936  1.00 35.00      D   O
ATOM   2506  OH2 TIP D  47      87.094  72.945   7.502  1.00 42.72      D   O
ATOM   2507  OH2 TIP D  48      94.871  49.318  21.499  1.00 39.92      D   O
ATOM   2508  OH2 TIP D  49     100.756  55.571  21.724  1.00 31.40      D   O
ATOM   2509  OH2 TIP D  50      82.454  52.955  20.704  1.00 36.98      D   O
ATOM   2510  OH2 TIP D  51      69.800  64.651  -2.536  1.00 31.05      D   O
ATOM   2511  OH2 TIP D  52      73.099  78.253   5.505  1.00 36.20      D   O
ATOM   2512  OH2 TIP D  53      79.769  76.220   7.412  1.00 31.24      D   O
ATOM   2513  OH2 TIP D  54      71.898  85.062  13.630  1.00 50.58      D   O
ATOM   2514  OH2 TIP D  56      99.519  45.955  31.814  1.00 36.45      D   O
ATOM   2515  OH2 TIP D  57      87.919  58.300  34.355  1.00 39.04      D   O
ATOM   2516  OH2 TIP D  58      85.799  60.950   7.150  1.00 42.00      D   O
ATOM   2517  OH2 TIP D  59      65.093  66.789   1.354  1.00 46.39      D   O
ATOM   2518  OH2 TIP D  60      71.751  40.562  35.341  1.00 59.42      D   O
ATOM   2519  OH2 TIP D  61      80.655  78.434   5.836  1.00 43.66      D   O
ATOM   2520  OH2 TIP D  63      84.594  41.520  28.336  1.00 42.32      D   O
ATOM   2521  OH2 TIP D  64      88.504  56.188  26.368  1.00 41.31      D   O
ATOM   2522  OH2 TIP D  65      92.630  68.084  22.198  1.00 43.36      D   O
ATOM   2523  OH2 TIP D  66     101.241  46.460  27.660  1.00 34.13      D   O
ATOM   2524  OH2 TIP D  67      96.808  63.335  10.988  1.00 48.01      D   O
ATOM   2525  OH2 TIP D  68      60.980  69.570  18.017  1.00 52.93      D   O
ATOM   2526  OH2 TIP D  69      89.268  74.040   8.746  1.00 40.53      D   O
ATOM   2527  OH2 TIP D  70      77.314  55.224  32.650  1.00 37.75      D   O
ATOM   2528  OH2 TIP D  71     101.867  43.990  29.397  1.00 43.64      D   O
```

FIGURE 1A-46

```
ATOM   2529  OH2 TIP D   72      95.628  70.670   8.615  1.00 52.13      D    O
ATOM   2530  OH2 TIP D   73      87.015  39.998  27.885  1.00 49.75      D    O
ATOM   2531  OH2 TIP D   74      78.723  48.928  19.173  1.00 39.82      D    O
ATOM   2532  OH2 TIP D   75     100.785  51.623  22.275  1.00 43.55      D    O
ATOM   2533  OH2 TIP D   76      97.821  71.144  15.670  1.00 45.95      D    O
ATOM   2534  OH2 TIP D   77      87.264  54.019  15.393  1.00 58.39      D    O
ATOM   2535  OH2 TIP D   78      81.307  62.907  39.328  1.00 47.42      D    O
ATOM   2536  OH2 TIP D   79      83.656  59.770  13.537  1.00 50.41      D    O
ATOM   2537  OH2 TIP D   80      82.241  79.835   7.530  1.00 53.69      D    O
ATOM   2538  OH2 TIP D   81     104.367  72.958  13.056  1.00 58.86      D    O
ATOM   2539  OH2 TIP D   82      85.016  52.580  53.353  1.00 67.94      D    O
ATOM   2540  OH2 TIP D   83      87.773  71.012   5.203  1.00 52.82      D    O
ATOM   2541  OH2 TIP D   84      60.930  77.675  30.433  1.00 57.61      D    O
ATOM   2542  OH2 TIP D   85      74.002  47.789  50.463  1.00 68.63      D    O
ATOM   2543  OH2 TIP D   86      86.841  59.629   9.548  1.00 47.19      D    O
ATOM   2544  OH2 TIP D   87      95.087  73.736   9.647  1.00 50.78      D    O
ATOM   2545  OH2 TIP D   88      88.687  74.541  22.595  1.00 50.85      D    O
ATOM   2546  OH2 TIP D   89      73.945  52.542   8.409  1.00 57.14      D    O
ATOM   2547  OH2 TIP D   90      99.069  63.260  24.901  1.00 50.64      D    O
ATOM   2548  OH2 TIP D   91      77.188  47.798  17.174  1.00 47.77      D    O
ATOM   2549  OH2 TIP D   92      90.990  62.527  39.644  1.00 56.26      D    O
ATOM   2550  OH2 TIP D   93      98.554  45.440  28.769  1.00 47.83      D    O
ATOM   2551  OH2 TIP D   94      73.253  56.190  23.137  1.00 60.72      D    O
ATOM   2552  OH2 TIP D   95      84.523  68.785  37.989  1.00 51.01      D    O
ATOM   2553  OH2 TIP D   96     104.858  47.182  26.122  1.00 41.99      D    O
ATOM   2554  OH2 TIP D   97      98.270  60.544  32.347  1.00 66.90      D    O
ATOM   2555  OH2 TIP D   98      71.563  47.183  40.204  1.00 54.63      D    O
ATOM   2556  OH2 TIP D   99      82.475  39.510  28.445  1.00 55.03      D    O
ATOM   2557  OH2 TIP D  100      91.762  60.414  12.150  1.00 51.97      D    O
ATOM   2558  OH2 TIP D  101      73.327  43.646  17.565  1.00 60.06      D    O
ATOM   2559  OH2 TIP D  102      98.974  45.291  25.559  1.00 39.67      D    O
ATOM   2560  OH2 TIP D  103     103.239  44.761  23.372  1.00 47.55      D    O
ATOM   2561  OH2 TIP D  104      88.171  66.004   0.314  1.00 54.60      D    O
ATOM   2562  OH2 TIP D  105      69.791  57.638  21.790  1.00 51.56      D    O
ATOM   2563  OH2 TIP D  106      99.370  54.414  41.036  1.00 43.40      D    O
ATOM   2564  OH2 TIP D  107      90.875  65.406  37.722  1.00 47.70      D    O
ATOM   2565  OH2 TIP D  109      87.298  65.473  17.190  1.00 45.34      D    O
ATOM   2566  OH2 TIP D  110      57.199  78.077  29.142  1.00 58.52      D    O
ATOM   2567  OH2 TIP D  111      88.197  41.331  15.192  1.00 53.82      D    O
ATOM   2568  OH2 TIP D  112      96.356  62.518  31.074  1.00 60.34      D    O
ATOM   2569  OH2 TIP D  113     101.678  48.714  19.566  1.00 42.67      D    O
ATOM   2570  OH2 TIP D  114      94.486  53.437  22.813  1.00 45.58      D    O
ATOM   2571  OH2 TIP D  116      95.716  73.739  14.342  1.00 59.75      D    O
ATOM   2572  OH2 TIP D  117      86.541  33.439  48.712  1.00 49.60      D    O
ATOM   2573  OH2 TIP D  118      70.967  57.629  18.028  1.00 46.56      D    O
ATOM   2574  OH2 TIP D  119      92.436  55.212  16.672  1.00 68.71      D    O
ATOM   2575  OH2 TIP D  120      74.777  54.536  33.188  1.00 34.16      D    O
ATOM   2576  OH2 TIP D  121      69.697  55.681  41.509  1.00 71.03      D    O
ATOM   2577  OH2 TIP D  122      77.610  55.424  39.937  1.00 40.02      D    O
ATOM   2578  OH2 TIP D  123      89.928  75.679  30.645  1.00 50.68      D    O
ATOM   2579  OH2 TIP D  124      78.648  40.325  27.132  1.00 61.34      D    O
ATOM   2580  OH2 TIP D  125      91.558  53.625  20.965  1.00 75.98      D    O
ATOM   2581  OH2 TIP D  126      70.804  44.609  15.928  1.00 72.84      D    O
ATOM   2582  OH2 TIP D  127      67.369  74.333   7.149  1.00 35.36      D    O
ATOM   2583  OH2 TIP D  128      72.242  69.703  40.450  1.00 66.99      D    O
ATOM   2584  OH2 TIP D  129      71.113  54.280  18.808  1.00 70.38      D    O
```

FIGURE 1A-47

```
ATOM   2585  OH2 TIP D 130      67.375  56.319  40.505  1.00 60.96      D   O
ATOM   2586  OH2 TIP D 131      84.039  78.774  32.854  1.00 65.20      D   O
ATOM   2587  OH2 TIP D 132      83.020  46.696   8.151  1.00 44.86      D   O
ATOM   2588  OH2 TIP D 133      69.945  55.252  27.205  1.00 51.63      D   O
ATOM   2589  OH2 TIP D 134      58.523  62.410  33.007  1.00 70.34      D   O
ATOM   2590  OH2 TIP D 135      68.056  64.410  36.813  1.00 54.18      D   O
ATOM   2591  OH2 TIP D 137     102.042  68.879   7.902  1.00 69.39      D   O
ATOM   2592  OH2 TIP D 138      88.921  81.410  17.416  1.00 62.79      D   O
ATOM   2593  OH2 TIP D 141      56.992  64.690  27.487  1.00 54.37      D   O
ATOM   2594  OH2 TIP D 142      87.064  51.715  11.666  1.00 61.55      D   O
ATOM   2595  OH2 TIP D 144      68.442  71.726   8.057  1.00 26.82      D   O
ATOM   2596  OH2 TIP D 145      69.675  54.027  31.522  1.00 67.61      D   O
ATOM   2597  OH2 TIP D 147      81.204  63.513  15.148  1.00 35.64      D   O
ATOM   2598  OH2 TIP D 149     100.249  44.103  27.485  1.00 34.80      D   O
ATOM   2599  OH2 TIP D 150      71.927  60.453   9.394  1.00 53.63      D   O
ATOM   2600  OH2 TIP D 151      86.760  53.924  42.402  1.00 48.70      D   O
ATOM   2601  OH2 TIP D 152      69.680  66.976  -0.646  1.00 46.61      D   O
ATOM   2602  OH2 TIP D 153      64.264  61.973   9.789  1.00 45.56      D   O
ATOM   2603  OH2 TIP D 154      84.584  65.675  16.145  1.00 38.92      D   O
ATOM   2604  OH2 TIP D 155      72.593  58.168  38.291  1.00 42.89      D   O
ATOM   2605  OH2 TIP D 156      84.744  79.982   7.374  1.00 45.13      D   O
ATOM   2606  OH2 TIP D 157      99.449  67.316  22.723  1.00 47.54      D   O
ATOM   2607  OH2 TIP D 158      72.681  54.995  31.628  1.00 40.25      D   O
ATOM   2608  OH2 TIP D 159      90.551  71.951   9.556  1.00 44.19      D   O
ATOM   2609  OH2 TIP D 160      87.769  49.413  12.940  1.00 56.83      D   O
ATOM   2610  OH2 TIP D 161      87.728  76.226  18.337  1.00 60.32      D   O
ATOM   2611  OH2 TIP D 162      93.349  79.621   8.370  1.00 53.49      D   O
ATOM   2612  OH2 TIP D 163      89.961  49.093  18.560  1.00 72.00      D   O
ATOM   2613  OH2 TIP D 164      78.720  70.587  36.469  1.00 66.88      D   O
ATOM   2614  OH2 TIP D 165      79.455  65.205  -3.050  1.00 43.30      D   O
ATOM   2615  OH2 TIP D 166      75.089  52.226  10.552  1.00 48.71      D   O
ATOM   2616  OH2 TIP D 167      80.944  54.190  17.568  1.00 55.16      D   O
ATOM   2617  OH2 TIP D 168      67.563  56.446  27.665  1.00 52.66      D   O
ATOM   2618  OH2 TIP D 169      80.074  77.905  -1.738  1.00 41.73      D   O
ATOM   2619  OH2 TIP D 170      76.234  59.218  38.289  1.00 50.96      D   O
ATOM   2620  OH2 TIP D 171      75.343  46.537  14.718  1.00 56.07      D   O
ATOM   2621  OH2 TIP D 172      88.389  58.506  36.924  1.00 48.21      D   O
ATOM   2622  OH2 TIP D 173      95.647  69.216  15.474  1.00 41.21      D   O
ATOM   2623  OH2 TIP D 174      70.482  51.386  39.769  1.00 53.87      D   O
ATOM   2624  OH2 TIP D 175      67.052  59.978  -0.495  1.00 46.03      D   O
ATOM   2625  OH2 TIP D 176      83.496  57.847  14.847  1.00 51.20      D   O
ATOM   2626  OH2 TIP D 177      68.063  63.093  -3.307  1.00 54.34      D   O
ATOM   2627  OH2 TIP D 178      57.570  62.592  22.629  1.00 51.41      D   O
ATOM   2628  OH2 TIP D 179      96.286  60.732  12.381  1.00 51.27      D   O
ATOM   2629  OH2 TIP D 180      82.091  57.051  49.846  1.00 67.64      D   O
ATOM   2630  OH2 TIP D 181     105.412  69.972   8.075  1.00 69.74      D   O
ATOM   2631  OH2 TIP D 183     103.124  42.446  30.858  1.00 73.66      D   O
ATOM   2632  OH2 TIP D 184      72.505  55.243   7.479  1.00 53.76      D   O
ATOM   2633  OH2 TIP D 185      98.423  49.201  44.087  1.00 57.99      D   O
ATOM   2634  OH2 TIP D 186      98.385  42.990  34.929  1.00 66.48      D   O
ATOM   2635  OH2 TIP D 187      69.393  80.908   9.493  1.00 53.09      D   O
ATOM   2636  OH2 TIP D 188      83.985  54.074  12.540  1.00 53.12      D   O
ATOM   2637  OH2 TIP D 189      87.544  50.868   5.477  1.00 57.79      D   O
ATOM   2638  OH2 TIP D 190      81.712  77.759   3.032  1.00 55.34      D   O
ATOM   2639  OH2 TIP D 191      93.597  72.958  22.657  1.00 53.79      D   O
ATOM   2640  OH2 TIP D 192      68.883  47.110  36.920  1.00 51.49      D   O
```

FIGURE 1A-48

```
ATOM   2641  OH2 TIP D 193      71.381  54.247  25.377  1.00 66.88      D    O
ATOM   2642  OH2 TIP D 194      88.440  49.774  42.145  1.00 46.60      D    O
ATOM   2643  OH2 TIP D 195      87.287  82.619  26.748  1.00 56.63      D    O
ATOM   2644  OH2 TIP D 196     105.094  65.047  19.568  1.00 66.33      D    O
ATOM   2645  OH2 TIP D 197      84.462  33.980  47.452  1.00 55.80      D    O
ATOM   2646  OH2 TIP D 198      92.222  70.996   7.628  1.00 71.01      D    O
ATOM   2647  OH2 TIP D 199      83.493  76.443   2.080  1.00 59.71      D    O
ATOM   2648  OH2 TIP D 200     101.572  63.264  24.812  1.00 57.36      D    O
ATOM   2649  OH2 TIP D 201      89.103  53.067  22.532  1.00 68.07      D    O
ATOM   2650  OH2 TIP D 202      90.188  73.709  32.432  1.00 71.95      D    O
ATOM   2651  OH2 TIP D 203      69.373  84.589  12.649  1.00 73.85      D    O
ATOM   2652  OH2 TIP D 204      83.885  75.476  -1.353  1.00 67.29      D    O
ATOM   2653  OH2 TIP D 205      75.957  41.813  22.662  1.00 62.37      D    O
ATOM   2654  OH2 TIP D 206      68.390  55.937  16.144  1.00 74.84      D    O
ATOM   2655  OH2 TIP D 207      95.637  49.471  18.644  1.00 58.29      D    O
ATOM   2656  OH2 TIP D 208      94.965  65.739   6.241  1.00 66.15      D    O
ATOM   2657  OH2 TIP D 209      99.363  51.681  17.418  1.00 50.51      D    O
ATOM   2658  OH2 TIP D 210      95.009  41.108  32.371  1.00 50.80      D    O
ATOM   2659  OH2 TIP D 211      96.605  44.181  28.748  1.00 54.17      D    O
ATOM   2660  OH2 TIP D 212      67.423  83.049  13.474  1.00 62.45      D    O
ATOM   2661  OH2 TIP D 213      65.324  79.337   5.733  1.00 53.45      D    O
ATOM   2662  OH2 TIP D 214      88.070  53.587  -1.691  1.00 80.48      D    O
ATOM   2663  OH2 TIP D 215      99.792  53.378  43.106  1.00 48.66      D    O
ATOM   2664  OH2 TIP D 216      90.360  50.766  22.126  1.00 61.98      D    O
ATOM   2665  OH2 TIP D 217      66.810  61.851   6.762  1.00 50.83      D    O
ATOM   2666  OH2 TIP D 218      65.466  64.237  35.681  1.00 53.42      D    O
ATOM   2667  OH2 TIP D 219      81.360  50.475  18.925  1.00 61.45      D    O
ATOM   2668  OH2 TIP D 220      70.155  48.228  23.231  1.00 69.23      D    O
ATOM   2669  OH2 TIP D 221      81.988  55.467  14.894  1.00 48.50      D    O
ATOM   2670  OH2 TIP D 222      86.836  70.655   1.588  1.00 62.75      D    O
ATOM   2671  OH2 TIP D 223      91.124  55.241  23.859  1.00 75.05      D    O
ATOM   2672  OH2 TIP D 224      93.318  49.903  45.245  1.00 48.68      D    O
ATOM   2673  OH2 TIP D 225      79.646  71.907  40.113  1.00 73.20      D    O
ATOM   2674  OH2 TIP D 226      95.425  63.734  33.676  1.00 61.19      D    O
ATOM   2675  OH2 TIP D 227     102.894  44.029  25.858  1.00 60.42      D    O
ATOM   2676  OH2 TIP D 228      90.298  68.769  36.678  1.00 65.60      D    O
ATOM   2677  OH2 TIP D 229      75.269  85.280  21.227  1.00 64.41      D    O
ATOM   2678  OH2 TIP D 230      99.013  64.795  27.379  1.00 59.35      D    O
ATOM   2679  OH2 TIP D 231      81.497  80.006  34.209  1.00 61.86      D    O
ATOM   2680  OH2 TIP D 232      71.941  56.102  40.770  1.00 62.92      D    O
ATOM   2681  OH2 TIP D 233      91.118  38.657  31.680  1.00 76.33      D    O
ATOM   2682  OH2 TIP D 234      97.251  55.393  34.703  1.00 51.91      D    O
ATOM   2683  OH2 TIP D 235      91.276  45.928   4.590  1.00 77.93      D    O
ATOM   2684  OH2 TIP D 236      79.170  56.705  41.549  1.00 59.41      D    O
ATOM   2685  OH2 TIP D 237      95.473  44.594  16.017  1.00 76.93      D    O
ATOM   2686  OH2 TIP D 238      68.017  53.566  33.391  1.00 73.72      D    O
ATOM   2687  OH2 TIP D 239      77.983  83.551  14.908  1.00 51.06      D    O
ATOM   2688  OH2 TIP D 240      87.455  56.778   8.553  1.00 64.84      D    O
ATOM   2689  OH2 TIP D 241      98.274  42.061  26.558  1.00 80.92      D    O
ATOM   2690  OH2 TIP D 242      58.232  70.264  22.413  1.00 48.77      D    O
ATOM   2691  OH2 TIP D 245      93.372  59.103  37.480  1.00 63.72      D    O
ATOM   2692  OH2 TIP D 246      82.762  45.426   5.622  1.00 59.05      D    O
ATOM   2693  OH2 TIP D 247      72.740  43.487  14.365  1.00 75.91      D    O
ATOM   2694  OH2 TIP D 248      64.830  84.344  18.637  1.00 54.60      D    O
ATOM   2695  OH2 TIP D 249      67.841  57.210  18.229  1.00 64.63      D    O
ATOM   2696  OH2 TIP D 250      81.910  35.225  29.553  1.00 69.50      D    O
```

FIGURE 1A-49

```
ATOM   2697  OH2 TIP D 251      78.623  80.070   4.636  1.00 60.26      D   O
ATOM   2698  OH2 TIP D 252      91.580  84.581   8.965  1.00 71.44      D   O
ATOM   2699  OH2 TIP D 253     100.410  54.377  32.340  1.00 70.96      D   O
ATOM   2700  OH2 TIP D 254      80.198  58.270   1.204  1.00 54.06      D   O
ATOM   2701  OH2 TIP D 255      72.190  51.195  45.453  1.00 68.29      D   O
ATOM   2702  OH2 TIP D 256      55.293  74.286  26.522  1.00 68.92      D   O
ATOM   2703  OH2 TIP D 257      63.168  63.936  34.976  1.00 55.97      D   O
ATOM   2704  OH2 TIP D 258      81.621  82.476  19.225  1.00 60.35      D   O
ATOM   2705  OH2 TIP D 259      62.747  81.032  21.373  1.00 62.92      D   O
ATOM   2706  OH2 TIP D 260      86.128  72.096  32.473  1.00 51.12      D   O
ATOM   2707  OH2 TIP D 261      66.100  57.761  20.401  1.00 42.30      D   O
ATOM   2708  OH2 TIP D 262      79.536  80.246  10.772  1.00 53.87      D   O
ATOM   2709  OH2 TIP D 263      81.823  54.668  29.288  1.00 49.25      D   O
ATOM   2710  OH2 TIP D 264      68.567  59.233  11.190  1.00 51.08      D   O
ATOM   2711  OH2 TIP D 265      82.722  52.918  15.334  1.00 54.15      D   O
ATOM   2712  OH2 TIP D 266      83.294  50.728  17.285  1.00 45.31      D   O
ATOM   2713  OH2 TIP D 267     101.346  56.832  31.587  1.00 45.21      D   O
ATOM   2714  OH2 TIP D 270      87.107  38.311  20.470  1.00 52.13      D   O
ATOM   2715  OH2 TIP D 271      81.451  66.510  -1.929  1.00 61.77      D   O
ATOM   2716  OH2 TIP D 272      95.000  73.176  25.584  1.00 60.61      D   O
ATOM   2717  OH2 TIP D 273      71.687  53.954  29.710  1.00 64.94      D   O
ATOM   2718  OH2 TIP D 274      90.593  73.669  28.226  1.00 52.28      D   O
ATOM   2719  OH2 TIP D 275      94.715  62.420  37.139  1.00 53.04      D   O
ATOM   2720  OH2 TIP D 276      72.780  84.429  34.900  1.00 60.95      D   O
ATOM   2721  OH2 TIP D 277      93.530  41.645  30.278  1.00 58.11      D   O
ATOM   2722  OH2 TIP D 278      84.123  38.112  26.821  1.00 57.83      D   O
ATOM   2723  OH2 TIP D 279      83.568  61.155   5.051  1.00 53.46      D   O
ATOM   2724  OH2 TIP D 280      74.272  54.557  43.552  1.00 59.25      D   O
ATOM   2725  OH2 TIP D 282      86.409  50.887  14.481  1.00 73.09      D   O
ATOM   2726  OH2 TIP D 283      65.361  76.538   5.782  1.00 73.74      D   O
ATOM   2727  OH2 TIP D 284      68.226  51.900  38.535  1.00 65.76      D   O
ATOM   2728  OH2 TIP D 285      62.990  83.588  16.200  1.00 72.10      D   O
ATOM   2729  OH2 TIP D 286      79.362  54.949  30.242  1.00 60.23      D   O
ATOM   2730  OH2 TIP D 287      76.655  40.962  24.782  1.00 52.94      D   O
ATOM   2731  OH2 TIP D 288      63.354  80.203  17.928  1.00 72.80      D   O
ATOM   2732  OH2 TIP D 289      81.894  47.949   4.535  1.00 52.45      D   O
ATOM   2733  OH2 TIP D 290      80.701  38.583  38.496  1.00 61.07      D   O
ATOM   2734  OH2 TIP D 291      50.468  66.625  23.384  1.00 66.20      D   O
ATOM   2735  OH2 TIP D 292      88.140  61.779  42.070  1.00 57.77      D   O
ATOM   2736  OH2 TIP D 293      83.048  37.148  35.815  1.00 63.01      D   O
ATOM   2737  OH2 TIP D 294      94.628  70.623  17.468  1.00 57.32      D   O
ATOM   2738  OH2 TIP D 295      93.887  54.338  19.633  1.00 62.57      D   O
ATOM   2739  OH2 TIP D 296      88.803  71.656  33.389  1.00 52.47      D   O
ATOM   2740  OH2 TIP D 297      95.507  44.385  19.620  1.00 53.32      D   O
ATOM   2741  OH2 TIP D 298      71.832  44.673  44.581  1.00 66.34      D   O
ATOM   2742  OH2 TIP D 299      97.899  57.926  35.567  1.00 60.33      D   O
ATOM   2743  OH2 TIP D 300      77.632  37.193  24.441  1.00 59.99      D   O
ATOM   2744  OH2 TIP D 301      78.126  46.936  14.317  1.00 54.75      D   O
ATOM   2745  OH2 TIP D 302      75.396  43.541  50.505  1.00 75.80      D   O
ATOM   2746  OH2 TIP D 303      90.111  79.670  19.224  1.00 58.58      D   O
ATOM   2747  OH2 TIP D 304      92.881  75.003   9.357  1.00 65.63      D   O
ATOM   2748  OH2 TIP D 305      61.152  70.341  34.503  1.00 67.29      D   O
ATOM   2749  OH2 TIP D 306      57.680  62.549  25.099  1.00 63.37      D   O
ATOM   2750  OH2 TIP D 308      89.189  81.494   6.347  1.00 62.19      D   O
ATOM   2751  OH2 TIP D 309      96.659  39.052  33.096  1.00 62.28      D   O
ATOM   2752  OH2 TIP D 310      65.594  85.652  21.249  1.00 63.78      D   O
```

FIGURE 1A-50

```
ATOM   2753  OH2  TIP  D  311     71.787  44.731  40.388  1.00  59.62      D  O
ATOM   2754  OH2  TIP  D  312     80.879  37.868  31.693  1.00  68.42      D  O
ATOM   2755  OH2  TIP  D  313     64.227  74.642  35.825  1.00  58.91      D  O
ATOM   2756  OH2  TIP  D  314     93.273  52.464  44.884  1.00  70.13      D  O
ATOM   2757  OH2  TIP  D  315    106.525  72.261  15.441  1.00  74.82      D  O
ATOM   2758  OH2  TIP  D  316     98.253  53.163  31.578  1.00  65.27      D  O
ATOM   2759  OH2  TIP  D  317     93.911  69.648  23.700  1.00  44.83      D  O
ATOM   2760  OH2  TIP  D  318     84.564  82.729  17.435  1.00  67.13      D  O
ATOM   2761  OH2  TIP  D  320     84.923  34.275  35.560  1.00  69.34      D  O
ATOM   2762  OH2  TIP  D  321     69.697  45.652  24.909  1.00  63.84      D  O
ATOM   2763  OH2  TIP  D  322     84.735  55.675  43.911  1.00  68.73      D  O
ATOM   2764  OH2  TIP  D  323     82.270  57.207   1.139  1.00  72.67      D  O
ATOM   2765  OH2  TIP  D  324     62.962  58.414  23.745  1.00  56.73      D  O
ATOM   2766  OH2  TIP  D  325     88.235  54.646  50.742  1.00  64.13      D  O
ATOM   2767  OH2  TIP  D  326     69.016  72.273  35.593  1.00  56.54      D  O
ATOM   2768  OH2  TIP  D  327     56.902  74.153  24.036  1.00  67.23      D  O
ATOM   2769  OH2  TIP  D  328     78.663  60.295  39.952  1.00  75.61      D  O
ATOM   2770  OH2  TIP  D  329     75.120  69.391  40.898  1.00  69.21      D  O
TER    2771       TIP  D  329                                              D
END
```

CRYSTAL STRUCTURE OF FMS-LIKE TYROSINE KINASE

CROSS-REFERENCE TO RELATED APPLICATIONS

The present application claims the benefit under 35 U.S.C. § 119 of U.S. Provisional patent application No. 60/503,270, filed Sep. 15, 2003, and U.S. Provisional patent application No. 60/540,391, filed Jan. 29, 2004, the entire contents of both applications being incorporated herein by reference.

TECHNICAL FIELD OF INVENTION

The present invention relates to human FMS-like tyrosine kinase (FLT3), FLT3 binding pockets or FLT3-like binding pockets. The present invention provides a computer comprising a data storage medium encoded with the structure coordinates of such binding pockets. This invention also relates to methods of using the structure coordinates to solve the structure of homologous proteins or protein complexes. In addition, this invention relates to methods of using the structure coordinates to screen for and design compounds, including inhibitory compounds, that bind to FLT3 protein, FLT3 protein complexes, homologues thereof, or FLT3-like protein or FLT3-like protein complexes. The invention also relates to crystallizable compositions and crystals comprising FLT3 cytoplasmic domain.

BACKGROUND OF THE INVENTION

The FMS-like tyrosine kinase (FLT3) is a type III receptor tyrosine kinase that is thought to play a key role in hematopoiesis. Certain classes of FLT3 mutations cause constitutively activated forms of the receptor that are found in significant numbers of patients with acute myeloid leukemia (AML). The mutations occur in either the activation loop, for example, as point mutations of Asp835, or as internal tandem duplication (ITD) sequences in the juxtamembrane (JM) domain.

FLT3 (FMS-like tyrosine kinase 3) (Gilliland, D. G., and Griffin, J. D., *Blood* 100: 1532-1542 (2002); D. Kottaridis, P., et. al., *Br. J. Haematol.* 122, 523-538 (2003); Stirewalt, D. L. and Radich, J. P. *Nat. Rev. Cancer* 3: 650-665 (2003)), also known as FLK-2 (fetal liver kinase 2) and STK-1 (human stem cell kinase 1), belongs to a family of type III receptor tyrosine kinases (RTKs) (Rosnet, O., et. al., *Oncogene* 6: 1641-1650 (1991); Rosnet, O., et. al., *Genomics* 9: 380-385 (1991); Small, D., et. al., *Proc. Natl. Acad. Sci. USA* 91, 459-463 (1994); Matthews, W., et. al., *Cell* 65: 1143-1152 (1991)). Members of a subset of this family include FLT3, platelet-derived growth factor receptors α and β (PDGFRα and PDGFRβ) (Yarden, Y., et. al., *Nature* 323: 226-232 (1986); Claesson-Welsh, L., et. al., *Methods Enzymol.* 198: 72-77 (1991); Claesson-Welsh, L et. al., *Proc. Natl. Acad. Sci. USA* 86: 4917-4921 (1989); Matsui, T., et. al., *Science* 243: 800-804 (1989)), FMS (Stanley, E. R., et. al., *J. Cell. Biochem.* 21:151-159 (1983)) and cKIT (Yarden, Y et. al., *EMBO J.* 6: 3341-3351 (1987); Mol, C. D., et. al., *J. Biol. Chem.* 278: 31461-31464 (2003)) and are characterized by an extracellular domain consisting of five immunoglobulin-like (Ig-like) domains, a single transmembrane region, a cytoplasmic juxtamembrane domain (JM) and a cytoplasmic tyrosine kinase domain interrupted by a kinase insert domain (KID) (Agnes, F., et. al., *Gene* 145: 283-288 (1994); Rosnet, O., and Birnbaum, D. (1993) Crit. Rev. Oncog. 4, 595-61; Scheijen, B., and Griffin, J. D. *Oncogene* 21: 3314-3333 (2002)). Two groups independently reported the cloning of the flt3 gene (Rosnet, O., et. al., *Oncogene*, supra; Rosnet, O., et. al., *Genomics*, supra; Matthews, W et. al., supra).

Subsequently, FL, the ligand for FLT3, and a type I transmembrane protein was cloned from mouse (Lyman, S. D., et. al., *Stem Cells* 12 Suppl 1: 99-107; discussion 108-110 (1994); Lyman, S. D et. al., *Oncogene* 11: 1165-1172 (1995); Hannum, C., et. al., *Nature* 368: 643-648 (1994); Savvides, S. N., et. al., *Nat. Struct. Biol.* 7: 486-491 (2000)). The binding of FL leads to dimerization, activation and autophosphorylation of the receptor and subsequent activation of several signaling pathways including STAT5 (Zhang, S., et. al., *J. Exp. Med.* 192: 719-728 (2000)), Ras/mitogen-activated protein kinase (MAPK) and phosphatidylinositol 3 kinase (PI3K)/AKT pathways. The human flt3 gene encodes a 993 amino acid protein of which residues 572-603 and 604-958 represent the JM and tyrosine kinase domains, respectively (Rosnet, O., et. al., *Blood* 82: 1110-1119 (1993)).

FLT3 is primarily expressed in immature hematopoietic cells (Rosnet, O., et. al., *Genomics*, supra; deLapeyriere, O., et. al., *Differentiation* 58: 351-359 (1995)) and is essential for the normal function of stem cells and the immune system (deLapeyriere, O., et. al., supra; Brasel, K., et. al., *Leukemia* 9: 1212-1218 (1995); Turner, A. M., et. al., *Blood* 88: 3383-3390 (1996)). FLT3 is also found in placenta, gonads and brain (Maroc, N., et. al., *Oncogene* 8: 909-918 (1993)) and is expressed in high levels in a wide range of hematopoietic malignancies including 70-100% of acute myelogenous leukemia (AML), acute lymphoblastic leukemia (ALL) and chronic myelogenous leukemia (Rosnet, O., et. al., *Acta Haematol.* 95: 218-223 (1996); Drexler, H. G. *Leukemia* 10: 588-599 (1996)).

Two distinct types of FLT3 mutations have been identified in up to 41% of AML patients. Internal tandem duplication (ITD) mutations within the JM domain contribute to about 17-34% of FLT3 activating mutations in AML (Nakao, M., et. al., *Leukemia* 10: 1911-1918 (1996); Thiede, C., et. al., *Blood* 99: 4326-4335 (2002)). FLT3-ITD has also been detected at low frequency in myelodysplastic syndrome (MDS) (Yokota, S., et. al., *Leukemia* 11: 1605-1609 (1997)); Horiike, S., et. al., *Leukemia* 11: 1442-1446 (1997)). The ITDs are always in-frame, and are limited to the JM domain. However, they vary in length and position from patient to patient. These repeat sequences may serve to disrupt the autoinhibitory activity of the JM domain resulting in the constitutive activation of FLT3. Point mutations at aspartate 835 within the activation loop of the FLT3 kinase domain represent a second class of activating mutations (Yamamoto, Y., et. al., *Blood* 97: 2434-2439 (2001); Abu-Duhier, F. M., et. al., *Br. J. Haematol.* 113: 983-988 (2001)). FLT3-Asp835 mutations also lead to constitutive activation of the receptor and have been reported in 7% of AML, 3% of MDS and 3% of all cases. The most common substitution is Asp835Tyr, but other substitutions including Asp835Val, Asp835His, Asp835Glu and Asp835Asn have also been reported (Yamamoto, Y., et. al., supra). Both FLT3-ITD and FLT3-Asp835 mutations are associated with FLT3 autophosphorylation and phosphorylation of downstream targets (Yamamoto, Y., et. al., supra; Mizuki, M., et. al., *Blood* 96: 3907-3914 (2000); Mizuki, M., et. al., *Blood* 101: 3164-3173 (2003); Hayakawa, F., et. al., *Oncogene* 19: 624-631 (2000)).

A novel class of constitutively activated FLT3 mutants has been recently identified in AML patients in which isoleucine 836 is either deleted (FLT3-Ile836del) or substituted with methionine and arginine (FLT3-Ile836Met+Arg) (Thiede, C., et. al., supra). In mice, injection of FLT3-ITD transformed cells results in leukemia-like syndrome (Mizuki, M., et. al., (2000), supra). Several FLT3 inhibitors, such as PKC412 (N-benzoyl staurosporine) (Fabbro, D., et. al., *Anticancer Drug Des.* 15: 17-28 (2000); Weisberg, E., et. al., *Cancer Cell* 1: 433-443 (2002)), CT53518 (also known as MLN518) (Kelly, L. M., et. al., *Cancer Cell* 1: 421-432 (2002)), SU11248 (O'Farrell, A. M., et. al., *Blood* 101: 3597-3605 (2003)), SU5614 (Spiekermann, K., et. al., *Blood* 101: 1494-1504 (2003)), and SU5416 (Giles, F. J., et. al., *Blood* 102: 795-801 (2003)), have been shown to have antitumor activity. Collectively, these data suggest that FLT3 is an attractive therapeutic target for the development of kinase inhibitors for AML and other associated diseases.

SUMMARY OF THE INVENTION

The present invention provides the first time the crystal structure of the autoinhibited, unphosphorylated form of FLT3 comprised of the kinase domain (minus the KID) and the JM domain. This structure shows, for the first time, the autoinhibitory conformation of a complete JM domain in type III class receptor tyrosine kinases. The structure of FLT3 provides direct insight into the mechanism by which the JM domain exerts its autoinhibitory effect on the catalytic activity of the kinase domain, which is likely utilized by other members of the type III receptor tyrosine kinases. The role of the internal tandem duplication (ITD) in the constitutive activation of FLT3 in acute myeloid leukemia (AML) patients is also revealed. This structure provides a framework to explain the aberrant behavior of FLT3 in disease and to understand the possible mechanisms by which the ITD can switch FLT3 from an inactive to a catalytically active form. An analysis of the sequence alignment of other members of the PDGFR family suggests that the FLT3 mechanism of autoinhibition may be a general one applicable to all members of this family. The structure also presents a rationale for the structure-based design of small molecule FLT3 inhibitors as therapeutic agents, thus addressing the need for novel drugs for the treatment of AML and related diseases.

The present invention also provides molecules comprising FLT3 binding pockets, or FLT3-like binding pockets that have similar three-dimensional shapes. In one embodiment, the molecules are FLT3 or FLT3-like proteins, protein complexes, or homologues thereof. In another embodiment, the molecules are FLT3 cytoplasmic domains or homologues thereof. In another embodiment, the molecules are in crystalline form.

The invention provides crystallizable compositions and crystal compositions comprising the cytoplasmic domain of human FLT3 or a homologue thereof with or without a chemical entity.

The invention provides a computer comprising a machine-readable storage medium, comprising a data storage material encoded with machine-readable data, wherein the data defines the binding pockets or domains according to the structure coordinates of molecules or molecular complexes of FLT3 or FLT3-like proteins, protein complexes or homologues thereof. The invention also provides a computer comprising the data storage medium. Such storage medium when read and utilized by a computer programmed with appropriate software can display, on a computer screen or similar viewing device, a three-dimensional graphical representation of such binding pockets or domains. In one embodiment, the structure coordinates of said molecules or molecular complexes are produced by homology modeling of the coordinates of FIG. 1A.

The invention also provides methods for designing, selecting, evaluating and identifying and/or optimizing compounds which bind to the molecules or molecular complexes or their binding pockets. Such compounds are potential inhibitors of FLT3, FLT3-like proteins or their homologues.

The invention also provides a method for determining at least a portion of the three-dimensional structure of molecules or molecular complexes which contain at least some structurally similar features to FLT3, particularly FLT3 homologues. This is achieved by using at least some of the structure coordinates obtained from a FLT3 cytoplasmic domain.

The invention provides a crystal comprising a cytoplasmic domain of an FMS-like tyrosine kinase protein or a homologue thereof, wherein the cytoplasmic domain of the FMS-like tyrosine kinase protein is selected from the group consisting of amino acid residues 564-993 of SEQ ID NO:1, amino acid residues 564-958 of SEQ ID NO:1, amino acid residues 564-710 and 762-958 of SEQ ID NO:1, amino acid residues 570-710 and 783-947 of SEQ ID NO:1, amino acid residues 570-958 of SEQ ID NO:1, and amino acid residues 570-710 and 762-958 of SEQ ID NO:1.

The invention also provides a crystal according to paragraph 14, wherein the cytoplasmic domain of the FMS-like tyrosine kinase protein comprises amino acid residues 564-710 and 762-958 of SEQ ID NO:1.

The invention provides a crystallizable composition comprising a cytoplasmic domain of an FMS-like tyrosine kinase protein or a homologue thereof, wherein the cytoplasmic domain of the FMS-like tyrosine kinase protein is selected from the group consisting of amino acid residues 564-993 of SEQ ID NO:1, amino acid residues 564-958 of SEQ ID NO:1, amino acid residues 564-710 and 762-958 of SEQ ID NO:1, amino acid residues 570-710 and 783-947 of SEQ ID NO:1, amino acid residues 570-958 of SEQ ID NO:1, and amino acid residues 570-710 and 762-958 of SEQ ID NO:1.

The invention also provides a crystallizable composition according to paragraph 16, wherein the cytoplasmic domain of the FMS-like tyrosine kinase protein comprises amino acid residues 564-710 and 762-958 of SEQ ID NO:1.

The invention provides a computer comprising:
(a) a machine-readable data storage medium, comprising a data storage material encoded with machine-readable data, wherein the data defines a binding pocket or domain selected from the group consisting of:
  (i) a set of amino acid residues which are identical to human FMS-like tyrosine kinase (FLTs) amino acid residues H809, R810, and D811 according to FIG. 1A, wherein the root mean square deviation of the backbone atoms between the set of amino acid residues and the FLT3 amino acid residues is not greater than about 2.0 Å;
  (ii) a set of amino acid residues comprising at least five amino acid residues which are identical to human FMS-like tyrosine kinase amino acid residues F621, E661, M664, L802, V808, R810, D829, and L832 according to FIG. 1A, wherein the root mean square deviation of the backbone atoms between the at least five amino acid residues and the FLT3 amino acid residues which are identical is not greater than about 2.0 Å;
  (iii) a set of amino acid residues comprising at least six amino acid residues which are identical to human FMS-like tyrosine kinase amino acid residues F621, K644, A657, L658, E661, M664, L802, K805, S806, C807, V808, H809, R810, D811, C828, D829, F830, G831, and L832 according to FIG. 1A, wherein the root mean square deviation of the backbone atoms between the at least six amino acid residues and the FLT3 amino acid residues which are identical is not greater than about 2.0 Å; and (iv) a set of amino acid residues that are identical to FLT3 amino acid residues according to FIG. 1A, wherein the root mean square deviation between the set of amino acid residues and the FLT3 amino acid residues is not more than about 3.0 Å;

(b) a working memory for storing instructions for processing the machine-readable data;

(c) a central processing unit coupled to the working memory and to the machine-readable data storage medium for processing the machine-readable data and a means for generating three-dimensional structural information of the binding pocket or domain; and (d) output hardware coupled to the central processing unit for outputting said three-dimensional structural information of the binding pocket or domain, or information produced using the three-dimensional structural information of the binding pocket or domain.

The invention also provides the computer according to paragraph 18, wherein the binding pocket is produced by homology modeling of the structure coordinates of the FMS-like tyrosine kinase amino acid residues according to FIG. 1A. The invention further provides the computer according to paragraph 18, wherein means for generating three-dimensional structural information is provided by means for generating a three-dimensional graphical representation of the binding pocket or domain.

The invention provides the computer according to paragraph 18, wherein the output hardware is a display terminal, a printer, CD or DVD recorder, ZIP™ or JAZ™ drive, a disk drive, or other machine-readable data storage device.

The invention provides a method of using a computer for selecting an orientation of a chemical entity that interacts favorably with a binding pocket or domain selected from the group consisting of:

(i) a set of amino acid residues which are identical to human FMS-like tyrosine kinase (FLT3) amino acid residues H809, R810, and D811 according to FIG. 1A, wherein the root mean square deviation of the backbone atoms between the set of amino acid residues and the FLT3 amino acid residues is not greater than about 2.0 Å;

(ii) a set of amino acid residues comprising at least five amino acid residues which are identical to human FMS-like tyrosine kinase amino acid residues F621, E661, M664, L802, V808, R810, D829, and L832 according to FIG. 1A, wherein the root mean square deviation of the backbone atoms between the at least five amino acid residues and the FLT3 amino acid residues which are identical is not greater than about 2.0 Å;

(iii) a set of amino acid residues comprising at least six amino acid residues which are identical to human FMS-like tyrosine kinase amino acid residues F621, K644, A657, L658, E661, M664, L802, K805, S806, C807, V808, H809, R810, D811, C828, D829, F830, G831, and L832 according to FIG. 1A, wherein the root mean square deviation of the backbone atoms between the at least six amino acid residues and the FLT3 amino acid residues which are identical is not greater than about 2.0 Å; and (iv) a set of amino acid residues that are identical to FLT3 amino acid residues according to FIG. 1A, wherein the root mean square deviation between the set of amino acid residues and the FLT3 amino acid residues is not more than about 3.0 Å;

the method comprising the steps of:
(a) providing the structure coordinates of the binding pocket or domain on a computer comprising means for generating three-dimensional structural information from the structure coordinates;

(b) employing computational means to dock a first chemical entity in the binding pocket or domain;

(c) quantifying the association between the chemical entity and all or part of the binding pocket or domain for different orientations of the chemical entity; and (d) selecting the orientation of the chemical entity with the most favorable interaction based on the quantified association.

The invention also provides the method according to paragraph 21, further comprising the step of (e) generating a three-dimensional graphical representation of the binding pocket or domain prior to step (b). The invention further provides the method according to paragraph 21, wherein energy minimization, molecular dynamics simulations, or rigid-body minimizations are performed simultaneously with or following step (b). The invention provides the method according to paragraph 21, further comprising the steps of:

(e) repeating steps (b) through (d) with a second chemical entity; and (f) selecting at least one of the first or second chemical entity that interacts more favorably with the binding pocket or domain based on the quantified association of the first or second chemical entity.

The invention provides a method of using a computer for selecting an orientation of a chemical entity with a favorable shape complementarity in a binding pocket selected from the group consisting of:

(i) a set of amino acid residues which are identical to human FMS-like tyrosine kinase (FLT3) amino acid residues H809, R810, and D811 according to FIG. 1A, wherein the root mean square deviation of the backbone atoms between the set of amino acid residues and the FLT3 amino acid residues is not greater than about 2.0 Å;

(ii) a set of amino acid residues comprising at least five amino acid residues which are identical to human FMS-like tyrosine kinase amino acid residues F621, E661, M664, L802, V808, R810, D829, and L832 according to FIG. 1A, wherein the root mean square deviation of the backbone atoms between the at least five amino acid residues and the FLT3 amino acid residues which are identical is not greater than about 2.0 Å;

(iii) a set of amino acid residues comprising at least six amino acid residues which are identical to human FMS-like tyrosine kinase amino acid residues F621, K644, A657, L658, E661, M664, L802, K805, S806, C807, V808, H809, R810, D811, C828, D829, F830, G831, and L832 according to FIG. 1A, wherein the root mean square deviation of the backbone atoms between the at least six amino acid residues and the FLT3 amino acid residues which are identical is not greater than about 2.0 Å; and (iv) a set of amino acid residues that are identical to FLT3 amino acid residues according to FIG. 1A, wherein the root mean square deviation between the set of amino acid residues and the FLT3 amino acid residues is not more than about 3.0 Å;

the method comprising the steps of:
(a) providing the structure coordinates of the binding pocket and all or part of the JM-B binding motif bound therein on a computer comprising means for generating three-dimensional structural information from the structure coordinates;

(b) employing computational means to dock a first chemical entity in the binding pocket;

(c) quantitating the contact score of the chemical entity in different orientations; and (d) selecting the orientation with the highest contact score.

The invention also provides method according to paragraph 23, further comprising the step of:

(e) generating a three-dimensional graphical representation of the binding pocket and all or part of the JM-B binding motif bound therein prior to step (b). The invention also provides the method according to paragraph 23, further comprising the steps of:

(e) repeating steps (b) through (d) with a second chemical entity; and (f) selecting at least one of the first or second chemical entity that has a higher contact score based on the quantitated contact score of the first or second chemical entity.

The invention provides a method for identifying a candidate inhibitor of a molecule or molecular complex comprising a binding pocket or domain selected from the group consisting of:

(i) a set of amino acid residues which are identical to human FMS-like tyrosine kinase (FLT3) amino acid residues H809, R810, and D811 according to FIG. 1A, wherein the root mean square deviation of the backbone atoms between the set of amino acid residues and the FLT3 amino acid residues is not greater than about 2.0 Å;

(ii) a set of amino acid residues comprising at least five amino acid residues which are identical to human FMS-like tyrosine kinase amino acid residues F621, E661, M664, L802, V808, R810, D829, and L832 according to FIG. 1A, wherein the root mean square deviation of the backbone atoms between the at least five amino acid residues and the FLT3 amino acid residues which are identical is not greater than about 2.0 Å;

(iii) a set of amino acid residues comprising at least six amino acid residues which are identical to human FMS-like tyrosine kinase amino acid residues F621, K644, A657, L658, E661, M664, L802, K805, S806, C807, V808, H809, R810, D811, C828, D829, F830, G831, and L832 according to FIG. 1A, wherein the root mean square deviation of the backbone atoms between the at least six amino acid residues and the FLT3 amino acid residues which are identical is not greater than about 2.0 Å; and (iv) a set of amino acid residues that are identical to FLT3 amino acid residues according to FIG. 1A, wherein the root mean square deviation between the set of amino acid residues and the FLT3 amino acid residues is not more than about 3.0 Å;

comprising the steps of:

(a) using a three-dimensional structure of the binding pocket or domain to design, select or optimize a plurality of chemical entities;

(b) contacting each chemical entity with the molecule or the molecular complex;

(c) monitoring an inhibitory effect of the catalytic activity of the molecule or molecular complex by each chemical entity; and (d) selecting a chemical entity based on the inhibitory effect of the chemical entity on the catalytic activity of the molecule or molecular complex.

The invention provides a method of designing a compound or complex that interacts with a binding pocket or domain selected from the group consisting of:

(i) a set of amino acid residues which are identical to human FMS-like tyrosine kinase (FLT3) amino acid residues H809, R810, and D811 according to FIG. 1A, wherein the root mean square deviation of the backbone atoms between the set of amino acid residues and the FLT3 amino acid residues is not greater than about 2.0 Å;

(ii) a set of amino acid residues comprising at least five amino acid residues which are identical to human FMS-like tyrosine kinase amino acid residues F621, E661, M664, L802, V808, R810, D829, and L832 according to FIG. 1A, wherein the root mean square deviation of the backbone atoms between the at least five amino acid residues and the FLT3 amino acid residues which are identical is not greater than about 2.0 Å;

(iii) a set of amino acid residues comprising at least six amino acid residues which are identical to human FMS-like tyrosine kinase amino acid residues F621, K644, A657, L658, E661, M664, L802, K805, S806, C807, V808, H809, R810, D811, C828, D829, F830, G831, and L832 according to FIG. 1A, wherein the root mean square deviation of the backbone atoms between the at least six amino acid residues and the FLT3 amino acid residues which are identical is not greater than about 2.0 Å; and (iv) a set of amino acid residues that are identical to FLT3 amino acid residues according to FIG. 1A, wherein the root mean square deviation between the set of amino acid residues and the FLT3 amino acid residues is not more than about 3.0 Å;

comprising the steps of:

(a) providing the structure coordinates of the binding pocket or domain on a computer comprising means for generating three-dimensional structural information from the structure coordinates;

(b) using the computer to dock a first chemical entity in part of the binding pocket or domain;

(c) docking at least a second chemical entity in another part of the binding pocket or domain;

(d) quantifying the association between the first or second chemical entity and part of the binding pocket or domain;

(e) repeating steps (b) to (d) with another first and second chemical entity, (f) selecting a first and a second chemical entity based on the quantified association of both the first and second chemical entity;

(g) optionally, visually inspecting the relationship of the selected first and second chemical entity to each other in relation to the binding pocket or domain on a computer screen using the three-dimensional graphical representation of the binding pocket or domain and the first and second chemical entity; and (h) assembling the selected first and second chemical entity into a compound or complex that interacts with said binding pocket or domain by model building.

The method provides a method of utilizing molecular replacement to obtain structural information about a molecule or a molecular complex of unknown structure, wherein the molecule is sufficiently homologous to a cytoplasmic domain of an FLT3 protein, comprising the steps of:

(a) crystallizing the molecule or molecular complex;

(b) generating an X-ray diffraction pattern from the crystallized molecule or molecular complex; and (c) applying at least a portion of the structure coordinates set forth in FIG. 1A or a homology model thereof to the X-ray diffraction pattern to generate a three-dimensional electron density map of at least a portion of the molecule or molecular complex of unknown structure; and (d) generating a structural model of the molecule or molecular complex from the three-dimensional electron density map.

The invention also provides a method according to paragraph 27, wherein the molecule is selected from the group consisting of the FMS-like tyrosine kinase protein, and a homologue of a cytoplasmic domain of the FMS-like tyrosine kinase protein.

The invention provides the method according to paragraph 27, wherein the molecular complex is selected from the group consisting of the FMS-like tyrosine kinase protein complex and a homologue of the cytoplasmic domain of FMS-like tyrosine cytoplasmic complex.

The invention provides a method for identifying a candidate inhibitor that interacts with a binding site of an FMS-like tyrosine kinase protein or a homologue thereof, comprising the steps of:

(a) obtaining a crystal comprising a cytoplasmic domain of said FMS-like tyrosine kinase protein or said homologue thereof, wherein the crystal is characterized with space group $P4_32_12$ and has unit cell parameters of a=b=80.67 Å, c=150.16 Å;

(b) obtaining the structure coordinates of amino acids of the crystal of step (a), wherein the structure coordinates are set forth in FIG. 1A-1 to 1A-50;

(c) generating a three-dimensional model of the cytoplasmic domain of said FMS-like tyrosine kinase protein or said homologue thereof using the structure coordinates of the amino acids obtained in step (b), a root mean square deviation from backbone atoms of said amino acids of not more than ±2.0 Å;

(d) determining a binding site of the cytoplasmic domain of said FMS-like tyrosine kinase protein or said homologue thereof from said three-dimensional model; and (e) performing computer fitting analysis to identify the candidate inhibitor which interacts with said binding site.

The invention provides the method according to paragraph 30, further comprising the step of: (f) contacting the identified candidate inhibitor with the cytoplasmic domain of said FMS-like tyrosine kinase protein or said homologue thereof in order to determine the effect of the inhibitor on FMS-like tyrosine kinase protein activity.

The invention provides the method according to paragraph 30, wherein the binding site of the cytoplasmic domain of said FMS-like tyrosine kinase protein or said homologue thereof determined in step (d) comprises the structure coordinates according to FIG. 1A-1 to 1A-50 of amino acid residues H809, R810, and D811, wherein the root mean square deviation from the backbone atoms of said amino acids is not more than ±2.0 Å.

The invention provides the method according to paragraph 30, wherein the binding site of the cytoplasmic domain of said FMS-like tyrosine kinase protein or said homologue thereof determined in step (d) comprises the structure coordinates according to FIG. 1A-1 to 1A-50 of amino acid residues F621, E661, M664, L802, V808, R810, D829, and L832, wherein the root mean square deviation from the backbone atoms of said amino acids is not more than ±2.0 Å.

The invention provides the method according to paragraph 30, wherein the binding site of the cytoplasmic domain of said FMS-like tyrosine kinase protein or said homologue thereof determined in step (d) comprises the structure coordinates according to FIG. 1A-1 to 1A-50 of amino acid residues F621, K644, A657, E661, M664, L802, S806, C807, V808, H809, R810, D811, D829, and L832, wherein the root mean square deviation from the backbone atoms of said amino acids is not more than ±2.0 Å.

The invention provides a method for identifying a candidate inhibitor that interacts with a binding site of a cytoplasmic domain of an FMS-like tyrosine kinase protein or a homologue thereof, comprising the steps of:

(a) obtaining a crystal comprising the cytoplasmic domain of said FMS-like tyrosine kinase protein or said homologue thereof, wherein the crystal is characterized with space group $P4_32_12$ and has unit cell parameters of a=b=80.67 Å, c=150.16 Å;

(b) obtaining the structure coordinates of amino acids of the crystal of step (a);

(c) generating a three-dimensional model of said FMS-like tyrosine kinase protein or said homologue thereof using the structure coordinates of the amino acids generated in step (b), a root mean square deviation from backbone atoms of said amino acids of not more than ±2.0 Å;

(d) determining a binding site of the cytoplasmic domain of said FMS-like tyrosine kinase protein or said homologue thereof from said three-dimensional model; and (e) performing computer fitting analysis to identify the candidate inhibitor which interacts with said binding site.

The invention provides the method according to paragraph 35, further comprising the step of:

(f) contacting the identified candidate inhibitor with the cytoplasmic domain of said FMS-like tyrosine kinase protein or said homologue thereof in order to determine the effect of the inhibitor on FMS-like tyrosine kinase protein activity.

The invention provides the method according to paragraph 35, wherein the binding site of the cytoplasmic domain of said FMS-like tyrosine kinase protein or said homologue thereof determined in step (d) comprises the structure coordinates according to FIG. 1A-1 to 1A-50 of amino acid residues H809, R810, and D811, wherein the root mean square deviation from the backbone atoms of said amino acids is not more than ±2.0 Å.

The invention provides the method according to paragraph 35, wherein the binding site of the cytoplasmic domain of said FMS-like tyrosine kinase protein or said homologue thereof determined in step (d) comprises the structure coordinates according to FIG. 1A-1 to 1A-50 of amino acid residues F621, E661, M664, L802, V808, R810, D829, and L832, wherein the root mean square deviation from the backbone atoms of said amino acids is not more than ±2.0 Å.

The method according to paragraph 35, wherein the binding site of the cytoplasmic domain of said FMS-like tyrosine kinase protein or said homologue thereof determined in step (d) comprises the structure coordinates according to FIG. 1A-1 to 1A-50 of amino acid residues F621, K644, A657, E661, M664, L802, S806, C807, V808, H809, R810, D811, D829, and L832, wherein the root mean square deviation from the backbone atoms of said amino acids is not more than ±2.0 Å.

The invention provides a method for identifying a candidate inhibitor that interacts with a binding site of a cytoplasmic domain of an FMS-like tyrosine kinase protein or a homologue thereof, comprising the step of determining a binding site of the cytoplasmic domain of said FMS-like tyrosine kinase protein or the homologue thereof from a three-dimensional model to design or identify the candidate inhibitor which interacts with said binding site.

The invention provides the method according to paragraph 40, wherein the binding site of the cytoplasmic domain of said FMS-like tyrosine kinase protein or said homologue thereof determined comprises the structure coordinates according to FIG. 1A-1 to 1A-50 of amino acid residues H809, R810, and D811, wherein the root mean square deviation from the backbone atoms of said amino acids is not more than ±2.0 Å.

The invention provides the method according to paragraph 40, wherein the binding site of the cytoplasmic domain of said FMS-like tyrosine kinase protein or said homologue thereof determined comprises the structure coordinates according to FIG. 1A-1 to 1A-50 of amino acid residues F621, E661, M664, L802, V808, R810, D829, and L832, wherein the root mean square deviation from the backbone atoms of said amino acids is not more than ±2.0 Å.

The invention provides the method according to paragraph 40, wherein the binding site of the cytoplasmic domain of said FMS-like tyrosine kinase protein or said homologue thereof determined comprises the structure coordinates according to FIG. 1A-1 to 1A-50 of amino acid residues F621, K644, A657, L658, E661, M664, L802, K805, S806, C807, V808, H809, R810, D811, C828, D829, F830, G831, and L832, wherein the root mean square deviation from the backbone atoms of said amino acids is not more than ±2.0 Å.

The invention provides a method for identifying a candidate inhibitor of a molecule or molecular complex comprising a binding pocket or domain selected from the group consisting of:
(i) a set of amino acid residues which are identical to human FMS-like tyrosine kinase (FLT3) amino acid residues H809, R810, and D811 according to FIG. 1A, wherein the root mean square deviation of the backbone atoms between said set of amino acid residues and said FMS-like tyrosine kinase amino acid residues is not greater than about 2.0 Å;
(ii) a set of amino acid residues comprising at least five amino acid residues which are identical to human FMS-like tyrosine kinase amino acid residues F621, E661, M664, L802, V808, R810, D829, and L832 according to FIG. 1A, wherein the root mean square deviation of the backbone atoms between said at least five amino acid residues and said FMS-like tyrosine kinase amino acid residues which are identical is not greater than about 2.0 Å;
(iii) a set of amino acid residues comprising at least six amino acid residues which are identical to human FMS-like tyrosine kinase amino acid residues F621, K644, A657, L658, E661, M664, L802, K805, S806, C807, V808, H809, R810, D811, C828, D829, F830, G831, and L832 according to FIG. 1A, wherein the root mean square deviation of the backbone atoms between said at least six amino acid residues and said FMS-like tyrosine kinase amino acid residues which are identical is not greater than about 2.0 Å; and
(iv) a set of amino acid residues that are identical to FMS-like tyrosine kinase amino acid residues according to FIG. 1A, wherein the root mean square deviation between said set of amino acid residues and said FMS-like tyrosine kinase amino acid residues is not more than about 3.0 Å;
comprising the steps of:
(a) using a three-dimensional structure of the binding pocket or domain to design, select or optimize a plurality of chemical entities; and
(b) selecting said candidate inhibitor based on the inhibitory effect of said chemical entities on a cytoplasmic domain of a FMS-like tyrosine kinase protein or a cytoplasmic domain of a FMS-like tyrosine kinase protein homologue on the catalytic activity of the molecule or molecular complex.

BRIEF DESCRIPTION OF THE FIGURES

The following abbreviations are used in FIG. 1A:

"Atom type" refers to the element whose coordinates are measured. The first letter in the column defines the element.

"Resid" refers to the amino acid residue in the molecular model.

"X, Y, Z" define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in the molecules.

FIG. 1A (1A-1 to 1A-50) lists the atomic coordinates for human FLT3 (amino acid residues 570-710 and 783-947 of the cytoplasmic domain of human FLT3 protein (GenBank accession no. NP_004110; SEQ ID NO:1)) as derived from X-ray diffraction. Residues 649-654 were not included in the final model. The coordinates are shown in Protein Data Bank (PDB) format. Residues "PO4 B", "CAP C" and "TIP D" represent phosphate, CAPS (3-cyclohexylamino-1-propanesulfonic acid) and water molecules, respectively.

Figure 2A:
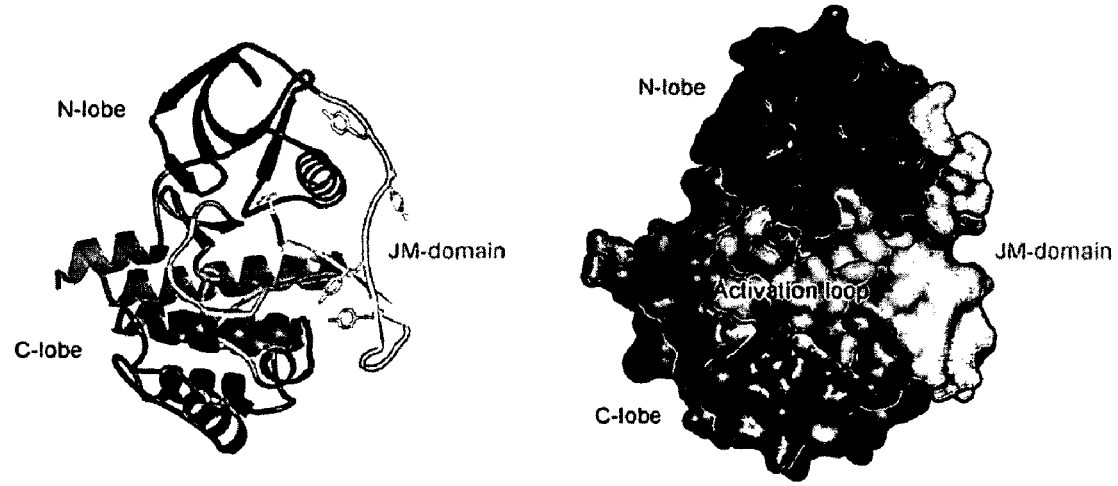

FIG. 2A depicts the structure of autoinhibited FLT3 using ribbon diagram (shown on left) and surface diagram (shown on right) and highlights the spatial arrangement of the various structural elements of the FLT3 molecule. The N-terminal kinase domain (labeled and shown in dark gray) and the C-terminal kinase domain (labeled and shown in medium gray) comprise the standard kinase fold. The activation loop (labeled in the right diagram) is folded up between the two kinase domains. The JM domain (labeled and shown in light gray) nearly spans the length of the molecule. All tyrosines in the JM domain and the activation loop are displayed as 'stick' representations.

Figure 2B:
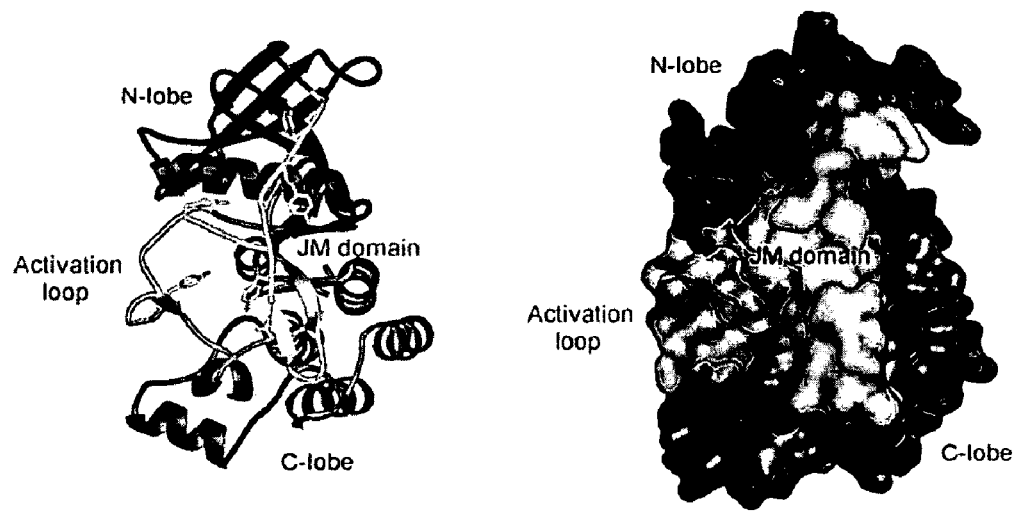

FIG. 2B is the same as FIG. 2A except the molecule is rotated 90 degrees clockwise when viewed down the vertical axis.

Figure 3A:
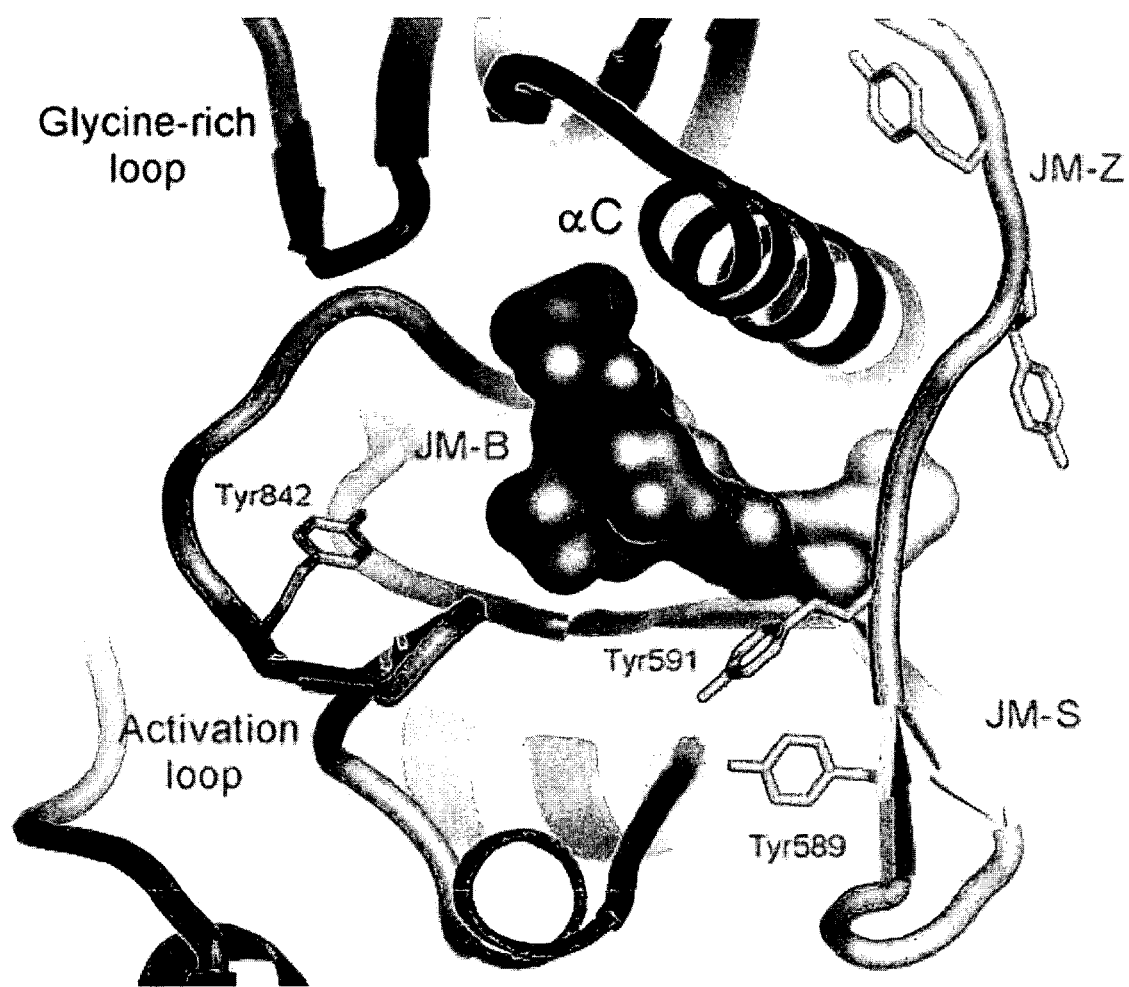

FIG. 3A depicts a ribbon representation of FLT3 highlighting the JM domain. A molecular surface representation of the JM-B shows its central position relative to the activation loop, αC, glycine-rich loop, JM-S and JM-Z.

Figure 3B:

FIG. 3B depicts a stereoview of a ribbon representation of FLT3. The JM domain is displayed as a 'stick' model.

Figure 4:
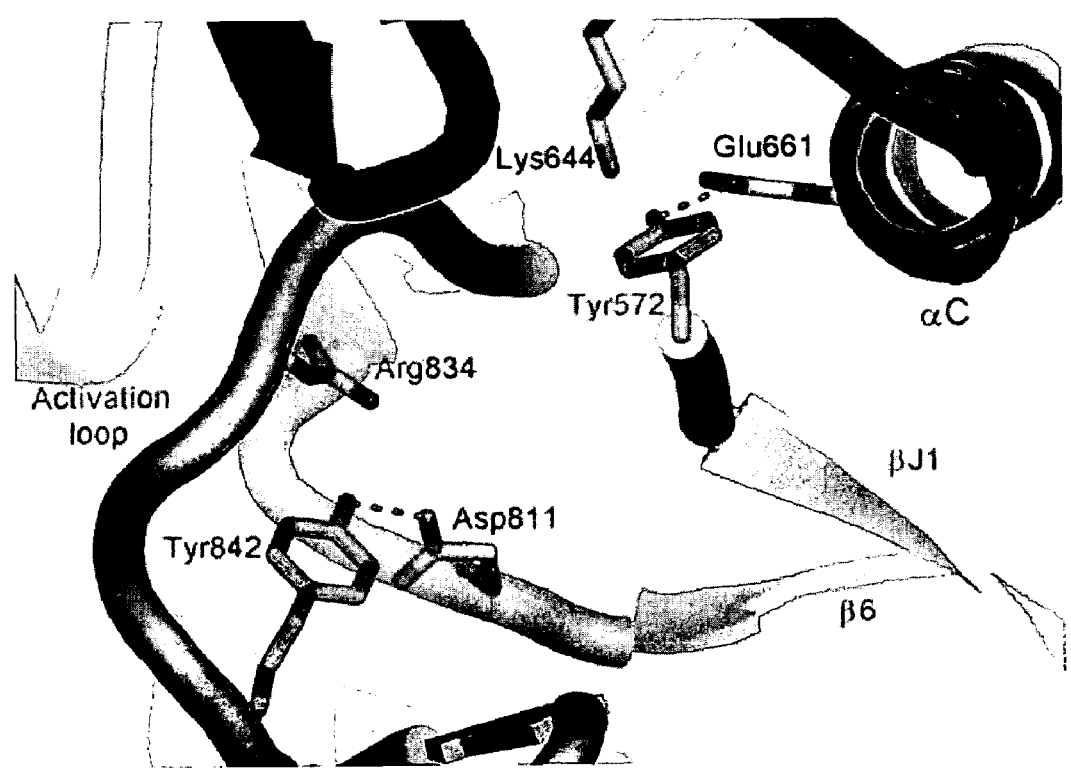

FIG. 4 shows a closeup view of the active site region of FLT3. Tyr572 and Tyr842 have hydrogen bonds to Glu661 and Asp811, respectively, which in turn are involved in salt bridges.

Figure 5A:
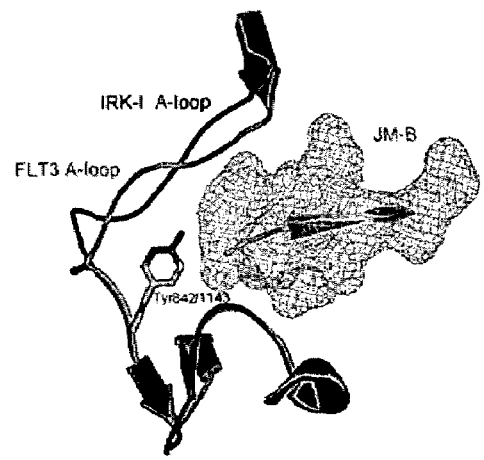

FIG. 5A shows a superposition of the closed activation loop from FLT3 on the closed IRK-I activation loop (dark gray).

Figure 5B:
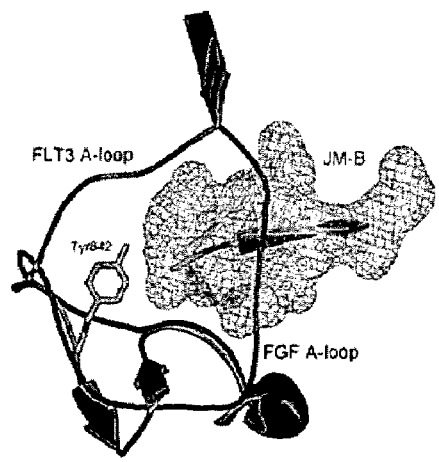

FIG. 5B shows a superposition of the closed activation loop from FLT3 on the partially open FGFR activation loop (dark gray).

Figure 5C:
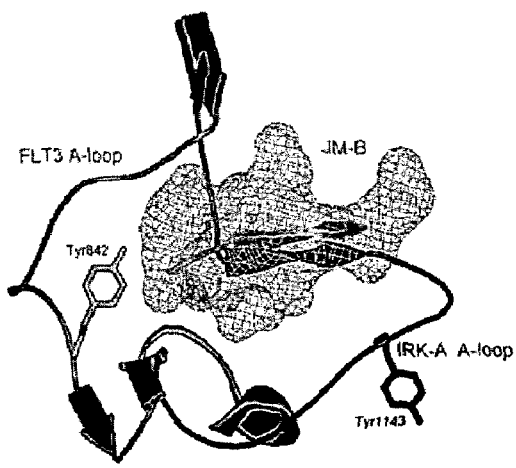

FIG. 5C shows a superposition of the closed activation loop from FLT3 on the fully open IRK-A activation loop (dark gray).

Figure 6A:
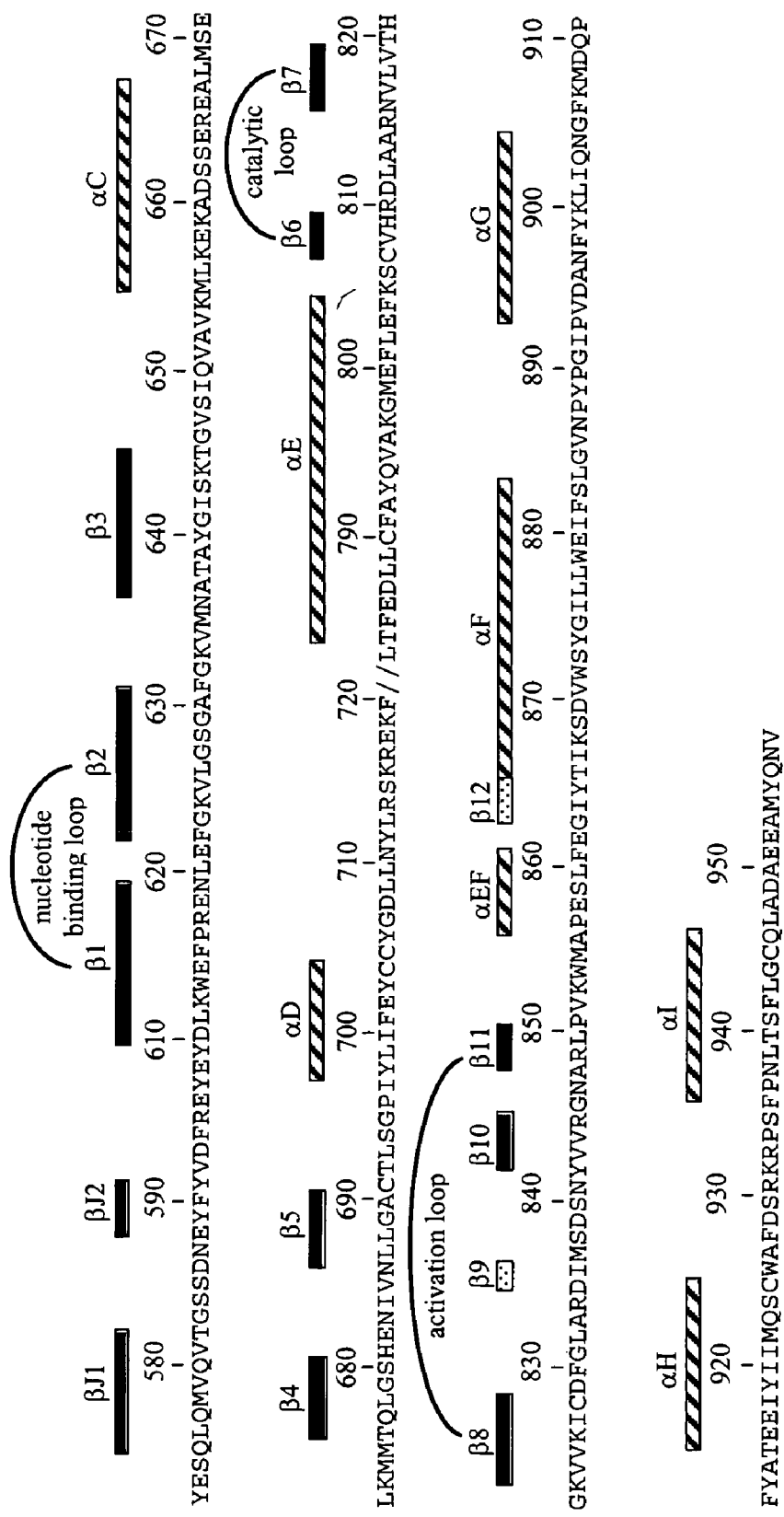

FIG. 6A shows the secondary structure assignments for FLT3 (amino acid residues 572-958 of the cytoplasmic domain (full length protein: GenBank accession no. NP_004110; SEQ ID NO:1)) in which α-helices and β-strands are represented by striped and solid bars, respectively. Dotted bars delineate secondary structures that are present in IRK3P (Hubbard et. al., 1997, supra), but not in autoinhibited FLT3.

Figure 6B:
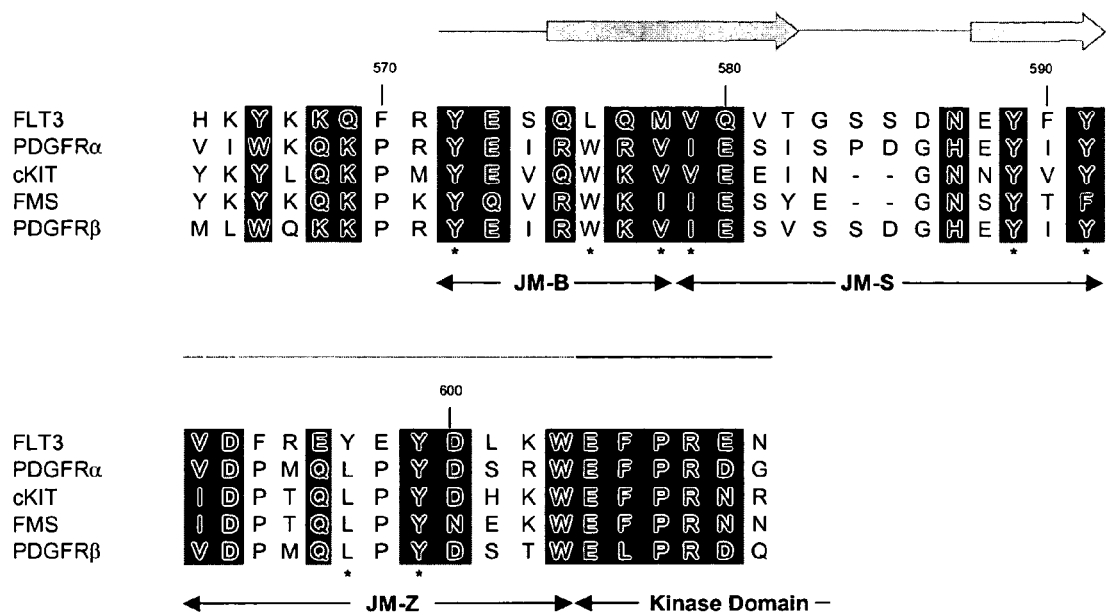

FIG. 6B show a sequence alignment of the JM domain for FLT3 (amino acid residues 564-609 of the cytoplasmic domain (full length protein: GenBank accession no. NP_004110; SEQ ID NO:1)), PDGFRα (SEQ ID NO:2), PDGFRβ (SEQ ID NO:3), cKIT (SEQ ID NO:4), and FMS (SEQ ID NO:5). Identical and homologous residues are shaded in gray. Gray arrows above the sequence alignment represent β-strands. Asterisks denote location of residues in PDGFRβ which when mutated to alanine give rise to constitutive activation. These PDGFRβ mutations include: Y530A, W534A, V536A, I537A, L555A, Y557A and the double mutant Y547A/Y549A (PDGFRβ numbers are given).

Figure 7:
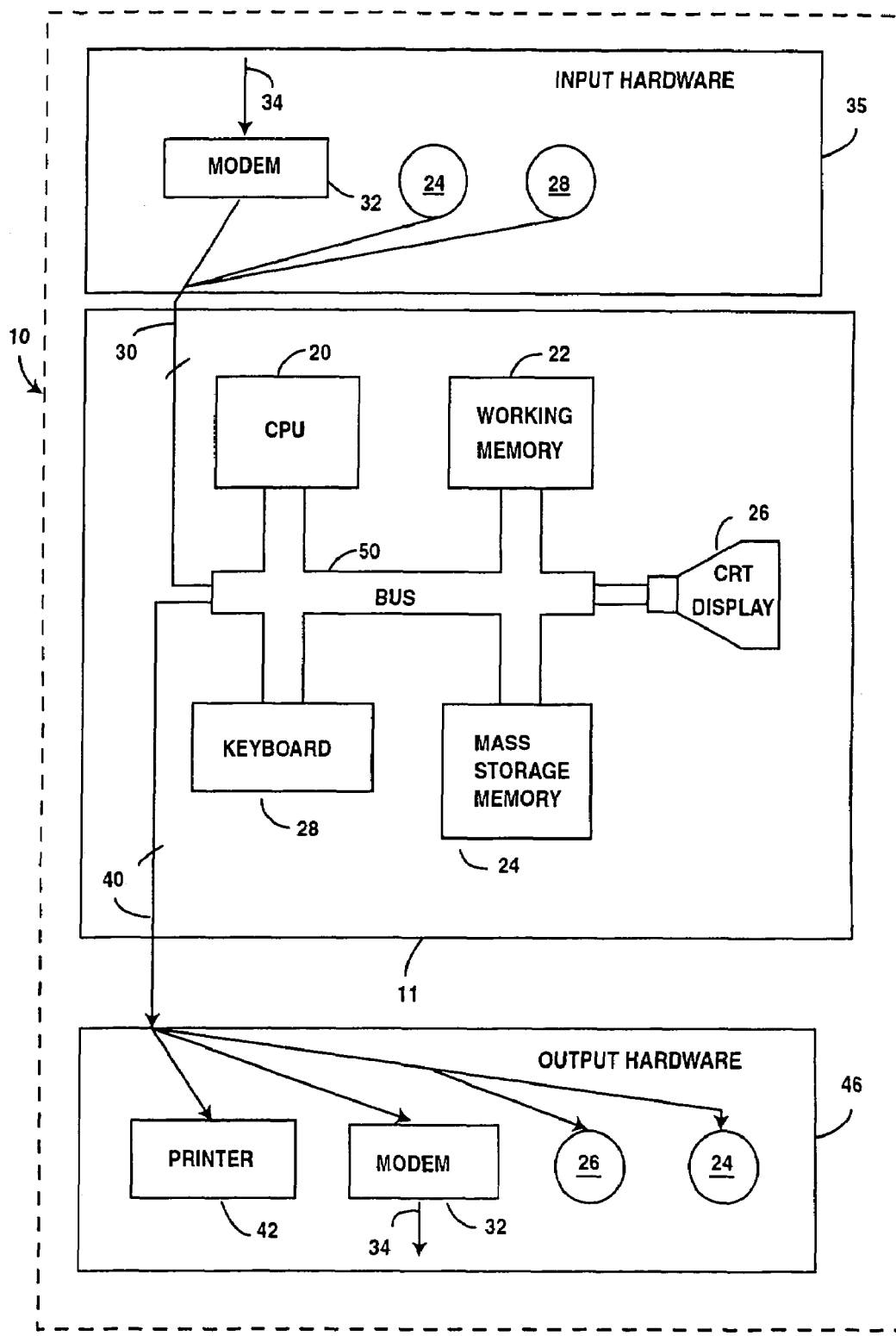
Figure 8:
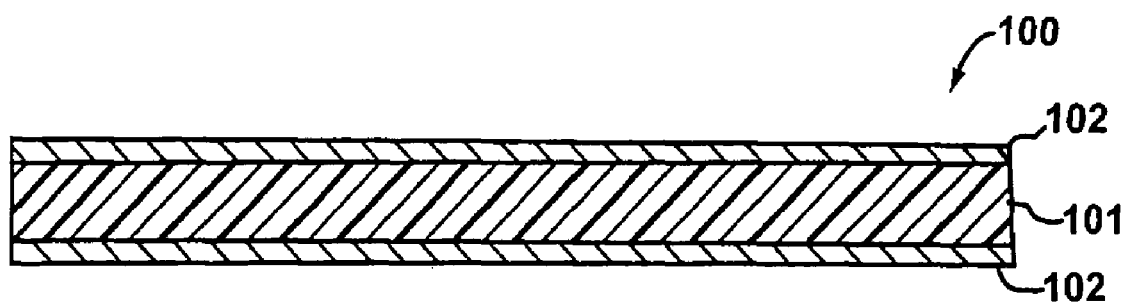
Figure 9:
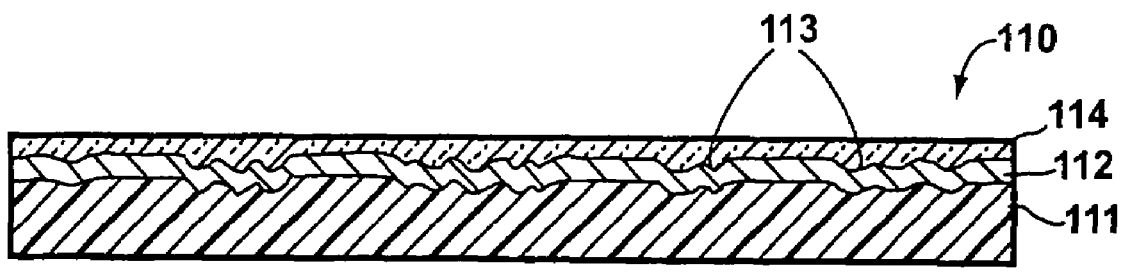

FIG. 7 shows a diagram of a system used to carry out the instructions encoded by the storage medium of FIGS. 8 and 9.

FIG. 8 shows a cross section of a magnetic storage medium.

FIG. 9 shows a cross section of a optically-readable data storage medium.

DETAILED DESCRIPTION OF THE INVENTION

In order that the invention described herein may be more fully understood, the following detailed description is set forth.

Throughout the specification, the word "comprise" or variations such as "comprises" or "comprising" will be understood to imply the inclusion of a stated integer or groups of integers but not the exclusion of any other integer or groups of integers.

The following abbreviations are used throughout the application:

| | | | | | |
|---|---|---|---|---|---|
| A = | Ala = | Alanine | T = | Thr = | Threonine |
| V = | Val = | Valine | C = | Cys = | Cysteine |
| L = | Leu = | Leucine | Y = | Tyr = | Tyrosine |
| I = | Ile = | Isoleucine | N = | Asn = | Asparagine |
| P = | Pro = | Proline | Q = | Gln = | Glutamine |
| F = | Phe = | Phenylalanine | D = | Asp = | Aspartic Acid |
| W = | Trp = | Tryptophan | E = | Glu = | Glutamic Acid |
| M = | Met = | Methionine | K = | Lys = | Lysine |
| G = | Gly = | Glycine | R = | Arg = | Arginine |
| S = | Ser = | Serine | H = | His = | Histidine |

As used herein, the following definitions shall apply unless otherwise indicated.

The term "about" when used in the context of root mean square deviation (RMSD) values takes into consideration the standard error of the RMSD value, which is ±0.1 Å.

The term "associating with" refers to a condition of proximity between a chemical entity or compound, or portions thereof, and a binding pocket or binding site on a protein. The association may be non-covalent—wherein the juxtaposition is energetically favored by hydrogen bonding, hydrophobic, van der Waals or electrostatic interactions—or it may be covalent.

The term "binding pocket" refers to a region of a molecule or molecular complex, that, as a result of its shape, favorably associates with a chemical entity. The term "pocket" includes, but is not limited to, cleft, channel or site. FLT3, FLT3-like molecules or homologues thereof may have binding pockets which include, but are not limited to, peptide or substrate binding, JM-B binding and ATP-binding sites. The shape of a first binding pocket may be largely pre-formed before binding of a chemical entity, may be formed simultaneously with binding of a chemical entity, or may be formed by the binding of another chemical entity to a different binding pocket of the molecule, which in turn induces a change in shape of the first binding pocket.

The term "catalytic active site" or "active site" refers to the portion of the protein kinase to which nucleotide substrates bind. For example, the catalytic active site of FLT3 is at the interface between the N-lobe and the C-lobe.

The term "chemical entity" refers to chemical compounds, complexes of at least two chemical compounds, and fragments of such compounds or complexes. The chemical entity can be, for example, a ligand, substrate, nucleotide triphosphate, nucleotide diphosphate, phosphate, nucleotide, agonist, antagonist, inhibitor, antibody, peptide, protein or drug. In one embodiment, the chemical entity is an inhibitor or substrate for the active site of FLT3 proteins or protein complexes, or homologues thereof. The first and second chemical entities referred to in the present invention may be identical or distinct from each other. When iterative steps of using first and second chemical entities are carried out, taken as a pair, the first and second chemical entities used in repeated steps should be different from the first and second chemical entities of the steps.

The term "complex" or "molecular complex" refers to a protein associated with a chemical entity.

The term "conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et. al., *Atlas of Protein Sequence and Structure*, 5: 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

The term "contact score" refers to a measure of shape complementarity between the chemical entity and binding pocket, which is correlated with an RMSD value obtained from a least square superimposition between all or part of the atoms of the chemical entity and all or part of the atoms of the ligand bound (for example, AMP-PNP or an inhibitor) in the binding pocket according to FIG. 1 or 2. The docking process may be facilitated by the contact score or RMSD values. For example, if the chemical entity moves to an orientation with high RMSD, the system will resist the motion. A set of orientations of a chemical entity can be ranked by contact score. A lower RMSD value will give a higher contact score. See Meng et. al. *J. Comp. Chem.*, 4, 505-524 (1992).

The term "correspond to" or "corresponding amino acids", when used in the context of amino acid residues that correspond to FLT3 amino acids, refers to particular amino acids or analogues thereof in a tyrosine kinase that correspond to amino acids in the human FLT3 protein. The corresponding amino acid may be an identical, mutated, chemically modified, conserved, conservatively substituted, functionally equivalent or homologous amino acid, when compared to the FLT3 amino acid to which it corresponds. For example, the following are examples of FLT3 amino acid residues that correspond to cKIT amino acid residues: F570:P551 and L576:W557 (the identity of the FLT3 residue is listed first; its position is indicated using FLT3 sequence numbering; and the identity of cKIT residue is given at the end).

Methods for identifying a corresponding amino acid are known in the art and are based upon sequence, structural alignment, its functional position or a combination thereof, as compared to the FLT3 protein. For example, corresponding amino acids may be identified by superimposing the backbone atoms of the amino acids in FLT3 and another protein using well known software applications, such as QUANTA (Molecular Simulations, Inc., San Diego, Calif. ©1998, 2000; Accelrys ©2001, 2002). The corresponding amino acids may also be identified using sequence alignment programs such as the "bestfit" program or CLUSTAL W Alignment Tool (Higgins D. G., et. al., *Methods Enzymol.*, 266: 383-402 (1996)).

The term "crystallization solution" refers to a solution which promotes crystallization comprising at least one agent, including a buffer, one or more salts, a precipitating agent, one or more detergents, sugars or organic compounds, lanthanide ions, a poly-ionic compound, and/or stabilizer.

The term "docking" refers to orienting, rotating, or translating a chemical entity in the binding pocket, domain, molecule or molecular complex or portion thereof based on distance geometry or energy. Docking may be performed by distance geometry methods that find sets of atoms of a chemical entity that match sets of sphere centers of the binding pocket, domain, molecule or molecular complex or portion thereof. See Meng et. al. *J. Comp. Chem.*, 4, 505-524 (1992). Sphere centers are generated by providing an extra radius of given length from the atoms (excluding hydrogen atoms) in the binding pocket, domain, molecule or molecular complex or portion thereof. Real-time interaction energy calculations, energy minimizations or rigid-body minimizations (Gschwend, et. al., *J. Mol. Recognition*, 9:175-186 (1996)) can be performed during or after orientation of the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen, et. al., *J. Med. Chem.* 33:889-894 (1990)). Docking can also be performed by combining a Monte Carlo search technique with rapid energy evaluation using molecular affinity potentials. See Goodsell and Olson, *Proteins: Structure, Function and Genetics* 8:195-202 (1990). Software programs that carry out docking functions include but are not limited to MATCHMOL (Cory et. al., *J Mol. Graphics*, 2, 39 (1984); MOLFIT (Redington, *Comput. Chem.*, 16, 217 (1992)) and DOCK (Meng et. al., supra).

The term "domain" refers to a structural unit of the FLT3 protein or homologue. The domain can comprise a binding pocket, a sequence or structural motif.

The term "full-length FLT3" refers to the complete human FLT3 protein, which includes an extracellular domain consisting of five immunoglobulin-like (Ig-like) domains, a single transmembrane region, and a cytoplasmic domain (amino acid residues 1 to 993; GenBank accession no. NP_004110; SEQ ID NO:1). The cytoplasmic domain includes a cytoplasmic juxtamembrane domain (JM) and a cytoplasmic kinase domain interrupted by a kinase insert domain (KID).

The term "FLT3-like" refers to all or a portion of a molecule or molecular complex that has a commonality of shape with all or a portion of the FLT3 protein. For example, in the FLT3-like JM-B binding pocket, the commonality of shape is defined by a root mean square deviation of the structure coordinates of the backbone atoms between the amino acids in the FLT3-like JM-B binding pocket and the FLT3 amino acids in the FLT3 JM-B binding pocket (as set forth in FIG. 1A). Compared to the amino acids of the FLT3 binding pocket, the corresponding amino acid residues in the FLT3-like binding pocket may or may not be identical. Depending on the set of FLT3 amino acid residues that define the FLT3 JM-B binding pocket, one skilled in the art would be able to locate the corresponding amino acids that define an FLT3-like binding pocket in a protein based on sequence or structural homology.

The term "FLT3 protein complex" or "FLT3 homologue complex" refers to a molecular complex formed by associating the FLT3 protein or FLT3 homologue with a chemical entity, for example, a ligand, a substrate, nucleotide triphosphate, nucleotide diphosphate, phosphate, an agonist or antagonist, inhibitor, antibody, drug or compound.

The term "generating a three-dimensional structure" or "generating a three-dimensional representation" refers to converting the lists of structure coordinates into structural models or graphical representations in three-dimensional space. This can be achieved through commercially or publicly available software. A model of a three-dimensional structure of a molecule or molecular complex can thus be constructed on a computer screen by a computer that is given the structure coordinates and that comprises the correct software. The three-dimensional structure may be displayed or used to perform computer modeling or fitting operations. In addition, the structure coordinates themselves, without the displayed model, may be used to perform computer-based modeling and fitting operations.

The term "homologue of FLT3 cytoplasmic domain" or "FLT3 cytoplasmic domain homologue" refers to the cytoplasmic domain of a protein in the type III class of receptor tyrosine kinases that is at least 70%, 80%, 90%, 95%, 96%, 97%, 98%, 99% or greater than 99% identical in sequence to the cytoplasmic domain (approximately amino acid residues 564-993 of SEQ ID NO:1) of human FLT3 protein and retains FLT3 kinase activity. In one embodiment, the homologue is at least 95%, 96%, 97%, 98% or 99% identical in sequence to human FLT3 cytoplasmic domain, and has conservative mutations as compared to human FLT3 cytoplasmic domain. The homologue can be an FLT3 cytoplasmic domain from another species, or the foregoing human FLT3 cytoplasmic domain with mutations, conservative substitutions, additions, deletions or a combination thereof. Such animal species include, but are not limited to, mouse, rat, a primate such as monkey or other primates.

The term "homology model" refers to a structural model derived from known three-dimensional structure(s). Generation of the homology model, termed "homology modeling", can include sequence alignment, residue replacement, residue conformation adjustment through energy minimization, or a combination thereof.

The term "interaction energy" refers to the energy determined for the interaction of a chemical entity and a binding pocket, domain, molecule or molecular complex or portion thereof. Interactions include but are not limited to one or more of covalent interactions, non-covalent interactions such as hydrogen bond, electrostatic, hydrophobic, aromatic, van der Waals interactions, and non-complementary electrostatic interactions such as repulsive charge-charge, dipole-dipole and charge-dipole interactions. As interaction energies are measured in negative values, the lower the value the more favorable the interaction.

The term "JM-B binding motif" or "JM-B" refers to a short segment in the FLT3 cytoplasmic domain or homologue thereof including amino acid residues Tyr572-Met578.

The term "JM-B binding pocket" refers to the binding pocket for the JM-B binding motif. The JM-B binding pocket comprises the kinase domain amino acid residues found within the near vicinity of the heptapeptide section of the autoinhibitory JM-B binding motif of FLT3 cytoplasmic domain or homologue thereof (amino acid residues YESQLQM (residues 572-578 of SEQ ID NO:1)).

The term "motif" refers to a group of amino acid residues in the FLT3 protein or homologue that defines a structural compartment or carries out a function in the protein or homologue, for example, catalysis or structural stabilization, or phosphorylation. The motif may be conserved in sequence, structure and function. The motif can be contiguous in primary sequence or three-dimensional space. An example of a motif includes but is not limited to the activation loop.

The term "part of a binding pocket" refers to less than all of the amino acid residues that define the binding pocket. The structure coordinates of amino acid residues that constitute part of a binding pocket may be specific for defining the chemical environment of the binding pocket, or useful in designing fragments of an inhibitor that may interact with those residues. For example, the portion of amino acid residues may be key residues that play a role in ligand binding, or may be residues that are spatially related and define a three-dimensional compartment of the binding pocket. The amino acid residues may be contiguous or non-contiguous in primary sequence. In one embodiment, part of the binding pocket has at least two amino acid residues, preferably at least three, eight, fourteen or fifteen amino acid residues.

The term "part of an FLT3 protein" or "part of an FLT3 homologue" refers to less than all of the amino acid residues of an FLT3 protein or homologue. In one embodiment, part of the FLT3 protein or homologue defines the binding pockets, domains, sub-domains, and motifs of the protein or homologue. The structure coordinates of amino acid residues that constitute part of an FLT3 protein or homologue may be specific for defining the chemical environment of the protein, or useful in designing fragments of an inhibitor that interact with those residues. The portion of amino acid residues may also be residues that are spatially related and define a three-dimensional compartment of the binding pocket, motif or domain. The amino acid residues may be contiguous or non-contiguous in primary sequence. For example, the portion of amino acid residues may be key residues that play a role in ligand or substrate binding, peptide binding, antibody binding, catalysis, structural stabilization or degradation.

The term "quantified association" refers to calculations of distance geometry and energy. Energy can include but is not limited to interaction energy, free energy and deformation energy. See Cohen, supra.

The term "root mean square deviation" or "RMSD" refers to the square root of the arithmetic mean of the squares of the deviations from the mean. It is a way to express the deviation or variation from a trend or object. For purposes of this invention, the "root mean square deviation" defines the variation in the backbone of a protein from the backbone of FLT3, a binding pocket, a motif, a domain, or portion thereof, as defined by the structure coordinates of FLT3 described herein. It would be readily apparent to those skilled in the art that the calculation of RMSD involves standard error of ±0.1 Å.

The term "soaked" refers to a process in which a crystal is transferred to a solution containing a compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "sub-domain" refers to a portion of a domain.

The term "substantially all of an FLT3 binding pocket" or "substantially all of an FLT3 protein" refers to all or almost all of the amino acids in the FLT3 binding pocket or protein. For example, substantially all of an FLT3 binding pocket can be 100%, 95%, 90%, 80%, or 70% of the residues defining the FLT3 binding pocket or protein.

The term "substrate binding pocket" refers to the binding pocket for a substrate of FLT3 or homologue thereof. A substrate is generally defined as the molecule upon which an enzyme performs catalysis. Natural substrates, synthetic substrates or peptides, or mimics of a natural substrates of FLT3 or homologue thereof may associate with the substrate binding pocket.

The term "sufficiently homologous to FLT3" refers to a protein that has a sequence identity of at least 25% compared to FLT3 protein. In other embodiments, the sequence identity is at least 40%. In other embodiments, the sequence identity is at least 50%, 60%, 70%, 80%, 90%, 95%, 96%, 97%, 98% or 99%.

The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for an FLT3 molecule or molecular complex or homologues thereof, calculating or minimizing energies for an association of an FLT3 molecule or molecular complex, or homologues thereof to a chemical entity.

Crystallizable Compositions and Crystals of an FLT3 Cytoplasmic Domain and Complexes Thereof In one embodiment, the invention provides a crystallizable composition comprising an FLT3 cytoplasmic domain or its homologue. In another embodiment, the crystallizable composition further comprises a buffer that maintains pH between about 8.0 and 12.0, 0.1-5 M sodium phosphate, 0.1-5 M potassium phosphate, and 50-500 mM lithium sulfate. In certain embodiments, the crystallizable composition comprises equal volumes of a solution of an FLT3 cytoplasmic domain or a homologue thereof (10 mg/ml) in the presence of 2 mM AMP-PNP and 4 mM $MgCl_2$, and 1.2 M sodium phosphate, 1.2 M potassium phosphate, 0.1 M CAPS (pH 10.5) and 0.2 M lithium sulfate.

According to another embodiment, the invention provides a crystal comprising an FLT3 cytoplasmic domain or its homologue. Preferably, the native crystal has a unit cell dimension of a=b=80.65 Å c=150.13 Å and belongs to space group $P4_32_12$. It will be readily apparent to those skilled in the art that the unit cells of such a crystal composition may deviate ±1-2 Å from the above cell dimensions depending on the deviation in the unit cell calculations.

As used herein, the FLT3 cytoplasmic domain in the crystallizable compositions or crystals can be amino acids 564-993 of SEQ ID NO:1; amino acids 564-958 of SEQ ID NO:1; amino acids 564-947 of SEQ ID NO:1; (removing residues spanning H711-H761) amino acids 564-710 and 762-958 of SEQ ID NO:1; (removing residues spanning 711-782) amino acids 564-710 and 783-958 of SEQ ID NO:1; (removing residues spanning H711-H761) amino acids 570-710 and 762-958 of SEQ ID NO:1; (removing residues spanning 711-782) amino acids 570-710 and 783-958 of SEQ ID NO:1; amino acid residues 570-958 of SEQ ID NO:1; amino acid residues 570-947 of SEQ ID NO:1; (removing residues spanning H711-H761) amino acid residues 570-710 and 762-947 of SEQ ID NO:1; (removing residues spanning 711-782) amino acid residues 570-710 and 783-947 of SEQ ID NO:1; (removing residues spanning H711-H761) amino acid residues 564-710 and 762-947 of SEQ ID NO:1; and (removing residues spanning 711-782) amino acid residues 564-710 and 783-947 of SEQ ID NO:1. The homologue thereof can be any of the aforementioned amino acids with conservative substitutions, deletions or additions, to the extent that any substitutions, deletions or additions maintains an FLT3 kinase activity in the homologue; preferably the homologue with substitutions, deletions or additions is at least 70%, 80%, 90%, 95%, 96%, 97%, 98%, or 99% identical to one of the aforementioned. Preferably, the homologue with substitutions, deletions or additions is at least 80%, 90%, 95%, 96%, 97%, 98%, or 99% identical to one of the aforementioned.

```
1
MPALARDAGT VPLLVVFSAM IFGTITNQDL PVIKCVLINH KNNDSSVGKS    SEQ ID NO:1

51
SSYPMVSESP EDLGCALRPQ SSGTVYEAAA VEVDVSASIT LQVLVDAPGN

101
ISCLWVFKHS SLNCQPHFDL QNRGVVSMVI LKMTETQAGE YLLFIQSEAT

151
NYTILFTVSI RNTLLYTLRR PYFRKMENQD ALVCISESVP EPIVEWVLCD

201
SQGESCKEES PAVVKKEEKV LHELFGTDIR CCARNELGRE CTRLFTIDLN

251
QTPQTTLPQL FLKVGEPLWI RCKAVHVNHG FGLTWELENK ALEEGNYFEM

301
STYSTNRTMI RILFAFVSSV ARNDTGYYTC SSSKHPSQSA LVTIVGKGFI

351
NATNSSEDYE IDQYEEFCFS VRFKAYPQIR CTWTFSRKSF PCEQKGLDNG

401
YSISKFCNHK HQPGEYIFHA ENDDAQFTKM FTLNIRRKPQ VLAEASASQA

451
SCFSDGYPLP SWTWKKCSDK SPNCTEEITE GVWNRKANRK VFGQWVSSST

501
LNMSEAIKGF LVKCCAYNSL GTSCETILLN SPGPFPFIQD NISFYATIGV

551
CLLFIVVLTL LICHKYKKQF RYESQLQMVQ VTGSSDNEYF YVDFREYEYD

601
LKWEFPRENL EFGKVLGSGA FGKVMNATAY GISKTGVSIQ VAVKMLKEKA

651
DSSEREALMS ELKMMTQLGS HENIVNLLGA CTLSGPIYLI FEYCCYGDLL

701
NYLRSKREKF HRTWTEIFKE HNFSFYPTFQ SHPNSSMPGS REVQIHPDSD

751
QISGLHGNSF HSEDEIEYEN QKRLEEEEDL NVLTFEDLLC FAYQVAKGME

801
FLEFKSCVHR DLAARNVLVT HGKVVKICDF GLARDIMSDS NYVVRGNARL

851
PVKWMAPESL FEGIYTIKSD VWSYGILLWE IFSLGVNPYP GIPVDANFYK

901
LIQNGFKMDQ PFYATEEIYI IMQSCWAFDS RKRPSFPNLT SFLGCQLADA

951
EEAMYQNVDG RVSECPHTYQ NRRPFSREMD LGLLSPQAQV EDS
```

The FLT3 protein or its homologue may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products.

Methods of Obtaining Crystals of an FLT3 Cytoplasmic Domain or Its Homologues

The invention also relates to a method of obtaining a crystal of an FLT3 cytoplasmic domain or homologue thereof, comprising the steps of:

a) optionally producing and purifying an FLT3 cytoplasmic domain or homologue thereof;
b) combining a crystallization solution with said FLT3 cytoplasmic domain or homologue thereof to produce a crystallizable composition; and
c) subjecting the composition to conditions which promote crystallization and obtaining said crystal.

In another embodiment, the invention provides methods of obtaining crystals of an FLT3 cytoplasmic domain protein, a homologue thereof, or complexes thereof using the steps set forth above. In one embodiment, step (b) is performed with an FLT3 cytoplasmic domain or homologue thereof bound to a chemical entity. In another embodiment, the above method further comprises the step of soaking said crystal in a solution comprising a chemical entity that binds to the FLT3 cytoplasmic domain or homologue thereof.

In certain embodiments, the method of making crystals of an FLT3 cytoplasmic domain, a homologue, or an FLT3 cytoplasmic domain protein or homologue complex includes the use of a device for promoting crystallizations. Devices for promoting crystallization can include but are not limited to the hanging-drop, sitting-drop, sandwich-drop, dialysis, microbatch or microtube batch devices (U.S. Pat. Nos. 4,886, 646, 5,096,676, 5,130,105, 5,221,410 and 5,400,741; Pav, S., et. al., *Proteins Struct. Funct. Genet.*, 20: 98-102 (1994); Chayen, *Acta. Cryst.*, D54: 8-15 (1998), Chayen, *Structure*, 5: 1269-1274 (1997), D'Arcy et. al., *J. Cryst. Growth*, 168: 175-180 (1996) and Chayen, *J. Appl. Cryst.*, 30: 198-202 (1997), incorporated herein by reference). The hanging-drop, sitting-drop and some adaptations of the microbatch methods (D'Arcy et. al., *J. Cryst. Growth*, 168: 175-180 (1996) and Chayen, *J. Appl. Cryst.*, 30: 198-202 (1997)) produce crystals by vapor diffusion. The hanging drop and sitting drop containing the crystallizable composition is equilibrated against a reservoir containing a higher or lower concentration of precipitant. As the drop approaches equilibrium with the reservoir, the saturation of protein in the solution leads to the formation of crystals.

Microseeding may be used to increase the size and quality of crystals. In this instance, microcrystals are crushed to yield a stock seed solution. The stock seed solution is diluted in series. Using a needle, glass rod, micro-pipet, micro-loop or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It would be readily apparent to one of skill in the art to vary the crystallization conditions disclosed above to identify other crystallization conditions that would produce crystals of FLT3 protein, FLT3 protein complex, FLT3 cytoplasmic domain protein complex or homologue thereof, or FLT3 cytoplasmic domain homologue. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brji 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

In certain embodiments, the crystal comprising a cytoplasmic domain of an FMS-like tyrosine kinase protein or a homologue thereof diffract X-rays to a resolution of at least 2.1 Å. In other embodiments, the crystal comprising a cytoplasmic domain of an FLT3 cytoplasmic domain, a homologue, or an FLT3 cytoplasmic domain protein or homologue complex diffract X-rays to a resolution of at least 5.0 Å, at least 3.5 Å, at least 3.0 Å, at least 2.5 Å, or at least 2.3 Å.

In certain embodiments, the crystal comprising a cytoplasmic domain of an FMS-like tyrosine kinase protein, a homologue thereof, or complexes thereof can produce an electron density map having resolution of at least 2.1 Å. In other embodiments, the crystal comprising a cytoplasmic domain of an FLT3 cytoplasmic domain, a homologue, or an FLT3 cytoplasmic domain protein or homologue complex can produce an electron density map having resolution of at least 5.0 Å, at least 3.5 Å, at least 3.0 Å, at least 2.5 Å, or at least 2.3 Å.

In certain embodiments, the electron density map produced above are sufficient to determine the atomic coordinates a cytoplasmic domain of an FMS-like tyrosine kinase protein or a homologue thereof.

Binding Pockets of FLT3 Protein or Its Homologues

As disclosed herein, applicants have provided the three-dimensional X-ray structure of FLT3 containing the complete JM domain in autoinhibited form. The atomic coordinate data is presented in FIG. 1A.

To use the structure coordinates generated for the FLT3 cytoplasmic domain or one of its binding pockets or an FLT3-like binding pocket, it may be necessary to convert the structure coordinates, or portions thereof, into a three-dimensional shape (i.e., a three-dimensional representation of these proteins and binding pockets). This is achieved through the use of a computer comprising commercially available software that is capable of generating three-dimensional representations or structures of molecules or molecular complexes, or portions thereof, from a set of structure coordinates. These three-dimensional representations may be displayed on a computer screen.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The binding pockets of this invention are useful and important for drug design.

The conformations of FLT3 and other proteins at a particular amino acid site, along the polypeptide backbone, can be compared using well-known procedures for performing sequence alignments of the amino acids. Such sequence alignments allow for the equivalent sites on these proteins to be compared. Such methods for performing sequence alignment include, but are not limited to, the "bestfit" program and CLUSTAL W Alignment Tool, Higgins et. al., supra.

The JM-B binding pocket comprises the kinase domain amino acid residues found within the near vicinity of the heptapeptide section of the autoinhibitory JM-B binding motif of FLT3 (amino acid residues YESQLQM (residues 572-578 of SEQ ID NO:1)).

In one embodiment, the JM-B binding pocket comprises amino acid residues F621, K644, A657, E661, M664, L802, S806, C807, V808, H809, R810, D811, D829, and L832 according to the structure of the autoinhibited conformation of FLT3 in FIG. 1A. The above-identified amino acid residues were within 5 Å ("5 Å sphere amino acids") of the heptapeptide section of the autoinhibitory JM-B binding motif of FLT3 (amino acid residues YESQLQM (residues 572-578 of SEQ ID NO:1)) in the binding pocket. These residues were identified using the program InsightII, which allow the display of the structure, and a software program to calculate the residues within 5 Å of the heptapeptide section of the autoinhibitory JM-B binding motif of FLT3 (amino acid residues YESQLQM (residues 572-578 of SEQ ID NO:1)). QUANTA (Molecular Simulations, Inc., San Diego, Calif. ©1998, 2000; Accelrys ©2001, 2002), O (T. A. Jones et. al., *Acta Cryst., A*47: 110-119 (1991)) and RIBBONS (Carson, *J. Appl. Cryst.,* 24: 958-961 (1991)) may also be used to obtain the above residues.

In another embodiment, the JM-B binding pocket comprises amino acids F621, K644, A657, L658, E661, M664, L802, K805, S806, C807, V808, H809, R810, D811, C828, D829, F830, G831, and L832 according to the structure of FLT3 protein in FIG. 1A. These amino acid residues were within 8 Å ("8 Å sphere amino acids") of heptapeptide section of the autoinhibitory JM-B binding motif of FLT3 (amino acid residues YESQLQM (residues 572-578 of SEQ ID NO:1)). These residues were identified using the above-mentioned programs. QUANTA, O and RIBBONS, supra may also be used to obtain the above residues.

In another embodiment, the JM-B binding pocket comprises amino acids F621, K644, A657, E661, M664, L802, S806, C807, V808, H809, R810, D811, D829, and L832 according to the structure of FLT3 protein in FIG. 1A. These amino acid residues within 3.8 Å of the JM-B binding motif (amino acid residues 572 to 578). These residues were identified using the program QUANTA (Molecular Simulations, Inc., San Diego, Calif. ©1998, 2000; Accelrys ©2001, 2002).

In another embodiment, the JM-B binding pocket comprises amino acids F621, E661, M664, L802, V808, R810, D829, and L832 according to the structure of FLT3 protein in FIG. 1A. These amino acid residues make contacts less than 3.8 Å in length with residues of the JM-B binding motif (F621, M664, L802 and L832 have hydrophobic interactions or van der Waals contacts; E661, V808, R810 and D829 form hydrogen bonds; and R810 is also involved in an ionic pairing with Glu573). These residues were identified using the program QUANTA (Molecular Simulations, Inc., San Diego, Calif. ©1998, 2000; Accelrys ©2001, 2002).

In another embodiment, the JM-B binding pocket comprises amino acids H809, R810, D811, D829, F830 and G831 according to the structure of FLT3 protein in FIG. 1A.

In another embodiment, the JM-B binding pocket comprises amino acids H809, R810, and D811 according to the structure of FLT3 protein in FIG. 1A.

It will be readily apparent to those of skill in the art that the numbering of amino acid residues in homologues of human FLT3 may be different than that set forth for human FLT3. Corresponding amino acid residues in homologues of FLT3 are easily identified by visual inspection of the amino acid sequences or by using commercially available homology software programs. Homologues of FLT3 include, for example, FLT3 from other species, such as non-humans primates, mouse, rat, etc.

Those of skill in the art understand that a set of structure coordinates for an enzyme or an enzyme-complex, or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated because of mathematical manipulations of the FLT3 structure coordinates. For example, the structure coordinates set forth in FIG. 1A could undergo crystallographic permutations, fractionalization, integer additions or subtractions, inversion, or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by this invention. Thus, for example, a ligand that bound to the binding pocket of FLT3 would also be expected to bind to another binding pocket whose structure coordinates defined a shape that fell within the acceptable root mean square deviation.

Various computational analyses may be necessary to determine whether a molecule or the binding pocket or portion thereof is sufficiently similar to the FLT3 binding pockets described above. Such analyses may be carried out using well known software applications, such as ProFit (A. C. R. Martin, SciTech Software, ProFit version 1.8, University College London, www.bioinf.org.uk/software), Swiss-Pdb Viewer (Guex et. al., Electrophoresis, 18: 2714-2723 (1997)), the Molecular Similarity application of QUANTA (Molecular Simulations, Inc., San Diego, Calif. ©1998, 2000; Accelrys ©2001, 2002) and as described in the accompanying User's Guide, which are incorporated herein by reference.

The above programs permit comparisons between different structures, different conformations of the same structure, and different parts of the same structure. The procedure used in QUANTA (Molecular Simulations, Inc., San Diego, Calif. ©1998, 2000; Accelrys ©2001, 2002) and Swiss-Pdb Viewer to compare structures is divided into four steps: 1) load the structures to be compared; 2) define the atom equivalences in these structures; 3) perform a fitting operation on the structures; and 4) analyze the results.

The procedure used in ProFit to compare structures includes the following steps: 1) load the structures to be compared; 2) specify selected residues of interest; 3) define the atom equivalences in the selected residues; 4) perform a fitting operation on the selected residues; and 5) analyze the results.

Each structure in the comparison is identified by a name. One structure is identified as the target (i.e., the fixed structure); all remaining structures are working structures (i.e., moving structures). Since atom equivalency within QUANTA (Molecular Simulations, Inc., San Diego, Calif. ©1998, 2000; Accelrys ©2001, 2002) is defined by user input, for the purpose of this invention we will define equivalent atoms as protein backbone atoms N, C, O and Cα for all corresponding amino acids between the two structures being compared.

The corresponding amino acids may be identified by sequence alignment programs such as the "bestfit" program available from the Genetics Computer Group which uses the local homology algorithm described by Smith and Waterman in *Advances in Applied Mathematics* 2, 482-489 (1981), which is incorporated herein by reference. A suitable amino acid sequence alignment will require that the proteins being aligned share a minimum percentage of identical amino acids. Generally, a first protein being aligned with a second protein should share in excess of about 35% identical amino acids (Hanks, S. K., et. al., *Science*, 241, 42-52 (1988); Hanks, S. K. and Quinn, A. M. *Methods in Enzymology*, 200: 38-62 (1991)). The identification of equivalent residues can also be assisted by secondary structure alignment, for example, aligning the α-helices, β-sheets in the structure. The program Swiss-Pdb Viewer has its own best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer program sets an RMSD cutoff for eliminating pairs of equivalent atoms that have high RMSD values. An RMSD cutoff value can be used to exclude pairs of equivalent atoms with extreme individual RMSD values. In the program ProFit, the RMSD cutoff value can be specified by the user.

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in FIG. 1A are encompassed by this invention.

One embodiment of this invention provides a crystalline molecule comprising a protein defined by structure coordinates of a set of amino acid residues that are identical to FLT3 amino acid residues according to FIG. 1A, wherein the RMSD between said set of amino acid residues and said FLT3 amino acid residues is not more than about 5.0 Å. In other embodiments, the RMSD between said set of amino acid residues and said FLT3 amino acid residues is not greater than about 4.0 Å, not greater than about 3.0 Å, not greater than about 2.0 Å, not greater than about 1.5 Å, not greater than about 1.0 Å, or not greater than about 0.5 Å.

In one embodiment, the present invention provides a crystalline molecule comprising all or part of a binding pocket defined by a set of amino acid residues comprising at least six amino acid residues which are identical to human FLT3 amino acid residues F621, K644, A657, L658, E661, M664, L802, K805, S806, C807, V808, H809, R810, D811, C828, D829, F830, G831, and L832 according to FIG. 1A, wherein the RMSD of the backbone atoms between said FLT3 amino acid residues and said at least six amino acid residues which are identical is not greater than about 3.0 Å. In other embodiments, the RMSD is not greater than about 2.0 Å, 1.0 Å, 0.8, 0.5 Å, 0.3 Å, or 0.2 Å. In other embodiments, the binding pocket is defined by a set of amino acid residues comprising at least four, six, eight, twelve or fifteen amino acid residues which are identical to said FLT3 amino acid residues.

In one embodiment, the present invention provides a crystalline molecule comprising all or part of a binding pocket defined by a set of amino acid residues which are identical to human FLT3 amino acid residues F621, E661, M664, L802, V808, R810, D829, and L832 according to FIG. 1A, wherein the RMSD of the backbone atoms between said FLT3 amino acid residues and said set of amino acid residues which are identical is not greater than about 3.0 Å. In other embodiments, the RMSD is not greater than about 2.0 Å, 1.0 Å, 0.8, 0.5 Å, 0.3 Å, or 0.2 Å. In other embodiments, the binding pocket is defined by a set of amino acid residues comprising at least four, five, six or seven amino acid residues which are identical to said FLT3 amino acid residues.

In one embodiment, the present invention provides a crystalline molecule comprising all or part of a binding pocket defined by a set of amino acid residues comprising a set of amino acid residues which are identical to human FLT3 amino acid residues H809, R810, and D811 according to FIG. 1A, wherein the RMSD of the backbone atoms between said FLT3 amino acid residues and said set of amino acid residues which are identical is not greater than about 3.0 Å. In other embodiments, the RMSD is not greater than about 2.0 Å, 1.0 Å, 0.8, 0.5 Å, 0.3 Å, or 0.2 Å.

In one embodiment, the above molecule is FLT3 protein, FLT3 cytoplasmic domain or homologues thereof. In another embodiment, the above molecules are in crystalline form. An FLT3 protein may be human FLT3. Homologues of human FLT3 can be FLT3 from another species, such as a mouse, a rat or a non-human primate.

Computer Systems

According to another embodiment, this invention provides a machine-readable data storage medium, comprising a data storage material encoded with machine-readable data, wherein said data defines the above-mentioned molecules or molecular complexes or binding pockets thereof. In one embodiment, the data defines the above-mentioned binding pockets by comprising the structure coordinates of said amino acid residues according to FIG. 1A. To use the structure coordinates generated for FLT3, homologues thereof, or one of its binding pockets, it is at times necessary to convert them into a three-dimensional shape or to extract three-dimensional structural information from them. This is achieved through the use of commercially or publicly available software that is capable of generating a three-dimensional structure or a three-dimensional representation of molecules or portions thereof from a set of structure coordinates. In one embodiment, three-dimensional structure or representation may be displayed graphically.

Therefore, according to another embodiment, this invention provides a machine-readable data storage medium comprising a data storage material encoded with machine readable data. In one embodiment, a machine programmed with instructions for using said data is capable of generating a three-dimensional structure or three-dimensional representation of any of the molecules, or molecular complexes or binding pockets thereof, that are described herein.

This invention also provides a computer comprising:
  (a) a machine-readable data storage medium, comprising a data storage material encoded with machine-readable data, wherein said data defines any one of the above molecules or molecular complexes;
  (b) a working memory for storing instructions for processing said machine-readable data;
  (c) a central processing unit (CPU) coupled to said working memory and to said machine-readable data storage medium for processing said machine readable data and means for generating three-dimensional structural information of said molecule or molecular complex; and (d) output hardware coupled to said central processing unit for outputting three-dimensional structural information of said molecule or molecular complex, or information produced by using said three-dimensional structural information of said molecule or molecular complex.

In one embodiment, the data defines the binding pocket of the molecule or molecular complex.

Three-dimensional data generation may be provided by an instruction or set of instructions, such as a computer program or commands for generating a three-dimensional structure or graphical representation from structure coordinates, or by subtracting distances between atoms, calculating chemical energies for an FLT3 molecule or molecular complex or homologues thereof, or calculating or minimizing energies for an association of an FLT3 molecule or molecular complex or homologues thereof to a chemical entity. The graphical representation can be generated or displayed by commercially available software programs. Examples of software programs include but are not limited to QUANTA (Accelrys ©2001, 2002), O (Jones et. al., *Acta Crystallogr.* A47: 110-119 (1991)) and RIBBONS (Carson, *J. Appl. Crystallogr.*, 24: 9589-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

Information about said binding pocket or information produced by using said binding pocket can be outputted through display terminals, touchscreens, facsimile machines, modems, CD-ROMs, printers, a CD or DVD recorder, ZIP™ or JAZ™ drives or disk drives. The information can be in graphical or alphanumeric form.

In one embodiment, the computer is executing an instruction such as a computer program for generating three-dimensional structure or docking. In another embodiment, the computer further comprises a commercially available software program to display the information as a graphical representation. Examples of software programs include but as not limited to, QUANTA (Accelrys ©2001, 2002), O (Jones et. al., *Acta Crystallogr.* A47: 110-119 (1991)) and RIBBONS (Carson, *J. Appl. Crystallogr.*, 24: 9589-961 (1991)), all of which are incorporated herein by reference.

FIG. 7 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives, CD-ROM drives or DVD-ROM drives), one or more cathode-ray tube ("CRT") display terminals (26), one or more keyboards (28), one or more input lines (30), and one or more output lines (40), all of which are, interconnected by a conventional bi-directional system bus (50).

Input hardware (35), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (35) may comprise CD-ROM or DVD-ROM drives or disk drives (24). In conjunction with display terminal (26), keyboard (28) may also be used as an input device.

Output hardware (46), coupled to computer (11) by output lines (40), may similarly be implemented by conventional devices. By way of example., output hardware (46) may include CRT display terminal (26) for displaying a graphical representation of a binding pocket of this invention using a program such as QUANTA (Molecular Simulations, Inc., San Diego, Calif. ©1998, 2000; Accelrys ©2001, 2002) as described herein. Output hardware may also include a printer (42), so that hard copy output may be produced, or a disk drive (24), to store system output for later use. Output hardware may also include a display terminal, touchscreens, facsimile machines, modems, a CD or DVD recorder, ZIP™ or JAZ™ drives, disk drives, or other machine-readable data storage device.

In operation, CPU (20) coordinates the use of the various input and output devices (35), (46), coordinates data accesses from mass storage (24) and accesses to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

FIG. 8 shows a cross section of a magnetic data storage medium (100) which can be encoded with a machine-readable data that can be carried out by a system such as system (10) of FIG. 7. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) are polarized or oriented so as to encode in manner which may be conventional, machine readable data such as that described herein, for execution by a system such as system (10) of FIG. 7.

FIG. 9 shows a cross section of an optically-readable data storage medium (110) which also can be encoded with such a machine-readable data, or set of instructions, which can be carried out by a system such as system (10) of FIG. 7. Medium (110) can be a conventional compact disk read only memory (CD-ROM) or a rewritable medium such as a magneto-optical disk which is optically readable and magneto-optically writable. Medium (100) preferably has a suitable substrate (111), which may be conventional, and a suitable coating (112), which may be conventional, usually of one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

In one embodiment, the structure coordinates of said molecules or molecular complexes or binding pockets are produced by homology modeling of at least a portion of the structure coordinates of FIG. 1A. Homology modeling can be used to generate structural models of FLT3 homologues or other homologous proteins based on the known structure of FLT3 cytoplasmic domain. This can be achieved by performing one or more of the following steps: performing sequence alignment between the amino acid sequence of a molecule (possibly an unknown molecule) against the amino acid sequence of FLT3; identifying conserved and variable regions by sequence or structure; generating structure coordinates for structurally conserved residues of the unknown structure from those of FLT3; generating conformations for the structurally variable residues in the unknown structure; replacing the non-conserved residues of FLT3 with residues in the unknown structure; building side chain conformations; and refining and/or evaluating the unknown structure.

Software programs that are useful in homology modeling include XALIGN (Wishart, D. S., et. al., *Comput. Appl. Biosci.*, 10: 687-88 (1994)) and CLUSTAL W Alignment Tool, Higgins et. al., supra. See also, U.S. Pat. No. 5,884,230. These references are incorporated herein by reference.

To perform the sequence alignment, programs such as the "bestfit" program available from the Genetics Computer Group (Waterman in Advances in *Applied Mathematics* 2, 482 (1981), which is incorporated herein by reference) and CLUSTAL W Alignment Tool (Higgins et. al., supra, which is incorporated by reference) can be used. To model the amino acid side chains of homologous molecules, the amino acid residues in FLT3 can be replaced, using a computer graphics program such as "O" (Jones et al, (1991) *Acta Cryst. Sect. A*, 47: 110-119), by those of the homologous protein, where they differ. The same orientation or a different orientation of the amino acid can be used. Insertions and deletions of amino acid residues may be necessary where gaps occur in the sequence alignment. However, certain portions of the active site of FLT3 and its homologues are highly conserved with essentially no insertions and deletions.

Homology modeling can be performed using, for example, the computer programs SWISS-MODEL available through Glaxo Wellcome Experimental Research in Geneva, Switzerland; WHATIF available on EMBL servers; Schnare et. al., *J. Mol. Biol*, 256: 701-719 (1996); Blundell et. al., *Nature* 326: 347-352 (1987); Fetrow and Bryant, *Bio/Technology* 11:479-484 (1993); Greer, *Methods in Enzymology* 202: 239-252 (1991); and Johnson et al, *Crit. Rev. Biochem. Mol. Biol.* 29:1-68 (1994). An example of homology modeling can be found, for example, in Szklarz G. D., *Life Sci.* 61: 2507-2520 (1997). These references are incorporated herein by reference.

Thus, in accordance with the present invention, data capable of generating the three-dimensional structure or three-dimensional representation of the above molecules or molecular complexes, or binding pockets thereof, can be stored in a machine-readable storage medium, which is capable of displaying structural information or a graphical three-dimensional representation of the structure. In one embodiment, means of generating three-dimensional information is provided by means for generating a three-dimensional structural representation of the binding pocket or protein or protein complex.

Rational Drug Design

The FLT3 structure coordinates or the three-dimensional graphical representation generated from these coordinates may be used in conjunction with a computer for a variety of purposes, including drug discovery.

For example, the structure encoded by the data may be computationally evaluated for its ability to associate with chemical entities. Chemical entities that associate with FLT3 may inhibit or activate FLT3 or its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

In one embodiment, the invention provides a method of using a computer for selecting an orientation of a chemical entity that interacts favorably with a binding pocket or domain comprising the steps of:

(a) providing the structure coordinates of said binding pocket or domain on a computer comprising means for generating three-dimensional structural information from said structure coordinates;

(b) employing computational means to dock a first chemical entity in the binding pocket or domain;

(c) quantifying the association between said chemical entity and all or part of the binding pocket or domain for different orientations of the chemical entity; and (d) selecting the orientation of the chemical entity with the most favorable interaction based on said quantified association.

In one embodiment, the docking is facilitated by said quantified association.

In one embodiment, the above method further comprises the following steps before step (a):

(e) producing a crystal of a molecule or molecular complex comprising an FLT3 cytoplasmic domain or homologue thereof;

(f) determining the three-dimensional structure coordinates of the molecule or molecular complex by X-ray diffraction of the crystal; and (g) identifying all or part of a binding pocket that corresponds to said binding pocket.

Three-dimensional structural information in step (a) may be generated by instructions such as a computer program or commands that can generate a three-dimensional representation; subtract distances between atoms; calculate chemical energies for an FLT3 molecule, molecular complex or homologues thereof; or calculate or minimize the chemical energies of an association of FLT3 molecule, molecular complex or homologues thereof to a chemical entity. These types of computer programs are known in the art. The graphical representation can be generated or displayed by commercially available software programs. Examples of software programs include but are not limited to QUANTA (Molecular Simulations, Inc., San Diego, Calif. ©1998, 2000; Accelrys ©2001, 2002), O (Jones et. al., *Acta Crystallogr.* A47: 110-119 (1991)) and RIBBONS (Carson, *J. Appl. Crystallogr.*, 24: 9589-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

The above method of paragraphs 160 and 161 may further comprise the following step after step (d): outputting said quantified association to a suitable output hardware, such as a CRT display terminal, a CD or DVD recorder, ZIP™ or JAZ™ drive, a disk drive, or other machine-readable data storage device, as described previously. The method may further comprise generating a three-dimensional structure, graphical representation thereof, or both, of the protein, binding pocket, molecule or molecular complex prior to step (b).

One embodiment of this invention provides the above method, wherein energy minimization, molecular dynamics simulations, or rigid body minimizations are performed simultaneously with or following step (b).

The above method may further comprise the steps of:
(e) repeating steps (b) through (d) with a second chemical entity; and
(f) selecting at least one of said first or second chemical entity that interacts more favorably with said binding pocket or domain based on said quantified association of said first or second chemical entity.

In another embodiment, the invention provides the method of using a computer for selecting an orientation of a chemical entity with a favorable shape complementarity in a binding pocket comprising the steps of:
(a) providing the structure coordinates of said binding pocket and all or part of the JM-B binding motif bound therein on a computer comprising means for generating three-dimensional structural information from said structure coordinates;
(b) employing computational means to dock a first chemical entity in the binding pocket;
(c) quantitating the contact score of said chemical entity in different orientations in the binding pocket; and
(d) selecting an orientation with the highest contact score.

In one embodiment, the docking is monitored and directed or facilitated by the contact score.

The method above may further comprise the step of generating a three-dimensional graphical representation of the binding pocket and all or part of the JM-B binding motif bound therein prior to step (b).

The method above may further comprise the steps of:
(e) repeating steps (b) through (d) with a second chemical entity; and
(f) selecting at least one of said first or second chemical entity that has a higher contact score based on said quantitated contact score of said first or second chemical entity.

In another embodiment, the invention provides a method for screening a plurality of chemical entities to associate at a deformation energy of binding of no greater than 7 kcal/mol with said binding pocket:
(a) employing computational means, which utilize said structure coordinates to dock one of said chemical entities from the plurality of chemical entities and said binding pocket;
(b) quantifying the deformation energy of binding between the chemical entity and the binding pocket;
(c) repeating steps (a) and (b) for each remaining chemical entity; and
(d) outputting a set of chemical entities that associate with the binding pocket at a deformation energy of binding of not greater than 7 kcal/mol to a suitable output hardware.

In another embodiment, the method comprises the steps of:
(a) constructing a computer model of a binding pocket of a molecule or molecular complex;
(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an FLT3 protein, or homologue thereof to produce said chemical entity;
(c) employing computational means to dock said chemical entity to be evaluated in said binding pocket in order to provide an energy-minimized configuration of said chemical entity in the binding pocket; and
(d) evaluating the results of said docking to quantify the association between said chemical entity and the binding pocket.

Alternatively, the structure coordinates of the FLT3 binding pockets may be utilized in a method for identifying a candidate inhibitor of a molecule or molecular complex comprising a binding pocket of FLT3. This method comprises the steps of:
(a) using a three-dimensional structure of the binding pocket or domain of FLT3 to design, select or optimize a plurality of chemical entities;
(b) contacting each chemical entity with the molecule and molecular complex;
(c) monitoring the inhibition to the catalytic activity of the molecule or molecular complex by the chemical entity; and
(d) selecting a chemical entity based on the effect of the chemical entity on the activity of the molecule or molecular complex.

In one embodiment, step (a) is carried out using a three-dimensional structure of the binding pocket or domain or portion thereof of the molecule or molecular complex. In another embodiment, the three-dimensional structure is displayed as a graphical representation.

In another embodiment, the method comprises the steps of:
(a) constructing a computer model of a binding pocket of the molecule or molecular complex;
(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an FLT3 protein or homologue thereof to produce said chemical entity;
(c) employing computational means to dock said chemical entity to be evaluated and said binding pocket in order to provide an energy-minimized configuration of said chemical entity in the binding pocket; and
(d) evaluating the results of said docking to quantify the association between said chemical entity and the binding pocket;
(e) synthesizing said chemical entity; and
(f) contacting said chemical entity with said molecule or molecular complex to determine the ability of said chemical entity to activate or inhibit said molecule.

In one embodiment, the invention provides a method of designing a compound or complex that associates with all or part of the binding pocket of a cytoplasmic domain of an FLT3 protein comprising the steps of:
(a) providing the structure coordinates of said binding pocket or domain on a computer comprising means for generating three-dimensional structural information from said structure coordinates;
(b) using the computer to dock a first chemical entity in part of the binding pocket or domain;
(c) docking a second chemical entity in another part of the binding pocket or domain;
(d) quantifying the association between the first and second chemical entity and part of the binding pocket or domain;
(e) repeating steps (b) to (d) with another first and second chemical entity and selecting a first and a second chemical entity based on said quantified association of all of said first and second chemical entity;
(f) optionally, visually inspecting the relationship of the first and second chemical entity to each other in relation to the binding pocket or domain on a computer screen using the three-dimensional graphical representation of the binding pocket or domain and said first and second chemical entity; and (g) assembling the first and second chemical entity into a compound or complex that interacts with said binding pocket by model building.

For the first time, the present invention permits the use of molecular design techniques to identify, select and design chemical entities, including inhibitory compounds, capable of binding to FLT3 or FLT3-like binding pockets and domains.

Applicants' elucidation of binding pockets of FLT3 provides the necessary information for designing new chemical entities and compounds that may interact with FLT3 substrate, active site, JM-B binding pockets or FLT3-like substrate, active site or JM-B binding pockets, in whole or in part.

Throughout this section, discussions about the ability of a chemical entity to bind to, interact with or inhibit FLT3 binding pockets refer to features of the entity alone.

The design of compounds that bind to or inhibit FLT3 binding pockets according to this invention generally involves consideration of two factors. First, the chemical entity must be capable of physically and structurally associating with parts or all of the FLT3 binding pockets. Non-covalent molecular interactions important in this association include hydrogen bonding, van der Waals interactions, hydrophobic interactions and electrostatic interactions.

Second, the chemical entity must be able to assume a conformation that allows it to associate with the FLT3 binding pockets directly. Although certain portions of the chemical entity will not directly participate in these associations, those portions of the chemical entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of a chemical entity comprising several chemical entities that directly interact with the FLT3 or FLT3-like binding pockets.

The potential inhibitory or binding effect of a chemical entity on FLT3 binding pockets may be analyzed prior to its actual synthesis and testing by the use of computer modeling techniques. If the theoretical structure of the given entity suggests insufficient interaction and association between it and the FLT3 binding pockets, testing of the entity is obviated. However, if computer modeling indicates a strong interaction, the molecule may then be synthesized and tested for its ability to bind to an FLT3 binding pocket. This may be achieved by testing the ability of the molecule to inhibit FLT3 using the assays described in Chan, P. M., et. al., *Mol. Cell. Biol.* 23: 3067-3078 (2003), which is incorporated herewith by reference.

A potential inhibitor of an FLT3 binding pocket may be computationally evaluated by means of a series of steps in which chemical entities or fragments are screened and selected for their ability to associate with the FLT3 binding pockets.

One skilled in the art may use one of several methods to screen chemical entities or fragments or moieties thereof for their ability to associate with the binding pockets described herein. This process may begin by visual inspection of, for example, any of the binding pockets on the computer screen based on the FLT3 structure coordinates FIG. 1A, or other coordinates which define a similar shape generated from the machine-readable storage medium. Selected chemical entities, or fragments or moieties thereof may then be positioned in a variety of orientations, or docked, within that binding pocket as defined supra. Docking may be accomplished using software such as QUANTA (Accelrys ©2001, 2002) and Sybyl (Tripos Associates, St. Louis, Mo.), followed by, or performed simultaneously with, energy minimization, rigid-body minimization (Gshwend, supra) and molecular dynamics with standard molecular mechanics force fields, such as CHARMM and AMBER.

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", *J. Med. Chem.*, 28: 849-857 (1985)). GRID is available from Oxford University, Oxford, UK.

2. MCSS (Miranker, A., et. al., "Functionality Maps of Binding Sites: A Multiple Copy Simultaneous Search Method." *Proteins Struct. Funct. Genet.*, 11: 29-34 (1991)). MCSS is available from Molecular Simulations, San Diego, Calif.

3. AUTODOCK (Goodsell, D. S., et. al., "Automated Docking of Substrates to Proteins by Simulated Annealing", *Proteins Struct., Funct., and Genet.*, 8: 195-202 (1990)). AUTODOCK is available from Scripps Research Institute, La Jolla, Calif.

4. DOCK (Kuntz, I. D., et. al., "A Geometric Approach to Macromolecule-Ligand Interactions", *J. Mol. Biol.*, 161: 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of FLT3. This would be followed by manual model building using software such as QUANTA (Accelrys ©2001, 2002) or Sybyl (Tripos Associates, St. Louis, Mo.).

Useful programs to aid one of skill in the art in connecting the individual chemical entities or fragments include:

1. CAVEAT (Bartlett, P. A., et. al., "CAVEAT: A Program to Facilitate the Structure-Derived Design of Biologically Active Molecules", in *Molecular Recognition in Chemical and Biological Problems*, S. M. Roberts, Ed., Royal Society of Chemistry, Special Publication No. 78: pp. 182-196 (1989); Lauri, G. and Bartlett, P. A., "CAVEAT: A Program to Facilitate the Design of Organic Molecules", *J. Comp. Aid. Molec. Design*, 8: 51-66 (1994)). CAVEAT is available from the University of California, Berkeley, Calif.

2. 3D Database systems such as ISIS (MDL Information Systems, San Leandro, Calif.). This area is reviewed in Martin, Y. C., "3D Database Searching in Drug Design", J. Med. Chem., 35: 2145-2154 (1992).

3. HOOK (Eisen, M. B., et. al., "HOOK: A Program for Finding Novel Molecular Architectures that Satisfy the Chemical and Steric Requirements of a Macromolecule Binding Site", *Proteins Struct., Funct., Genet.*, 19: 199-221 (1994)). HOOK is available from Molecular Simulations, San Diego, Calif.

Instead of proceeding to build an inhibitor of an FLT3 binding pocket in a step-wise fashion one fragment or chemical entity at a time as described above, inhibitory or other FLT3 binding compounds may be designed as a whole or "de novo" using either an empty binding pocket or optionally including some portion(s) of a known inhibitor(s). There are many de novo ligand design methods including:

1. LUDI (Böhm, H.-J., "The Computer Program LUDI: A New Method for the De Novo Design of Enzyme Inhibitors", *J. Comp. Aid. Molec. Design*, 6: pp. 61-78 (1992)). LUDI is available from Molecular Simulations Incorporated, San Diego, Calif.

2. LEGEND (Nishibata, Y., et. al., *Tetrahedron*, 47: 8985-8990 (1991)). LEGEND is available from Molecular Simulations Incorporated, San Diego, Calif.

3. LeapFrog (available from Tripos Associates, St. Louis, Mo.).

4. SPROUT (Gillet, V., et. al., "SPROUT: A Program for Structure Generation)", *J. Comp. Aid. Molec. Design*, 7: 127-153 (1993)). SPROUT is available from the University of Leeds, UK.

Other molecular modeling techniques may also be employed in accordance with this invention (see, e.g., Cohen, N. C., et. al., "Molecular Modeling Software and Methods for Medicinal Chemistry, *J. Med. Chem.*, 33: 883-894 (1990); see also, Navia, M. A. and Murcko, M. A., "The Use of Structural Information in Drug Design", Current Opinions in Structural Biology, 2: 202-210 (1992); Balbes, L. M., et. al., "A Perspective of Modern Methods in Computer-Aided Drug Design", in *Reviews in Computational Chemistry*, K. B. Lipkowitz and D. B. Boyd, Eds., VCH Publishers, New York, 5: pp. 337-379 (1994); see also, Guida, W. C., "Software For Structure-Based Drug Design", *Curr. Opin. Struct. Biology*, 4: 777-781 (1994)).

Once a chemical entity has been designed or selected by the above methods, the efficiency with which that entity may bind to any of the above binding pockets may be tested and optimized by computational evaluation. For example, an effective binding pocket inhibitor must preferably demonstrate a relatively small difference in energy between its bound and free states (i.e., a small deformation energy of binding). Thus, the most efficient binding pocket inhibitors should preferably be designed with a magnitude of deformation energy of binding of not greater than about 10 kcal/mole, more preferably, not greater than 7 kcal/mole. Binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

A chemical entity designed or selected as binding to any one of the above binding pockets may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Accelrys ©2001, 2002); Insight II/Discover (Molecular Simulations, Inc., San Diego, Calif. ©1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention is the computational screening of small molecule databases for chemical entities or compounds that can bind in whole, or in part, to any of the above binding pocket. In this screening, the quality of fit of such entities to the binding pocket may be judged either by shape complementarity or by estimated interaction energy (Meng, E. C., et. al., *J. Comp. Chem.*, 13: 505-524 (1992)).

According to another embodiment, the invention provides chemical entities which associate with an FLT3 binding pocket produced or identified by the method set forth above.

Another particularly useful drug design technique enabled by this invention is iterative drug design. Iterative drug design is a method for optimizing associations between a protein and a chemical entity by determining and evaluating the three-dimensional structures of successive sets of protein/chemical entity complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. High throughput crystallization assays may be used to find a new crystallization condition or to optimize the original protein crystallization condition for the new complex. Alternatively, a pre-formed protein crystal may be soaked in the presence of an inhibitor, thereby forming a protein/compound complex and obviating the need to crystallize each individual protein/compound complex.

Any of the above methods may be used to design peptide or small molecule mimics of the JM-B binding motif which may have inhibitory effects on full-length FLT3 protein or fragments thereof, or on full-length FLT3 protein which is mutated in or fragments of the mutated protein thereof.

In one embodiment, the present invention provides a method for identifying a candidate inhibitor that interacts with a binding site of an FMS-like tyrosine kinase protein or a homologue thereof, comprising the steps of:

(a) obtaining a crystal comprising a cytoplasmic domain of said FMS-like tyrosine kinase protein or said homologue thereof, wherein the crystal is characterized with space group $P4_32_12$ and has unit cell parameters of a=b=80.67 Å, c=150.16 Å;

(b) obtaining the structure coordinates of amino acids of the crystal of step (a), wherein the structure coordinates are set forth in FIG. 1A-1 to 1A-50;

(c) generating a three-dimensional model of the cytoplasmic domain of said FMS-like tyrosine kinase protein or said homologue thereof using the structure coordinates of the amino acids generated in step (b), a root mean square deviation from backbone atoms of said amino acids of not more than ±2.0 Å;

(d) determining a binding site of the cytoplasmic domain of said FMS-like tyrosine kinase protein or said homologue thereof from said three-dimensional model; and (e) performing computer fitting analysis to identify the candidate inhibitor which interacts with said binding site.

In one embodiment, the present invention provides the method for identifying a candidate inhibitor that interacts with a binding site of an FMS-like tyrosine kinase protein or a homologue thereof, further comprising the step of: (f) contacting the identified candidate inhibitor with the cytoplasmic domain of said FMS-like tyrosine kinase protein or said homologue thereof in order to determine the effect of the inhibitor on FMS-like tyrosine kinase protein activity.

In one embodiment, the present invention provides the method for identifying a candidate inhibitor that interacts with a binding site of an FMS-like tyrosine kinase protein or a homologue thereof, wherein the binding site of the cytoplasmic domain of said FMS-like tyrosine kinase protein or said homologue thereof determined in step (d) comprises the structure coordinates according to FIGS. 1A-1 to 1A-50 of amino acid residues H809, R810, and D811, wherein the root mean square deviation from the backbone atoms of said amino acids is not more than ±2.0 Å.

In one embodiment, the present invention provides the method for identifying a candidate inhibitor that interacts with a binding site of an FMS-like tyrosine kinase protein or a homologue thereof, wherein the binding site of the cytoplasmic domain of said FMS-like tyrosine kinase protein or said homologue thereof determined in step (d) comprises the structure coordinates according to FIGS. 1A-1 to 1A-50 of amino acid residues F621, E661, M664, L802, V808, R810, D829, and L832, wherein the root mean square deviation from the backbone atoms of said amino acids is not more than ±2.0 Å.

In one embodiment, the present invention provides the method for identifying a candidate inhibitor that interacts with a binding site of an FMS-like tyrosine kinase protein or a homologue thereof, wherein the binding site of the cytoplasmic domain of said FMS-like tyrosine kinase protein or said homologue thereof determined in step (d) comprises the structure coordinates according to FIGS. 1A-1 to 1A-50 of amino acid residues F621, K644, A657, E661, M664, L802, S806, C807, V808, H809, R810, D811, D829, and L832, wherein the root mean square deviation from the backbone atoms of said amino acids is not more than ±2.0 Å.

In one embodiment, the present invention provides a method for identifying a candidate inhibitor that interacts with a binding site of a cytoplasmic domain of an FMS-like tyrosine kinase protein or a homologue thereof, comprising the steps of:
(a) obtaining a crystal comprising the cytoplasmic domain of said FMS-like tyrosine kinase protein or said homologue thereof, wherein the crystal is characterized with space group $P4_32_12$ and has unit cell parameters of a=b=80.67 Å, c=150.16 Å;
(b) obtaining the structure coordinates of amino acids of the crystal of step (a);
(c) generating a three-dimensional model of said FMS-like tyrosine kinase protein or said homologue thereof using the structure coordinates of the amino acids generated in step (b), a root mean square deviation from backbone atoms of said amino acids of not more than ±2.0 Å;
(d) determining a binding site of the cytoplasmic domain of said FMS-like tyrosine kinase protein or said homologue thereof from said three-dimensional model; and
(e) performing computer fitting analysis to identify the candidate inhibitor which interacts with said binding site. In one embodiment, the step of obtaining a crystal is optional.

In one embodiment, the present invention provides the method for identifying a candidate inhibitor that interacts with a binding site, further comprising the step of:
(f) contacting the identified candidate inhibitor with the cytoplasmic domain of said FMS-like tyrosine kinase protein or said homologue thereof in order to determine the effect of the inhibitor on FMS-like tyrosine kinase protein activity.

One embodiment of this invention provides the method for identifying a candidate inhibitor that interacts with a binding site, wherein the binding site of the cytoplasmic domain of said FMS-like tyrosine kinase protein or said homologue thereof determined in step (d) comprises the structure coordinates according to FIGS. 1A-1 to 1A-50 of amino acid residues H809, R810, and D811, wherein the root mean square deviation from the backbone atoms of said amino acids is not more than ±2.0 Å.

One embodiment of this invention provides the method for identifying a candidate inhibitor that interacts with a binding site, wherein the binding site of the cytoplasmic domain of said FMS-like tyrosine kinase protein or said homologue thereof determined in step (d) comprises the structure coordinates according to FIGS. 1A-1 to 1A-50 of amino acid residues F621, E661, M664, L802, V808, R810, D829, and L832, wherein the root mean square deviation from the backbone atoms of said amino acids is not more than ±2.0 Å.

In one embodiment, the present invention provides the method for identifying a candidate inhibitor that interacts with a binding site, wherein the binding site of the cytoplasmic domain of said FMS-like tyrosine kinase protein or said homologue thereof determined in step (d) comprises the structure coordinates according to FIGS. 1A-1 to 1A-50 of amino acid residues F621, K644, A657, E661, M664, L802, S806, C807, V808, H809, R810, D811, D829, and L832, wherein the root mean square deviation from the backbone atoms of said amino acids is not more than ±2.0 Å.

In one embodiment, the present invention provides a method for identifying a candidate inhibitor that interacts with a binding site of a cytoplasmic domain of an FMS-like tyrosine kinase protein or a homologue thereof, comprising the step of determining a binding site of the cytoplasmic domain of said FMS-like tyrosine kinase protein or the homologue thereof from a three-dimensional model to design or identify the candidate inhibitor which interacts with said binding site.

In one embodiment, the present invention provides the method for identifying a candidate inhibitor that interacts with a binding site of a cytoplasmic domain of an FMS-like tyrosine kinase protein or a homologue thereof, wherein the binding site of the cytoplasmic domain of said FMS-like tyrosine kinase protein or said homologue thereof determined comprises the structure coordinates according to FIGS. 1A-1 to 1A-50 of amino acid residues H809, R810, and D811, wherein the root mean square deviation from the backbone atoms of said amino acids is not more than ±2.0 Å.

In one embodiment, the present invention provides the method for identifying a candidate inhibitor that interacts with a binding site of a cytoplasmic domain of an FMS-like tyrosine kinase protein or a homologue thereof, wherein the binding site of the cytoplasmic domain of said FMS-like tyrosine kinase protein or said homologue thereof determined comprises the structure coordinates according to FIGS. 1A-1 to 1A-50 of amino acid residues F621, E661, M664, L802, V808, R810, D829, and L832, wherein the root mean square deviation from the backbone atoms of said amino acids is not more than ±2.0 Å.

In one embodiment, the present invention provides the method for identifying a candidate inhibitor that interacts with a binding site of a cytoplasmic domain of an FMS-like tyrosine kinase protein or a homologue thereof, wherein the binding site of the cytoplasmic domain of said FMS-like tyrosine kinase protein or said homologue thereof determined comprises the structure coordinates according to FIGS. 1A-1 to 1A-50 of amino acid residues F621, K644, A657, L658, E661, M664, L802, K805, S806, C807, V808, H809, R810, D811, C828, D829, F830, G831, and L832, wherein the root mean square deviation from the backbone atoms of said amino acids is not more than ±2.0 Å.

One embodiment of this invention provides a method for identifying a candidate inhibitor of a molecule or molecular complex comprising a binding pocket or domain selected from the group consisting of:

(i) a set of amino acid residues which are identical to human FMS-like tyrosine kinase amino acid residues H809, R810, and D811 according to FIG. 1A, wherein the root mean square deviation of the backbone atoms between said set of amino acid residues and said FMS-like tyrosine kinase amino acid residues is not greater than about 2.0 Å;

(ii) a set of amino acid residues comprising at least five amino acid residues which are identical to human FMS-like tyrosine kinase amino acid residues F621, E661, M664, L802, V808, R810, D829, and L832 according to FIG. 1A, wherein the root mean square deviation of the backbone atoms between said at least five amino acid residues and said FMS-like tyrosine kinase amino acid residues which are identical is not greater than about 2.0 Å;

(iii) a set of amino acid residues comprising at least six amino acid residues which are identical to human FMS-like tyrosine kinase amino acid residues F621, K644, A657, L658, E661, M664, L802, K805, S806, C807, V808, H809, R810, D811, C828, D829, F830, G831, and L832 according to FIG. 1A, wherein the root mean square deviation of the backbone atoms between said at least six amino acid residues and said FMS-like tyrosine kinase amino acid residues which are identical is not greater than about 2.0 Å; and (iv) a set of amino acid residues that are identical to FMS-like tyrosine kinase amino acid residues according to FIG. 1A, wherein the root mean square deviation between said set of amino acid residues and said FMS-like tyrosine kinase amino acid residues is not more than about 3.0 Å;

comprising the steps of:

(a) using a three-dimensional structure of the binding pocket or domain to design, select or optimize a plurality of chemical entities; and (b) selecting said candidate inhibitor based on the inhibitory effect of said chemical entities on said cytoplasmic domain of said FMS-like tyrosine kinase protein or said cytoplasmic domain of said FMS-like tyrosine kinase protein homologue on the catalytic activity of the molecule.

In one embodiment, the present invention provides a method of using a crystal of a cytoplasmic domain of said FMS-like tyrosine kinase protein or a homologue in an inhibitor screening assay comprising:

(a) selecting a potential inhibitor by performing rational drug design with a three-dimensional structure determined for the crystal, wherein said selecting is performed in conjunction with computer modeling;

(b) contacting the potential inhibitor with a kinase; and (c) detecting the ability of the potential inhibitor for inhibiting the kinase.

In certain embodiments, the ability of the potential inhibitor for inhibiting the kinase is assesed using an enzyme inhibition assay. In other embodiments, the ability of the potential inhibitor for inhibiting the kinase is performed using a cellular-based assay.

In one embodiment, the present invention provides a method for identifying a candidate inhibitor that interacts with a binding site of an FMS-like tyrosine kinase protein or a homologue thereof comprising:

(a) obtaining a crystal of an FMS-like tyrosine kinase protein or a homologue thereof;

(b) obtaining the atomic coordinates of the crystal; and (c) using the atomic coordinates and one or more molecular modeling techniques to identify the candidate inhibitor that interacts with a binding site of an FMS-like tyrosine kinase protein or a homologue thereof. In certain embodiments, the crystal comprising a cytoplasmic domain of an FMS-like tyrosine kinase protein or a homologue thereof. In one embodiment, the step of obtaining a crystal is optional.

In one embodiment, the present invention provides the method for identifying a candidate inhibitor that interacts with a binding site of an FMS-like tyrosine kinase protein or a homologue thereof, wherein the one or more molecular modeling techniques are selected from the group consisting of graphic molecular modeling and computational chemistry.

In one embodiment, the present invention provides the method for identifying a candidate inhibitor that interacts with a binding site of an FMS-like tyrosine kinase protein or a homologue thereof, further comprising the candidate inhibitor with the FMS-like tyrosine kinase protein or the homologue and detecting binding of the candidate inhibitor to the FMS-like tyrosine kinase protein or the homologue.

In one embodiment, the present invention provides a method of struture-based identification of candidate compounds for binding to an FMS-like tyrosine kinase protein or a homologue thereof, comprising:

(a) constructing a three-dimensional structure of the FMS-like tyrosine kinase protein or a homologue thereof;

(b) performing computer-assisted structure-based drug design with said structure of the FMS-like tyrosine kinase protein or a homologue; and (c) identifying at least one candidate inhibitor that is predicted to have a compatible conformation with a binding site of the structure of the FMS-like tyrosine kinase protein or a homologue.

In certain embodiments, the present invention provides for methods wherein the three-dimensional structure is visualized as a computer image generated when said atomic coordinates determined by X-ray diffraction are analyzed on a computer using a graphical display software program to create an electronic file of the image and visualizing the electronic file on a computer capable of representing the electronic file as a three-dimensional image.

Structure Determination of Other Molecules

The structure coordinates set forth in FIG. 1A can also be used in obtaining structural information about other crystallized molecules or molecular complexes. This may be achieved by any of a number of well-known techniques, including molecular replacement.

According to one embodiment, the machine-readable data storage medium comprises a data storage material encoded with a first set of machine readable data which comprises the Fourier transform of at least a portion of the structure coordinates set forth in FIG. 1A or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex having an unknown structure, wherein said computer comprises:

(a) a machine-readable data storage medium comprising a data storage material encoded with machine-readable data, wherein said data comprises at least a portion of the structure coordinates of FLT3 according to FIG. 1A or a homology model thereof;

(b) a machine-readable data storage medium comprising a data storage material encoded with machine-readable data, wherein said data comprises X-ray diffraction data obtained from said molecule or molecular complex having an unknown structure; and (c) instructions for performing a Fourier transform of the machine-readable data of (a) and for processing said machine-readable data of (b) into structure coordinates.

For example, the Fourier transform of at least a portion of the structure coordinates set forth in FIG. 1A or homology model thereof may be used to determine at least a portion of the structure coordinates of the molecule or molecular complex.

Therefore, another embodiment this invention provides a method of utilizing molecular replacement to obtain structural information about a molecule or a molecular complex of unknown structure wherein the molecule or molecular complex is sufficiently homologous to FLT3, comprising the steps of:

(a) crystallizing said molecule or molecular complex of unknown structure;

(b) generating an X-ray diffraction pattern from said crystallized molecule or molecular complex;

(c) applying at least a portion of the FLT3 structure coordinates set forth in one of FIG. 1A or a homology model thereof to the X-ray diffraction pattern to generate a three-dimensional electron density map of at least a portion of the molecule or molecular complex whose structure is unknown; and (d) generating a structural model of the molecule or molecular complex from the three-dimensional electron density map.

In one embodiment, the method is performed using a computer. In another embodiment, the molecule is selected from the group consisting of FLT3 protein and FLT3 cytoplasmic domain homologues. In another embodiment, the molecular complex is FLT3 cytoplasmic domain complex or homologue thereof.

By using molecular replacement, all or part of the structure coordinates of FLT3 as provided by this invention (and set forth in FIG. 1A) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of FLT3 protein according to FIG. 1A within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.*, 115: 55-77 (1985); M. G. Rossmann, ed., "The Molecular Replacement Method", Int. Sci. Rev. Ser., No. 13, Gordon & Breach, New York (1972)).

The structure of any portion of any crystallized molecule or molecular complex that is sufficiently homologous to any portion of the structure of human FLT3 protein can be resolved by this method.

In one embodiment, the method of molecular replacement is utilized to obtain structural information about an FLT3 homologue. The structure coordinates of FLT3 as provided by this invention are particularly useful in solving the structure of FLT3 complexes that are bound by ligands, substrates and inhibitors.

Furthermore, the structure coordinates of FLT3 as provided by this invention are useful in solving the structure of FLT3 proteins that have amino acid substitutions, additions and/or deletions (referred to collectively as "FLT3 mutants", as compared to naturally occurring FLT3). These FLT3 mutants may optionally be crystallized in co-complex with a chemical entity. The crystal structures of a series of such complexes may then be solved by molecular replacement and compared with that of wild-type FLT3. Potential sites for modification within the various binding pockets of the enzyme may thus be identified. This information provides an additional tool for determining the most efficient binding interactions, for example, increased hydrophobic interactions, between FLT3 and a chemical entity or compound.

The structure coordinates are also particularly useful in solving the structure of crystals of the cytoplasmic domain of FLT3 or homologues co-complexed with a variety of chemical entities. This approach enables the determination of the optimal sites for interaction between chemical entities, including candidate FLT3 inhibitors. For example, high resolution X-ray diffraction data collected from crystals exposed to different types of solvent allows the determination of where each type of solvent molecule resides. Small molecules that bind tightly to those sites can then be designed and synthesized and tested for their FLT3 inhibition activity.

All of the molecules and complexes referred to above may be studied using well-known X-ray diffraction techniques and may be refined using 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzymol.*, vol. 114 & 115, H. W. Wyckoff et. al., eds., Academic Press (1985)) or CNS (Brunger et. al., *Acta Cryst.*, D54: 905-921, (1998)).

In order that this invention be more fully understood, the following examples are set forth. These examples are for the purpose of illustration only and are not to be construed as limiting the scope of the invention in any way.

EXAMPLE 1

FLT3 Expression and Purification

The cytoplasmic domain (H564-S993) of FLT3 (full length sequence, amino acid residues 1 to 993; GenBank accession no. NP_004110; SEQ ID NO:1) was cloned from cDNA bone marrow library (Clonetech, CA, USA). The expressed protein (H564-S958) was engineered with an internal deletion, removing the residues spanning H711-H761, and containing an N-terminal hexa-histidine tagged protein with a thrombin cleavage site. Cloned into the baculoviral transfer vector pBEV10, for insect cell expression, the recombinant virus generated was plaque purified and amplified to obtain a high-titer clonal viral stock. For production, High-5 insect cells grown to $2 \times 10^6$ cell/ml in Excell-405 medium (JRH Bioscience, KS, US) were infected with virus at a multiplicity of infection (MOI) of 2.5 and incubated 72-96 h at 27° C.

Frozen cell paste was thawed in 8 volumes of Buffer A (50 mM Hepes pH 8.2, 500 mM NaCl, 20% (v/v) glycerol, 0.1% (v/v) Triton X-100, 3 mM β-mercaptoethanol, 5 mM imidazole, 50 µM diisopropyl fluorophosphate, 2 µg/ml Pepstatin, 1 µg/ml leupeptin, 1 µg/ml E64 (Roche Diagnostics Corp., Indianapolis, Ind.), and 25 µl/L Benzonase) and mechanically lysed in a microfluidizer (Microfluidics, Newton, Mass.). The lysate was centrifuged at 54,000×g for 1 h, and the supernatant incubated with metal affinity resin (Ni-NTA agarose, Qiagen Inc. Valencia, Calif.) overnight at 4° C. After extensive washing with 20 column volumes of Buffer A, the protein was eluted with Buffer A containing 200 mM imidazole with the pH readjusted to 8.2. The elution pool was concentrated by ultrafiltration (30 KDa MWCO) in an Amicon stirred cell concentrator (Millipore, Billerica, Mass.) and loaded onto a HR 16/60 Superdex-200 size-exclusion column (Amersham Biosciences, Uppsala, Sweden) equilibrated in Buffer B (50 mM Hepes 8.2, 200 mM NaCl, 15% (v/v) glycerol, 5 mM DTT, and 0.1% (w/v) β-octylglucopyranoside). The FLT3 protein was pooled based on SDS-PAGE analysis. The protein was diluted two-fold with buffer containing 50 mM Hepes pH 8.2, 20% (v/v) glycerol, 5 mM DTT to reduce the salt concentration to 100 mM NaCl and loaded onto a MonoQ HR (5/5) column (Amersham Biosciences Corp, Uppsala, Sweden) pre-equilibrated in Buffer C (50 mM Hepes 8.2, 100 mM NaCl, 20% (v/v) glycerol, 5 mM DTT). A gradient was developed from Buffer C to Buffer C containing 1 M NaCl over 60 column volumes and FLT3 was eluted at ~250 mM NaCl. The protein was pooled based on SDS-PAGE analysis and the buffer exchanged to 25 mM Tris pH 8.1, 500 mM NaCl, 5% (v/v) glycerol and 5 mM DTT using a G25 column (Amersham Biosciences, Uppsala, Sweden). The protein containing fractions were pooled and concentrated to 10 mg/ml using a 30 KDa MWCO Vivaspin concentrator (Vivascience, Hanover, Germany) in the presence of 2 mM AMP-PNP and 4 mM $MgCl_2$.

EXAMPLE 2

Protein Crystallization for Native FLT3

Samples of the protein from Example 1 were subjected to ultracentrifugation at 90,000×g for 10 minutes prior to crystallization.

Crystals were grown in hanging drops by the vapor diffusion method where 0.5 µl each of FLT3 sample and reservoir solutions were combined. The reservoir condition was 1.2 M sodium phosphate, 1.2 M potassium phosphate, 0.1 M CAPS (3-cyclohexylamino-1-propanesulfonic acid) (pH 10.5) and 0.2 M lithium sulfate. Typically, the crystals took 1-3 weeks to appear and grew as hexagonal bipyramids to full size 2-4 days later. The morphology is representative of the space group $P4_32_12$ with a unit cell of dimensions a=b=80.67 Å, c=150.16 Å containing one molecule per asymmetric unit.

EXAMPLE 3

X-ray Diffraction and Structure Determination of FLT3

Prior to data collection the crystals were transferred stepwise to reservoir solutions containing 30% (v/v) glycerol then flash frozen in liquid nitrogen and stored in liquid nitrogen. Diffraction data were collected at −180° C. on a Rigaku R-AXIS IV++ imaging system mounted on a Rigaku RU-H3R rotating anode x-ray generator (CuKα) operated at 50 kV and 100 mA. Diffraction intensities were integrated and scaled with CrystalClear (Rigaku Intl. Corp). Table 1 summarizes information about the data collection.

The structure of FLT3 was solved by the molecular replacement method using AMoRe (Navaza, J., *Acta Cryst.* A50: 157-163 (1994)) in the CCP4 suite of programs (Collaborative Computational Project, Number 4, "The CCP4 Suite: Programs for Protein Crystallography," *Acta Cryst.* D50: 760-763 (1994)). The starting model for FLT3 was derived from the human vascular endothelial growth factor receptor 2 kinase domain (KDR) atomic coordinates (PDB entry 1VR2) where KDR residues identical to those in FLT3 were included in the search model. For those residues that were not identical, the side chains were pared back to the beta carbon atom.

Both the rotation and translation searches yielded a single consistent solution. The model corresponding to this solution was subjected to rigid body refinement, followed by torsional dynamics using CNX (Brünger, A. T., et al, *Acta Cryst.* D54: 905-921 (1998); (Accelrys, ©2000, 2001). All model building was performed using QUANTA (Molecular Simulations, Inc., San Diego, Calif. ©1998, 2000; Accelrys ©2001, 2002).

The electron density corresponding to side chains absent from the search model was generally clear and unambiguous in the kinase domain. Although, the electron density for certain regions of the activation loop and JM domain was visible, the entire course of each segment could not be traced in the preliminary electron density maps. The model was subjected to cycles of building/refinement. Composite difference electron maps were calculated which allowed the main chains of both the active site loop and the JM domain to be traced.

The final FLT3 structure contains the JM domain (residues 570 to 603), the kinase fold and activation loop (residues 604 to 710, 783 to 947), and 329 water molecules, one phosphate ion and one CAPS buffer molecule. During the course of the refinement, the electron density corresponding to residues 649-654 was poor and did not improve. Consequently, these residues that reside on the loop connecting β3 and αC were removed from the final model. Crystallographic refinement statistics are provided in Table 1.

EXAMPLE 4

Overview of FLT3 Structure

The principal features of the autoinhibited FLT3 structure include the bilobal kinase fold, the activation loop and the JM domain (FIGS. 2A and 2B). The kinase fold in FLT3 is that typically found in most protein kinases and consists of N- and C-terminal domains (N- and C-lobes) (Knighton, D. R., et. al., *Science* 253: 407-414 (1991)). The N-lobe contains a twisted five-stranded anti-parallel beta sheet adjacent to an α-helix.

According to the standard kinase nomenclature (FIG. 6A), the five β-strands in the N-lobe are termed β1-β5 and the sole N-lobe α-helix is termed αC. The secondary structure of the FLT3 C-lobe is predominantly α-helical, containing seven α-helices (αD, αE, αEF, αF-αI) and three β-strands (β6, β7 and β8). The activation loop is attached to the C-lobe and contains two additional β-strands (β10 and β11). These two β-strands comprise a small β-sheet that is characteristic of inactive kinases. This β-sheet is not present in activated kinase structures such as IRK (Hubbard et. al., 1997, supra) and cKIT (Mol et. al., supra) where the activation loop is fully open and the two β-strands are separated. However, in both activated structures, the unfolded activation loop generates β9 that pairs with β6. Even though β9 does not exist in the inactive FLT3 structure, β6 survives by forming a novel β-pair with βJ1 on the JM domain. The JM domain contains an additional β-strand termed βJ2.

Kinase N- and C-lobes are typically connected by a single flexible polypeptide strand that allows considerable rotational movement of the two domains relative to each other. This conformational diversity is observed in the multitude of available kinase structures (Huse, M., and Kuriyan, *J. Cell* 109: 275-282 (2002)) where the interlobe angular orientation can vary by approximately 20°. When the N-lobe is rotated away from the C-terminal domain, the kinase is in the catalytically 'inactive' form. Conversely, if the N-lobe is rotated towards the C-lobe, allowing key catalytic residues from both lobes to align, the kinase adopts the catalytically 'active' conformation. The crystal structure of autoinhibited FLT3 conforms to the prototypical conformation common to other inactive kinases that have a 'closed' activation loop folded between the two lobes of the 'inactive' kinase fold. A novel feature of the FLT3 structure is the presence of the complete JM domain that assumes its autoinhibited conformation and interacts with all key features of FLT3.

Activation Loop

Analogous to other kinases, the activation loop on FLT3 can be characterized as a long flexible peptide segment that connects β8 to αEF. The ends of the loop are delimited by the conserved three residue sequences Asp829-Phe830-Gly831 and Trp854-Met855-Ala856 located at the N- and C-terminal hinges of the loop, respectively. Asp829 is invariant in kinases and serves as the catalytic base in the phosphotransfer reaction (Bossemeyer, D., et. al., *EMBO J.* 12: 849-859 (1993)).

The crystal structures of FGFR (Mohammadi, M., et. al., supra), activated IRK (IRK-A) (Hubbard, S. R., supra) and inactive IRK (IRK-I) (Hubbard, S. R., et. al. (1994), supra) demonstrate the wide range of conformations available to the activation loop. In IRK-I, the activation loop is completely closed, allowing Tyr1143 to position itself in the active site, whereas the FGFR activation loop is partially unfolded and the IRK-A activation loop is fully open (FIG. 5A). These large conformational changes have been documented for other kinases as they transition from inactive to active states (Huse, M., and Kuriyan, supra). Kinase activation loops usually contain one to three tyrosine residues that can serve as phosphorylation sites. When these tyrosines are unphosphorylated, the activation loop typically assumes the closed conformation by folding into the cleft between the N- and C-lobes, thereby blocking access to the peptide substrate and ATP binding sites. In the activated state, which is associated with tyrosine phosphorylation, the activation loop adopts the open conformation and no longer restricts ATP and protein substrates from binding (Huse, M., and Kuriyan, supra).

The FLT3 activation loop in the crystal structure is similar to that observed in other inactive kinases such as IRK-I. The FLT3 loop contains a single unphosphorylated tyrosine residue (Tyr842) that adopts an orientation identical to its equivalent tyrosine in IRK-I (Tyr1143) and it is located in the same type of environment as its IRK-I analog. In particular, the phenolic ring points directly into the active site and is held in place by a hydrogen bond to an Asp side chain (Asp811) that, in turn, forms an ion pair with an arginine side chain (Arg834). The electron density corresponding to the Tyr842 side chain was one of the dominant features of the activation loop observed in the initial difference electron density maps. Except for the β10/β11 β-sheet, the electron density corresponding to the rest of the activation loop is significantly weaker, particularly for the residue segment running from Ile836 to Arg841. This is consistent with the IRK-I structure where the activation loop contains flexible peptide segments that are connected firmly to the C-lobe at each end and are held in place by the tightly bound tyrosine.

Point mutations of residues located on the activation loop generate constitutively activated forms of FLT3 that are implicated in AML (Yamamoto, Y., et. al., supra; Abu-Duhier, F. M., et. al., supra). The most common mutation is Asp835Tyr, however other mutations such as Asp835Thr and Asp835His have been reported (Yamamoto, Y., et. al., supra). Constitutive activation has also been reported for Ile836 mutations as well (Thiede, C., et. al., supra; Yamamoto, Y., et. al., supra). It has been suggested that Asp835 might provide essential stability to the closed form of the loop that is lost in the FLT3 mutants. Looking at Asp835 in the FLT3 structure, the side chain of Asp835 does indeed make a hydrogen bond with the main chain of Ser838. However, the significance of this, with respect to stability of the closed loop conformation, is not clear because the electron density in this region is relatively diffuse. Likewise, the possible role of Ile836 in stabilizing the closed conformation remains ambiguous due to the disorder and implied mobility of the activation loop in this region. Therefore, the electron density of the structure does not support the suggestion that Asp835 and/or Ile836 provides intrinsic stability to the closed form of the activation loop which, when lost in oncogenic mutants, prevents the closure of the activation loop.

Juxtamembrane Domain

The structure of the JM domain and its relation to the rest of the FLT3 structure is illustrated in FIGS. 2A, 2B, 3A and 3B. The JM domain can be divided into three distinct topological components: the JM binding motif (JM-B), the JM switch motif (JM-S) and the zipper or linker peptide segment (JM-Z) (FIGS. 3A and 3B). The JM-B (Tyr572-Met578) is termed the binding motif because it is nearly buried in the FLT3 structure. It is a short finger-like segment beginning with an invariant tyrosine (Tyr572) that resembles a 'hook'. Even though the JM-B consists of only seven residues, it makes contacts with virtually every structural component implicated in the activation/inactivation cycle of the FLT3 cytoplasmic domain (FIGS. 3A and 3B). The JM-S (Val579-Val592) is a two-stranded anti-parallel β-twist that is situated in an external location on the C-lobe. It is attached to the JM-B by a continuous extension of a β-strand termed βJ1. The JM-S is defined as a switching motif because it contains two key tyrosine residues whose state of phosphorylation is implicated in the activation and regulation of receptor enzymatic activity (Mol. C. D., et. al., supra). Lastly, the JM-Z (Asp593-Trp603) is located at the C-terminus of the JM domain and is associated primarily with the N-lobe as it loops around the outside of αC forming fairly extensive contacts with this key α-helix.

Looking at the FLT3 JM domain in more detail, particularly at the N-terminal region of the peptide sequence, the segment from His564 to Arg571, now defined as part of the linker connecting the JM and the transmembrane (TM) domains, is disordered and not present in the FLT3 structure. The first residue identified in the electron density map is Tyr572 located at the N-terminus of the JM-B. The side chain of Tyr572 sits in a tight pocket where the aromatic ring makes extensive hydrophobic contacts with surrounding residues. The Tyr572 phenolic hydroxyloxygen forms a hydrogen bond with a side chain oxygen on the highly conserved Glu661 which, together with sequence-invariant Lys644, forms an ion pair which is critical for nucleotide binding. It is interesting to note that Tyr842, which serves as an anchoring point on the activation loop, interacts with another ion pair (Asp811: Arg834) in a similar manner (FIG. 4). Proceeding in the C-terminal direction from Tyr572, the polypeptide chain runs inward three residues before making a perpendicular turn at Gln575. The Gln575 and the next three residues in the polypeptide chain interact with β6 to form an antiparallel β-sheet. The electron density in this segment (Tyr572-Met578) is excellent and indicative of a well-ordered conformation. The JM-B binds in a central strategic area of FLT3 and makes contacts with a number of key structural components (Knighton, et. al., supra) including the glycine-rich loop, the activation loop, and the catalytically important αC.

The JM-B is nearly buried in the crystal structure of autoinhibited FLT3. It loses 350 Å² of solvent accessible surface area as it attaches to its binding site. This accounts for 76% of the total accessible surface area available to the JM-B when it is not in contact with its neighboring structural elements in the crystal structure. This proportionally large area of contact suggests a stable interaction between the JM-B and the rest of the molecule. The strength of the interaction is likely enhanced by a moderate amount of interdigitation between side chains on the JM-B and those in the surrounding pocket as it is positioned between β6 on one side and αC on the other. Therefore, the JM-B can be thought of as a 'wedge' that stabilizes the inactive kinase conformation of FLT3 by preventing the N-lobe from rotating towards the C-lobe to generate the activated kinase fold.

An additional role of the JM-B in stabilizing the inactive kinase conformation is revealed by its proximity to the N-terminal hinge of the activation loop. This is shown in FIGS. 5A and 5C which depicts the relationship of the JM-B to the open and closed forms of the IRK activation loops. The autoinhibited FLT3 activation loop is in the closed conformation and, as long as the JM-B is in place, the activation loop cannot unfold in a manner similar to the fully open IRK-A form (FIG. 5C) or even to the partially open FGFR form (FIG. 5B). In fact, a segment of the IRK activation loop forms a β-strand (β9) that overlaps with the superposed βJ1 and similarly generates a β-pair with β6. This relationship between β9 and β6 exists in the activated structure of cKIT. Therefore, β6 can stabilize both the active and the inactive (autoinhibited) kinase conformation, depending on whether it interacts with the activation loop or JM domain, respectively.

The JM-S lies immediately adjacent to the JM-B and consists of fourteen residues that form a two-stranded β-twist motif. The JM-S starts as a four-residue extension to βJ1 where the transition from JM-B to JM-S occurs at Met578-Val579. The extended conformation of the βJ1 likely provides a rigid connection between the JM-B and JM-S that could directly transmit perturbations and movements from one motif to the other. βJ1 terminates at residue Val581 where a five-residue loop connects to a short four-residue β-strand (βJ2) that contains two conserved tyrosines (Tyr589 and Tyr591). The side chains on these tyrosines are adjacent to each other and lay between the JM-S and the C-lobe.

Unlike the JM-B, which is immersed in extensive intramolecular contacts, the JM-S interacts with the rest of the molecule in a less extensive, less complementary way. As shown in FIGS. 3A and 4, the JM-S protrudes from FLT3 as an extension of the βJ1. The JM-S appears to be held in place by the rigidity of the β-strand network consisting of β6, βJ1, and βJ1. Any significant change in the orientation of the JM-S relative to the C-lobe would likely disrupt the β-network and de-stabilize binding of the JM-B. A dominant feature of the JM-S is the tyrosine pair (Tyr589 and Tyr591) pointed directly at the C-lobe. In fact, this tyrosine pair is the principal contact between the JM-S β-sheet and the C-lobe. Neither of the tyrosine side chains binds in a tight complementary pocket similar to Tyr572 and Tyr599. As such, the JM-S does not provide a significant amount of binding interface between it and the C-lobe that can directly enhance the attachment of the JM-B. Rather, the spatial arrangement of the JM-S relative to the C-lobe suggests the role of the JM-S is to provide a rigid and properly oriented framework requisite for the interposition of Tyr589 and Tyr591 between it and the C-lobe.

The remaining eleven residues of the JM domain comprise the JM-Z that folds up alongside the N-lobe. It is a simple peptide segment that loops over αC and terminates in the hinge region of the JM domain. Recent crystallographic studies on IRK, cKIT and other RTKs show that the JM-Z region can undergo large amplitude rotations away from the N-lobe by pivoting about its attachment point. This is demonstrated in the crystal structure of cKIT (PDB entry, 1PKG) that contains two independent copies of the activated molecule. The JM-Z on one molecule adopts the 'attached' conformation as it lays alongside the N-lobe, while the JM-Z on the other molecule in the asymmetric unit is 'unattached' or 'unzipped' from the N-lobe. The conformation of the FLT3 JM-Z is very similar to the 'attached' conformation observed in activated cKIT and inactivated IRK crystal structures. However, the JM-B and the N-terminal half of the JM-S in these structures are either missing or disordered.

FLT3 Tyr599 is conserved across the PDGFR family and is located near the JM hinge region. Like its cKIT equivalent on the 'attached' JM-Z, the tyrosine side chain is buried in a pocket where the hydroxyl group is hydrogen bonded to the equally conserved Glu604. In the 'unattached' cKIT JM-Z, the tyrosine is pulled out of its insertion pocket and is exposed to solvent. There is no biochemical or crystallographic evidence to suggest that Tyr599, or its equivalents in cKIT or IRK, are autophosphorylation sites. Thus, the principal function of Tyr599 could be one of providing the proper orientation and guidance to the JM hinge region as the JM domain transitions from the 'unattached' to the 'attached' conformation.

The JM Domain Autoinhibitory Mechanism

The activation of FLT3 is a stepwise process that is described for all the type III RTKs (Rosnet, O., and Birnbaum, D. *Crit. Rev. Oncog.* 4: 595-613 (1993)). It is initiated when FL, its specific endogenous ligand, binds to the extracellular domain of FLT3. This promotes dimerization of the receptor and concomitant juxtapositioning of the cytoplasmic domains. Once the dimer is formed, transphosphorylaton of specific tyrosine residues on the JM domain can take place. This activates full kinase activity which induces multiple signaling pathways that are involved in cell proliferation and activation (Turner, A. M., et. al., supra; Heldin, C. H. *Cell* 80: 213-223 (1995)). The kinase activity is negatively modulated by tyrosine phosphatases that dephosphorylate the tyrosines on the unbound JM domain. This allows the JM domain to adopt its autoinhibitory conformation.

There has been considerable speculation on how the JM domain regulates the activity of type III RTKs. Certainly, the phosphorylation state of key tyrosine residues plays a central role, but the precise nature of regulation has not been understood. However, the structure of autoinhibited FLT3 suggests a simple mechanism for kinase modulation by the JM domain. As shown earlier, the tyrosine pair (Tyr589 and Tyr591) is positioned between the JM-S β-sheet and the C-lobe. As such, it cannot accommodate the charged, bulky phosphate moieties of phosphorylated tyrosines and still maintain the bound conformation of the JM-B/JM-S complex. Without being bound by theory, when one or both of these tyrosines is phosphorylated, the JM-S cannot fold up properly and/or position itself next to the C-lobe in a manner conducive to the autoinhibited state. Conversely, when the phosphates are removed from the tyrosines by regulatory phosphatases, the JM-S can position itself next to the C-lobe and allow the JM-B to insert into its autoinhibitory binding site. This role of the JM domain is supported by Chan et. al. (Chan, P. M., et. al., *Mol. Cell. Biol.* 23: 3067-3078 (2003)) who synthesized the JM domain of cKIT, approximately 39 amino acid long, and showed that this peptide alone inhibits a cKIT construct that had the JM domain entirely deleted. Furthermore, other JM constructs that were either mutated or phosphorylated did not 'autoinhibit' the JM-minus cKIT construct.

According to this suggested mechanism, the role of the JM-Z is to correctly align and maintain the JM-S in the proper register during and after the transition between activated and inactive states of FLT3. Therefore the length of the JM-S is critical and should be conserved across all members of the PDGFR family. This is confirmed by analysis of the aligned sequences of the PDGFR family (FIG. 6B) where the lengths of all structural elements in the JM domain are conserved. The only exception occurs in the loop connecting the two JM-S β-strands. The variability in this loop region is inconsequential because it is located between the two aligned strands of the β-sheet that does not affect the position of the JM-S relative to the JM-B and the JM-Z.

Autoinhibitory Mechanism of the PDGRF Family

The amino acid sequence of the JM domain shows a high degree of homology across the PDGFR family (FIG. 6B). This homology likely correlates with conserved structural and mechanistic features of all the members. Irusta et. al. (Irusta, P. M., et al, *J. Biol. Chem.* 277, pp 38627-38634 (2002)) carried out a systematic alanine-scanning mutational analysis of the JM domain of murine PDGFRβ and identified a number of residues, namely Y530A, W534A, V536A, 1537A, L555A, Y557A, and the double mutant Y547A/Y549A that resulted in constitutive receptor activation (PDGFRβ numbers are given). These residues in PDGFRβ when mutated to alanine, result in constitutive activation, and therefore, correspond to key residues in the JM domain observed in the FLT3 structure. For example, substitution of alanine for residues corresponding to Tyr572 and Leu576, two key anchoring points for the JM-B, resulted in receptor activation. Conversely, mutation of amino acid residues corresponding to FLT3 amino acid residues that are not involved in interactions with the kinase domain, such as Gln580, Gly583 and Glu588, did not result in activation of PDGFRβ. In another experiment, an alanine was inserted between positions Ser574 and Gln575 and between positions Asp586 and Asn587 in the PDGFRβ sequence. These insertions fall within the JM-B region and within the JM-S loop region, respectively. Not surprisingly, the JM-B insertion resulted in constitutive activation while the loop insertion did not. The results of these mutational experiments, together with own structural analysis, strongly suggests that the JM sequence of the PDGFR family constitutes a common inhibitory domain that utilizes the autoinhibitory mechanism described for FLT3.

The common autoinhibitory mechanism for the PDGFR kinase family is the result of a highly conserved amino acid sequence in the JM region. Other kinases, with different JM amino acid sequences, utilize distinctly different autoregulatory mechanisms. For example, the JM region of Type I TGFβ receptor, in association with FKBP12, forms an autoinhibitory structure that interacts with the kinase domain to block catalytic activity, most significantly by displacing the critical αC helix in the N-lobe of the kinase domain and disrupting the conformation of the ATP-binding site (Huse M., et. al., *Cell* 96: 425-436 (1999)). In a similar manner, the autoinhibitory mechanism of EphB2 is facilitated by the JM domain as it interacts with the αC helix. Specifically, a helix on the JM domain introduces a kink in αC that stabilizes the inactive conformation (Wybenga-Groot, L. E., et. al., supra). All three of these distinct autoinhibitory mechanisms are examples of the conformational plasticity of protein kinases described by Huse and Kuriyan, supra.

Structural Implications for ITDs Found in AML

The internal tandem duplications (ITDs) found in AML patients (Nakao, M., et. al., supra; Thiede, C., et. al., supra) range from four to about sixty-eight amino acid residues (Kottaridis, P. D., et. al., supra). This insert domain made FLT3 autoinhibition 'leaky', as described by Schlessinger et. al. (Irusta, P. M., et. al., supra), allowing it to switch FLT3 from the inactive to the catalytically active conformation without the presence of its endogenous ligand FL. The ITD insertions generally occur in the JM-Z near the JM hinge region which, among other things, offsets the position of the JM-S in the FLT3 structure. This likely disturbs or prevents the optimal orientation of JM-S as it tries to position the JM-B in its binding site. In addition to this, the presence of an ITD could simply obviate the complementary interaction that exists between the normal JM-Z and the N-lobe. As such, the aberrant JM-S could be stuck in the 'unattached' conformation permanently.

While we have described a number of embodiments of this invention, it is apparent that our basic constructions may be altered to provide other embodiments which utilize the products, processes and methods of this invention.

All cited documents are incorporated herein by reference.

TABLE 1

| Data Collection and Refinement Statistics | |
|---|---|
| Data set | Native |
| Data collection | |
| X-ray source | Rigaku RU-H3R |
| Space group | P4₃2₁2 |
| Unit cell parameters (Å) | a = b = 80.65; c = 150.13 |
| Resolution (Å) | 30 – 2.1 |
| Unique reflections | 29690 |
| Redundancy | 6.82 |

TABLE 1-continued

Data Collection and Refinement Statistics

| Data set | Native |
|---|---|
| Completeness (%)* | 99.3 (94.1) |
| $R_{merge}$* | 0.056 (0.265) |
| $<I/\sigma>$* | 18.6 (57) |
| Refinement | |
| Reflections used | 29428 |
| Test reflections | 1706 |
| R-factor | 0.209 |
| free R-factor (% data) | 0.246 (5.0) |
| RMS deviation | |
| Bond lengths (Å) | 0.009 |
| Bond angles (°) | 1.59 |
| Protein atoms | 2439 |
| Solvent atoms | 329 |
| Phosphate atoms | 5 |
| CAPS atoms | 13 |

*Values for the highest resolution shell are shown in parentheses.

$$R_{merge} = \sum_{hkl}\sum_{i} |I(hkl)_i - \langle I(hkl) \rangle| / \sum_{hkl}\sum_{i} \langle I(hkl)_i \rangle$$

over i observations of reflection hkl.

$$R\text{-factor} = \sum ||F_{obs}| - |F_{calc}|| / \sum |F_{obs}|$$

where $F_{obs}$ and $F_{calc}$ are the observed and calculated structure factors, respectively.

Free R-factor is calculated from a randomly chosen subset of reflections not used for refinement.

---

We claim:

1. A crystal of a cytoplasmic domain of an FMS-like tyrosine kinase 3 (FLT3) protein wherein said cytoplasmic domain is unphosphorylated and consists of, in the following order: an N-terminal hexa-histidine tag containing a thrombin cleavage site fused to the N-terminus of FLT3 amino acids 564-958 of SEQ ID NO:1, except for an internal deletion of amino acids 711-761, and wherein said crystal is characterized as having space group $P4_32_12$ with unit cell parameters of a=b=80.67 Å and c=150.16 Å.

2. A crystallizable composition of a cytoplasmic domain of an FMS-like tyrosine kinase 3 (FLT3) protein wherein said cytoplasmic domain consists of, in the following order, an N-terminal hexa-histidine tag containing a thrombin cleavage site fused to the N-terminus of the polypeptide of amino acids 564-958 of SEQ ID NO:1, except for an internal deletion of amino acids 711-761 and wherein said crystallizable composition forms isomorphous crystals.

3. A method for identifying a candidate inhibitor that interacts with a binding site of an FMS-like tyrosine kinase 3 (FLT3) protein, comprising the steps of:

(a) diffracting the crystal according to claim 1 with X-rays to obtain a set of diffraction patterns;

(b) using the diffraction patterns in step a) to solve the three-dimensional protein structure and obtain structure coordinates for the amino acids of the crystal of step (a), wherein the structure coordinates are set forth in FIG. 1A-1 to 1A-50;

(c) generating a three-dimensional model of the cytoplasmic domain of said FLT3 protein using the structure coordinates of the amino acids obtained in step (b), wherein said structure coordinates have a root mean square deviation from the backbone atoms of said amino acids of no more than ±2.0 Å;

(d) determining a binding site of the cytoplasmic domain of said FLT3 protein from said three-dimensional model; and (e) performing computer fitting analysis to identify a candidate inhibitor or inhibitors which interact with said binding site, wherein the candidate inhibitor or inhibitors that interact with said binding site are identified as a candidate inhibitor or inhibitors of FLT3.

4. The method according to claim 3, further comprising the step of:

(f) contacting the identified candidate inhibitor or inhibitors with the cytoplasmic domain of said FLT3 protein in vitro in order to determine the effect of the inhibitor on FLT3 protein activity.

5. The method according to claim 3, wherein the binding site of the cytoplasmic domain of said FLT3 protein determined in step (d) comprises the structure coordinates according to FIGS. 1A-1 to 1A-50 of amino acid residues His 809, Arg 810, and Asp 811, wherein the root mean square deviation from the backbone atoms of said amino acids is not more than ±2.0 Å.

6. The method according to claim 3, wherein the binding site of the cytoplasmic domain of said FLT3 protein determined in step (d) comprises the structure coordinates according to FIGS. 1A-1 to 1A-50 of amino acid residues Phe 621, Glu 661, Met 664, Leu 802, Val 808, Arg 810, Asp 829, and Leu 832, wherein the root mean square deviation from the backbone atoms of said amino acids is not more than ±2.0 Å.

7. The method according to claim 3, wherein the binding site of the cytoplasmic domain of said FLT3 protein determined in step (d) comprises the structure coordinates according to FIGS. 1A-1 to 1A-50 of amino acid residues Phe 621, Lys 644, Ala 657, Glu 661, Met 664, Leu 802, Ser 806, Cys 807, Val 808, His 809, Arg 810, Asp 811, Asp 829, and Leu 832, wherein the root mean square deviation from the backbone atoms of said amino acids is not more than ±2.0 Å.

8. A method for identifying a candidate inhibitor that interacts with a binding site of the cytoplasmic domain of an FLT3 protein, comprising the steps of:

(a) diffracting the crystal according to claim 1 with X-rays to obtain a set of diffraction patterns;

(b) using the diffraction patterns in step a) to solve the three-dimensional protein structure and obtain structure coordinates for the amino acids of the crystal of step (a);

(c) generating a three-dimensional model of said FLT3 protein using the structure coordinates of the amino acids generated in step (b), wherein the structure coordinates have a root mean square deviation from backbone atoms of said amino acids of not more than ±2.0 Å;

(d) determining a binding site of the cytoplasmic domain of said FLT3 protein from said three-dimensional model; and (e) performing computer fitting analysis to identify a candidate inhibitor which interacts with said binding site, wherein a candidate inhibitor that interacts with said binding site is identified as a candidate inhibitor of FLT3.

9. The method according to claim 8, further comprising the step of:

(f) contacting the identified candidate inhibitor with the cytoplasmic domain of said FLT3 protein in vitro in order to determine the effect of the inhibitor on FLT3 protein activity.

10. The method according to claim 8, wherein the binding site of the cytoplasmic domain of said FMS-like tyrosine kinase 3 protein determined in step (d) comprises amino acid residues His 809, Arg 810, and Asp 811.

11. The method according to claim 8, wherein the binding site of the cytoplasmic domain of said FLT3 protein determined in step (d) comprises amino acid residues Phe 621, Glu 661, Met 664, Leu 802, Val 808, Arg 810, Asp 829, and Leu 832.

12. The method according to claim 8, wherein the binding site of the cytoplasmic domain of said FLT3 protein determined in step (d) comprises amino acid residues Phe 621, Lys 644, Ala 657, Glu 661, Met 664, Leu 802, Ser 806, Cys 807, Val 808, His 809, Arg 810, Asp 811, Asp 829, and Leu 832.

* * * * *

SEQUENCE LISTING

<160> NUMBER OF SEQ ID NOS: 5

<210> SEQ ID NO 1
<211> LENGTH: 993
<212> TYPE: PRT
<213> ORGANISM: Homo sapiens

<400> SEQUENCE: 1

```
Met Pro Ala Leu Ala Arg Asp Ala Gly Thr Val Pro Leu Leu Val Val
 1               5                  10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
                35                  40                  45

Lys Ser Ser Ser Tyr Pro Met Val Ser Glu Ser Pro Glu Asp Leu Gly
50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
                115                 120                 125

Val Ile Leu Lys Met Thr Glu Thr Gln Ala Gly Glu Tyr Leu Leu Phe
            130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
                180                 185                 190

Ile Val Glu Trp Val Leu Cys Asp Ser Gln Gly Glu Ser Cys Lys Glu
                195                 200                 205

Glu Ser Pro Ala Val Val Lys Lys Glu Glu Lys Val Leu His Glu Leu
210                 215                 220
```

```
Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Gly Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
610                 615                 620

Met Asn Ala Thr Ala Tyr Gly Ile Ser Lys Thr Gly Val Ser Ile Gln
625                 630                 635                 640
```

```
Val Ala Val Lys Met Leu Lys Glu Lys Ala Asp Ser Ser Glu Arg Glu
            645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
        690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
            755                 760                 765

Glu Asn Gln Lys Arg Leu Glu Glu Glu Glu Asp Leu Asn Val Leu Thr
        770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 2
<211> LENGTH: 46
<212> TYPE: PRT
<213> ORGANISM: Homo sapiens

<400> SEQUENCE: 2

Val Ile Trp Lys Gln Lys Pro Arg Tyr Glu Ile Arg Trp Arg Val Ile
 1                5                  10                  15
```

-continued

```
Glu Ser Ile Ser Pro Asp Gly His Glu Tyr Ile Tyr Val Asp Pro Met
             20                  25                  30

Gln Leu Pro Tyr Asp Ser Arg Trp Glu Phe Pro Arg Asp Gly
         35                  40                  45

<210> SEQ ID NO 3
<211> LENGTH: 46
<212> TYPE: PRT
<213> ORGANISM: Homo sapiens

<400> SEQUENCE: 3

Met Leu Trp Gln Lys Lys Pro Arg Tyr Glu Ile Arg Trp Lys Val Ile
 1               5                  10                  15

Glu Ser Val Ser Ser Asp Gly His Glu Tyr Ile Tyr Val Asp Pro Met
             20                  25                  30

Gln Leu Pro Tyr Asp Ser Thr Trp Glu Leu Pro Arg Asp Gln
         35                  40                  45

<210> SEQ ID NO 4
<211> LENGTH: 44
<212> TYPE: PRT
<213> ORGANISM: Homo sapiens

<400> SEQUENCE: 4

Tyr Lys Tyr Leu Gln Lys Pro Met Tyr Glu Val Gln Trp Lys Val Val
 1               5                  10                  15

Glu Glu Ile Asn Gly Asn Asn Tyr Val Tyr Ile Asp Pro Thr Gln Leu
             20                  25                  30

Pro Tyr Asp His Lys Trp Glu Phe Pro Arg Asn Arg
         35                  40

<210> SEQ ID NO 5
<211> LENGTH: 44
<212> TYPE: PRT
<213> ORGANISM: Homo sapiens

<400> SEQUENCE: 5

Tyr Lys Tyr Lys Gln Lys Pro Lys Tyr Gln Val Arg Trp Lys Ile Ile
 1               5                  10                  15

Glu Ser Tyr Glu Gly Asn Ser Tyr Thr Phe Ile Asp Pro Thr Gln Leu
             20                  25                  30

Pro Tyr Asn Glu Lys Trp Glu Phe Pro Arg Asn Asn
         35                  40
```